(12) United States Patent
Georg et al.

(10) Patent No.: US 8,377,958 B2
(45) Date of Patent: Feb. 19, 2013

(54) LONIDAMINE ANALOGUES FOR FERTILITY MANAGEMENT

(75) Inventors: Ingrid Gunda Georg, St. Paul, MN (US); Joseph S. Tash, Leawood, KS (US); Ramappa Chakrasali, St. Paul, MN (US); Sudhakar Rao Jakkaraj, Falcon Heights, MN (US); Katherine Roby, Overland Park, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 12/830,681

(22) Filed: Jul. 6, 2010

(65) Prior Publication Data

US 2011/0060003 A1    Mar. 10, 2011

Related U.S. Application Data

(63) Continuation-in-part of application No. 12/395,521, filed on Feb. 27, 2009, which is a continuation-in-part of application No. 10/922,747, filed on Aug. 20, 2004, now Pat. No. 7,514,463.

(60) Provisional application No. 61/105,125, filed on Oct. 14, 2008, provisional application No. 61/223,330, filed on Jul. 6, 2009.

(51) Int. Cl.
*A61K 31/416* (2006.01)
*A61K 31/437* (2006.01)

(52) U.S. Cl. ........................... 514/303; 514/406
(58) Field of Classification Search .................. 514/303, 514/406
See application file for complete search history.

(56) References Cited

U.S. PATENT DOCUMENTS

| 3,895,026 A | 7/1975 | Palazzo et al. |
| 7,514,463 B2 * | 4/2009 | Georg et al. ................. 514/405 |
| 2006/0047126 A1 | 3/2006 | Georg et al. |

OTHER PUBLICATIONS

Grima et al., Biology of Reproduction (2001), 64(5), p. 1500-1508.*
Cheng et al., Biology of Reproduction (2001), 65(2), p. 449-461.*
Extended European Search Report dated Nov. 20, 2012 as received in Application No. EP 10 79 7717.
Cheng at al., "Two New Male Contraceptives Exert Their Effects by Depleting Germ Cells Prematurely from the Testis.", Biology of Reproduction, vol. 65, No. 2, Aug. 1, 2001, pp. 449-461.
Barcellona et al., "Effects of 1-p-chlorobenzyl-1H-indazol-3-carboxylic acid (AF 1312/TS) on the fertility of rats.", Journal of Reproduction and Fertility, vol. 50, No. 1, May 1977, pp. 159-161.

* cited by examiner

*Primary Examiner* — Yong Chu
(74) *Attorney, Agent, or Firm* — Maschoff Gilmore & Israelsen

(57) ABSTRACT

Fertility management can include: administering to the subject one or more doses of a compound according to Formula I so as to reduce fertility in the subject. Fertility management can also include administering an effective amount of the compound to: impair Sertoli cell function in a male subject; inhibit spermatogenesis in the subject; reduce testis weight in the subject; reduce ovary weight in a female subject; reduce serum progesterone in the female subject; impair ovarian follicle function in the female subject; causing reversible fertility in the subject. In order to return fertility, the method can include ceasing administration of the compound to the subject so as to return fertility in the subject. The compound can be administered for irreversibly sterilizing the subject.

24 Claims, 44 Drawing Sheets

RC-MC-86 200 mg/kg

RC-MC-110 1.0 mg/kg

US 8,377,958 B2

LONIDAMINE ANALOGUES FOR FERTILITY MANAGEMENT

CROSS-REFERENCE TO RELATED APPLICATIONS

The present patent application is a continuation-in-part of U.S. patent application Ser. No. 12/395,521, filed Feb. 27, 2009 which is a continuation-in-part of U.S. patent application Ser. No. 10/922,747, filed Aug. 20, 2004 now U.S. Pat. No. 7,514,463 and claims benefit U.S. Provisional Application Ser. No. 61/105,125, filed Oct. 14, 2008, and claims benefit to U.S. Provisional Application Ser. No. 61/223,330, filed Jul. 6, 2009, which applications are incorporated herein by specific reference in their entirety by specific reference.

This invention was made with government support under NO1-HD-1-3313 and P50 DK05301 awarded by the National Institutes of Health. The government has certain rights in the invention.

FIELD OF THE INVENTION

The present invention relates to novel analogues of lonidamine, such as gamendazole and H2-gamendazole, and others. In particular, some of the novel analogues of lonidamine, such as gamendazole and H2-gamendazole, are useful in sterilizing males and females and inhibiting reproduction potential.

BACKGROUND OF THE INVENTION

The prevention of unplanned pregnancy in humans and other mammals is of continuing concern for both the developing and the developed world. A variety of methods and products have been proposed or developed for the prevention of pregnancy. These products include: surgical sterilization, condoms, birth control pills containing progestin or a combination of progestin and estrogen, subdermal implants containing delayed release forms of progesterone, intrauterine devices, spermicidal creams or gels, and intravaginal barriers such as sponges or diaphragms.

Male contraceptive approaches have included the barrier methods, hormonal methods, the rhythm method, and immunological methods. More recently, researchers have begun investigating compounds which inhibit spermatogenesis by disrupting junctional complex sites between Sertoli cells and germ cells in the testes. One such compound is lonidamine (1-(2,4-dichlorobenzyl)-1H-indazole-3-carboxylic acid). Lonidamine belongs to a group of indazole-carboxylic acid compounds that was found to be a potent inhibitor of spermatogenesis. However, the antispermatogenic effects of lonidamine at high doses were found to be irreversible and toxic. See generally Lonidamine: A New Pharmacological Approach to the Study and Control of Spermatogenesis and Tumors, Chemotherapy, 27 Suppl. 2, 1-120 (1981a 1981b); Lonidamine, Proceedings of the 2nd International Symposium, Vancouver (1982).

Several analogues of lonidamine have recently been investigated as spermatogenic inhibitors. See Silvestrini et al., U.S. Pat. No. 6,001,865; Baiocchi et al., U.S. Pat. No. 5,112,986; Silvestrini, U.S. Pat. No. 4,282,237; Palazzo et al., U.S. Pat. No. 3,895,026; Cheng et al., Two New Male Contraceptives Exert Their Effects by Depleting Germ Cells Prematurely from the Testis, BIOLOGY OF REPRODUCTION 65, 449-461 (2001); Grima et al., Reversible Inhibition of Spermatogenesis in Rats Using a New Male Contraceptive 1-(2,4-dichlorobenzyl)-indazole-3-carbohydrazide, BIOLOGY OF REPRODUCTION 64, 1500-1508 (2001); Corsi et al., 1-Halobenzyl-1H-indazole-3-carboxylic acids: A New Class of Antispermatogenic Agents, J. MED. CHEM., Vol. 19, No. 6, 778-783 (1976); Palazzo et al., Synthesis and pharmacological properties of 1-substituted 3-dimethylaminoalkoxy-1H-indazoles, J. MED. CHEM. Vol. 9, 38-41 (1966). Despite these advances, there remains a need for compounds which are antispermatogenic but preferably do not exhibit toxic side effects.

The somatic form of eEF-1 alpha (eEF-1 alpha S) mRNA is virtually undetectable in male and female germ cells of the adult gonad but is very abundant in embryonic cells after the neurula stage. In contrast, another form of eEF-1 alpha (eEF-1 alpha O) mRNA is highly concentrated in oogonia and in previtellogenic oocytes but is undetectable in eggs and embryos. eEF-1 alpha O mRNA is also present in spermatogonia and spermatocytes of adult testis. The latter finding identifies eEF-1 alpha O mRNA as a germ cell-specific gene product. Although germ cells contain very little eEF-1 alpha S mRNA, several eEF-1 alpha S retropseudogenes exist in *X. laevis* chromosomes. These genes are thought to arise in germ cells from reverse transcription of mRNA and subsequent integration of the cDNA copies into chromosomal DNA. It is suggested that eEF-1 alpha S pseudogenes are generated in primordial germ cells of the embryo before they differentiate into oogonia or spermatogonia. See Abdallah et al., Germ cell-specific expression of a gene encoding eukaryotic translation elongation factor 1 alpha (eEF-1 alpha) and generation of eEF-1 alpha retropseudogenes in *Xenopus laevis*, Proc. Natl. Acad. Sci. U.S.A. 88: 9277-9281 (1991).

Protein synthesis is believed to be under control of the cell cycle during meiosis and mitosis. Any relationship between substrates for cdc2 kinase and components of the protein synthetic apparatus would therefore be of prime importance. During meiosis of *Xenopus laevis* oocytes one of the substrates for this kinase is a p47 protein, which is complexed to two other proteins, P36 and P30. Judged from partial amino acid sequence data on P47 and P30, the P30 and P47 proteins were reported to resemble the protein synthetic elongation factors (EF) 1 beta and 1 gamma from *Artemia salina*. See Belle et al., A purified complex from *Xenopus* oocytes contains a p47 protein, an in vivo substrate of MPF, and a p30 protein respectively homologous to elongation factors EF-1 gamma and EF-1 beta. FEBS Lett. 255: 101-104 (1989). This paper shows that the complex composed of P30, P47, and P36 from *Xenopus* is identical to the complex of EF-1 beta, EF-1 gamma, and EF-1 delta from *Artemia* according to two criteria. 1) Both stimulate elongation factor 1 alpha-mediated transfer RNA binding to ribosomes and exchange of guanine nucleotides on elongation factor 1 alpha to a comparable degree. 2) Each of the three subunits of the protein complex P30.P47.P36 from *Xenopus* shows a structural homology with one of the corresponding subunits of EF-1 beta gamma delta from *Artemia*. Presumably the phosphorylation of EF-1 gamma, which associates with tubulin at least in vitro, is important in processes following the onset of meiosis which is accompanied by a rise of protein synthesis. See Janssen et al., A major substrate of maturation promoting factor identified as elongation factor 1 beta gamma delta in *Xenopus laevis*. J. Biol. Chem. 266: 14885-14888 (1991).

BRIEF SUMMARY OF THE INVENTION

The present invention is directed to novel compounds which are useful in methods for managing fertility, such as reducing fertility in a subject for a period of time and then restoring fertility. Such a fertility management can include:

administering to the subject one or more doses of a compound according to Formula I so as to reduce fertility in the subject:

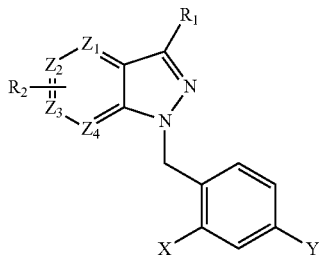

Formula I

In Formula I: $R_1$ is carboxyl, acryl, or carboxylic acid hydrazide; $R_2$ is hydrogen, halogen, alcohol, alkyl, alkoxy, aralkyl, cycloalkyl, haloalkyl, haloalkoxy, amino, or carboxyl; X and Y are the same or different from each other and are halogen or lower alkyl; and $Z_1$, $Z_2$, $Z_3$, and $Z_4$ are independently nitrogen or carbon. The compound can also be pharmaceutically acceptable salts and esters of Formula I. In one embodiment, when $R_2$ is hydrogen, then either: at least one of $Z_1$, $Z_2$, $Z_3$, and $Z_4$ is nitrogen and the remainder are independently carbon or nitrogen; or $R_1$ is not —COOH, —CONHNH$_2$, —CONHN(CH$_3$)$_2$, —CH=CHCOOH.

In one embodiment, the compound is selected from the group consisting of: 3-[1-(2,4-dichlorobenzyl)-6-trifluoromethyl-1H-indazol-3-yl]acrylic acid; 6-chloro-1-(2,4-dichlorobenzyl)-1H-indazole-3-carboxylic acid hydrazide; 1-(2,4-dichlorobenzyl)-6-fluoro-1H-indazole-3-carboxylic acid methyl ester; 6-fluoro-1-(2,4-dichlorobenzyl)-1H-indazole-3-carboxylic acid hydrazide; 3-[1-(2,4-dichlorobenzyl)-6-fluoro-1H-indazol-3-yl]-acrylic acid;

3-[1-(2,4-dichlorobenzyl)-6-chloro-1H-indazol-3-yl]-acrylic acid; 3-[1-(2,4-dichlorobenzyl)-6-trifluoromethoxy-1H-indazol-3-yl]acrylic acid; 3-[1-(2,4-dichlorobenzyl)-6-chloro-1H-indazol-3-yl]-propionic acid; 3-[1-(2,4-dichlorobenzyl)-6-trifluoromethyl-1H-indazol-3-yl]-propionic acid; and pharmaceutically acceptable salts and esters thereof.

In one embodiment, the compound is selected from the group consisting of: gamendazole; 3-[1-(2,4-dichlorobenzyl)-6-trifluoromethyl-1H-indazol-3-yl]-propionic acid (JWS-2-72 or H2-gamendazole); 3-[1-(2,4-dichlorobenzyl)-6-methyl-1H-indazol-3-yl]acrylic acid (TH 2-192); 1-(2,4-dichlorobenzyl)-6-methyl-1H-indazole-3-carboxylic acid (TH 2-178); 1-(2,4-dichlorobenzyl)-6-methyl-1H-indazole-3-carboxylic acid hydrazide (TH 2-179); 3-[1-(2,4-dichlorobenzyl)-6-chloro-1H-indazol-3-yl]-acrylic acid (JWS 1-190); 1-(2-chloro-4-fluorobenzyl)-6-chloro-1H-indazole-3-carboxylic acid hydrazide (JWS 2-22); 1-(2,4-difluorobenzyl)-6-chloro-1H-indazole-3-carboxylic acid hydrazide (JWS 1-282); and pharmaceutically acceptable salts and esters thereof.

Fertility management can also include administering an effective amount of the compound to impair Sertoli cell function in a male subject. For example, the compound can be administered in an effective amount to inhibit spermatogenisis in the subject. Also, the compound can be administered in an effective amount to reduce testis weight in the subject.

Fertility management can also include administering an effective amount of the compound to reduce ovary weight in a female subject. The compound can also be administered in a therapeutically effective amount to reduce serum progesterone in the female subject. The compound can be administered in an effective amount to impair ovarian follicle function in the female subject.

In one embodiment, the compound can be administered in an effective amount for causing reversible fertility in the subject. In order to return fertility, the method can include ceasing administration of the compound to the subject so as to return fertility in the subject.

In one embodiment, the compound can be administered in an effective amount for irreversibly sterilizing the subject. This can include one or more doses to impart sterility.

In one embodiment, the compound can be administered in an effective amount to induce sterility in the subject in a single dose. Alternatively, the compound can be administered in a multi-dose regimen to induce sterility in the subject.

In one embodiment, the fertility management can include inhibiting spermatogenesis in a male subject. Such a fertility management method can include administering to the male subject a compound according to Formula I so as to inhibit spermatogenesis, where Formula I is described herein. The male fertility management method can include administering the compound in an effective amount in accordance with at least one of the following: maintaining bodyweight of the subject; inhibiting production of inhibin B; increasing circulating follicle-stimulating hormone (FSH); inhibiting compound-associated toxicity; reducing structured spermatogenic cell-type layering; reducing spermatozoa; reducing spermatids; reducing spermatagonia; reducing germinal epithelium; reducing amount of germ cells; reducing testis weight; inhibiting heat shock protein HSP90AB1; inhibiting eukaryotic translation elongation factor 1 alpha 1 (EEF1A1); increasing production of an interleukin protein; or increasing production of NF-KappaB inhibitor alpha (Nfkbia). Male fertility can be reversible or irreversible depending on the amount and or dosing regimen. Higher dosing amounts can permanently impair the Sertoli cell function in a male subject. Lower doses can provide reversible infertility, where ceasing administration of the compound to the subject can return spermatogenesis potential in the subject.

In one embodiment, the compounds can be used in fertility management for women. The compounds can be administered alone or in combination of another fertility managing compound. The compound of the invention (e.g., Formula I) can be administered to a female subject so as to reduce fertility. The compound can be administered to the female subject in an effective amount in accordance with at least one of the following: maintaining bodyweight of the subject; inhibiting production of inhibin B; inhibiting production of estradiol; reducing ovary weight; reducing serum progesterone; inhibiting progesterone production; inducing atretic ovarian follicles; reducing number of viable ovarian follicles; reducing amount of germ cells; or inhibiting ovulation. Female fertility can be reversible or irreversible depending on the amount and or dosing regimen. Higher dosing amounts can permanently impair the ovarian follicles in a female subject. Lower doses can provide reversible infertility, where ceasing administration of the compound to the subject can return ovarian follicle potential in the female subject.

BRIEF DESCRIPTION OF THE DRAWINGS

FIG. 9A shows compounds administered at 25 mg/kg. FIG. 9B shows compounds administered at 200 mg/kg. Controls received 5 ml/kg of carrier (buffered DMSO).

FIG. 10A shows inhibin B: The limit of detection was 25 pg/ml. The human inhibin B standard was reconstituted in castrate rat serum; therefore, the results are relative to human inhibin B. FIG. 10B shows FSH: the limit of detection was 1.5 ng/ml. FIG. 10C shows testosterone: the limit of detection was 0.04 ng/ml.

FIG. 14 panel B shows rat testis cytosol protein affinity binding using gamendazole-BT: Lanes 1 and 2—the Coomassie-stained starting cytosol and pre-cleared avidin-agarose treated cytosol, respectively. The columns were eluted stepwise with 1.5 mM (Lanes 3-4), then 3.0 mM (Lanes 5-6) gamendazole, then 600 mM NaCl (Lanes 7-8). The first lane in each pair represents the eluate from the cytosol that was incubated with gamendazole-BT alone and the second lane, from the cytosol incubated with gamendazole-BT plus excess gamendazole. Arrow at 90 kDA indicates the band in lane 3 identified by MALDI-TOF MS as HSP90AB1. Arrow at 53 kDa indicates the band in lane 7 that was identified by MALDI-TOF MS as EEF1A1. The bottom two images in panel B depict Western blots of HSP90AB1 and EEF1A1 showing the corresponding regions of the gel indicated by the arrows at HSP90AB1 and EEF1A1, respectively.

FIG. 14 panel C shows ID8 Ovarian cancer cell cytosol protein affinity binding using biotinylated gamendazole (gamendazole-BT). Lanes represent treatments identical to panel A, above. Arrows in lane 3 and 7 indicates the bands corresponding to positions of HSP90AB1 and EEF1A1, respectively.

FIG. 15 panel B shows competition binding of 13.7 μM BT-UV-gamendazole with HSP90 inhibitors geldanamycin and KU-1 to purified yeast HSP82.

FIG. 15 panel C shows competitive binding of 13.7 μM BT-UV-gamendazole to purified *O. caniculus* EEF1A1 by gamendazole and LND.

FIG. 15 panel D shows direct binding of BT-UV-gamendazole to purified *S. cerevisiae* TEF1 and competitive binding by gamendazole.

FIG. 15 panel E shows direct binding of BT-UV-gamendazole to purified *S. cerevisiae* TEF1 and absence of binding to control proteins TEF3 and HSB1.

FIG. 18A shows the ability of gamendazole (closed circles) and novobiocin (open circles) to inhibit the HSP90-mediated refolding of thermally denatured firefly luciferase was determined as previously described. Values represent the mean±SE for one representative experiment performed in triplicate. Assays were replicated three times and the $IC_{50}$ of novobiocin correlated well with previously published values. FIG. 18B shows MCF-7 cells were incubated with gamendazole (closed circles) or novobiocin (open circles) at varying concentrations. Viable cells were quantitated using the MTS/PMS assay as described in the methods section. Values represent the mean±SE for one representative experiment performed in triplicate. Assays were replicated three times and the $IC_{50}$ of novobiocin correlated well with previously published values.

DETAILED DESCRIPTION OF PREFERRED EMBODIMENT

Figure 1A:
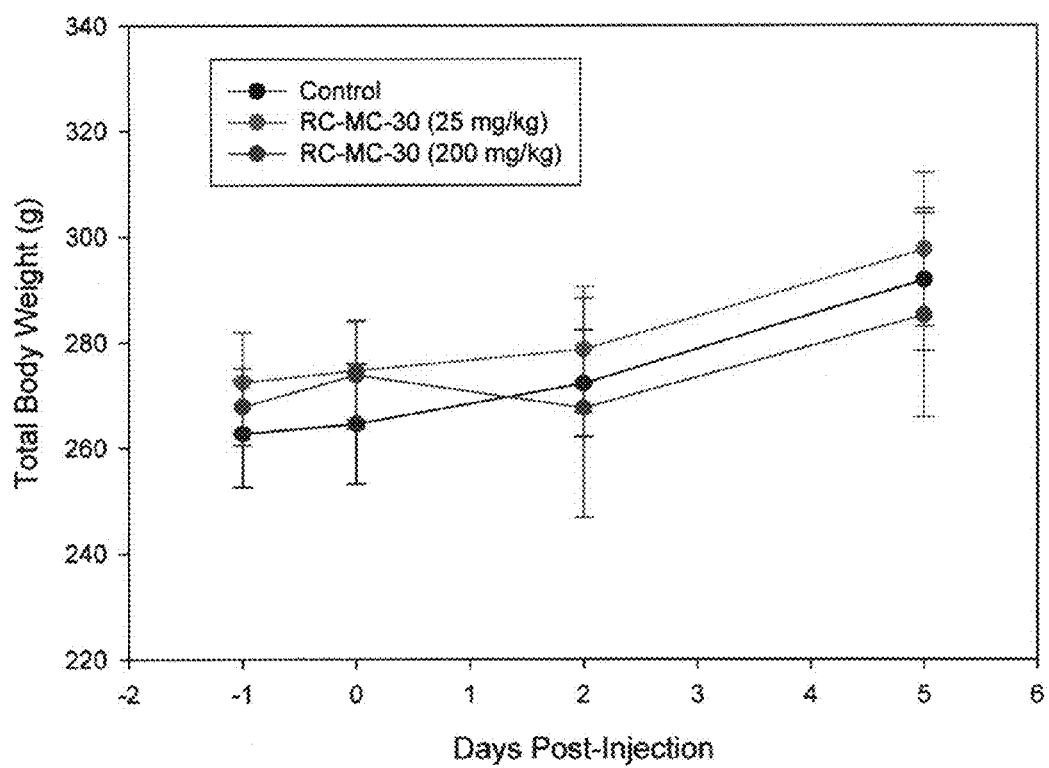
FIG. 1A illustrates the change in total body weight of animals receiving 25 mg/kg and 200 mg/kg of RC-MC-30 compared with the control.
Figure 1B:
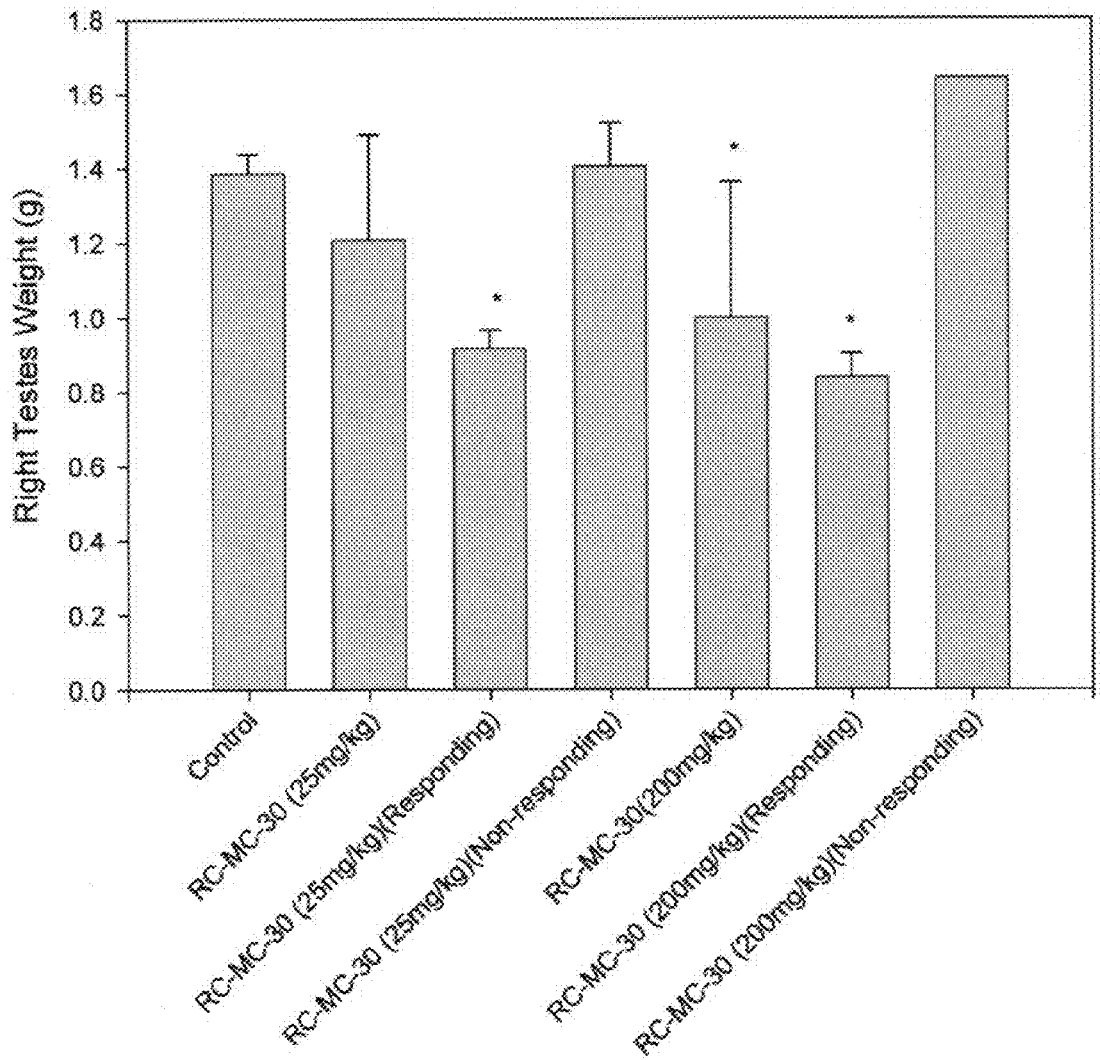
FIG. 1B illustrates the right testes weight of animals receiving 25 mg/kg and animals receiving 200 mg/kg of RC-MC-30 compared with the control.
Figure 1C:
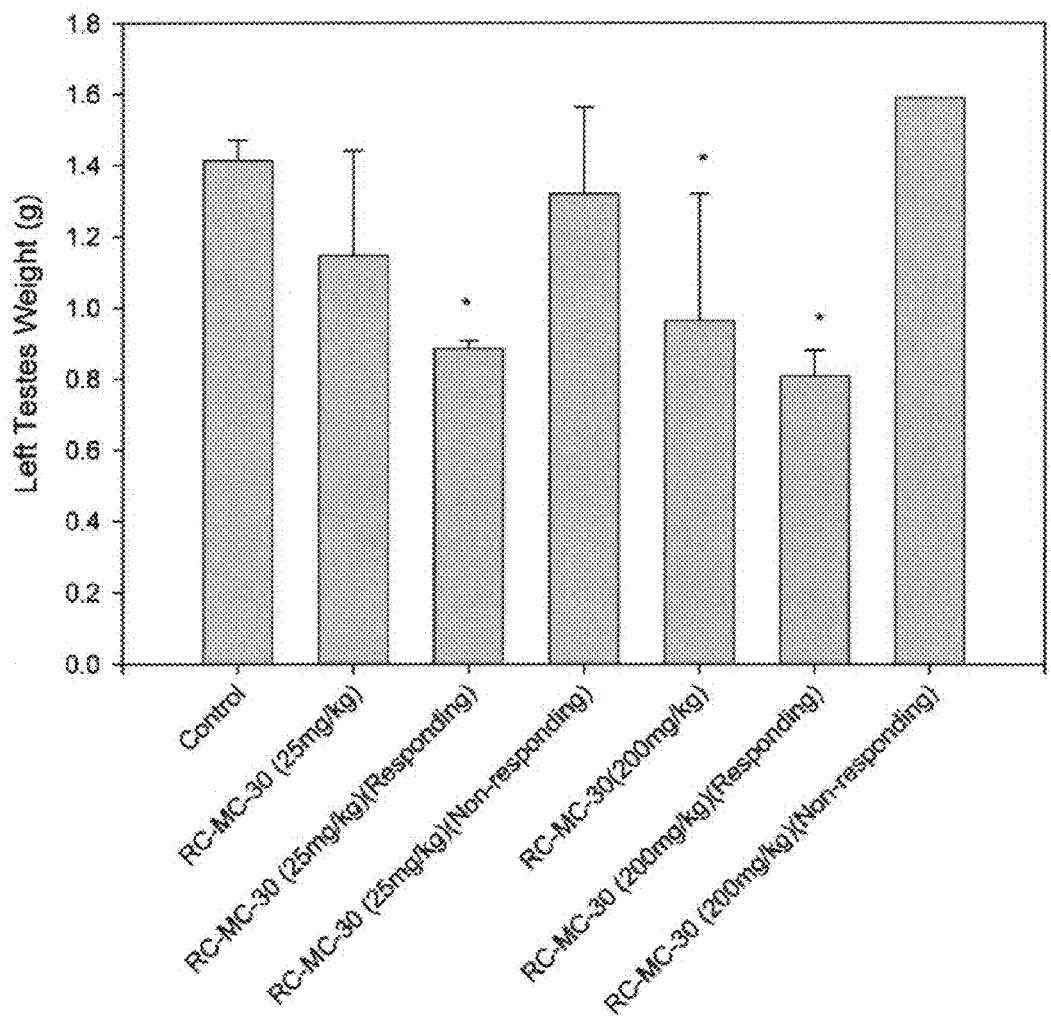
FIG. 1C illustrates the left testes weight of animals receiving 25 mg/kg and animals receiving 200 mg/kg of RC-MC-30 compared with the control.
Figure 1D:
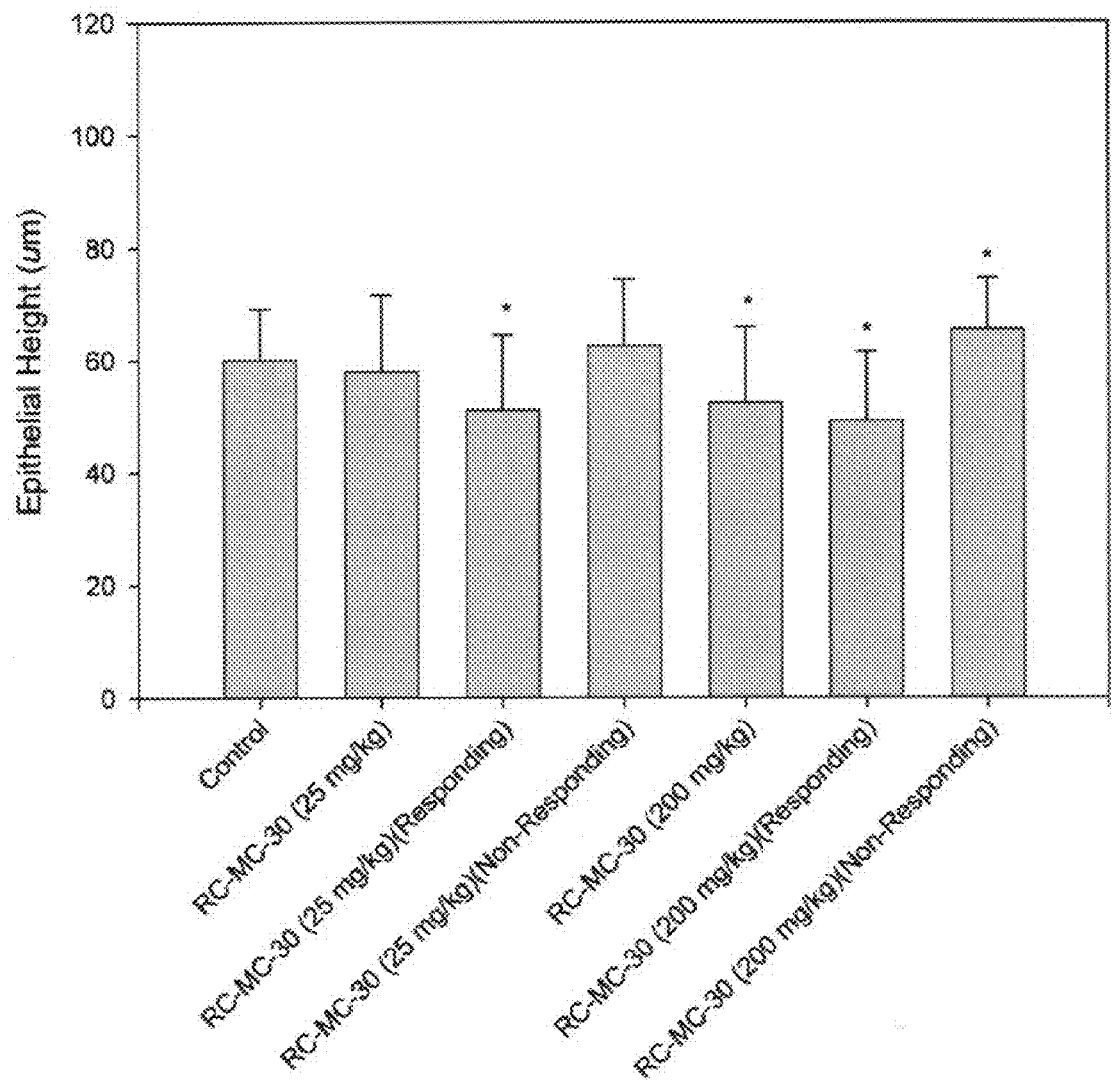
FIG. 1D illustrates the epithelial height of the seminiferous tubule epithelium of animals receiving 25 mg/kg and animals receiving 200 mg/kg of RC-MC-30 compared with the control.
Figure 1E:
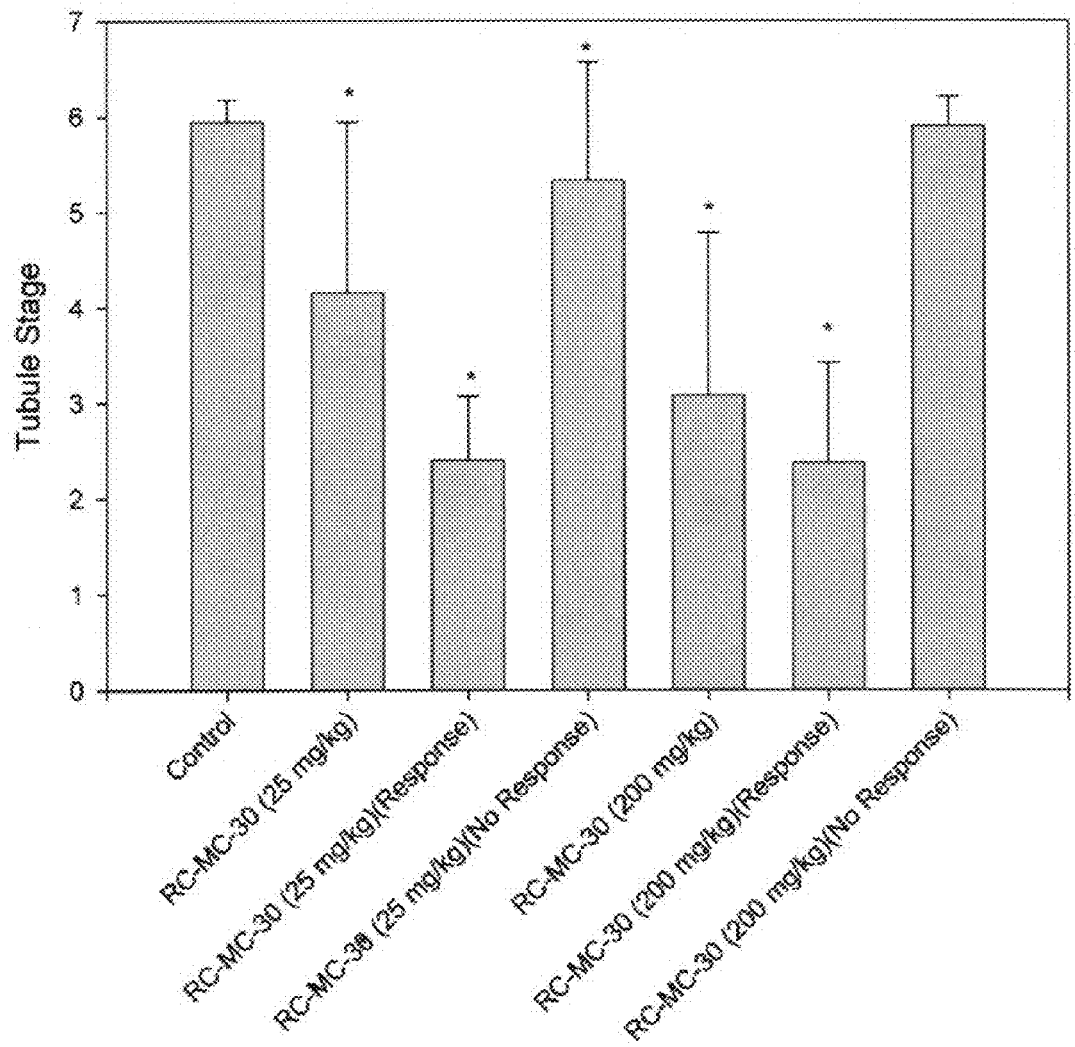
FIG. 1E illustrates seminiferous tubule staging of animals receiving 25 mg/kg and animals receiving 200 mg/kg of RC-MC-30 compared with the control.
Figure 2A:
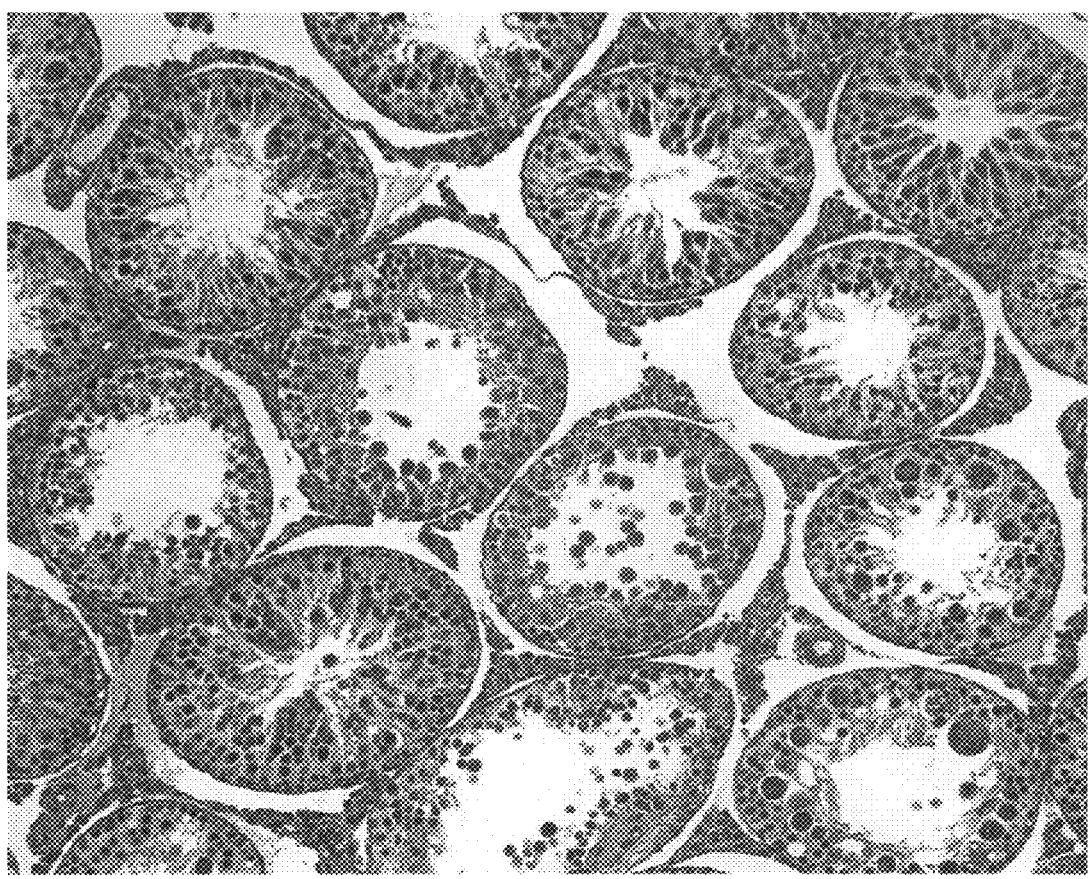
FIG. 2A is a histologic photograph of the testes of a rat receiving 25 mg/kg of RC-MC-30.
Figure 2B:
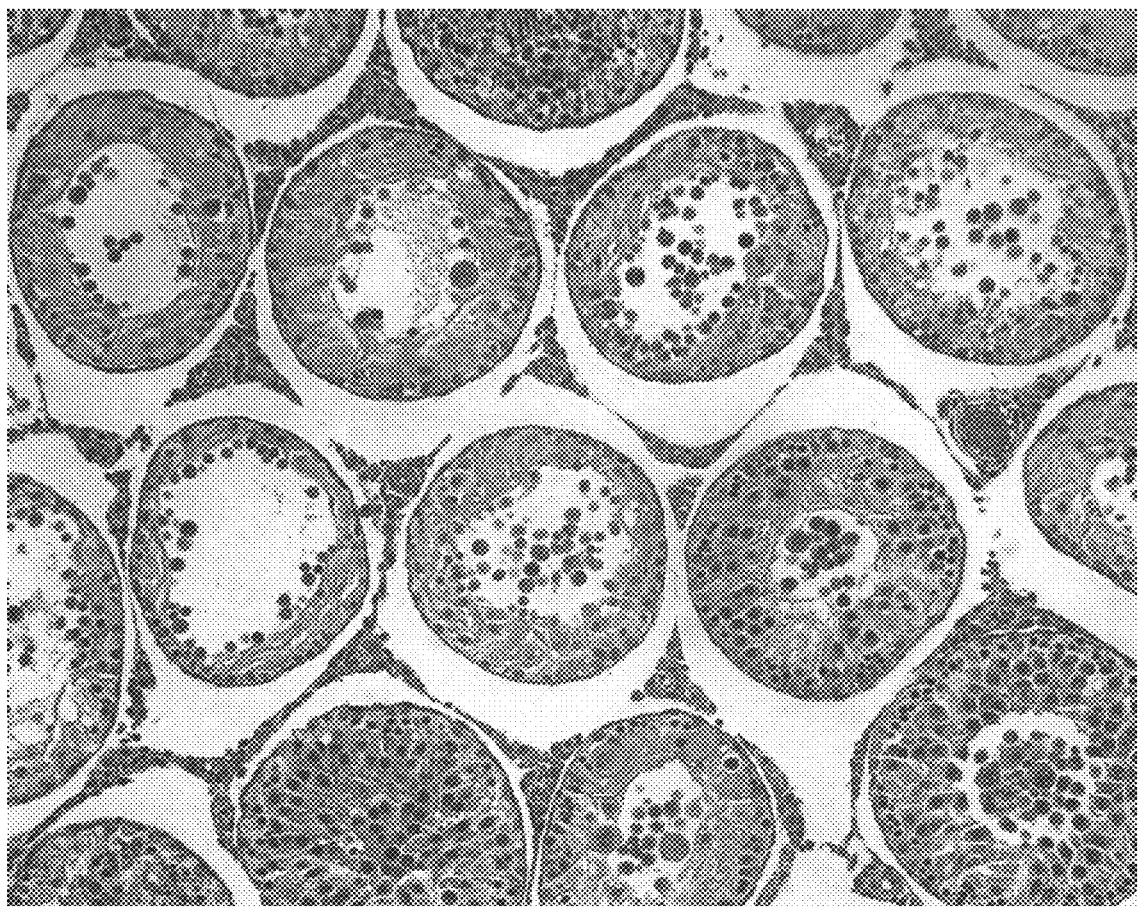
FIG. 2B is a histologic photograph of the testes of a rat receiving 200 mg/kg of RC-MC-30.
Figure 3A:
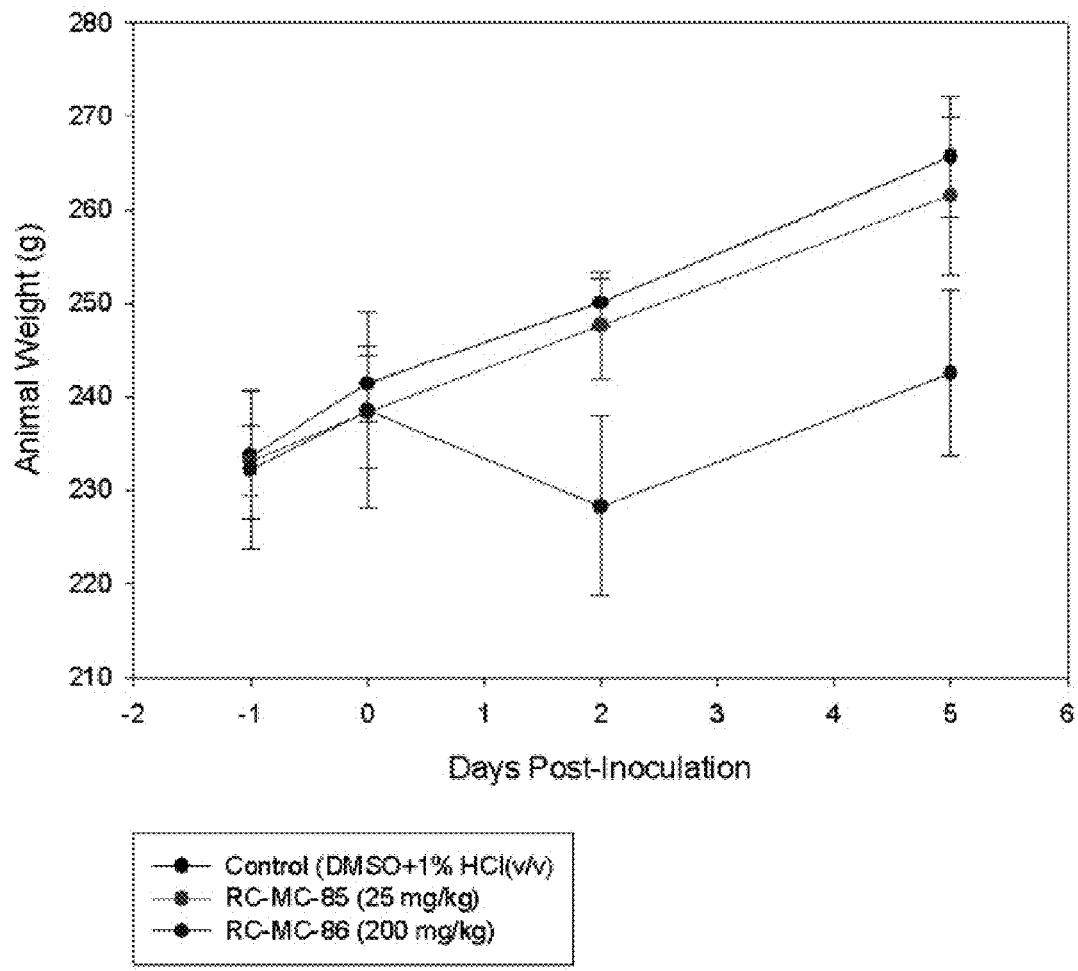
FIG. 3A illustrates the change in total body weight of animals receiving 25 mg/kg and 200 mg/kg of RC-MC-86 compared with the control.
Figure 3B:
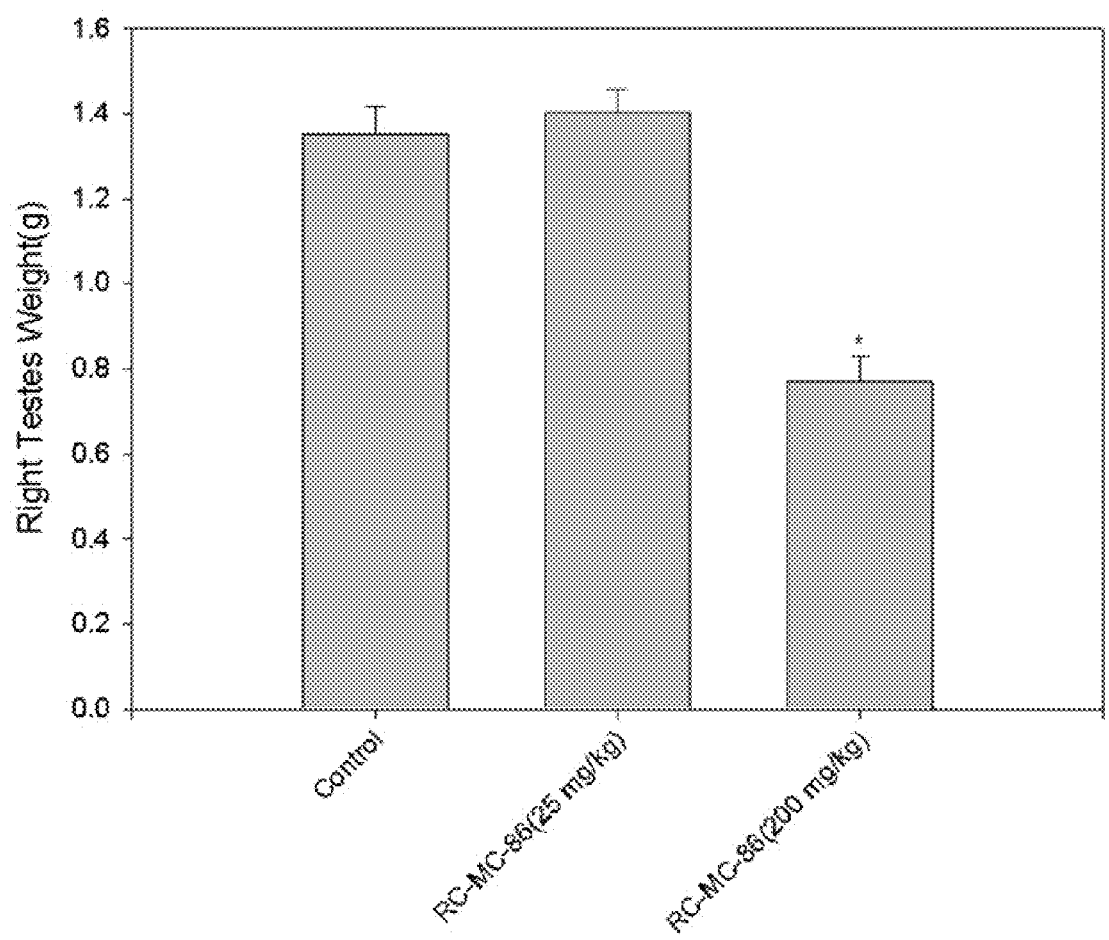
FIG. 3B illustrates the right testes weight of animals receiving 25 mg/kg and animals receiving 200 mg/kg of RC-MC-86 compared with the control.
Figure 3C:
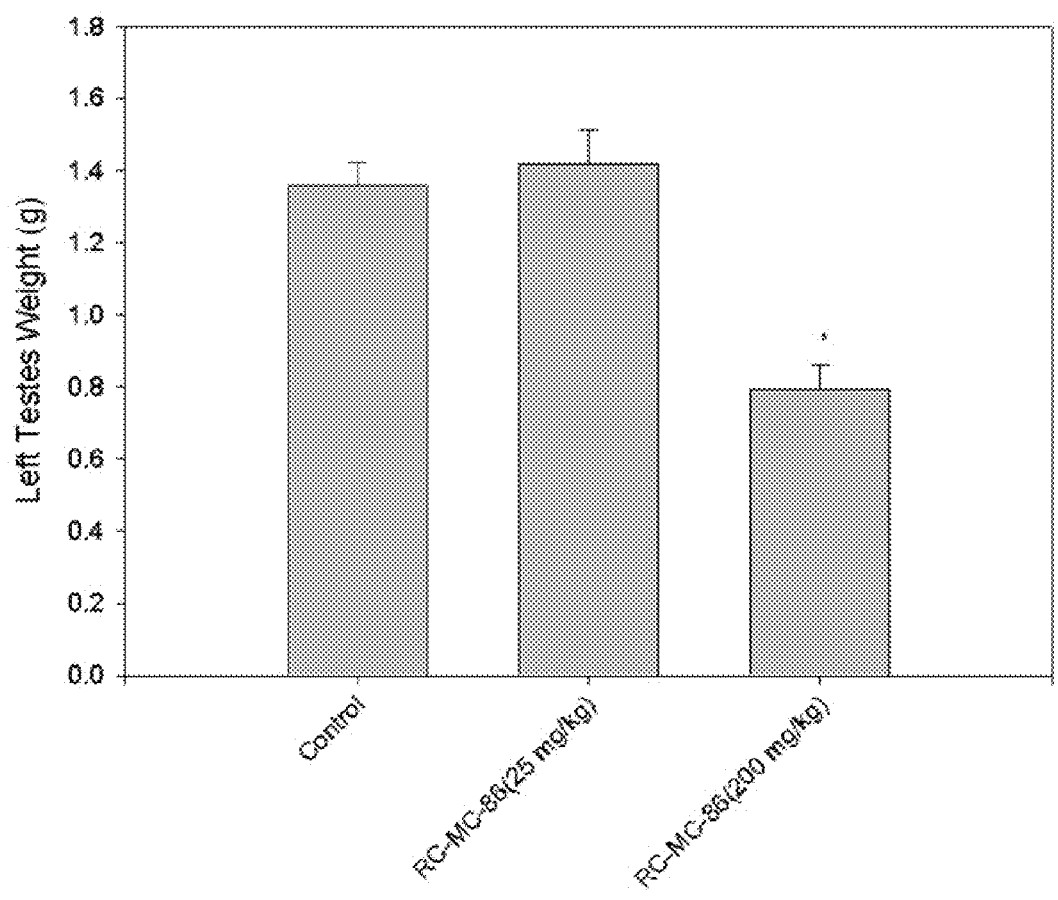
FIG. 3C illustrates the left testes weight of animals receiving 25 mg/kg and animals receiving 200 mg/kg of RC-MC-86 compared with the control.
Figure 3D:
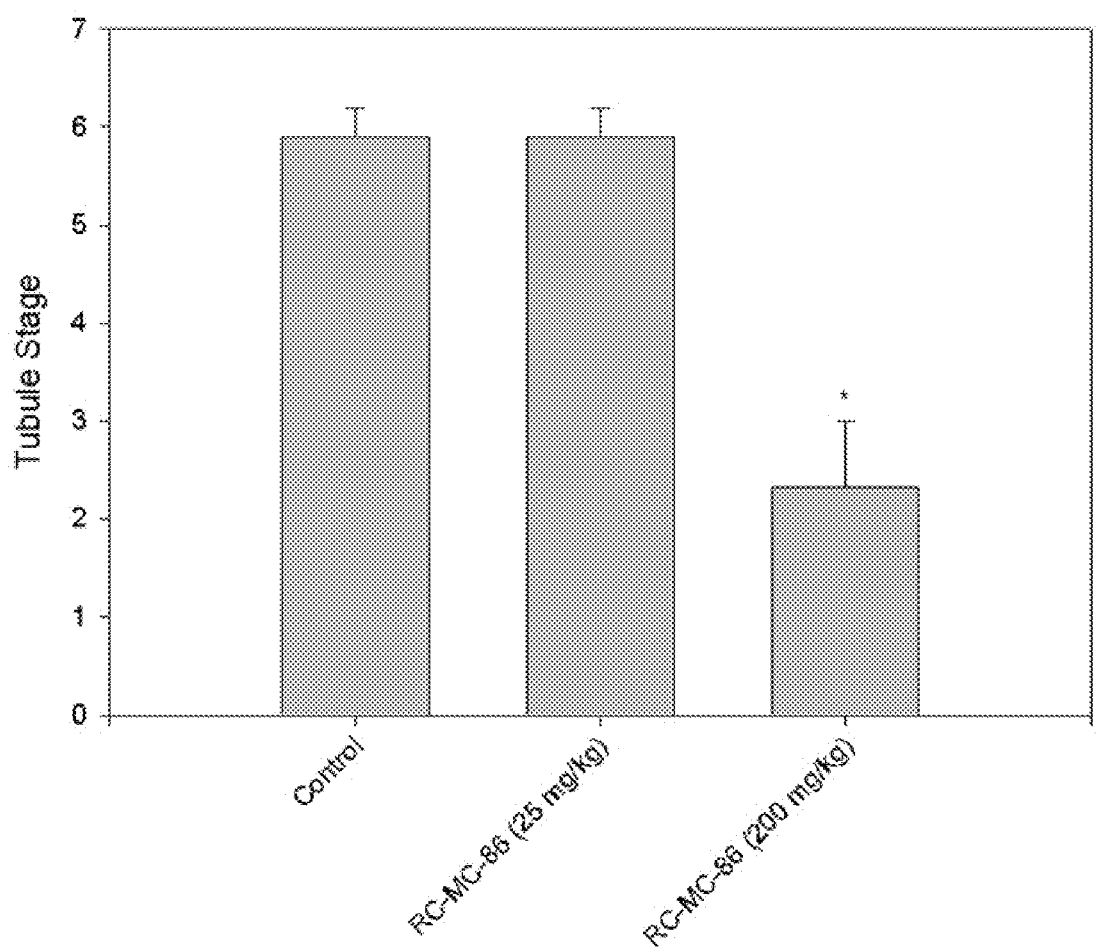
FIG. 3D illustrates the epithelial height of the seminiferous tubule epithelium of animals receiving 25 mg/kg and animals receiving 200 mg/kg of RC-MC-86 compared with the control.
Figure 3E:
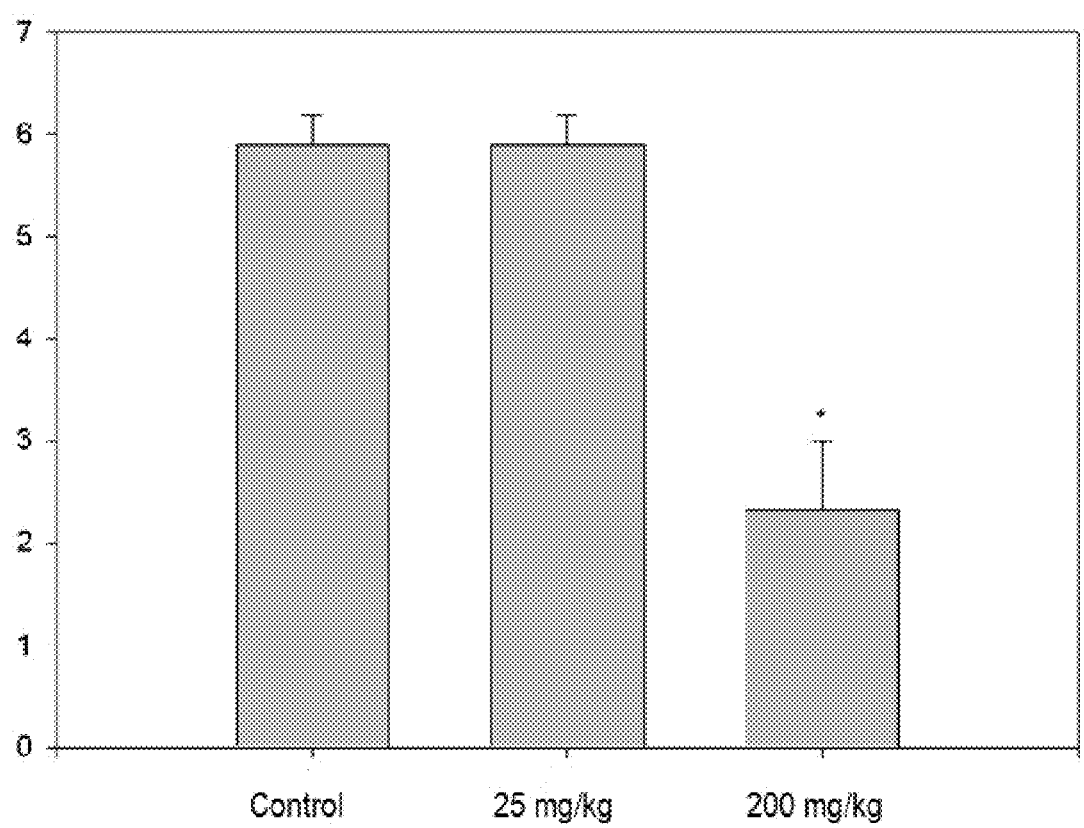
FIG. 3E illustrates seminiferous tubule staging of animals receiving 25 mg/kg and animals receiving 200 mg/kg of RC-MC-86 compared with the control.
Figure 4A:
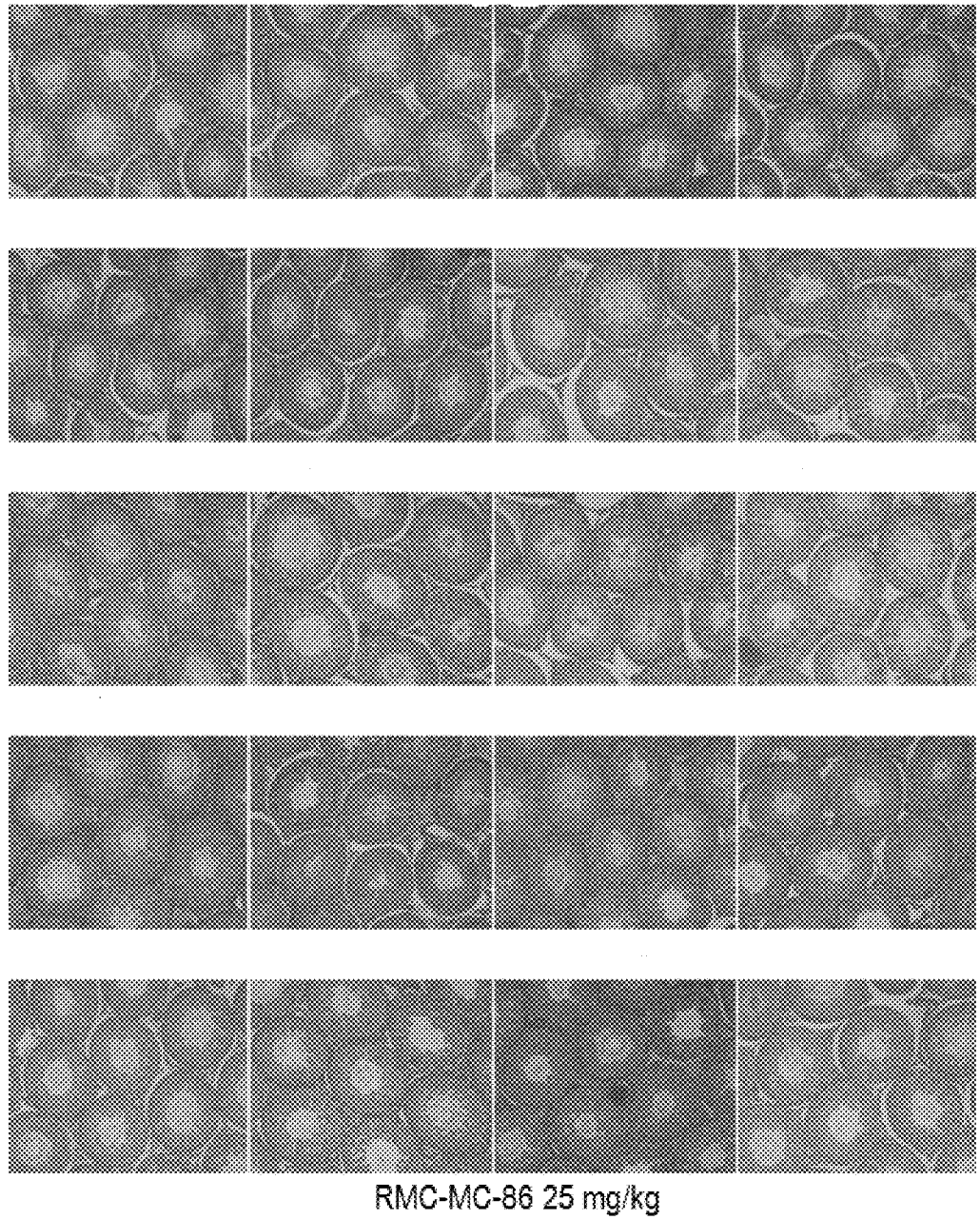
FIG. 4A is a histologic photograph of the testes of a rat receiving 25 mg/kg of RC-MC-86.
Figure 4B:
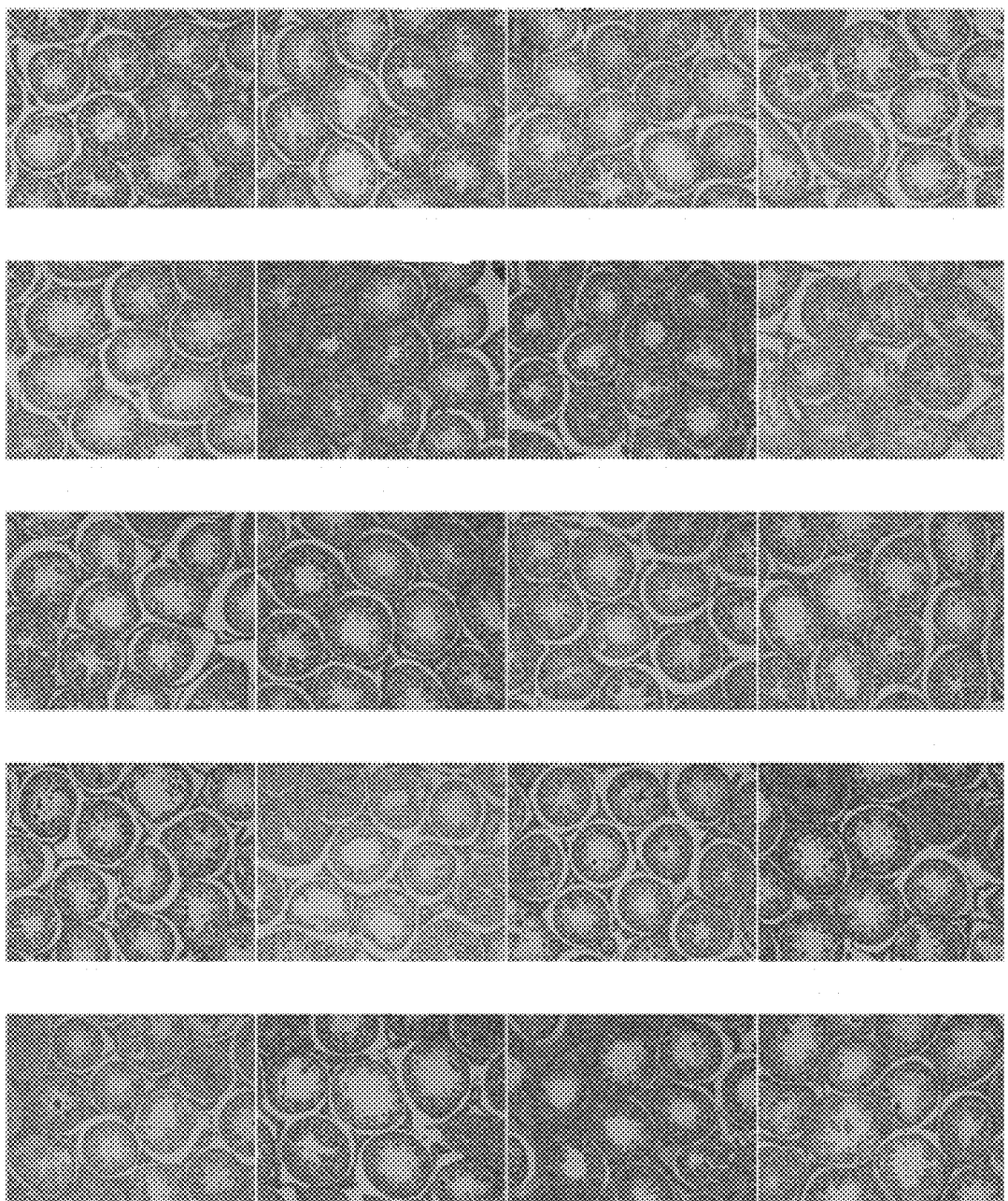
FIG. 4B is a histologic photograph of the testes of a rat receiving 200 mg/kg of RC-MC-86.
Figure 5A:
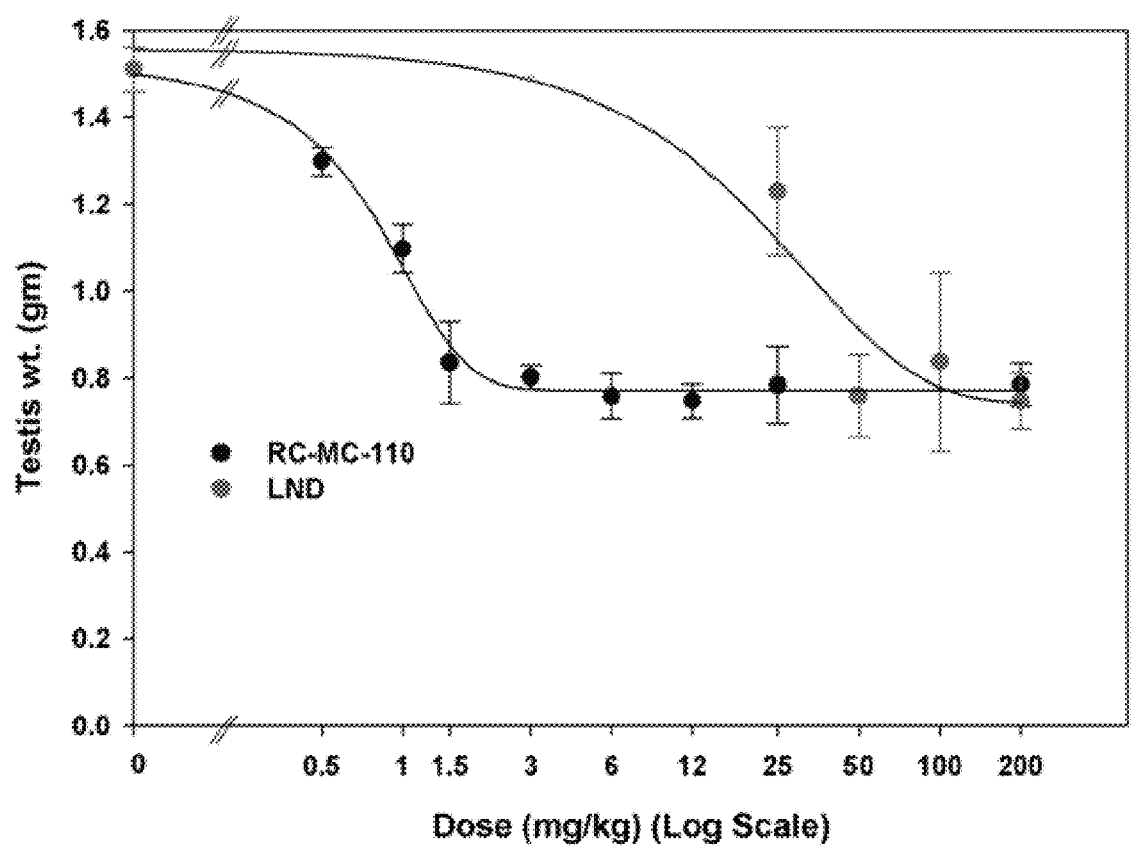
FIG. 5A illustrates the dose-dependent effects of lonidamine compared to RC-MC-110 on testes weight.
Figure 5B:
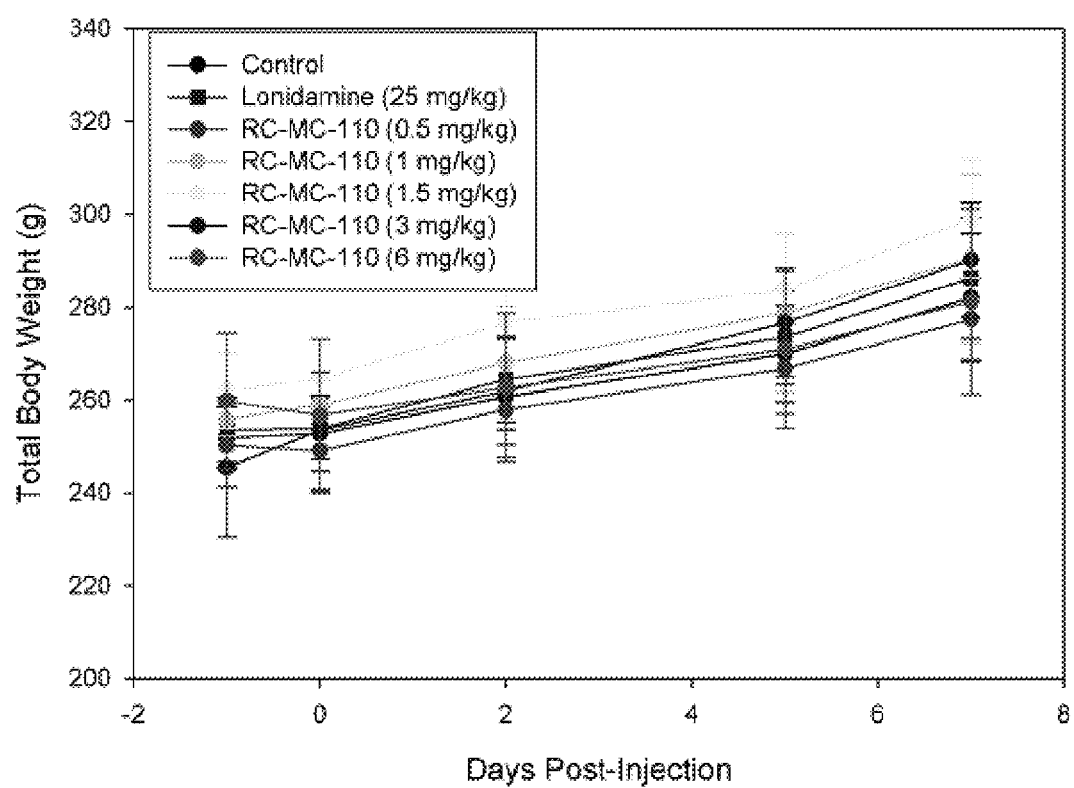
FIG. 5B illustrates the total body weight of animals receiving 6.0, 3.0, 1.5, 1, and 0.5 mg/kg of RC-MC-110 and animals compared to 25 mg/kg lonidamine and a control.
Figure 5C:
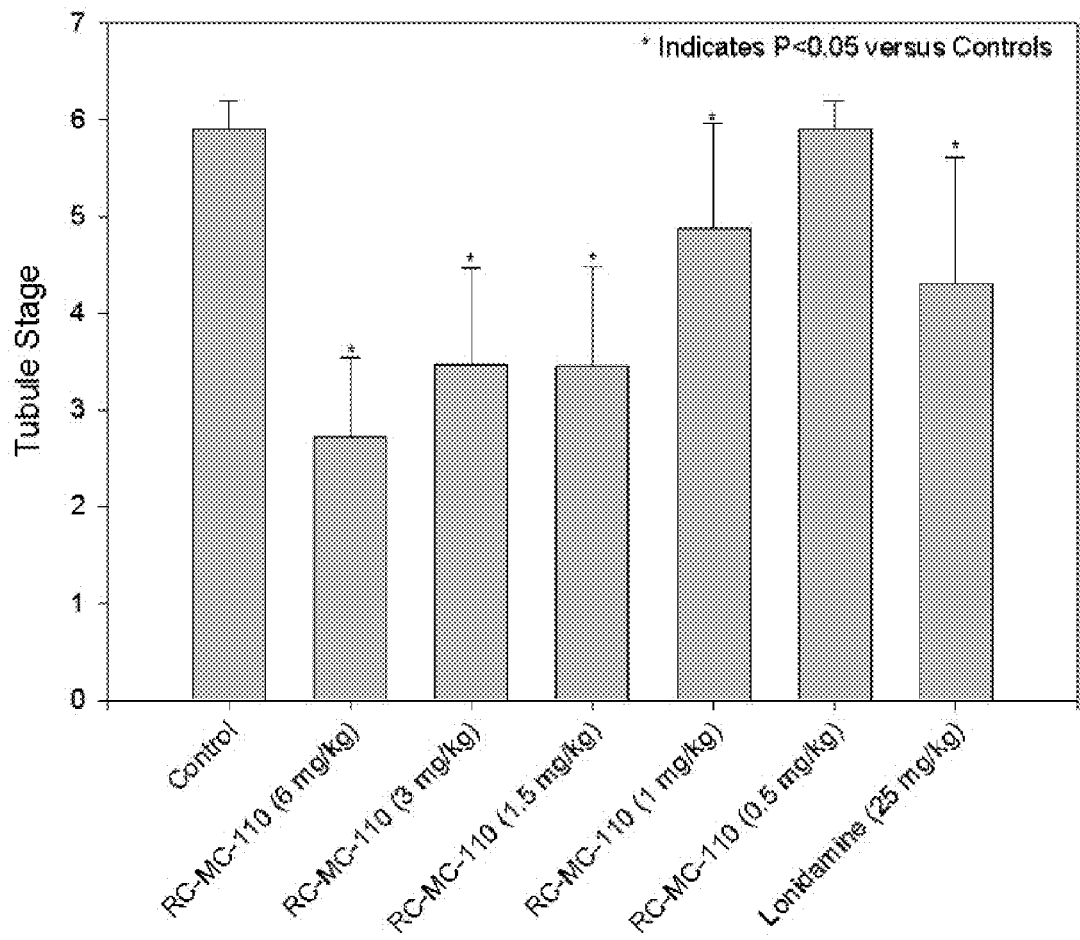
FIG. 5C illustrates tubule staging of animals receiving 6.0, 3.0, 1.5, 1, and 0.5 mg/kg of RC-MC-110 and animals compared to 25 mg/kg lonidamine and a control.
Figure 5D:
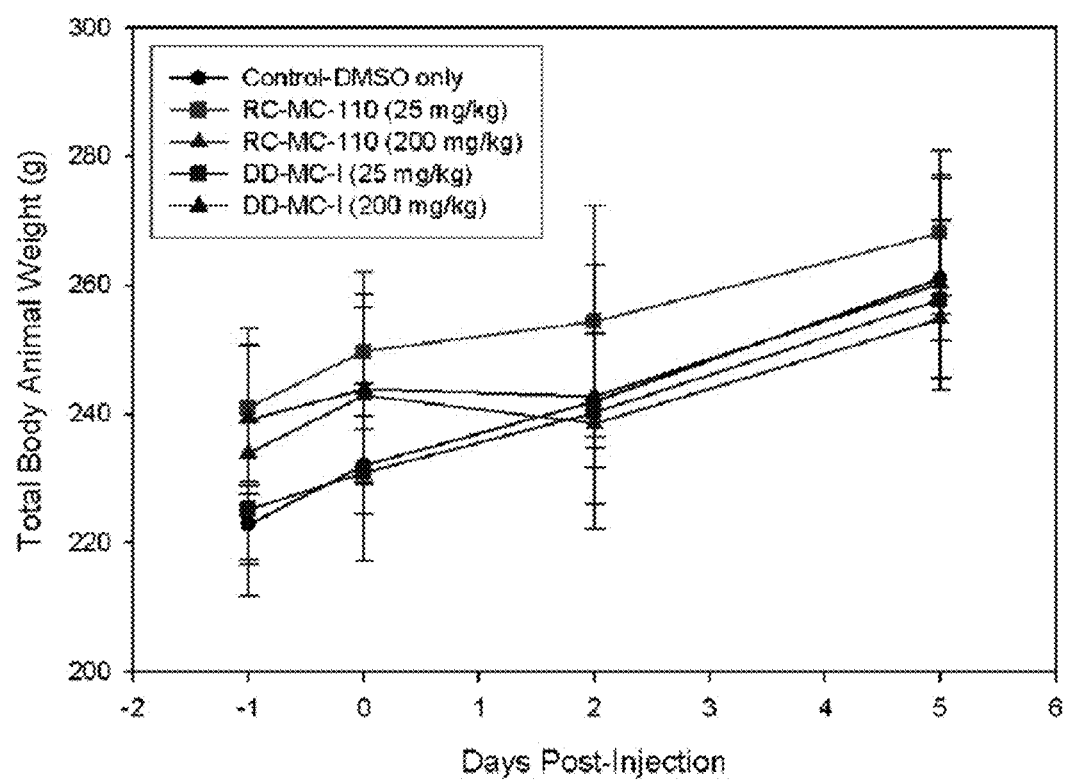
FIG. 5D illustrates the total body weight of animals receiving 25 mg/kg and 200 mg/kg of RC-MC-110 and DD-MC-I.
Figure 5E:
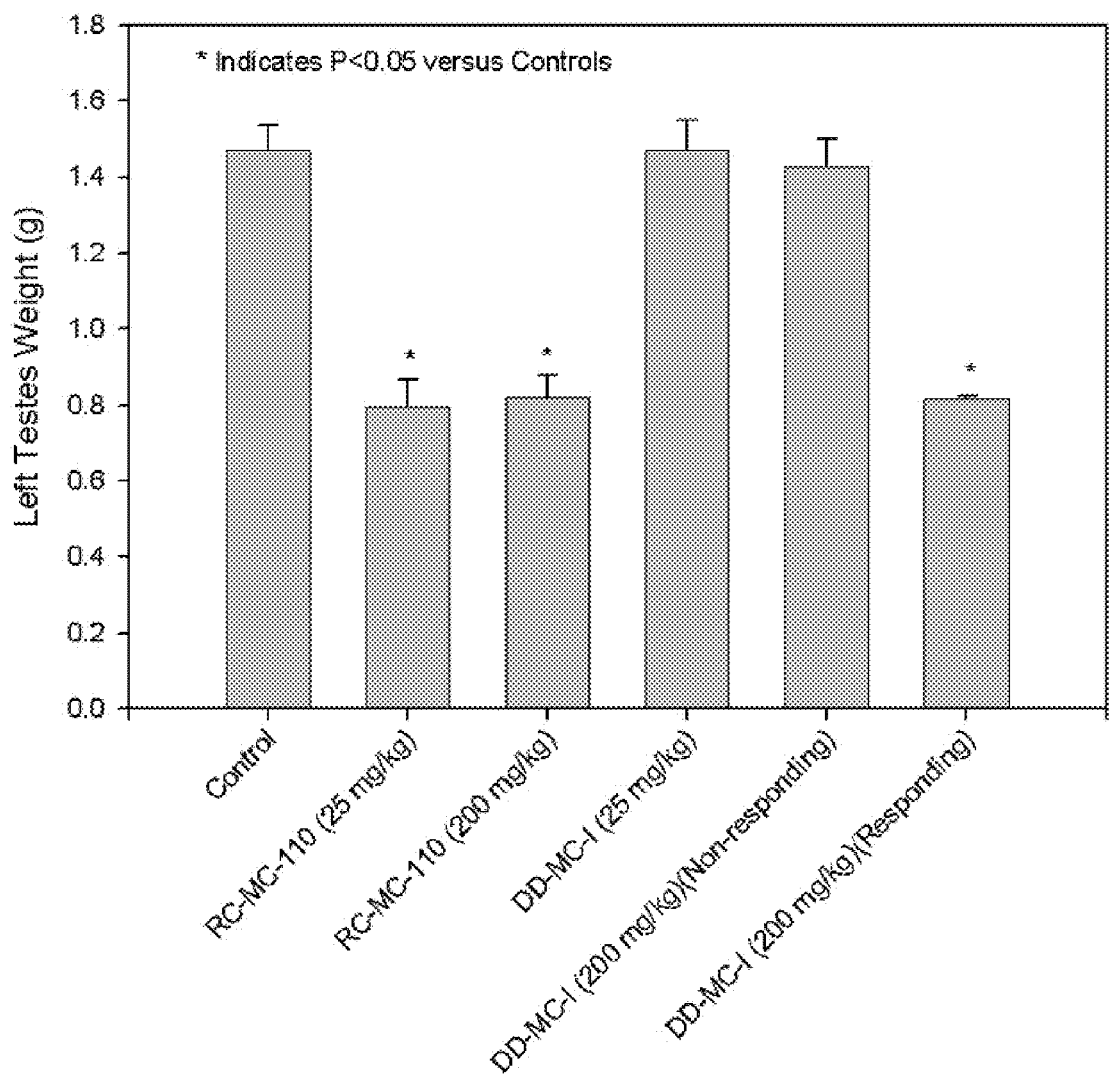
FIG. 5E illustrates the left testes weight of animals receiving 25 mg/kg and 200 mg/kg of RC-MC-110 compared to that of comparative compound, DD-MC-I (1-(2,4-dichlorobenzyl)-6-chloro-1H-indazole-3-carboxylic acid).
Figure 6A:
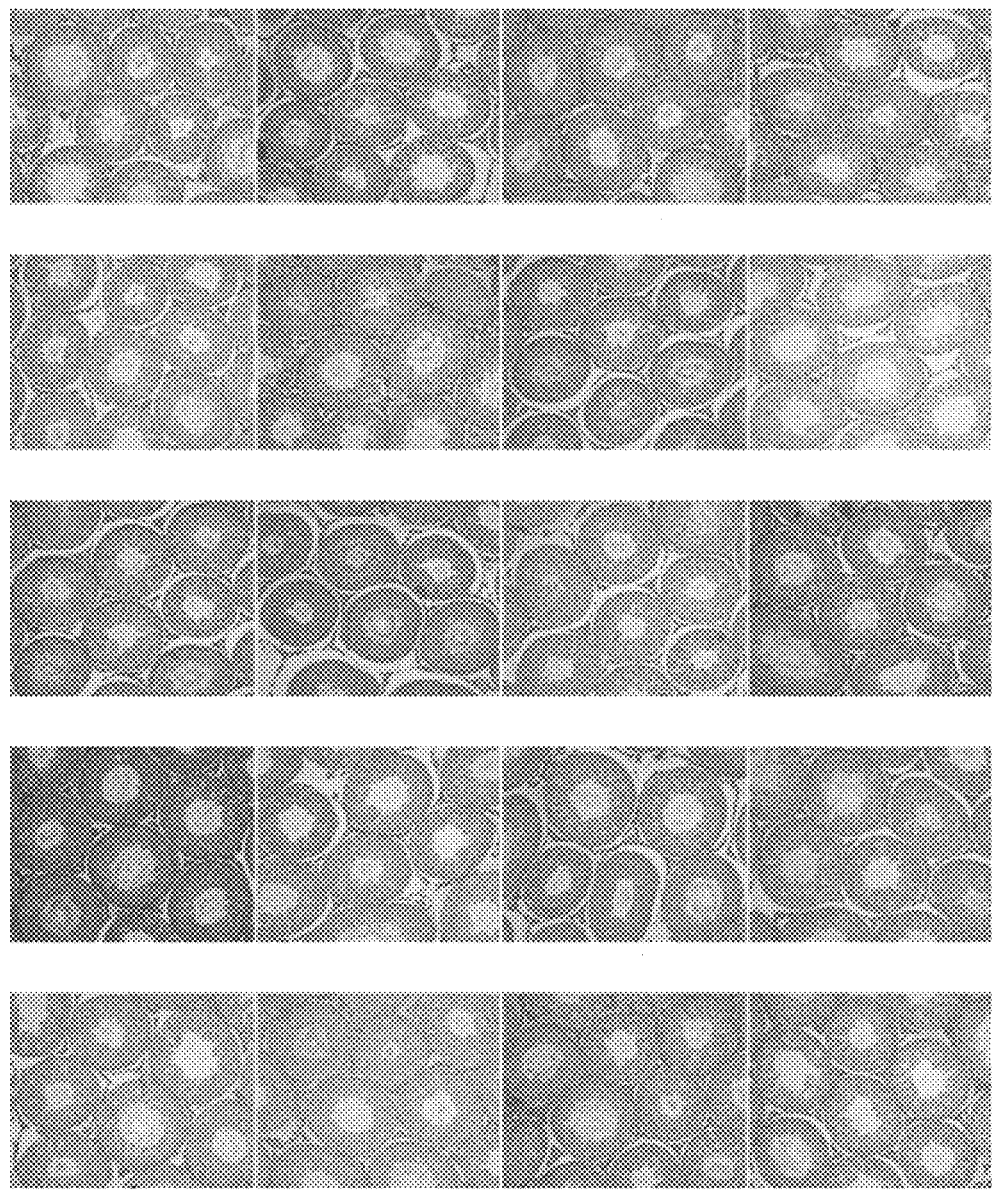
FIG. 6A is a histologic photograph of the testes of a rat receiving 0.5 mg/kg of RC-MC-110.
Figure 6B:
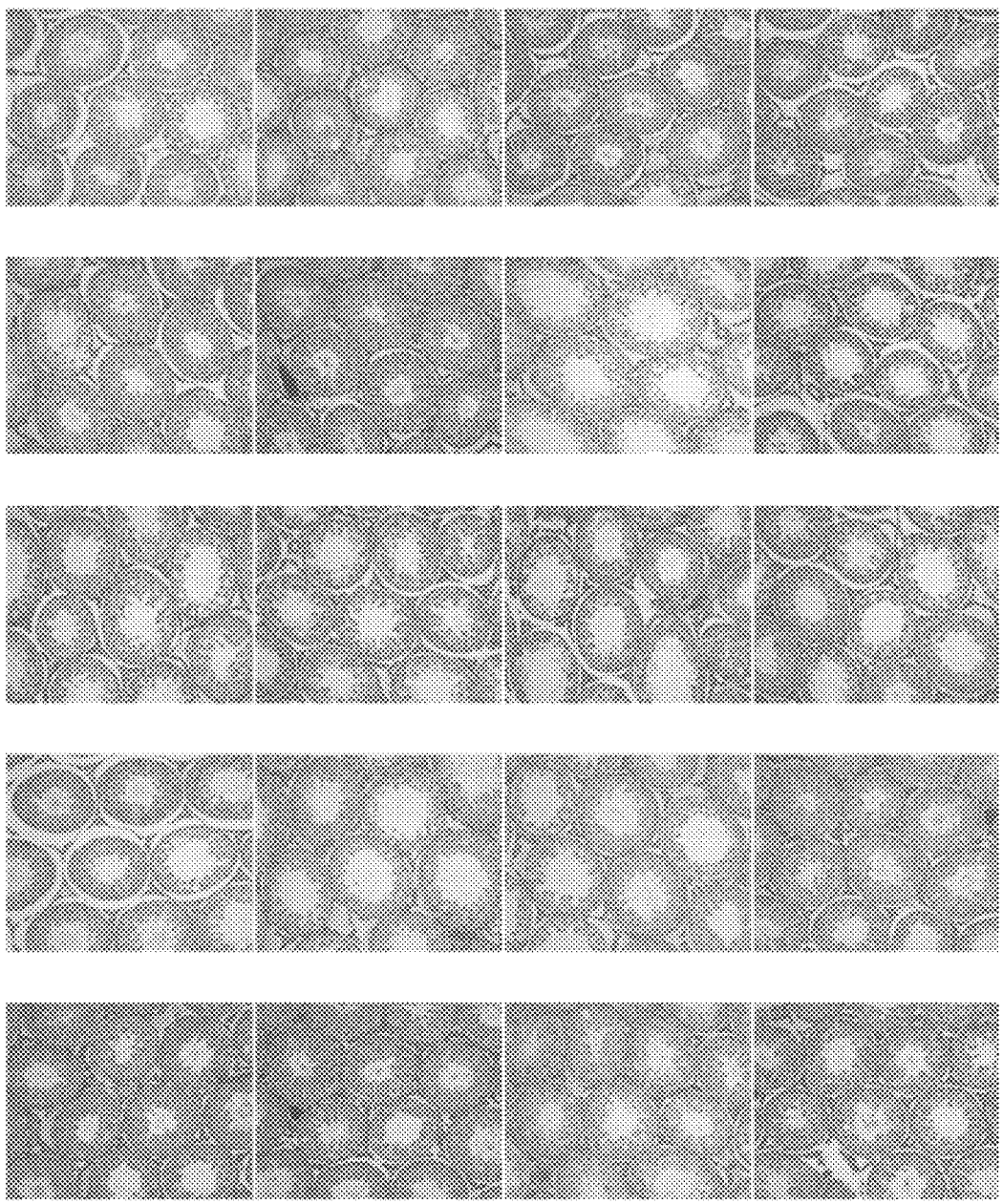
FIG. 6B is a histologic photograph of the testes of a rat receiving 1.0 mg/kg of RC-MC-110.
Figure 6C:
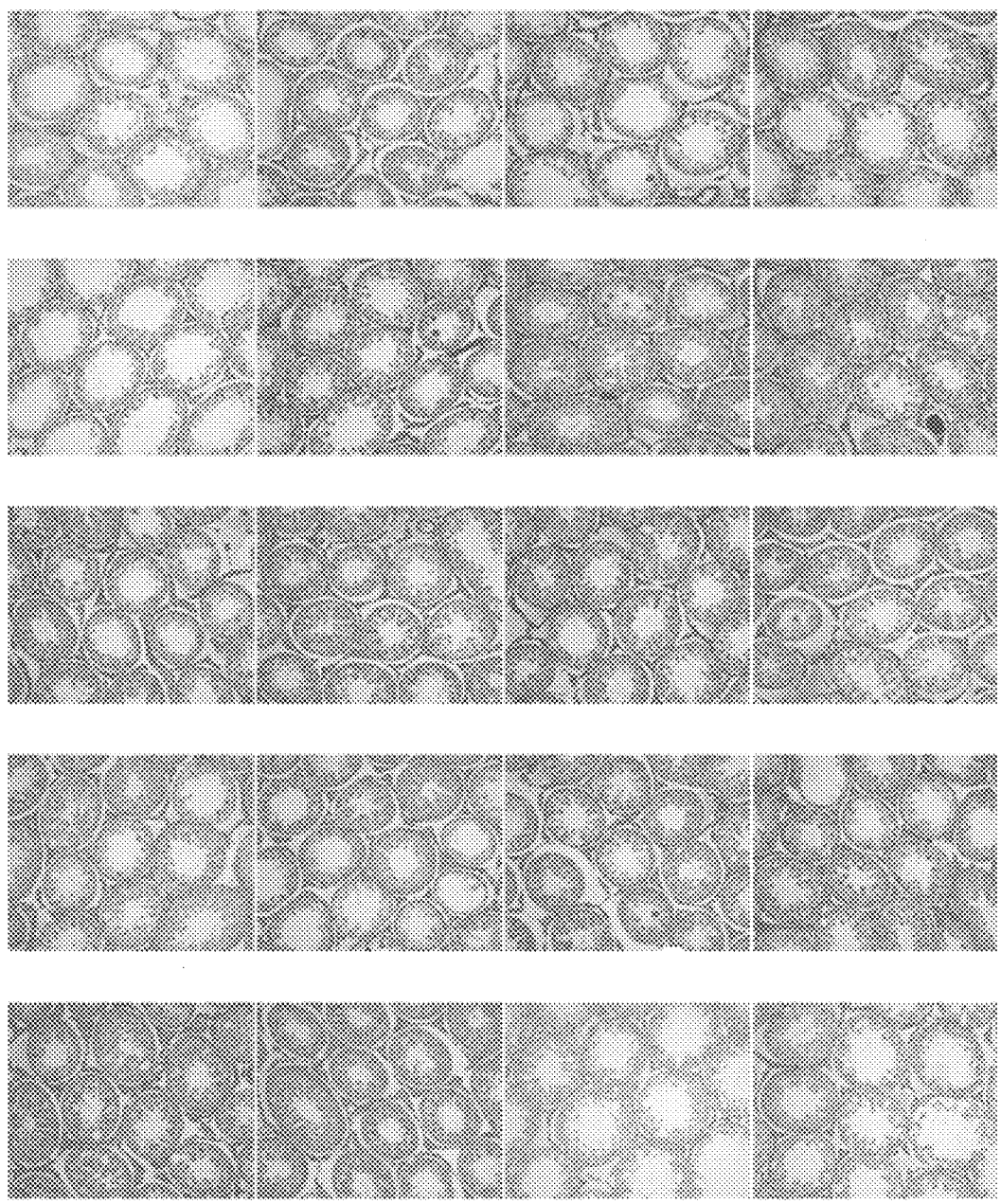
FIG. 6C is a histologic photograph of the testes of a rat receiving 1.5 mg/kg of RC-MC-110.
Figure 6D:
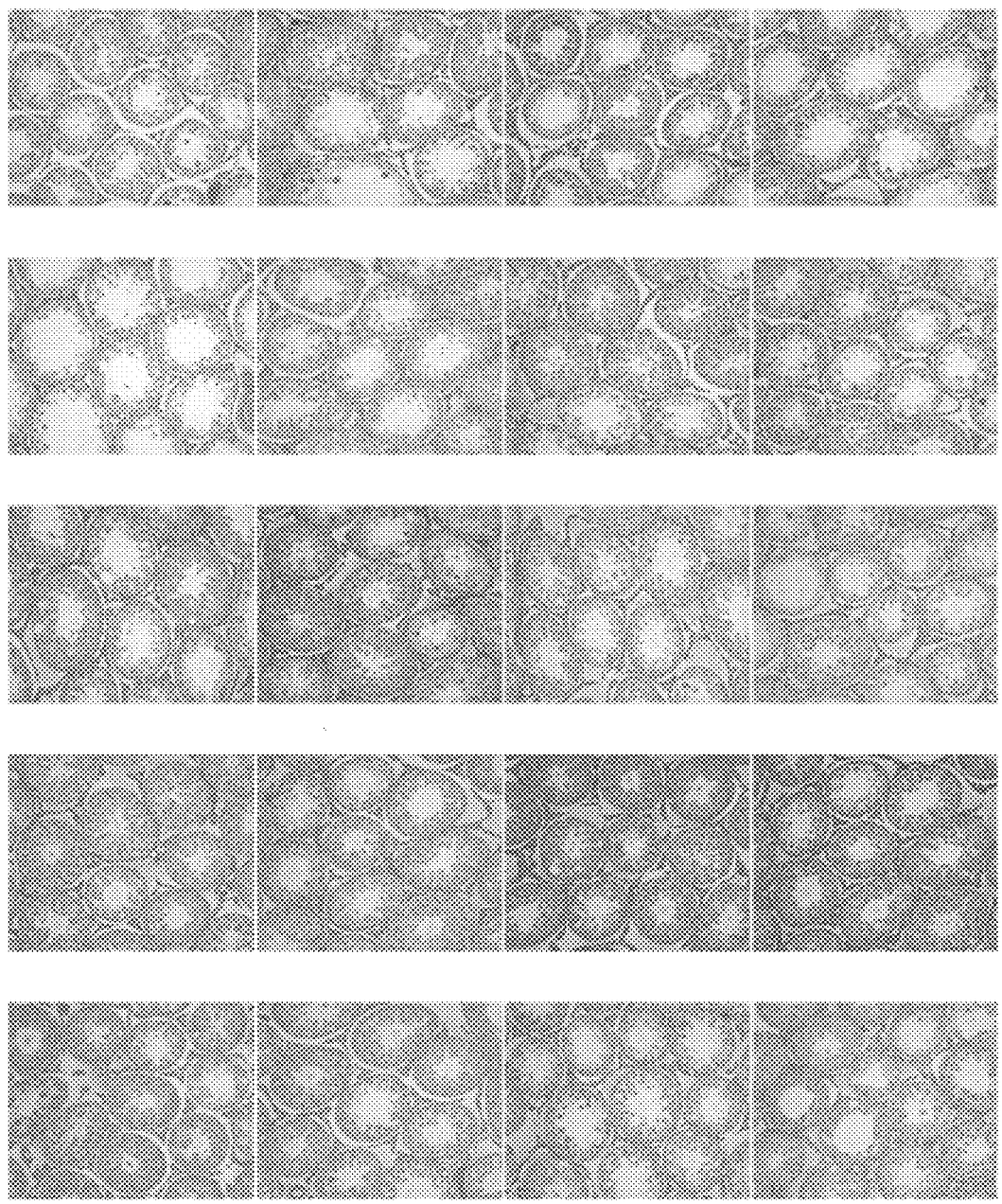
FIG. 6D is a histologic photograph of the testes of a rat receiving 3.0 mg/kg of RC-MC-110.
Figure 6E:
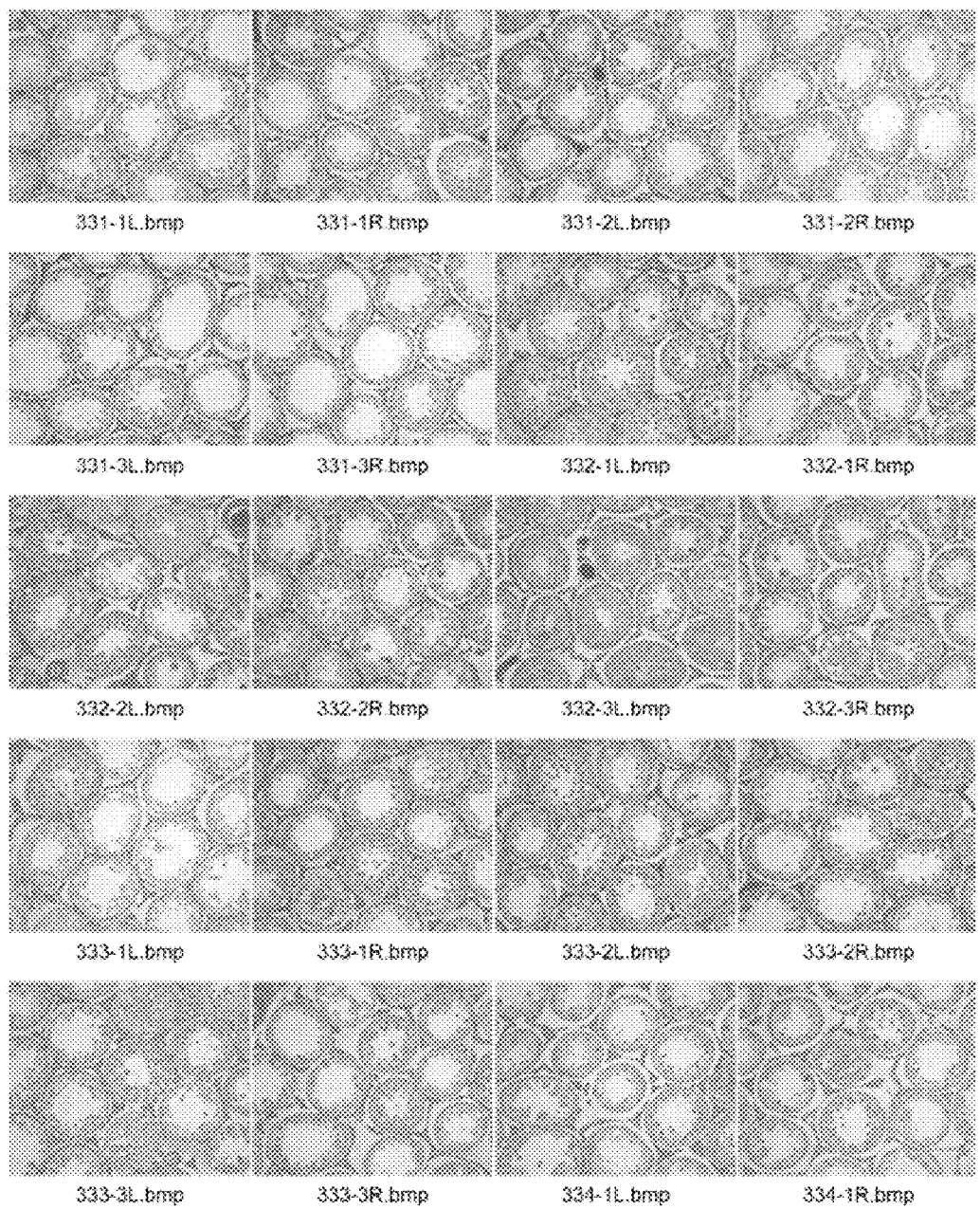
FIG. 6E is a histologic photograph of the testes of a rat receiving 6.0 mg/kg of RC-MC-110.
Figure 6F:
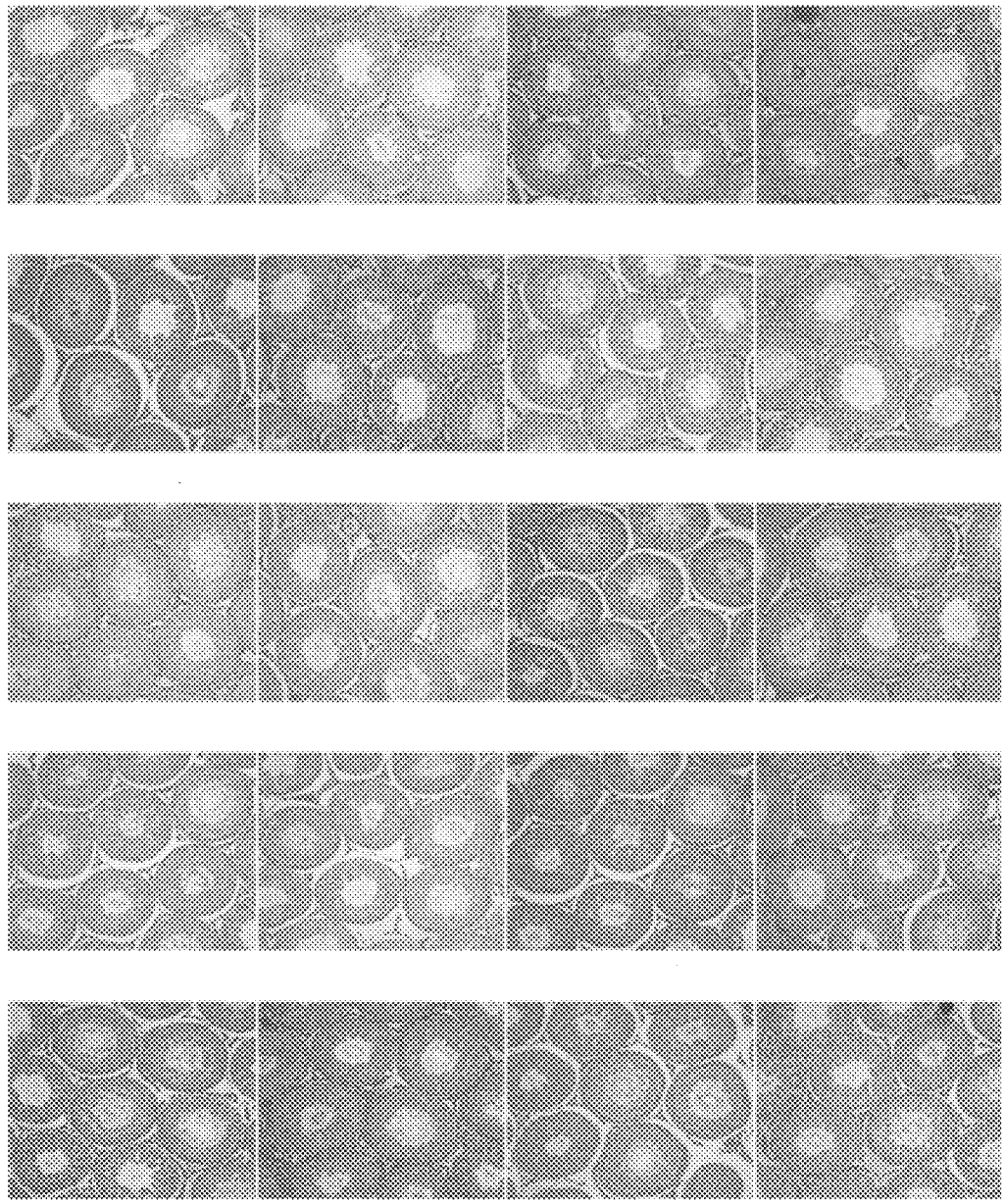
FIG. 6F is a histologic photograph of the testes of a rat receiving corn oil as a control for the RC-MC-110 studies.

It is contemplated that some of the compounds of the present invention exert their anti-fertility effects by binding either directly or indirectly to heat shock proteins or to chaperone proteins related to the heat shock proteins. It has been found that the compounds of the invention can inhibit heat shock protein HSP90AB1. It has also been found that the compounds described herein can inhibit eukaryotic translation elongation factor 1 alpha 1 (EEF1A 1). The compounds may also induce increases in interleukin 1 and/or NF-KappaB inhibitor alpha (Nfkbia). The compounds may also be able to preferentially target Sertoli cells and ovarian cells, such as ovarian follicles.

The 90 kDa heat shock proteins belong to a family of chaperones that regulate intracellular functions and are required for the refolding of denatured proteins following heat shock, as well as the conformational maturation of a large number of key proteins involved in cellular processes. Accordingly, inhibiting HSP90 proteins or associated proteins can be useful for inhibiting fertility. In yeast, a homologue of Hsp90 with a slightly lower molecular weight at 83 kDa (Hsp83) serves an identical function. The Hsp90 family of chaperones is comprised of four different isoforms. Hsp90 α and Hsp90 β are found predominately in the cytosol, the 94 kDa glucose-regulated protein ("GRP94") is localized to the endoplasmic reticulum, and Hsp75/tumour necrosis factor receptor associated protein 1 ("TRAP-1") resides mainly in the mitochondrial matrix. These Hsp90s bind to client proteins in the presence of cochaperones, immunophilins, and partner proteins to make the multiprotein complex responsible for conformational maturation of newly formed nascent peptides into biologically active three-dimensional structures.

As discussed more fully below, Hsp90 is an ATP-dependent protein with an ATP binding site in the N-terminal region of the active homodimer. Disruption of the ATPase activity of Hsp90 results in the stabilization of multiprotein complexes and subsequent ubiquitination of the client protein, which undergoes proteasome-mediated hydrolysis.

More specifically, in an ATP-dependent fashion, Hsp70 binds to newly synthesized proteins cotranslationally and/or posttranslationally to stabilize the nascent peptide by preventing aggregation. Stabilization of the Hsp70/polypeptide binary complex is dependent upon the binding of Hsp70 interacting protein ("HIP"), which occurs after Hsp70 binds to the newly formed peptide. Hsp70-Hsp90 organizing protein ("HOP") contains highly conserved TPRs (tetratricopeptide repeats) that are recognized by both Hsp70 and Hsp90, promoting the union of Hsp70/HIP and Hsp90, which results in a heteroprotein complex. In the case of telomerase and steroid hormone receptors, the client protein is transferred from the Hsp70 system to the Hsp90 homodimer with concomitant release of Hsp70, HIP, and HOP. Upon binding of ATP and an immunophilin with cis/trans prolyl-isomerase activity (FKBP51, FKBP-52, or CyP A), the ensemble folds the client protein into its three-dimensional structure. In a subsequent event, p23 binds Hsp90 near the N-terminal region promoting the hydrolysis of ATP and release of the folded protein Hsp90 partner proteins, and ADP.

Examples of proteins dependent upon Hsp90 for conformational maturation include: oncogenic Src kinase, Raf, p185, mutant p53 (not normal p53), telomerase, steroid hormone receptors, polo-like kinase ("PLK"), protein kinase B ("AKT"), death domain kinase ("RIP"), MET kinase, focal adhesion kinase ("FAK"), aryl hydrocarbon receptor, RNA-dependent protein kinase ("PKR"), nitric oxide synthase ("NOS"), centrosomal proteins, and others. In addition, other proteins, such as cyclin dependent kinase 4 ("CDK4"), cyclin dependent kinase 6 ("CDK6"), and human epidermal growth factor receptor 2 ("Her-2") are thought to be client proteins of Hsp90. Consequently, Hsp90 inhibition is a target for the development of therapeutics that inhibit fertility potential because multiple signaling pathways can be simultaneously inhibited by disruption of the Hsp90 protein folding machinery.

Accordingly, the present invention is directed to novel compounds (e.g., lonidamine analogs) which are based on the lonidamine structure, and methods of use that modulate fertility. Lonidamine (1-(2,4-dichlorobenzyl)-1H-indazole-3-carboxylic acid) belongs to a group of indazole-carboxylic acid compounds. Some examples of lonidamine analogs that can be used for inhibiting fertility potential are described as follows.

In one aspect of the present invention, compounds according to the Formula I are provided:

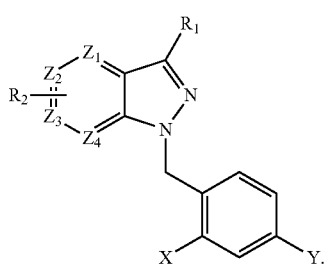

Formula I

In Formula 1: $R_1$ is carboxyl, acryl, or carboxylic acid hydrazide; wherein $R_2$ is hydrogen, halogen, alcohol, alkyl, alkoxy, aralkyl, cycloalkyl, haloalkyl, haloalkoxy, amino, or carboxyl; wherein X and Y are the same or different from each other and are halogen or lower alkyl; wherein $Z_1$, $Z_2$, $Z_3$, and $Z_4$ are independently nitrogen or carbon, and pharmaceutically salts and esters thereof.

When $R_2$ is anything other than hydrogen, $R_1$ can be —COOCH$_3$, —COOCH$_2$CH$_3$, —CH=CHCOOH, —CH=CHCOOCH$_3$, —CONHNH$_2$, —CONHNHCH$_3$, or —CONHN(CH$_3$)$_2$. When $R_2$ is hydrogen, then either: at least one of $Z_1$, $Z_2$, $Z_3$, and $Z_4$ is nitrogen and the remainder are independently carbon or nitrogen; or $R_1$ is not —COOH, —CONHNH$_2$, —CONHN(CH$_3$)$_2$, —CH=CHCOOH. Also, $R_1$ can be carboxylic acid or carboxylic acid ester selected from the group consisting of propionic acid, 2-methyl propionic acid, oxirane-carboxylic acid, cyclopropane carboxylic acid, propionic acid methyl ester, 2-methyl propionic acid methyl ester, oxirane-carboxylic acid methyl ester, cyclopropane carboxylic acid methyl ester In one aspect of the present invention, a compound comprising 1-(2,4-dichlorobenzyl)indazole-3-carboxylic acid methyl ester (also referred herein as RC-MC-30) is provided.

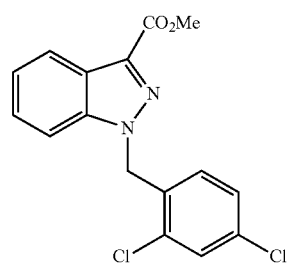 [SMILES: COC(=O)c1nn(Cc2ccc(Cl)cc2Cl)c2ccccc12]

In another aspect of the present invention, a compound comprising 1-[(2,4-dichlorobenzyl)-1H-indazole]-3-carboxylic acid ethyl ester (RC-MC-156) is provided.

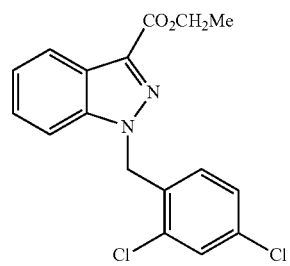

Still in another aspect of the present invention, a compound comprising 1-[(2,4-dichlorobenzyl)-1H-indazole]-3-carboxylic acid propyl ester (RC-MC-158) is provided.

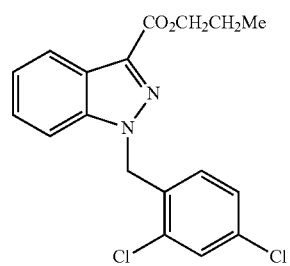

Still in another aspect of the present invention, a compound comprising 1-(2,4-dichlorobenzyl)-1H-indazole-3-carboxylic acid N-methyl hydrazide (RC-MC-120) is provided.

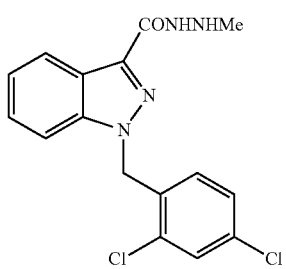

In another aspect of the present invention, a compound comprising 6-chloro-1-(2,4-dichlorobenzyl)-1H-indazole-3-carboxylic acid (DD-MC-I) is provided.

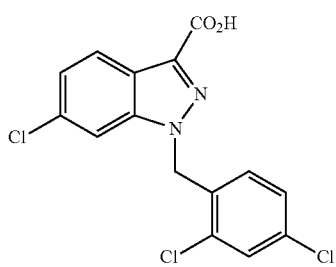 [SMILES: O=C(O)c1nn(Cc2ccc(Cl)cc2Cl)c2cc(Cl)ccc12]

In yet another aspect, the present invention includes a compound comprising 1-(2,4-difluorobenzyl)-6-chloro-1H-indazole-3-carboxylic acid (JSW-1-284).

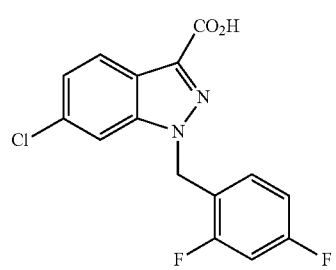 [SMILES: O=C(O)c1nn(Cc2ccc(F)cc2F)c2cc(Cl)ccc12]

Still in another aspect of the present invention, a compound comprising 1-(2-chloro-4-fluorobenzyl)-6-chloro-1H-indazole-3-carboxylic acid (JWS-2-20) is provided.

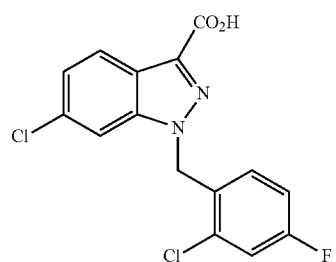 [SMILES: O=C(O)c1nn(Cc2ccc(F)cc2Cl)c2cc(Cl)ccc12]

Still in another aspect of the present invention, a compound comprising 1-(2,4-difluorobenzyl)-6-chloro-1H-indazole-3-carboxylic acid methyl ester (JWS-1-280) is provided.

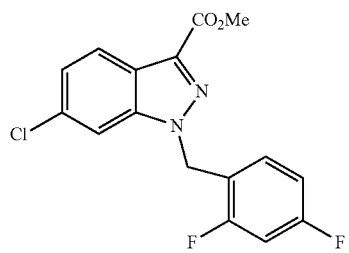 [SMILES: COC(=O)c1nn(Cc2ccc(F)cc2F)c2cc(Cl)ccc12]

Yet, still in another aspect of the present invention, a compound comprising 1-(2-chloro-4-fluorobenzyl)-6-chloro-1H-indazole-3-carboxylic acid methyl ester (JWS-2-18) is provided.

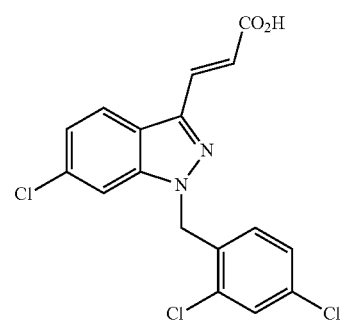 [SMILES: O=C(O)/C=C/c1nn(Cc2ccc(Cl)cc2Cl)c2cc(Cl)ccc12]

Still in another aspect of the present invention, a compound comprising 3-[1-(2,4-dichlorobenzyl)-6-chloro-1H-indazol-3-yl]-acrylic acid (JWS-1-190) is provided.

Still in another aspect of the present invention, a compound comprising 3-[1-(2,4-dichlorobenzyl)-6-chloro-1H-indazol-3-yl]-propionic acid is provided.

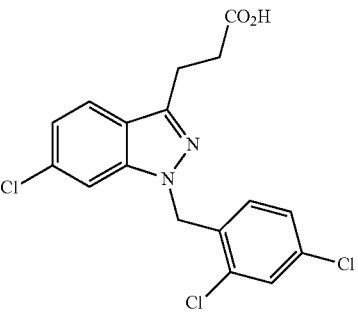 [SMILES: O=C(O)CCc1nn(Cc2ccc(Cl)cc2Cl)c2cc(Cl)ccc12]

Still in another aspect of the present invention, a compound comprising 3-[1-(2,4-difluorobenzyl)-6-chloro-1H-indazol-3-yl]-acrylic acid (JWS-1-298) is provided.

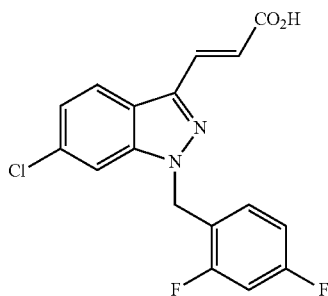 [SMILES: O=C(O)/C=C/c1nn(Cc2ccc(F)cc2F)c2cc(Cl)ccc12]

Still in another aspect of the present invention, a compound comprising 3-[1-(2-chloro, 4-fluorobenzyl)-6-chloro-1H-indazol-3-yl]-acrylic acid (JWS-2-36) is provided.

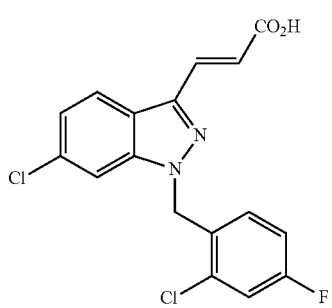 [SMILES: O=C(O)/C=C/c1nn(Cc2ccc(F)cc2Cl)c2cc(Cl)ccc12]

In yet another aspect of the present invention, a compound comprising 6-chloro-1-(2,4-dichlorobenzyl)-1H-indazole-3-carboxylic acid hydrazide (DD-MC-II) is provided.

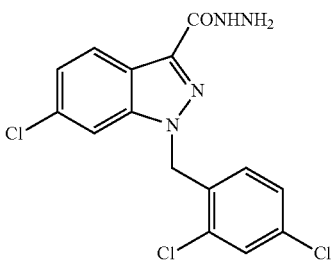

Still in another aspect of the present invention, a compound comprising 1-(2,4-difluorobenzyl)-6-chloro-1H-indazole-3-carboxylic acid hydrazide (JWS-1-282) is provided.

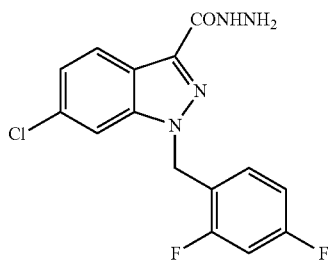

Still in another aspect of the present invention, a compound comprising 1-(2-chloro, 4-fluorobenzyl)-6-chloro-1H-indazole-3-carboxylic acid hydrazide (JWS-2-22) is provided.

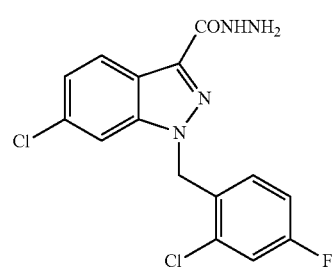

Still in another aspect of the present invention, a compound comprising 1-(2,4-dichlorobenzyl)-6-fluoro-1H-indazole-3-carboxylic acid (JWS-1-162) is provided.

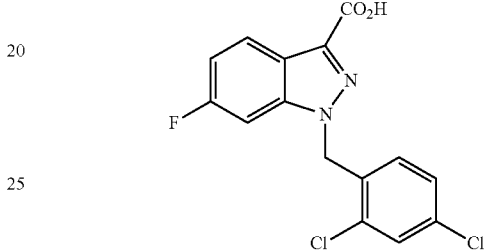

Still in another aspect of the present invention, a compound comprising 1-(2,4-dichlorobenzyl)-6-fluoro-1H-indazole-3-carboxylic acid methyl ester (JWS-1-158) is provided.

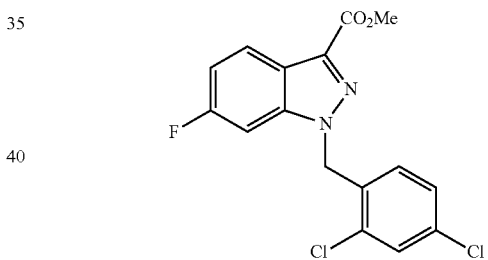

In still another aspect of the present invention, a compound comprising 3-[1-(2,4-dichlorobenzyl)-6-fluoro-1H-indazol-3-yl]-acrylic acid (JWS-1-170) is provided.

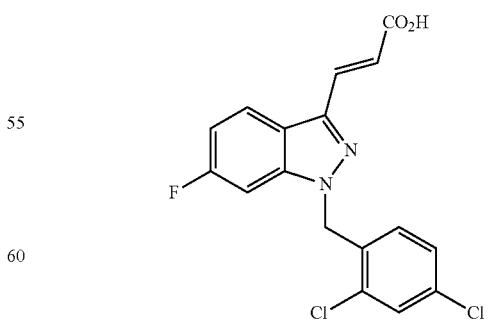

It is still another aspect of the present invention to provide a compound comprising 1-(2,4-dichlorobenzyl)-6-fluoro-1H-indazole-3-carboxylic acid hydrazide (JWS-1-160).

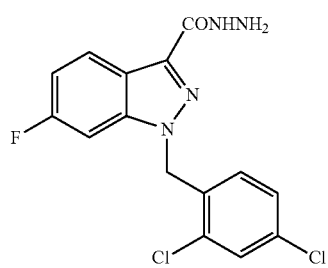

Still in another aspect of the present invention, a compound comprising 1-(2,4-dichlorobenzyl)-6-trifluoromethyl-1H-indazole-3-carboxylic acid (RC-MC-100) is provided.

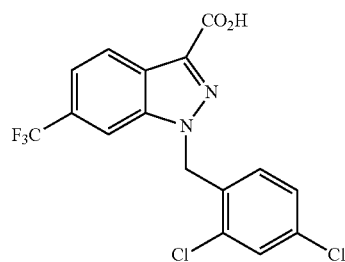 [SMILES: O=C(O)c1nn(Cc2ccc(Cl)cc2Cl)c2cc(C(F)(F)F)ccc12]

In a further aspect of the present invention, a compound comprising 1-(2,4-difluorobenzyl)-6-trifluoromethyl-1H-indazole-3-carboxylic acid (JWS-1-276) is provided.

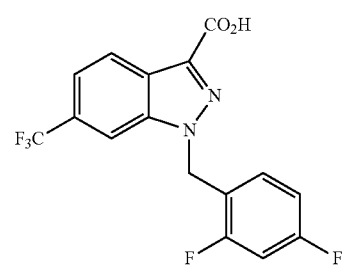 [SMILES: O=C(O)c1nn(Cc2ccc(F)cc2F)c2cc(C(F)(F)F)ccc12]

Further, in another aspect of the present invention, a compound comprising 1-(2-chloro-4-fluorobenzyl)-6-trifluoromethyl-1H-indazole-3-carboxylic acid (JWS-2-14) is provided.

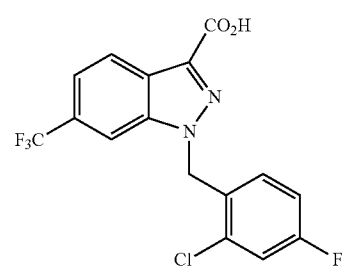 [SMILES: O=C(O)c1nn(Cc2ccc(F)cc2Cl)c2cc(C(F)(F)F)ccc12]

In another aspect of the present invention, a compound comprising 1-(2,4-difluorobenzyl)-6-trifluoromethyl-1H-indazole-3-carboxylic acid methyl ester (JWS-1-270) is provided.

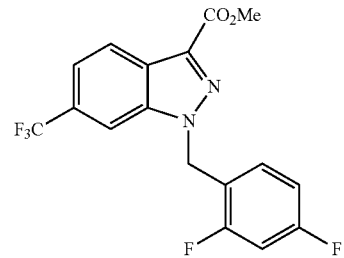

Still in another aspect of the present invention, a compound comprising 1-(2-fluoro-4-chlorobenzyl)-6-trifluoromethyl-1H-indazole-3-carboxylic acid methyl ester (JWS-2-12) is provided.

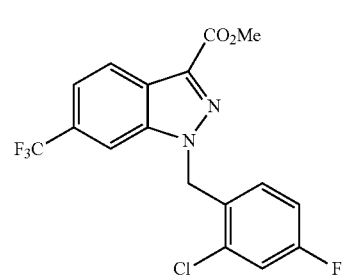

In still a further aspect of the present invention, a compound comprising cis 3-[1-(2,4-dichlorobenzyl)-6-trifluoromethyl-1H-indazol-3-yl]-acrylic acid (cis RC-MC-110) is provided

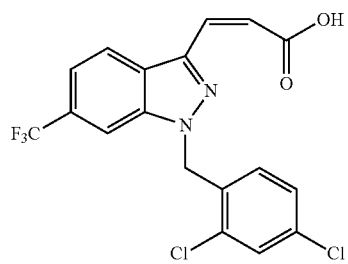 [SMILES: O=C(O)/C=C\c1nn(Cc2ccc(Cl)cc2Cl)c2cc(C(F)(F)F)ccc12]

Still in another aspect of the present invention, a compound comprising 3-[1-(2,4-difluorobenzyl)-6-trifluoromethyl-1H-indazol-3-yl]-acrylic acid (JWS-1-294) is provided.

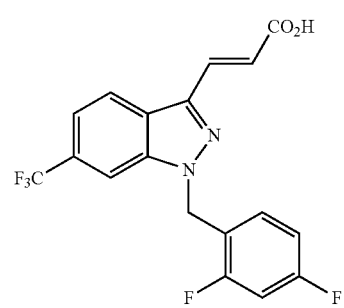 [SMILES: O=C(O)/C=C/c1nn(Cc2ccc(F)cc2F)c2cc(C(F)(F)F)ccc12]

Still in another aspect of the present invention, a compound comprising 3-[1-(2-chloro, 4-fluorobenzyl)-6-trifluoromethyl-1H-indazol-3-yl]-acrylic acid (JWS-2-40) is provided.

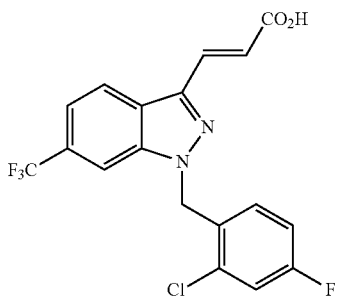 [SMILES: O=C(O)/C=C/c1nn(Cc2ccc(F)cc2Cl)c2cc(C(F)(F)F)ccc12]

In still a further aspect of the present invention, a compound comprising 3-[1-(2,4-dichlorobenzyl)-6-trifluoromethyl-1H-indazol-3-yl]-2-methyl-acrylic acid (RC-MC-217) is provided.

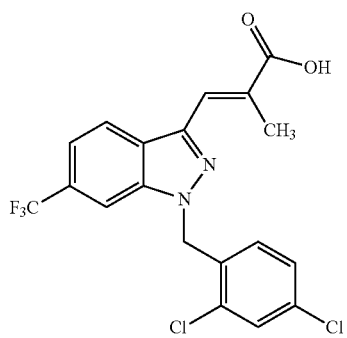 [SMILES: C/C(=C\c1nn(Cc2ccc(Cl)cc2Cl)c2cc(C(F)(F)F)ccc12)C(=O)O]

In a further aspect of the present invention, a compound comprising trans 3-[1-(2,4-dichlorobenzyl)-6-trifluoromethyl-1H-indazol-3-yl]-acrylic acid methyl ester (trans RC-MC-200) is provided.

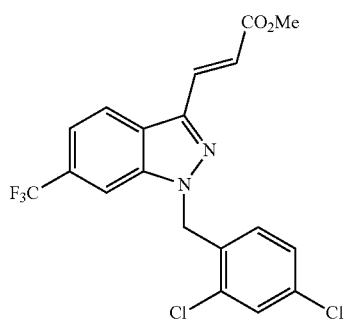 [SMILES: COC(=O)/C=C/c1nn(Cc2ccc(Cl)cc2Cl)c2cc(C(F)(F)F)ccc12]

In still a further aspect of the present invention, a compound comprising cis 3-[1-(2,4-dichlorobenzyl)-6-trifluoromethyl-1H-indazol-3-yl]-acrylic acid methyl ester (cis RC-MC-200) is provided.

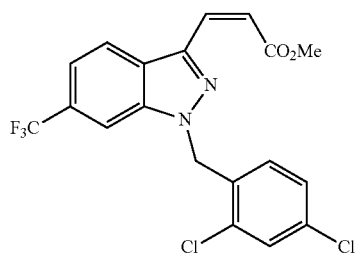 [SMILES: COC(=O)/C=C\c1nn(Cc2ccc(Cl)cc2Cl)c2cc(C(F)(F)F)ccc12]

Still in another aspect of the present invention, a compound comprising 1-(2,4-dichlorobenzyl)-6-trifluoromethyl-1H-indazole-3-carboxylic acid hydrazide (RC-MC-101) is provided.

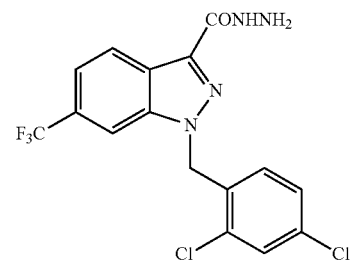

Still in another aspect of the present invention, a compound comprising 1-(2,4-difluorobenzyl)-6-trifluoromethyl-1H-indazole-3-carboxylic acid hydrazide (JWS-1-274) is provided.

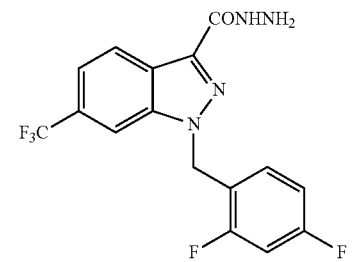

Still in another aspect of the present invention, a compound comprising 1-(2-chloro-4-fluorobenzyl)-6-trifluoromethyl-1H-indazole-3-carboxylic acid hydrazide (JWS-2-16) is provided.

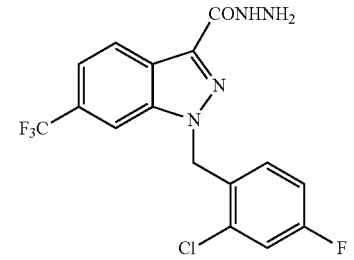

In still a further aspect of the present invention, a compound comprising 3-[1-(2,4-dichlorobenzyl)-6-trifluoromethyl-1H-indazol-3-yl]-propionic acid (JWS-2-72; H2-gamendazole) is provided.

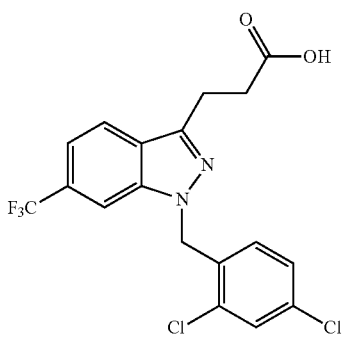 [SMILES: O=C(O)CCc1nn(Cc2ccc(Cl)cc2Cl)c2cc(C(F)(F)F)ccc12]

JWS-2-72 (H2 Gamandazole)

Still in another aspect of the present invention, a compound comprising trans 3-[1-(2,4-dichlorobenzyl)-6-trifluoromethyl-1H-indazol-3-yl]-acrylic acid (RC-MC-110), also known as gamendazole, is provided.

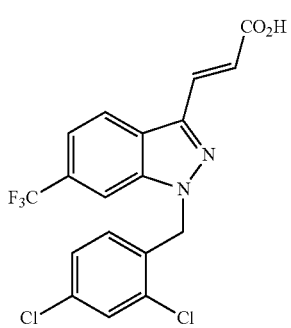 [SMILES: O=C(O)/C=C/c1nn(Cc2ccc(Cl)cc2Cl)c2cc(C(F)(F)F)ccc12]

Gamendazole (RC-MC-110)

In still a further aspect of the present invention, a compound comprising 3-[1-(2,4-dichlorobenzyl)-6-trifluoromethyl-1H-indazol-3-yl]-2-methylpropionic acid is provided (RC-MC-294).

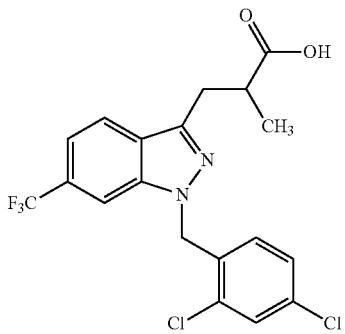 [SMILES: CC(Cc1nn(Cc2ccc(Cl)cc2Cl)c2cc(C(F)(F)F)ccc12)C(=O)O]

In still a further aspect of the present invention, a compound comprising 3-[1-(2,4-dichlorobenzyl)-6-trifluoromethyl-1H-indazol-3-yl]-propionic acid ethyl ester (JWS-2-70) is provided.

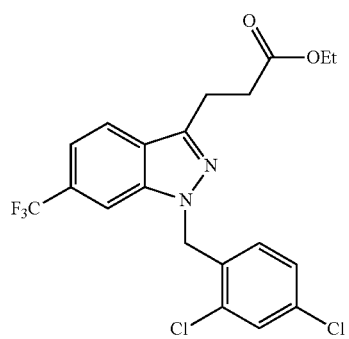

In still a further aspect of the present invention, a compound comprising 1-(4-chloro-2-methyl-benzyl)-6-trifluoromethyl-1H-indazole-3-carboxylic acid (JWS-2-212) is provided.

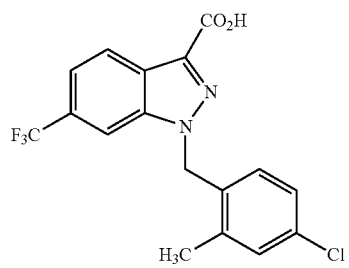 [SMILES: Cc1cc(Cl)ccc1Cn1nc(C(=O)O)c2ccc(C(F)(F)F)cc21]

In still a further aspect of the present invention, a compound comprising 1-(4-chloro-2-methyl-benzyl)-6-trifluoromethyl-1H-indazole-3-carboxylic acid methyl ester (JWS-2-210) is provided.

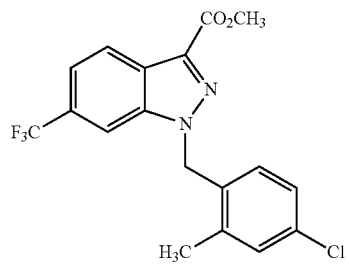 [SMILES: COC(=O)c1nn(Cc2ccc(Cl)cc2C)c2cc(C(F)(F)F)ccc12]

In still a further aspect of the present invention, a compound comprising 3-[1-(4-chloro-2-methyl-benzyl)-6-trifluoromethyl-1H-indazol-3-yl]-acrylic acid (JWS-2-224) is provided.

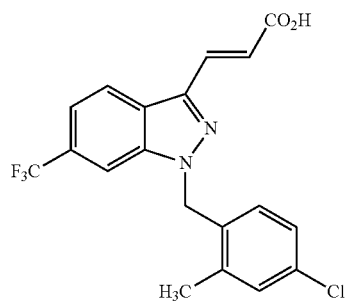 [SMILES: Cc1cc(Cl)ccc1Cn1nc(/C=C/C(=O)O)c2ccc(C(F)(F)F)cc21]

In still a further aspect of the present invention, compounds comprising cis- and trans-3-[1-(2,4-dichlorobenzyl)-6-trifluoromethyl-1H-indazol-3-yl]-oxirane-2-carboxylic acid (RC-MC-228) are provided.

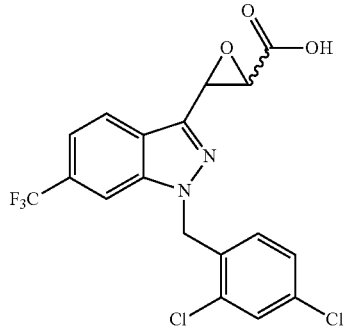 [SMILES: O=C(O)C1OC1c1nn(Cc2ccc(Cl)cc2Cl)c2cc(C(F)(F)F)ccc12]

In still a further aspect of the present invention, compounds comprising cis- and trans-2-[1-(2,4-dichloro-benzyl)-6-trifluoromethyl-1H-indazol-3-yl]-cyclopropanecarboxylic acid (JWS-3-6) are provided.

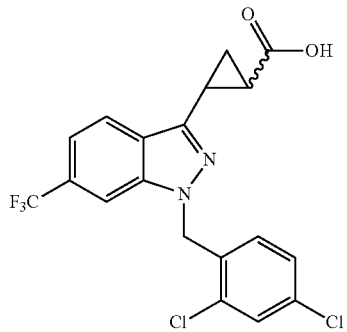 [SMILES: O=C(O)C1CC1c1nn(Cc2ccc(Cl)cc2Cl)c2cc(C(F)(F)F)ccc12]

In still a further aspect of the present invention, a compound comprising 3-[1-(2,4-dichlorobenzyl)-6-trifluoromethyl-1H-indazol-3-yl]-prop-2-en-1-ol (RC-MC-223) is provided.

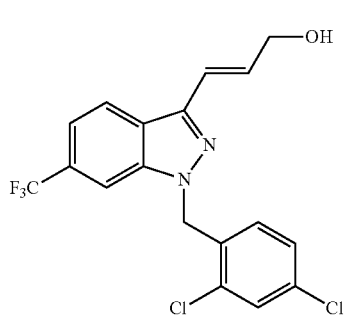 [SMILES: OC/C=C/c1nn(Cc2ccc(Cl)cc2Cl)c2cc(C(F)(F)F)ccc12]

In still a further aspect of the present invention, a compound comprising trans-3-[1-(2,4-dichlorobenzyl)-6-trifluoromethyl-1H-indazol-3-yl]-acrylonitrile is provided (RC-MC-222 Trans).

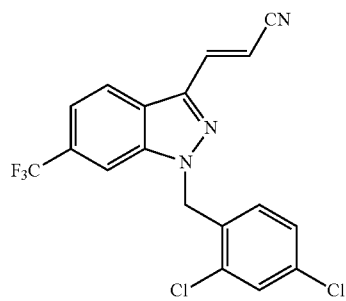 [SMILES: N#C/C=C/c1nn(Cc2ccc(Cl)cc2Cl)c2cc(C(F)(F)F)ccc12]

In still a further aspect of the present invention, a compound comprising cis-3-[1-(2,4-dichlorobenzyl)-6-trifluoromethyl-1H-indazol-3-yl]-acrylonitrile is provided (RC-MC-222 cis).

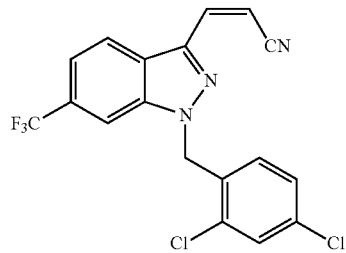 [SMILES: N#C/C=C\c1nn(Cc2ccc(Cl)cc2Cl)c2cc(C(F)(F)F)ccc12]

In still a further aspect of the present invention, a compound comprising 4-[1-(2,4-dichloro-benzyl)-6-trifluoromethyl-1H-indazol-3-yl]-but-3-en-2-one (RC-MC-216) is provided.

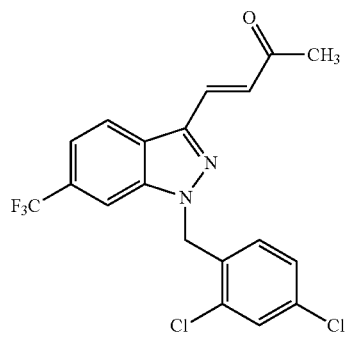 [SMILES: CC(=O)/C=C/c1nn(Cc2ccc(Cl)cc2Cl)c2cc(C(F)(F)F)ccc12]

In still a further aspect of the present invention, a compound comprising 1-(2,4-dichloro-benzyl)-3-[2-(1H-tetrazol-5-yl)-vinyl]-6-trifluoromethyl-1H-indazole (RC-MC-225) is provided.

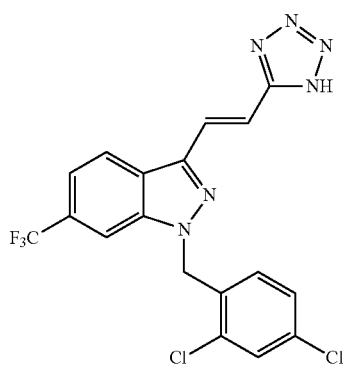 [SMILES: FC(F)(F)c1ccc2c(/C=C/c3nnn[nH]3)nn(Cc3ccc(Cl)cc3Cl)c2c1]

In a further aspect of the present invention, a compound comprising 3-[1-(2,4-dichlorobenzyl)-6-trifluoromethyl-1H-indazol-3-yl]-acrylic acid hydrazide (RC-MC-205) is provided.

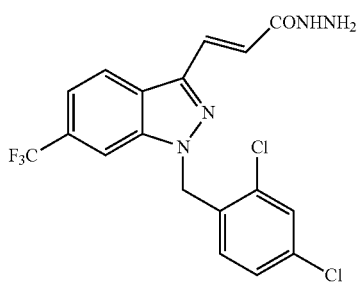

Further, in another aspect of the present invention, a compound comprising 1-(2,4-dichlorobenzyl)-6-difluoromethyl-1H-indazole-3-carboxylic acid (RC-MC-288) is provided.

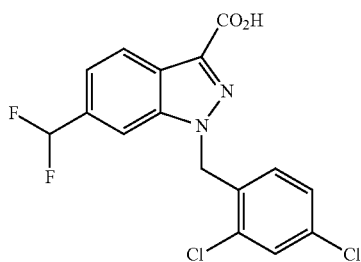 [SMILES: O=C(O)c1nn(Cc2ccc(Cl)cc2Cl)c2cc(C(F)F)ccc12]

Further, in another aspect of the present invention, a compound comprising 1-(2,4-dichlorobenzyl)-6-difluoromethyl-1-indazole-3-carboxylic acid methyl ester (RC-MC-287) is provided.

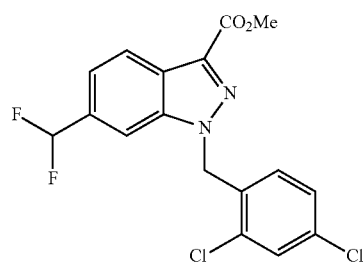 [SMILES: COC(=O)c1nn(Cc2ccc(Cl)cc2Cl)c2cc(C(F)F)ccc12]

Still in another aspect of the present invention, a compound comprising 3-[1-(2,4-dichlorobenzyl)-6-difluoromethyl-1H-indazol-3-yl]-acrylic acid (RC-MC-292) is provided.

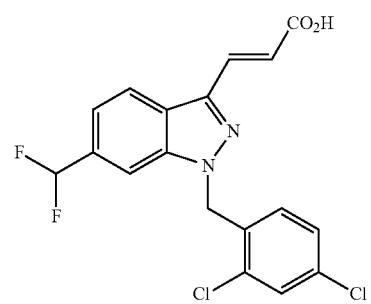 [SMILES: O=C(O)/C=C/c1nn(Cc2ccc(Cl)cc2Cl)c2cc(C(F)F)ccc12]

In a further aspect of the present invention, a compound comprising 3-[1-(2,4-dichlorobenzyl)-6-difluoromethyl-1H-indazol-3-yl]-acrylic acid methyl ester (RC-MC-291) is provided.

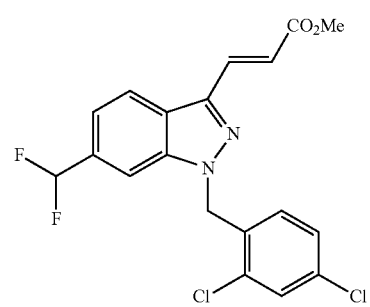 [SMILES: COC(=O)/C=C/c1nn(Cc2ccc(Cl)cc2Cl)c2cc(C(F)F)ccc12]

Further, in another aspect of the present invention, a compound comprising 1-(2,4-dichlorobenzyl)-6-fluoromethyl-1H-indazole-3-carboxylic acid (RC-MC-263) is provided.

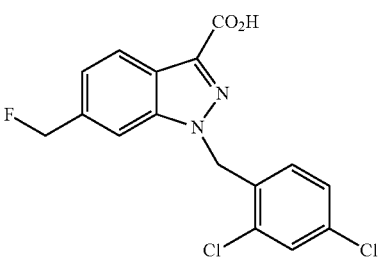 [SMILES: O=C(O)c1nn(Cc2ccc(Cl)cc2Cl)c2cc(CF)ccc12]

In still another aspect of the present invention, a compound comprising 1-(2,4-dichlorobenzyl)-6-fluoromethyl-1H-indazole-3-carboxylic acid methyl ester (RC-MC-262) is provided.

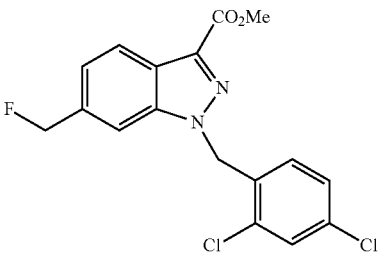 [SMILES: COC(=O)c1nn(Cc2ccc(Cl)cc2Cl)c2cc(CF)ccc12]

Still in another aspect of the present invention, a compound comprising 3-[1-(2,4-dichlorobenzyl)-6-fluoromethyl-1H-indazol-3-yl]-acrylic acid (RC-MC-265) is provided.

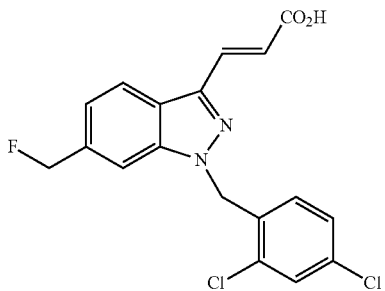 [SMILES: O=C(O)/C=C/c1nn(Cc2ccc(Cl)cc2Cl)c2cc(CF)ccc12]

In a further aspect of the present invention, a compound comprising 3-[1-(2,4-dichlorobenzyl)-6-fluoromethyl-1H-indazol-3-yl]-acrylic acid methyl ester (RC-MC-264) is provided.

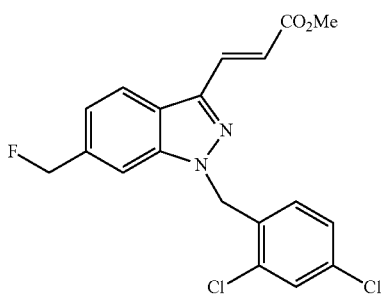 [SMILES: COC(=O)/C=C/c1nn(Cc2ccc(Cl)cc2Cl)c2cc(CF)ccc12]

In still a further aspect of the present invention, a compound comprising 1-(2,4-dichlorobenzyl)-6-trifluoromethoxy-1H-indazole-3-carboxylic acid (JWS-2-102) is provided.

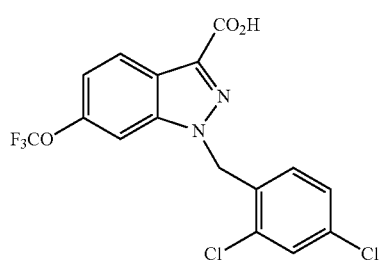 [SMILES: O=C(O)c1nn(Cc2ccc(Cl)cc2Cl)c2cc(OC(F)(F)F)ccc12]

In still a further aspect of the present invention, a compound comprising 1-(2,4-dichlorobenzyl)-6-trifluoromethoxy-1H-indazole-3-carboxylic acid methyl ester (JWS-2-100) is provided.

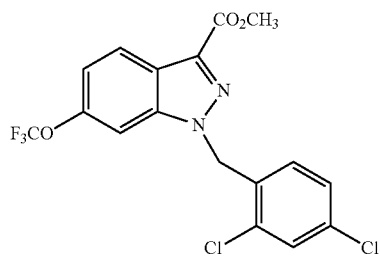 [SMILES: COC(=O)c1nn(Cc2ccc(Cl)cc2Cl)c2cc(OC(F)(F)F)ccc12]

In still a further aspect of the present invention, a compound comprising 3-[1-(2,4-dichlorobenzyl)-6-trifluoromethoxy-1H-indazol-3-yl]acrylic acid (JWS-2-112) is provided.

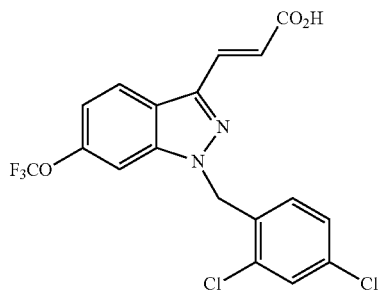 [SMILES: O=C(O)/C=C/c1nn(Cc2ccc(Cl)cc2Cl)c2cc(OC(F)(F)F)ccc12]

In still a further aspect of the present invention, a compound comprising 3-[1-(2,4-dichlorobenzyl)-6-trifluoromethoxy-1H-indazol-3-yl]acrylic acid methyl ester (JWS-2-110) is provided.

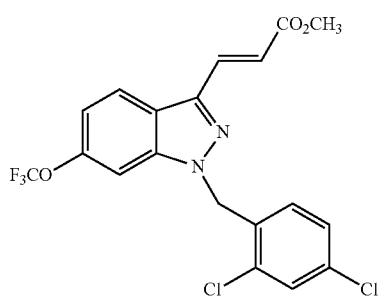 [SMILES: COC(=O)/C=C/c1nn(Cc2ccc(Cl)cc2Cl)c2cc(OC(F)(F)F)ccc12]

In still a further aspect of the present invention, a compound comprising 1-(2,4-dichlorobenzyl)-6-trifluoromethoxy-1H-indazole-3-carboxylic acid hydrazide (JWS-2-104) is provided.

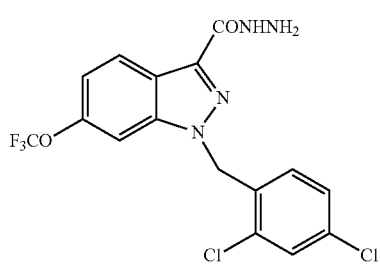

In still a further aspect of the present invention, a compound comprising 1-(4-chloro-2-methyl-benzyl)-6-trifluoromethoxy-1H-indazole-3-carboxylic acid (JWS-2-216) is provided.

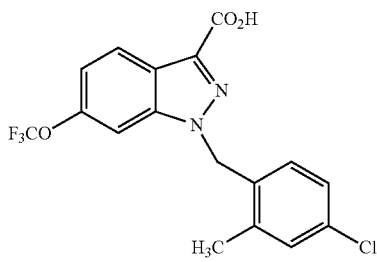 [SMILES: Cc1cc(Cl)ccc1Cn1nc(C(=O)O)c2ccc(OC(F)(F)F)cc21]

In still a further aspect of the present invention, a compound comprising 1-(4-chloro-2-methyl-benzyl)-6-trifluoromethoxy-1H-indazole-3-carboxylic acid methyl ester (JWS-2-214) is provided.

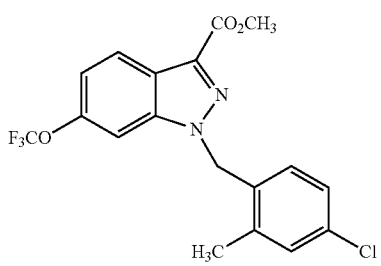 [SMILES: COC(=O)c1nn(Cc2ccc(Cl)cc2C)c2cc(OC(F)(F)F)ccc12]

In still a further aspect of the present invention, a compound comprising 3-[1-(4-chloro-2-methyl-benzyl)-6-trifluoromethoxy-1H-indazol-3-yl]-acrylic acid (JWS-2-232) is provided.

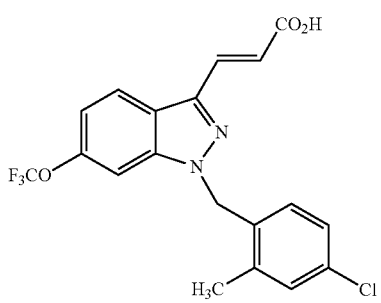 [SMILES: Cc1cc(Cl)ccc1Cn1nc(/C=C/C(=O)O)c2ccc(OC(F)(F)F)cc21]

Still in another aspect of the present invention, a compound comprising 1-(2,4-dichlorobenzyl)-6-methyl-1H-indazole-3-carboxylic acid (TH-2-178) is provided.

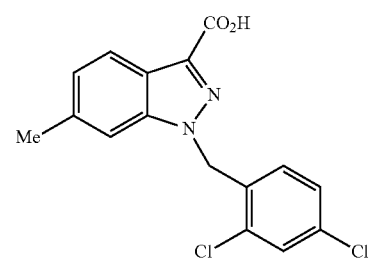 [SMILES: Cc1ccc2c(C(=O)O)nn(Cc3ccc(Cl)cc3Cl)c2c1]

In a further aspect of the present invention, a compound comprising 3-[1-(2,4-dichlorobenzyl)-6-methyl-1H-indazol-3-yl]acrylic acid (TH-2-192) is provided.

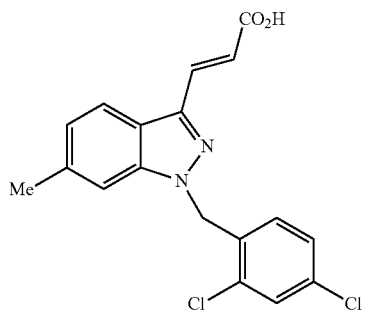 [SMILES: Cc1ccc2c(/C=C/C(=O)O)nn(Cc3ccc(Cl)cc3Cl)c2c1]

Still in another aspect of the present invention, a compound comprising 1-(2,4-dichlorobenzyl)-6-methyl-1H-indazole-3-carboxylic acid hydrazide (TH-2-179) is provided.

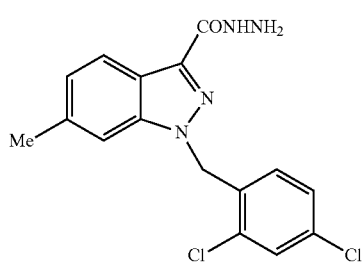

In still a further aspect of the present invention, a compound comprising 1-(2,4-dichlorobenzyl)-6-methoxy-1H-indazole-3-carboxylic acid (JWS-2-122) is provided.

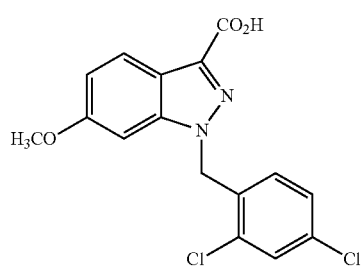 [SMILES: COc1ccc2c(C(=O)O)nn(Cc3ccc(Cl)cc3Cl)c2c1]

In still a further aspect of the present invention, a compound comprising 1-(2,4-dichlorobenzyl)-6-methoxy-1H-indazole-3-carboxylic acid methyl ester (JWS-2-120) is provided.

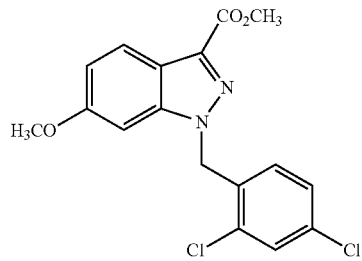 [SMILES: COC(=O)c1nn(Cc2ccc(Cl)cc2Cl)c2cc(OC)ccc12]

In still a further aspect of the present invention, a compound comprising 3-[1-(2,4-dichlorobenzyl)-6-methoxy-1H-indazol-3-yl]acrylic acid (JWS-2-132) is provided.

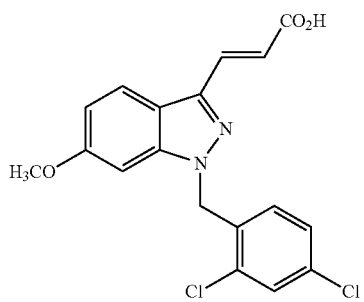 [SMILES: COc1ccc2c(/C=C/C(=O)O)nn(Cc3ccc(Cl)cc3Cl)c2c1]

In still a further aspect of the present invention, a compound comprising 1-(2,4-dichlorobenzyl)-6-methoxy-1H-indazole-3-carboxylic acid hydrazide (JWS-2-124) is provided.

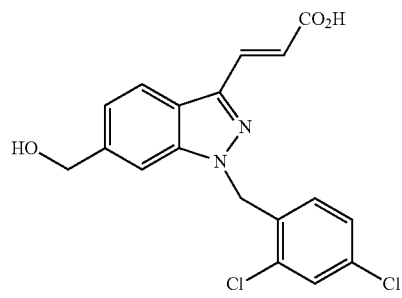

In still a further aspect of the present invention, a compound comprising 3-[1-(2,4-dichlorobenzyl)-6-hydroxymethyl-1H-indazol-3-yl]acrylic acid methyl ester (RC-MC-257) is provided.

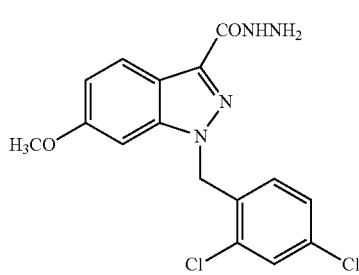

Yet, in another aspect of the present invention, a compound comprising 1-(2,4-dichlorobenzyl)-6-hydroxymethyl-1H-indazole-3-carboxylic acid (RC-MC-260) is provided.

Yet, in another aspect of the present invention, a compound comprising 1-(2,4-dichloro-benzyl)-1H-indazole-3,6-dicarboxylic acid (RC-MC-247) is provided.

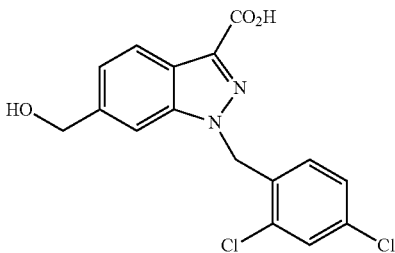 [SMILES: O=C(O)c1nn(Cc2ccc(Cl)cc2Cl)c2cc(CO)ccc12]

Yet, in another aspect of the present invention, a compound comprising 1-(2,4-dichlorobenzyl)-6-hydroxymethyl-1H-indazole-3-carboxylic acid methyl ester (RC-MC-251) is provided.

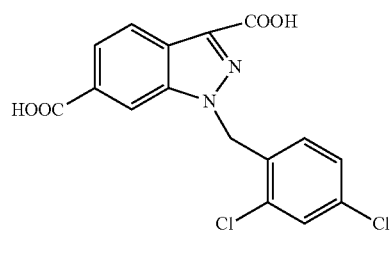

Yet, in another aspect of the present invention, a compound comprising 1-(2,4-dichloro-benzyl)-1H-indazole-3,6-dicarboxylic acid-3-methyl ester (RC-MC-252) is provided.

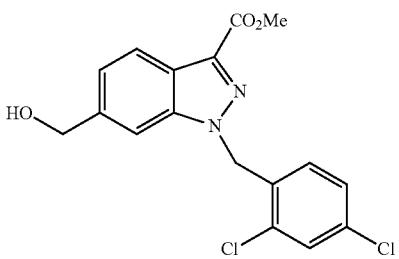 [SMILES: COC(=O)c1nn(Cc2ccc(Cl)cc2Cl)c2cc(CO)ccc12]

Still in another aspect of the present invention, a compound comprising 3-[1-(2,4-dichlorobenzyl)-6-hydroxymethyl-1H-indazol-3-yl]-acrylic acid (RC-MC-261) is provided.

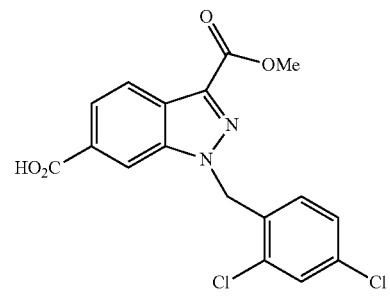 [SMILES: COC(=O)c1nn(Cc2ccc(Cl)cc2Cl)c2cc(C(=O)O)ccc12]

In still a further aspect of the present invention, a compound comprising 3-(2-carboxy-vinyl)-1-(2,4-dichloro-benzyl)-1H-indazole-6-carboxylic acid (RC-MC-259) is provided

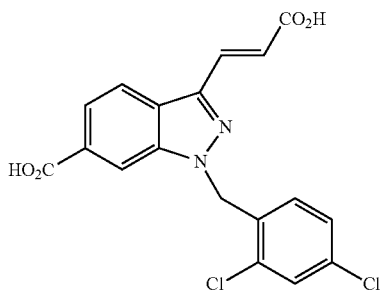 [SMILES: O=C(O)/C=C/c1nn(Cc2ccc(Cl)cc2Cl)c2cc(C(=O)O)ccc12]

In still a further aspect of the present invention, a compound comprising 1-(2,4-dichloro-benzyl)-3-(2-methoxycarbonyl-vinyl)-1H-indazole-6-carboxylic acid (RC-MC-258) is provided.

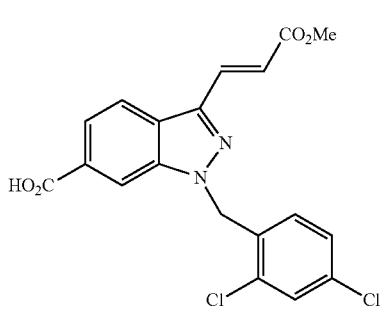 [SMILES: COC(=O)/C=C/c1nn(Cc2ccc(Cl)cc2Cl)c2cc(C(=O)O)ccc12]

Still in another aspect of the present invention, a compound comprising 1-(2,4-dichlorobenzyl)-5-trifluoromethyl-1H-indazole-3-carboxylic acid (JWS-1-260) is provided.

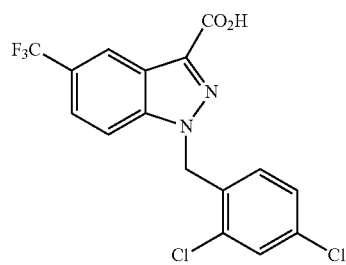 [SMILES: O=C(O)c1nn(Cc2ccc(Cl)cc2Cl)c2ccc(C(F)(F)F)cc12]

Still in another aspect of the present invention, a compound comprising 1-(2,4-difluorobenzyl)-5-trifluoromethyl-1H-indazole-3-carboxylic acid (JWS-2-1) is provided.

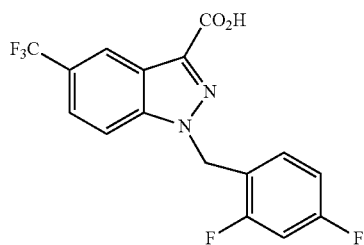 [SMILES: O=C(O)c1nn(Cc2ccc(F)cc2F)c2ccc(C(F)(F)F)cc12]

Yet, in another aspect of the present invention, a compound comprising 1-(2,4-dichlorobenzyl)-5-trifluoromethyl-1H-indazole-3-carboxylic acid methyl ester (JWS-1-254) is provided.

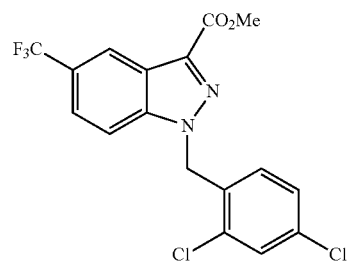 [SMILES: COC(=O)c1nn(Cc2ccc(Cl)cc2Cl)c2ccc(C(F)(F)F)cc12]

Still in another aspect of the present invention, a compound comprising 1-(2,4-difluorobenzyl)-5-trifluoromethyl-1H-indazole-3-carboxylic acid methyl ester (JWS-1-300) is provided.

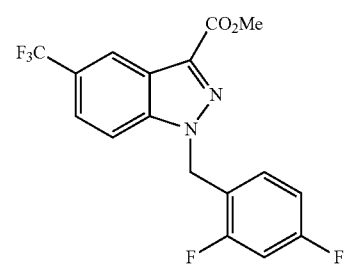 [SMILES: COC(=O)c1nn(Cc2ccc(F)cc2F)c2ccc(C(F)(F)F)cc12]

In yet another aspect of the present invention, a compound comprising 3-[1-(2,4-dichlorobenzyl)-5-trifluoromethyl-1H-indazol-3-yl]-acrylic acid (JWS-1-268) is provided.

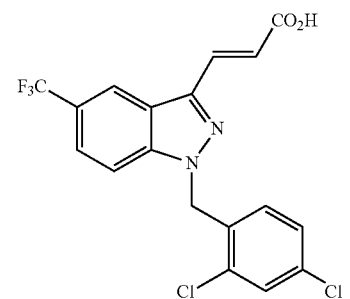 [SMILES: O=C(O)/C=C/c1nn(Cc2ccc(Cl)cc2Cl)c2ccc(C(F)(F)F)cc12]

Still in another aspect of the present invention, a compound comprising-3-[1-(2,4-difluorobenzyl)-5-trifluoromethyl-1H-indazol-3-yl]-acrylic acid (JWS-2-10) is provided.

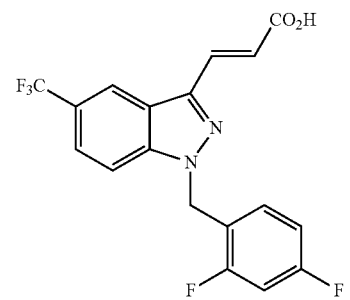 [SMILES: O=C(O)/C=C/c1nn(Cc2ccc(F)cc2F)c2ccc(C(F)(F)F)cc12]

Further, in another aspect of the present invention, a compound comprising 1-(2,4-dichlorobenzyl)-5-trifluoromethyl-1H-indazole-3-carboxylic acid hydrazide (JWS-1-258) is provided.

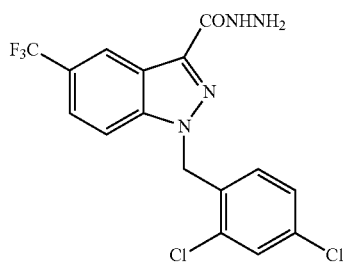

Still in another aspect of the present invention, a compound comprising 1-(2,4-difluorobenzyl)-5-trifluoromethyl-1H-indazole-3-carboxylic acid hydrazide (JWS-1-302) is provided.

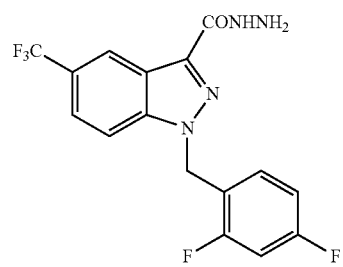

In still a further aspect of the present invention, a compound comprising 1-(2,4-dichloro-benzyl)-6-dimethylamino-1H-indazole-3-carboxylic acid (JWS-2-270) is provided.

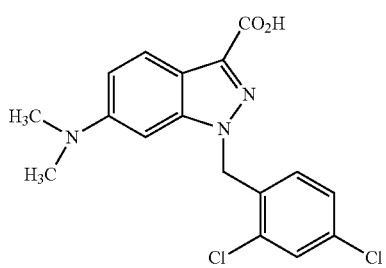 [SMILES: CN(C)c1ccc2c(C(=O)O)nn(Cc3ccc(Cl)cc3Cl)c2c1]

In still a further aspect of the present invention, a compound comprising 1-(2,4-dichloro-benzyl)-6-dimethylamino-1H-indazole-3-carboxylic acid methyl ester (JWS-2-268) is provided.

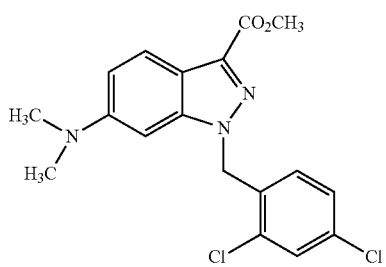 [SMILES: COC(=O)c1nn(Cc2ccc(Cl)cc2Cl)c2cc(N(C)C)ccc12]

In still a further aspect of the present invention, a compound comprising 3-[1-(2,4-dichlorobenzyl)-6-dimethylamino-1H-indazol-3-yl]-acrylic acid (JWS-2-278) is provided.

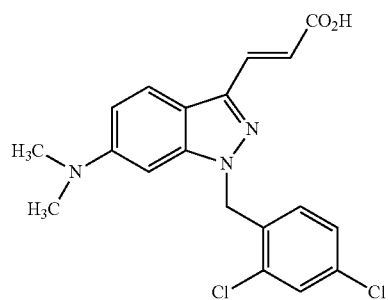 [SMILES: CN(C)c1ccc2c(/C=C/C(=O)O)nn(Cc3ccc(Cl)cc3Cl)c2c1]

In still a further aspect of the present invention, a compound comprising 1-(2,4-dichlorobenzyl)-4-methyl-1H-indazole-3-carboxylic acid (JWS-2-94) is provided.

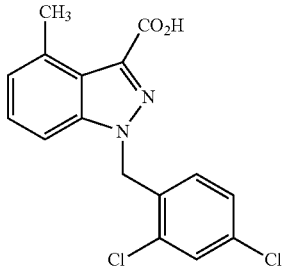 [SMILES: Cc1cccc2c1c(C(=O)O)nn2Cc1ccc(Cl)cc1Cl]

In still a further aspect of the present invention, a compound comprising 1-(2,4-dichlorobenzyl)-4-methyl-1H-indazole-3-carboxylic acid methyl ester (JWS-2-92) is provided.

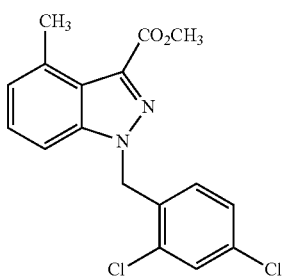 [SMILES: COC(=O)c1nn(Cc2ccc(Cl)cc2Cl)c2cccc(C)c12]

In still another aspect, compounds according to Formula II(A), are provided, where the substituents are the same as described in connection to Formula I:

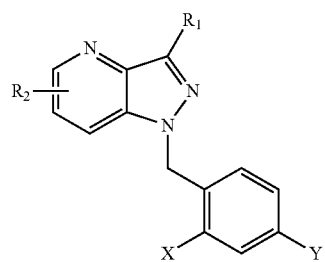

Examples of Formula II(A) derivatives include: 1-(2,4-difluorobenzyl)-1H-pyrazolo[4,3-b]pyridine-3-carboxylic acid; 1-(2-chloro-4-fluorobenzyl)-1H-pyrazolo[4,3-b]pyridine-3-carboxylic acid; 1-(2-fluoro-4-chlorobenzyl)-1H-pyrazolo[4,3-b]pyridine-3-carboxylic acid; 1-(2,4-difluorobenzyl)-1H-pyrazolo[4,3-b]pyridine]-3-carboxylic acid methyl ester; 1-(2-chloro-4-fluorobenzyl)-1H-pyrazolo[4,3-b]pyridine]-3-carboxylic acid methyl ester; 1-(2-fluoro-4-chlorobenzyl)-1H-pyrazolo[4,3-b]pyridine]-3-carboxylic acid methyl ester; 3-[1-(2,4-difluorobenzyl)-1H-pyrazolo[4,3-b]pyridin-3-yl]acrylic acid; 3-[1-(2-chloro-4-fluorobenzyl)-1H-pyrazolo[4,3-b]pyridin-3-yl]acrylic acid; 3-[1-(2-fluoro-4-chlorobenzyl)-1H-pyrazolo[4,3-b]pyridin-3-yl] acrylic acid; 1-(2,4-difluorobenzyl)-1H-pyrazolo[4,3-b]pyridine-3-carboxylic acid hydrazide; 1-(2-chloro-4-fluorobenzyl)-1H-pyrazolo[4,3-b]pyridine-3-carboxylic acid hydrazide; and 1-(2-fluoro-4-chlorobenzyl)-1H-pyrazolo[4,3-b]pyridine-3-carboxylic acid hydrazide. Additional examples are provided herein.

In still another aspect of the present invention, a compound comprising 1-(2,4-dichlorobenzyl)-1H-pyrazolo[4,3-b]pyridine-3-carboxylic acid (JWS-1-114) is provided.

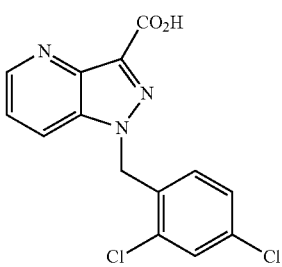 [SMILES: O=C(O)c1nn(Cc2ccc(Cl)cc2Cl)c2cccnc12]

In another aspect of the present invention, a compound comprising 1-(2,4-dichlorobenzyl)-1H-pyrazolo[4,3-b]pyridine]-3-carboxylic acid methyl ester (JWS-1-110) is provided.

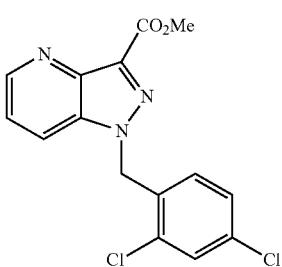

In still a further aspect of the present invention, a compound comprising 3-[1-(2,4-dichlorobenzyl)-1H-pyrazolo[4,3-b]pyridin-3-yl]acrylic acid (JWS-2-176) is provided.

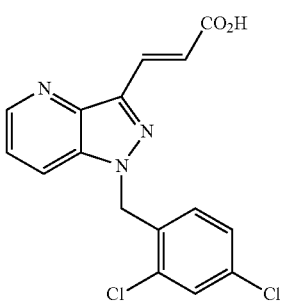 [SMILES: O=C(O)/C=C/c1nn(Cc2ccc(Cl)cc2Cl)c2cccnc12]

In still another aspect of the present invention, a compound comprising 1-(2,4-dichlorobenzyl)-1H-pyrazolo[4,3-b]pyridine-3-carboxylic acid hydrazide (JWS-1-112) is provided.

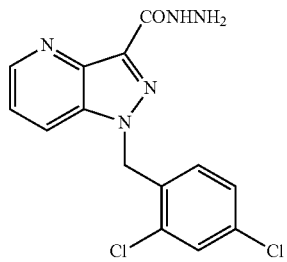

Further, the present invention includes a compound comprising 1-(2,4-dichlorobenzyl)-6-trifluoromethyl-1H-pyrazolo[4,3-b]pyridine-3-carboxylic acid (JWS-1-230).

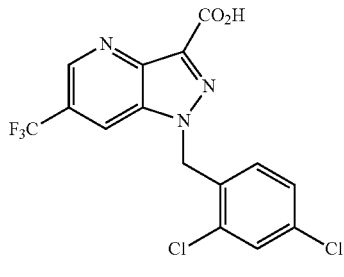 [SMILES: O=C(O)c1nn(Cc2ccc(Cl)cc2Cl)c2cc(C(F)(F)F)cnc12]

In another aspect of the present invention, a compound comprising 1-(2,4-dichlorobenzyl)-6-trifluoromethyl-1H-pyrazolo[4,3-b]pyridine-3-carboxylic acid methyl ester (JWS-1-228) is provided.

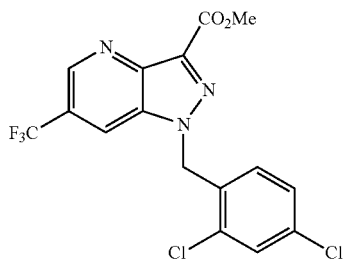 [SMILES: COC(=O)c1nn(Cc2ccc(Cl)cc2Cl)c2cc(C(F)(F)F)cnc12]

Further, the present invention includes a compound comprising 1-(2,4-dichlorobenzyl)-6-trifluoromethyl-1H-pyrazolo[4,3-b]pyridine-3-carboxylic acid hydrazide (JWS-1-232).

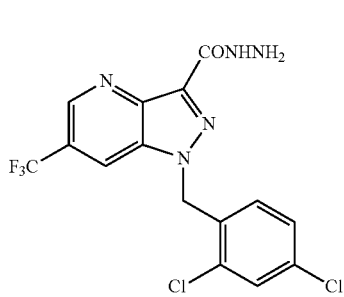

Further, the present invention includes a compound comprising 1-(2,4-dichlorobenzyl)-5-methoxy-1H-pyrazolo[4,3-b]pyridine-3-carboxylic acid (JWS-1-144).

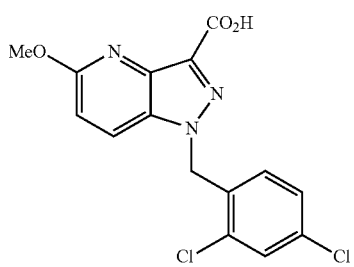 [SMILES: COc1ccc2c(n1)c(C(=O)O)nn2Cc1ccc(Cl)cc1Cl]

In another aspect of the present invention, a compound comprising 1-(2,4-dichlorobenzyl)-5-methoxy-1H-pyrazolo[4,3-b]pyridine-3-carboxylic acid methyl ester (JWS-1-142) is provided.

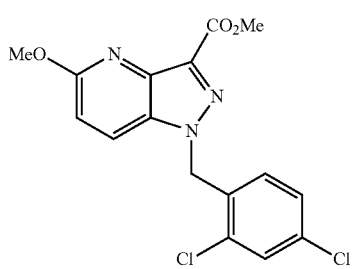 [SMILES: COC(=O)c1nn(Cc2ccc(Cl)cc2Cl)c2ccc(OC)nc12]

Further, the present invention includes a compound comprising 1-(2,4-dichlorobenzyl)-5-methoxy-1H-pyrazolo[4,3-b]pyridine-3-carboxylic acid hydrazide (JWS-1-146) is provided.

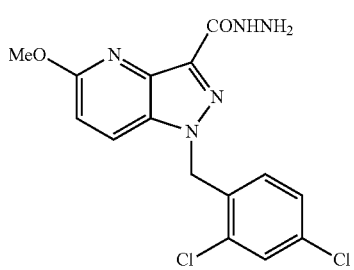

In yet another aspect, compounds according Formula II(B) are provided:

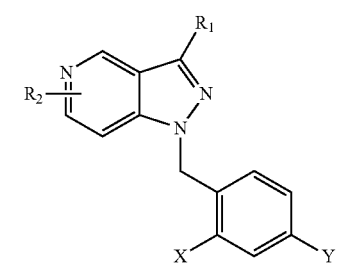

In still another aspect, the compounds according to Formula II(C) are provided, where the substituents are the same as described in connection to Formula I:

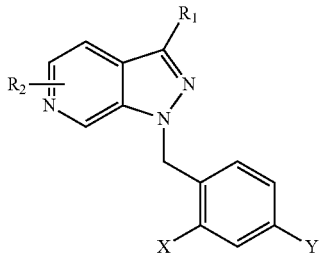

Examples of Formula II(C) derivatives include: 3-[1-(2,4-dichlorobenzyl)-1H-pyrazolo[3,4-c]pyridin-3-yl]acrylic acid; 1-(2,4-dichlorobenzyl)-1H-pyrazolo[3,4-c]pyridine-3-carboxylic acid hydrazide; 1-(2,4-dichlorobenzyl)-6-trifluoromethyl-1H-pyrazolo[3,4-c]pyridine-3-carboxylic acid; 1-(2,4-difluorobenzyl)-6-trifluoromethyl-1H-pyrazolo[3,4-c]pyridine-3-carboxylic acid; 1-(2,4-dichlorobenzyl)-6-trifluoromethyl-1H-pyrazolo[3,4-c]pyridine-3-carboxylic acid methyl ester; 1-(2,4-difluorobenzyl)-6-trifluoromethyl-1H-pyrazolo[3,4-c]pyridine-3-carboxylic acid methyl ester; 3-[1-(2,4-dichlorobenzyl)-6-trifluoromethyl-1H-pyrazolo[3,4-c]pyridin-3-yl]acrylic acid; 3-[1-(2,4-difluorobenzyl)-6-trifluoromethyl-1H-pyrazolo[3,4-c]pyridin-3-yl]acrylic acid; 1-(2,4-dichlorobenzyl)-6-trifluoromethyl-1H-pyrazolo[3,4-c]pyridine-3-carboxylic acid hydrazide; and 1-(2,4-difluorobenzyl)-6-trifluoromethyl-1H-pyrazolo[3,4-c]pyridine-3-carboxylic acid hydrazide. Additional examples are provided herein.

In still another aspect of the present invention, a compound comprising 1-(2,4-dichlorobenzyl)-1H-pyrazolo[3,4-c]pyridine-3-carboxylic acid (JWS-1-132) is provided.

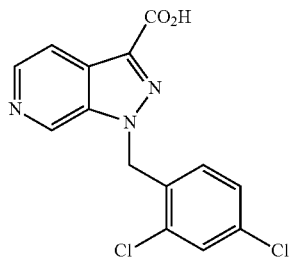 [SMILES: O=C(O)c1nn(Cc2ccc(Cl)cc2Cl)c2cnccc12]

In another aspect of the present invention, a compound comprising 1-(2,4-dichlorobenzyl)-1H-pyrazolo[3,4-c]pyridine-3-carboxylic acid methyl ester (JWS-1-130) is provided.

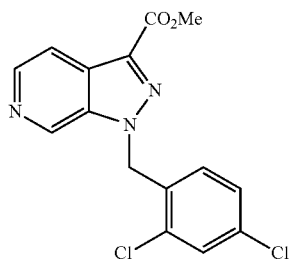 [SMILES: COC(=O)c1nn(Cc2ccc(Cl)cc2Cl)c2cnccc12]

In still another aspect, the compounds according to Formula II(D) are provided, where the substituents are the same as described in connection to Formula I:

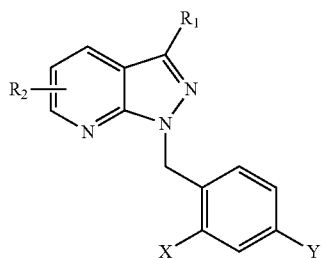

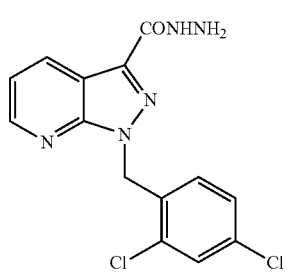

Examples of Formula II(D) derivatives include: 1-(2,4-dichlorobenzyl)-1H-pyrazolo[3,4-b]pyridine-3-carboxylic acid methyl ester; 1-(2,4-dichlorobenzyl)-6-trifluoromethyl-1H-pyrazolo[3,4-b]pyridine-3-carboxylic acid; 1-(2,4-dichlorobenzyl)-6-trifluoromethyl-1H-pyrazolo[3,4-b]pyridine-3-carboxylic acid methyl ester; 3-[1-(2,4-dichlorobenzyl)-6-trifluoromethyl-1H-pyrazolo[3,4-b]pyridine-3-yl]-acrylic acid; and 1-(2,4-dichlorobenzyl)-6-trifluoromethyl-1H-pyrazolo[3,4-b]pyridine-3-carboxylic acid hydrazide.

In still a further aspect of the present invention, a compound comprising 1-(2,4-dichlorobenzyl)-1H-pyrazolo[3,4-b]pyridine-3-carboxylic acid (RC-MC-86) is provided.

In still another aspect, the compounds encompassed by the Formula II(F) are provided, where the substituents are the same as described in connection to Formula I:

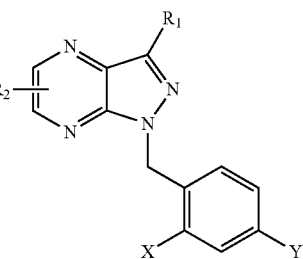

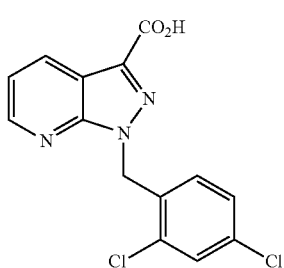 [SMILES: O=C(O)c1nn(Cc2ccc(Cl)cc2Cl)c2ncccc12]

In yet another aspect of the present invention, a compound comprising 3-[1-(2,4-dichlorobenzyl)-1H-pyrazolo[3,4-b]pyridine-3-yl]-acrylic acid (RC-MC-65) is provided.

Examples of Formula II(F) derivatives include: 1-(2,4-dichlorobenzyl)-1H-pyrazolo[3,4-b]pyrazine-3-carboxylic, acid hydrazide; 1-(2,4-dichlorobenzyl)-6-trifluoromethyl-1H-pyrazolo[3,4-b]pyrazin-3-carboxylic acid; 1-(2,4-dichlorobenzyl)-6-trifluoromethyl-1H-pyrazolo[3,4-b]pyrazin-3-carboxylic acid methyl ester; 3-[1-(2,4-dichlorobenzyl)-6-trifluoromethyl-1H-pyrazolo[3,4-b]pyrazin-3-yl]-acrylic acid; and 1-(2,4-dichlorobenzyl)-6-trifluoromethyl-1H-pyrazolo[3,4-b]pyrazin-3-carboxylic acid hydrazide.

In still a further aspect of the present invention, a compound comprising 1-(2,4-dichloro-benzyl)-1H-pyrazolo[3,4-b]pyrazine-3-carboxylic acid (JWS-2-298) is provided.

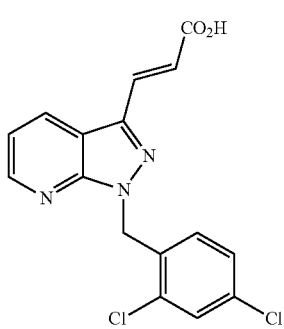 [SMILES: O=C(O)/C=C/c1nn(Cc2ccc(Cl)cc2Cl)c2ncccc12]

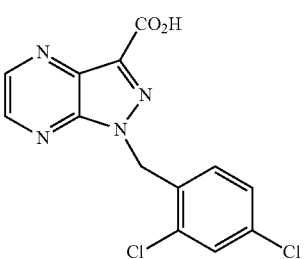 [SMILES: O=C(O)c1nn(Cc2ccc(Cl)cc2Cl)c2nccnc12]

In yet another aspect of the present invention, a compound comprising 1-(2,4-dichlorobenzyl)-1H-pyrazolo[3,4-b]pyridine-3-carboxylic acid hydrazide (RC-MC-60) is provided.

In still a further aspect of the present invention, a compound comprising 1-(2,4-dichloro-benzyl)-1H-pyrazolo[3,4-b]pyrazine-3-carboxylic acid methyl ester (JWS-2-296) is provided.

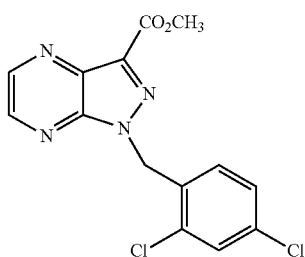 [SMILES: COC(=O)c1nn(Cc2ccc(Cl)cc2Cl)c2nccnc12]

In still a further aspect of the present invention, a compound comprising 3-[1-(2,4-dichlorobenzyl)-1H-pyrazolo[3,4-b]pyrazin-3-yl]-acrylic acid (JWS-3-1) is provided.

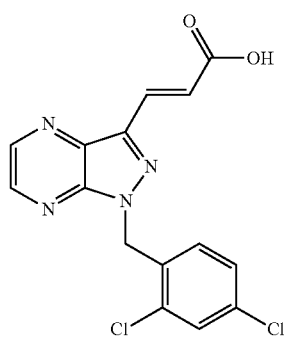 [SMILES: O=C(O)/C=C/c1nn(Cc2ccc(Cl)cc2Cl)c2nccnc12]

In yet another aspect, the compounds according encompassed by the Formula II(E) are provided, where the substituents are the same as described in connection to Formula I:

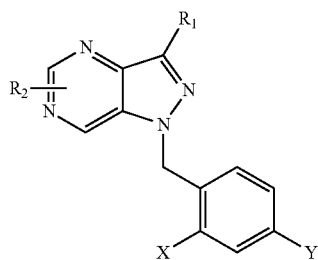

Examples of Formula II(E) derivatives include: 1-(2,4-dichlorobenzyl)-1H-pyrazolo[4,3-d]pyrimidine-3-carboxylic acid hydrazide; 1-(2,4-dichlorobenzyl)-6-trifluoromethyl-1H-pyrazolo[4,3-d]pyrimidine-3-carboxylic acid; 1-(2,4-dichlorobenzyl)-6-trifluoromethyl-1H-pyrazolo[4,3-d]pyrimidine-3-carboxylic acid methyl ester; 3-[1-(2,4-dichlorobenzyl)-6-trifluoromethyl-1H-pyrazolo[4,3-d]pyrimidin-3-yl]-acrylic acid; and 1-(2,4-dichlorobenzyl)-6-trifluoromethyl-1H-pyrazolo[4,3-d]pyrimidin-3-carboxylic acid hydrazide.

In still a further aspect of the present invention, a compound comprising 1-(2,4-dichloro-benzyl)-1H-pyrazolo[4,3-d]pyrimidine-3-carboxylic acid (JWS-2-256) is provided.

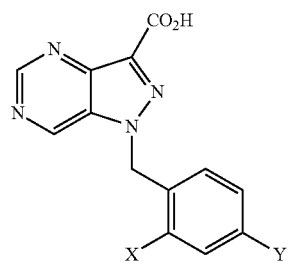

In still a further aspect of the present invention, a compound comprising [1-(2,4-dichloro-benzyl)-1H-pyrazolo[4,3-d]pyrimidine-3-carboxylic acid methyl ester (JWS-2-246) is provided.

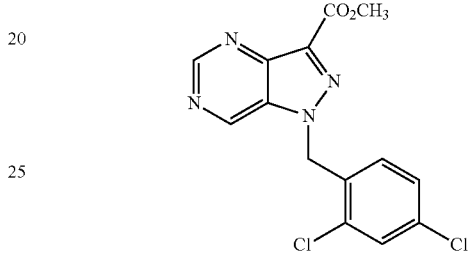

In still a further aspect of the present invention, a compound comprising 3-[1-(2,4-dichloro-benzyl)-1H-pyrazolo[4,3-d]pyrimidin-3-yl]-acrylic acid (JWS-2-254) is provided.

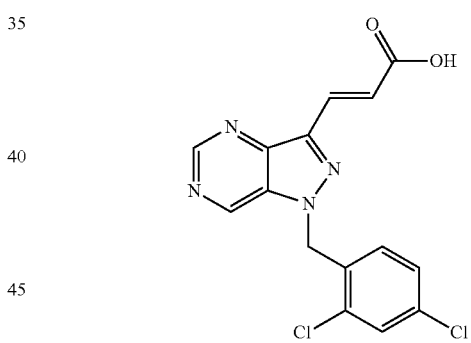

The present invention is further described by the following description, which should not be construed as a limitation on the invention.

In addition to the foregoing, the derivatives in accordance with Formula I can include $R_2$ at the 6-position being halogen, alkoxy, or carboxylic acid such as: 1-(2,4-dichlorobenzyl)-6-chloro-1H-indazole-3-carboxylic acid methyl ester; 1-(2-fluoro-4-chlorobenzyl)-6-chloro-1H-indazole-3-carboxylic acid methyl ester; 3-[1-(2-fluoro-4-chlorobenzyl)-6-chloro-1H-indazol-3-yl]-acrylic acid; 3-[1-(2,4-dichlorobenzyl)-6-chloro-1H-indazol-3-yl]-acrylic acid methyl ester; 3-[1-(2,4-difluorobenzyl)-6-chloro-1H-indazol-3-yl]-acrylic acid methyl ester; 3-[1-(2-chloro-4-fluorobenzyl)-6-chloro-1H-indazol-3-yl]-acrylic acid methyl ester; 3-[1-(2-fluoro-4-chlorobenzyl)-6-chloro-1H-indazol-3-yl]-acrylic acid; 1-(2-fluoro-4-chlorobenzyl)-6-chloro-1H-indazole-3-carboxylic acid hydrazide; 1-(2,4-dichlorobenzyl)-5-chloro-1H-indazole-3-carboxylic acid methyl ester; 1-(2,4-difluorobenzyl)-5-chloro-1H-indazole-3-carboxylic acid methyl ester; 1-(2- chloro-4-fluorobenzyl)-5-chloro-1H-indazole-3-carboxylic acid methyl ester; 1-(2-fluoro-4-chlorobenzyl)-5-chloro-1H-indazole-3-carboxylic acid methyl ester; 3-[1-(2,4-dichlorobenzyl)-5-chloro-1H-indazol-3-yl]-acrylic acid; 3-[1-(2,4-difluorobenzyl)-5-chloro-1H-indazol-3-yl]-acrylic acid; 3-[1-(2-chloro-4-fluorobenzyl)-5-chloro-1H-indazol-3-yl]-acrylic acid; 3-[1-(2-fluoro-4-chlorobenzyl)-5-chloro-1H-indazol-3-yl]-acrylic acid; 3-[1-(2,4-dichlorobenzyl)-5-chloro-1H-indazol-3-yl]-acrylic acid methyl ester; 3-[1-(2,4-difluorobenzyl)-5-chloro-1H-indazol-3-yl]-acrylic acid methyl ester; 3-[1-(2-chloro-4-fluorobenzyl)-5-chloro-1H-indazol-3-yl]-acrylic acid methyl ester; 3-[1-(2-fluoro-4-chlorobenzyl)-5-chloro-1H-indazol-3-yl]-acrylic acid; 5-chloro-1-(2,4-dichlorobenzyl)-1H-indazole-3-carboxylic acid hydrazide; 1-(2,4-difluorobenzyl)-5-chloro-1H-indazole-3-carboxylic acid hydrazide; 1-(2-chloro-4-fluorobenzyl)-5-chloro-1H-indazole-3-carboxylic acid hydrazide; 1-(2-fluoro-4-chlorobenzyl)-5-chloro-1H-indazole-3-carboxylic acid hydrazide; 1-(2,4-difluorobenzyl)-6-fluoro-1H-indazole-3-carboxylic acid methyl ester; 1-(2-chloro-4-fluorobenzyl)-6-fluoro-1H-indazole-3-carboxylic acid methyl ester; 1-(2-fluoro-4-chlorobenzyl)-6-fluoro-1H-indazole-3-carboxylic acid methyl ester; 3-[1-(2,4-difluorobenzyl)-6-fluoro-1H-indazol-3-yl]-acrylic acid; 3-[1-(2-chloro-4-fluorobenzyl)-6-fluoro-1H-indazol-3-yl]-acrylic acid; 3-[1-(2-fluoro-4-chlorobenzyl)-6-fluoro-1H-indazol-3-yl]-acrylic acid; 1-(2,4-difluorobenzyl)-6-fluoro-1H-indazole-3-carboxylic acid hydrazide; 1-(2-chloro-4-fluorobenzyl)-6-fluoro-1H-indazole-3-carboxylic acid hydrazide; 1-(2-fluoro-4-chlorobenzyl)-6-fluoro-1H-indazole-3-carboxylic acid hydrazide; 1-(2,4-difluorobenzyl)-6-methoxy-1H-indazole-3-carboxylic acid methyl ester; 1-(2-chloro-4-fluorobenzyl)-6-methoxy-1H-indazole-3-carboxylic acid methyl ester; 1-(2-fluoro-4-chlorobenzyl)-6-methoxy-1H-indazole-3-carboxylic acid methyl ester; 3-[1-(2,4-difluorobenzyl)-6-methoxy-1H-indazol-3-yl]-acrylic acid; 3-[1-(2-chloro-4-fluorobenzyl)-6-methoxy-1H-indazol-3-yl]-acrylic acid; 3-[1-(2-fluoro-4-chlorobenzyl)-6-methoxy-1H-indazol-3-yl]-acrylic acid; 1-(2,4-difluorobenzyl)-6-methoxy-1H-indazole-3-carboxylic acid hydrazide; 1-(2-chloro-4-fluorobenzyl)-6-methoxy-1H-indazole-3-carboxylic acid hydrazide; 1-(2-fluoro-4-chlorobenzyl)-6-methoxy-1H-indazole-3-carboxylic acid hydrazide; 1-(2,4-difluoro-benzyl)-1H-indazole-3,6-dicarboxylic acid-3-methyl ester; 1-(2-chloro-4-fluoro-benzyl)-1H-indazole-3,6-dicarboxylic acid-3-methyl ester; 1-(2-fluoro-4-chloro-benzyl)-1H-indazole-3,6-dicarboxylic acid-3-methyl ester; 3-(2-carboxy-vinyl)-1-(2,4-difluoro-benzyl)-1H-indazole-6-carboxylic acid; 3-(2-carboxy-vinyl)-1-(2-chloro-4-fluoro-benzyl)-1H-indazole-6-carboxylic acid; 3-(2-carboxy-vinyl)-1-(2-fluoro-4-chloro-benzyl)-1H-indazole-6-carboxylic acid; 1-(2,4-difluoro-benzyl)-3-(2-methoxycarbonyl-vinyl)-1H-indazole-6-carboxylic acid; 1-(2-chloro-4-fluoro-benzyl)-3-(2-methoxylcarbonyl-vinyl)-1H-indazole-6-carboxylic acid; and 1-(2-fluoro-4-chloro-benzyl)-3-(2-methoxycarbonyl-vinyl)-1H-indazole-6-carboxylic acid.

In addition to the foregoing, the derivatives in accordance with Formula I can include $R_2$ as trihaloalkyl: 1-(2,4-dichlorobenzyl)-6-trifluoromethyl-1H-indazole-3-carboxylic acid methyl ester; 1-(2-fluoro-4-chlorobenzyl)-6-trifluoromethyl-1H-indazole-3-carboxylic acid methyl ester; 1-(4-fluoro-2-methyl-benzyl)-6-trifluoromethyl-1H-indazole-3-carboxylic acid methyl ester; 1-(4-methyl-2-chloro-benzyl)-6-trifluoromethyl-1H-indazole-3-carboxylic acid methyl ester; 1-(4-methyl-2-fluoro-benzyl)-6-trifluoromethyl-1H-indazole-3-carboxylic acid methyl ester; 3-[1-(2-fluoro-4-chlorobenzyl)-6-trifluoromethyl-1H-indazol-3-yl]-acrylic acid; 3-[1-(4-fluoro-2-methyl-benzyl)-6-trifluoromethyl-1H-indazol-3-yl]-acrylic acid; 3-[1-(4-methyl-2-chloro-benzyl)-6-trifluoromethyl-1H-indazol-3-yl]-acrylic acid; 3-[1-(4-methyl-2-fluoro-benzyl)-6-trifluoromethyl-1H-indazol-3-yl]-acrylic acid; 3-[1-(2,4-difluorobenzyl)-6-trifluoromethyl-1H-indazol-3-yl]-2-methyl-acrylic acid; trans 3-[1-(2,4-difluorobenzyl)-6-trifluoromethyl-1H-indazol-3-yl]-acrylic acid methyl ester; cis 3-[1-(2,4-dichlorobenzyl)-6-trifluoromethyl-1H-indazol-3-yl]-acrylic acid methyl ester; 1-(2-fluoro-4-chlorobenzyl)-6-trifluoromethyl-1H-indazole-3-carboxylic acid hydrazide; 3-[1-(2,4-difluorobenzyl)-6-trifluoromethyl-1H-indazol-3-yl]-acrylic acid hydrazide; 3-[1-(2-chloro-4-fluorobenzyl)-6-trifluoromethyl-1H-indazol-3-yl]-acrylic acid hydrazide; 3-[1-(2-fluoro-4-chlorobenzyl)-6-trifluoromethyl-1H-indazol-3-yl]-acrylic acid hydrazide; 3-[1-(2,4-difluorobenzyl)-6-trifluoromethyl-1H-indazol-3-yl]-propionic acid ethyl ester; 3-[1-(2-chloro-4-fluorobenzyl)-6-trifluoromethyl-1H-indazol-3-yl]-propionic acid ethyl ester; 3-[1-(2-fluoro-4-chlorobenzyl)-6-trifluoromethyl-1H-indazol-3-yl]-propionic acid ethyl ester; 1-(2-chloro-4-fluorobenzyl)-5-trifluoromethyl-1H-indazole-3-carboxylic acid methyl ester; 1-(2-fluoro-4-chlorobenzyl)-5-trifluoromethyl-1H-indazole-3-carboxylic acid methyl ester; 3-[1-(2-chloro-4-fluorobenzyl)-5-trifluoromethyl-1H-indazol-3-yl]-acrylic acid; 3-[1-(2-fluoro-4-chlorobenzyl)-5-trifluoromethyl-1H-indazol-3-yl]-acrylic acid; 3-[1-(2,4-dichlorobenzyl)-5-trifluoromethyl-1H-indazol-3-yl]-acrylic acid methyl ester; 3-[1-(2,4-difluorobenzyl)-5-trifluoromethyl-1H-indazol-3-yl]-acrylic acid methyl ester; 3-[1-(2-chloro-4-fluorobenzyl)-5-trifluoromethyl-1H-indazol-3-yl]-acrylic acid methyl ester; 3-[1-(2-fluoro-4-chlorobenzyl)-5-trifluoromethyl-1H-indazol-3-yl]-acrylic acid methyl ester; 1-(2-chloro-4-fluorobenzyl)-5-trifluoromethyl-1H-indazole-3-carboxylic acid hydrazide; 1-(2-fluoro-4-chlorobenzyl)-5-trifluoromethyl-1H-indazole-3-carboxylic acid hydrazide; 3-[1-(2,4-dichlorobenzyl)-5-trifluoromethyl-1H-indazol-3-yl]-acrylic acid hydrazide; 3-[1-(2,4-difluorobenzyl)-5-trifluoromethyl-1H-indazol-3-yl]-acrylic acid hydrazide; 3-[1-(2-chloro-4-fluorobenzyl)-5-trifluoromethyl-1H-indazol-3-yl]-acrylic acid hydrazide; 3-[1-(2-fluoro-4-chlorobenzyl)-5-trifluoromethyl-1H-indazol-3-yl]-acrylic acid hydrazide; 3-[1-(2,4-dichlorobenzyl)-5-trifluoromethyl-1H-indazol-3-yl]-propionic acid ethyl ester; 3-[1-(2,4-difluorobenzyl)-5-trifluoromethyl-1H-indazol-3-yl]-propionic acid ethyl ester; 3-[1-(2-chloro-4-fluorobenzyl)-5-trifluoromethyl-1H-indazol-3-yl]-propionic acid ethyl ester; and 3-[1-(2-fluoro-4-chlorobenzyl)-5-trifluoromethyl-1H-indazol-3-yl]-propionic acid ethyl ester.

In addition to the foregoing, the derivatives in accordance with Formula I can include $R_2$ as a lower alkyl: 1-(2,4-dichlorobenzyl)-6-methyl-1H-indazole-3-carboxylic acid methyl ester; 1-(2,4-difluorobenzyl)-6-methyl-1H-indazole-3-carboxylic acid methyl ester; 1-(2-chloro-4-fluorobenzyl)-6-methyl-1H-indazole-3-carboxylic acid methyl ester; 1-(2-fluoro-4-chlorobenzyl)-6-methyl-1H-indazole-3-carboxylic acid methyl ester; 3-[1-(2,4-difluorobenzyl)-6-methyl-1H-indazol-3-yl]-acrylic acid; 3-[1-(2-chloro-4-fluorobenzyl)-6-methyl-1H-indazol-3-yl]-acrylic acid; 3-[1-(2-fluoro-4-chlorobenzyl)-6-methyl-1H-indazol-3-yl]-acrylic acid; 3-[1-(2,4-dichlorobenzyl)-6-methyl-1H-indazol-3-yl]-acrylic acid methyl ester; 3-[1-(2,4-difluorobenzyl)-6-methyl-1H-indazol-3-yl]-acrylic acid methyl ester; 3-[1-(2-chloro-4-fluorobenzyl)-6-methyl-1H-indazol-3-yl]-acrylic acid methyl ester; 3-[1-(2-fluoro-4-chlorobenzyl)-6-methyl-1H-indazol-3-yl]-acrylic acid methyl ester; 1-(2,4-difluorobenzyl)-6-methyl-1H-indazole-3-carboxylic acid hydrazide; 1-(2-chloro-4-fluorobenzyl)-6-methyl-1H-indazole-3-carboxylic acid hydrazide; 1-(2-fluoro-4-chlorobenzyl)-6-methyl-1H-indazole-3-carboxylic acid hydrazide; 3-[1-(2,4-dichlorobenzyl)-6-methyl-1H-indazol-3-yl]-acrylic acid hydrazide; 3-[1-(2,4-difluorobenzyl)-6-methyl-1H-indazol-3-yl]-acrylic acid hydrazide; 3-[1-(2-chloro-4-fluorobenzyl)-6-methyl-1H-indazol-3-yl]-acrylic acid hydrazide; 3-[1-(2-fluoro-4-chlorobenzyl)-6-methyl-1H-indazol-3-yl]-acrylic acid hydrazide; 3-[1-(2,4-dichlorobenzyl)-6-methyl-1H-indazol-3-yl]-propionic acid ethyl ester; 3-[1-(2,4-difluorobenzyl)-6-methyl-1H-indazol-3-yl]-propionic acid ethyl ester; 3-[1-(2-chloro-4-fluorobenzyl)-6-methyl-1H-indazol-3-yl]-propionic acid ethyl ester; and 3-[1-(2-fluoro-4-chlorobenzyl)-6-methyl-1H-indazol-3-yl]-propionic acid ethyl ester.

In addition to the foregoing, the derivatives in accordance with Formula I can include $R_2$ as a dihaloalkyl: 1-(2,4-difluorobenzyl)-6-difluoromethyl-1H-indazole-3-carboxylic acid methyl ester; 1-(2-chloro-4-fluorobenzyl)-6-difluoromethyl-1H-indazole-3-carboxylic acid methyl ester; 1-(2-fluoro-4-chlorobenzyl)-6-difluoromethyl-1H-indazole-3-carboxylic acid methyl ester; 3-[1-(2,4-difluorobenzyl)-6-difluoromethyl-1H-indazol-3-yl]-acrylic acid; 3-[1-(2-chloro-4-fluorobenzyl)-6-difluoromethyl-1H-indazol-3-yl]-acrylic acid; 3-[1-(2-fluoro-4-chlorobenzyl)-6-difluoromethyl-1H-indazol-3-yl]-acrylic acid; 3-[1-(2,4-difluorobenzyl)-6-difluoromethyl-1H-indazol-3-yl]-acrylic acid methyl ester; 3-[1-(2-chloro-4-fluorobenzyl)-6-difluoromethyl-1H-indazol-3-yl]-acrylic acid methyl ester; 3-[1-(2-fluoro-4-chlorobenzyl)-6-difluoromethyl-1H-indazol-3-yl]-acrylic acid methyl ester; 1-(2,4-dichlorobenzyl)-6-difluoromethyl-1H-indazole-3-carboxylic acid hydrazide; 1-(2,4-difluorobenzyl)-6-difluoromethyl-1H-indazole-3-carboxylic acid hydrazide; 1-(2-chloro-4-fluorobenzyl)-6-difluoromethyl-1H-indazole-3-carboxylic acid hydrazide; 1-(2-fluoro-4-chlorobenzyl)-6-difluoromethyl-1H-indazole-3-carboxylic acid hydrazide; 3-[1-(2,4-dichlorobenzyl)-6-difluoromethyl-1H-indazol-3-yl]-acrylic acid hydrazide; 3-[1-(2,4-difluorobenzyl)-6-difluoromethyl-1H-indazol-3-yl]-acrylic acid hydrazide; 3-[1-(2-chloro-4-fluorobenzyl)-6-difluoromethyl-1H-indazol-3-yl]-acrylic acid hydrazide; and 3-[1-(2-fluoro-4-chlorobenzyl)-6-difluoromethyl-1H-indazol-3-yl]-acrylic acid hydrazide.

In addition to the foregoing, the derivatives in accordance with Formula I can include $R_2$ as a monohaloalkyl: 1-(2,4-difluorobenzyl)-6-fluoromethyl-1H-indazole-3-carboxylic acid methyl ester; 1-(2-chloro-4-fluorobenzyl)-6-fluoromethyl-1H-indazole-3-carboxylic acid methyl ester; 1-(2-fluoro-4-chlorobenzyl)-6-fluoromethyl-1H-indazole-3-carboxylic acid methyl ester; 3-[1-(2,4-difluorobenzyl)-6-fluoromethyl-1H-indazol-3-yl]-acrylic acid; 3-[1-(2-chloro-4-fluorobenzyl)-6-fluoromethyl-1H-indazol-3-yl]-acrylic acid; 3-[1-(2-fluoro-4-chlorobenzyl)-6-fluoromethyl-1H-indazol-3-yl]-acrylic acid; 3-[1-(2,4-difluorobenzyl)-6-fluoromethyl-1H-indazol-3-yl]-acrylic acid methyl ester; 3-[1-(2-chloro-4-fluorobenzyl)-6-fluoromethyl-1H-indazol-3-yl]-acrylic acid methyl ester; 3-[1-(2-fluoro-4-chlorobenzyl)-6-fluoromethyl-1H-indazol-3-yl]-acrylic acid methyl ester; 1-(2,4-dichlorobenzyl)-6-fluoromethyl-1H-indazole-3-carboxylic acid hydrazide; 1-(2,4-difluorobenzyl)-6-fluoromethyl-1H-indazole-3-carboxylic acid hydrazide; 1-(2-chloro-4-fluorobenzyl)-6-fluoromethyl-1H-indazole-3-carboxylic acid hydrazide; 1-(2-fluoro-4-chlorobenzyl)-6-fluoromethyl-1H-indazole-3-carboxylic acid hydrazide; 3-[1-(2,4-dichlorobenzyl)-6-fluoromethyl-1H-indazol-3-yl]-acrylic acid hydrazide; 3-[1-(2,4-difluorobenzyl)-6-fluoromethyl-1H-indazol-3-yl]-acrylic acid hydrazide; 3-[1-(2-chloro-4-fluorobenzyl)-6-fluoromethyl-1H-indazol-3-yl]-acrylic acid hydrazide; and 3-[1-(2-fluoro-4-chlorobenzyl)-6-fluoromethyl-1H-indazol-3-yl]-acrylic acid hydrazide.

In addition to the foregoing, the derivatives in accordance with Formula I can include $R_2$ as an alcohol: 1-(2,4-difluorobenzyl)-6-hydroxymethyl-1H-indazole-3-carboxylic acid methyl ester; 1-(2-chloro-4-fluorobenzyl)-6-hydroxymethyl-1H-indazole-3-carboxylic acid methyl ester; 1-(2-fluoro-4-chlorobenzyl)-6-hydroxymethyl-1H-indazole-3-carboxylic acid methyl ester; 3-[1-(2,4-difluorobenzyl)-6-hydroxymethyl-1H-indazol-3-yl]-acrylic acid; 3-[1-(2-chloro-4-fluorobenzyl)-6-hydroxymethyl-1H-indazol-3-yl]-acrylic acid; 3-[1-(2-fluoro-4-chlorobenzyl)-6-hydroxymethyl-1H-indazol-3-yl]acrylic acid; 3-[1-(2,4-difluorobenzyl)-6-hydroxymethyl-1H-indazol-3-yl]-acrylic acid methyl ester; 3-[1-(2-chloro-4-fluorobenzyl)-6-hydroxymethyl-1H-indazol-3-yl]-acrylic acid methyl ester; 3-[1-(2-fluoro-4-chlorobenzyl)-6-hydroxymethyl-1H-indazol-3-yl]-acrylic acid methyl ester; 1-(2,4-dichlorobenzyl)-6-hydroxymethyl-1H-indazole-3-carboxylic acid hydrazide; 1-(2,4-difluorobenzyl)-6-hydroxymethyl-1H-indazole-3-carboxylic acid hydrazide; 1-(2-chloro-4-fluorobenzyl)-6-hydroxymethyl-1H-indazole-3-carboxylic acid hydrazide; 1-(2-fluoro-4-chlorobenzyl)-6-hydroxymethyl-1H-indazole-3-carboxylic acid hydrazide; 3-[1-(2,4-dichlorobenzyl)-6-hydroxymethyl-1H-indazol-3-yl]-acrylic acid hydrazide; 3-[1-(2,4-difluorobenzyl)-6-hydroxymethyl-1H-indazol-3-yl]-acrylic acid hydrazide; 3-[1-(2-chloro-4-fluorobenzyl)-6-hydroxymethyl-1H-indazol-3-yl]-acrylic acid hydrazide; and 3-[1-(2-fluoro-4-chlorobenzyl)-6-hydroxymethyl-1H-indazol-3-yl]-acrylic acid hydrazide.

In addition to the foregoing, the derivatives in accordance with Formula I can include $R_2$ as an alcohol: 1-(2,4-difluorobenzyl)-6-trifluoromethoxy-1H-indazole-3-carboxylic acid methyl ester; 1-(2-chloro-4-fluorobenzyl)-6-trifluoromethoxy-1H-indazole-3-carboxylic acid methyl ester; 1-(2-fluoro-4-chlorobenzyl)-6-trifluoromethoxy-1H-indazole-3-carboxylic acid methyl ester; 1-(4-fluoro-2-methyl-benzyl)-6-trifluoromethoxy-1H-indazole-3-carboxylic acid methyl ester; 1-(4-methyl-2-chloro-benzyl)-6-trifluoromethoxy-1H-indazole-3-carboxylic acid methyl ester; 1-(4-methyl-2-fluoro-benzyl)-6-trifluoromethoxy-1H-indazole-3-carboxylic acid methyl ester; 3-[1-(2,4-difluorobenzyl)-6-trifluoromethoxy-1H-indazol-3-yl]acrylic acid; 3-[1-(2-chloro-4-fluorobenzyl)-6-trifluoromethoxy-1H-indazol-3-yl]acrylic acid; 3-[1-(2-fluoro-4-chlorobenzyl)-6-trifluoromethoxy-1H-indazol-3-yl]acrylic acid; 3-[1-(4-fluoro-2-methyl-benzyl)-6-trifluoromethoxy-1H-indazol-3-yl]-acrylic acid; 3-[1-(4-methyl-2-chloro-benzyl)-6-trifluoromethoxy-1H-indazol-3-yl]-acrylic acid; 3-[1-(4-methyl-2-fluoro-benzyl)-6-trifluoromethoxy-1H-indazol-3-yl]-acrylic acid; 3-[1-(2,4-difluorobenzyl)-6-trifluoromethoxy-1H-indazol-3-yl]acrylic acid methyl ester; 3-[1-(2-chloro-4-fluorobenzyl)-6-trifluoromethoxy-1H-indazol-3-yl]acrylic acid methyl ester; 3-[1-(2-fluoro-4-chlorobenzyl)-6-trifluoromethoxy-1H-indazol-3-yl]acrylic acid methyl ester; 1-(2,4-difluorobenzyl)-6-trifluoromethoxy-1H-indazole-3-carboxylic acid hydrazide; 1-(2-chloro-4-fluorobenzyl)-6-trifluoromethoxy-1H-indazole-3-carboxylic acid hydrazide; 1-(2-fluoro-4-chlorobenzyl)-6-trifluoromethoxy-1H-indazole-3-carboxylic acid hydrazide; 3-[1-(2,4-dichlorobenzyl)-6-trifluoromethoxy-1H-indazol-3-yl]-acrylic acid hydrazide; 3-[1-(2,4-difluorobenzyl)-6-trifluoromethoxy-1H-indazol-3-yl]-acrylic acid hydrazide; 3-[1-(2-chloro-4-fluorobenzyl)-6-trifluoromethoxy-1H-indazol-3-yl]-acrylic acid hydrazide; and 3-[1-(2-fluoro-4-chlorobenzyl)-6-trifluoromethoxy-1H-indazol-3-yl]-acrylic acid hydrazide.

In addition to the foregoing, the derivatives in accordance with Formula I can include $R_2$ as an amino: 1-(2,4-difluorobenzyl)-6-dimethylamino-1H-indazole-3-carboxylic acid methyl ester; 1-(2-chloro-4-fluorobenzyl)-6-dimethylamino-1H-indazole-3-carboxylic acid methyl ester; 1-(2-fluoro-4-chlorobenzyl)-6-dimethylamino-1H-indazole-3-carboxylic acid methyl ester; 3-[1-(2,4-difluorobenzyl)-6-dimethylamino-1H-indazol-3-yl]acrylic acid; 3-[1-(2-chloro-4-fluorobenzyl)-6-dimethylamino-1H-indazol-3-yl]acrylic acid; 3-[1-(2-fluoro-4-chlorobenzyl)-6-dimethylamino-1H-indazol-3-yl]acrylic acid; 3-[1-(2,4-dichlorobenzyl)-6-dimethylamino-1H-indazol-3-yl]acrylic acid methyl ester; 3-[1-(2,4-difluorobenzyl)-6-dimethylamino-1H-indazol-3-yl]acrylic acid methyl ester; 3-[1-(2-chloro-4-fluorobenzyl)-6-dimethylamino-1H-indazol-3-yl]acrylic acid methyl ester; 3-[1-(2-fluoro-4-chlorobenzyl)-6-dimethylamino-1H-indazol-3-yl]acrylic acid methyl ester; 1-(2,4-dichlorobenzyl)-6-dimethylamino-1H-indazole-3-carboxylic acid hydrazide; 1-(2,4-difluorobenzyl)-6-dimethylamino-1H-indazole-3-carboxylic acid hydrazide; 1-(2-chloro-4-fluorobenzyl)-6-dimethylamino-1H-indazole-3-carboxylic acid hydrazide; 1-(2-fluoro-4-chlorobenzyl)-6-dimethylamino-1H-indazole-3-carboxylic acid hydrazide; 3-[1-(2,4-dichlorobenzyl)-6-dimethylamino-1H-indazol-3-yl]-acrylic acid hydrazide; 3-[1-(2,4-difluorobenzyl)-6-dimethylamino-1H-indazol-3-yl]-acrylic acid hydrazide; 3-[1-(2-chloro-4-fluorobenzyl)-6-dimethylamino-1H-indazol-3-yl]-acrylic acid hydrazide; and 3-[1-(2-fluoro-4-chlorobenzyl)-6-dimethylamino-1H-indazol-3-yl]-acrylic acid hydrazide.

In addition to the foregoing, the derivatives in accordance with Formula I can include $R_1$ according to the Formula I(A):

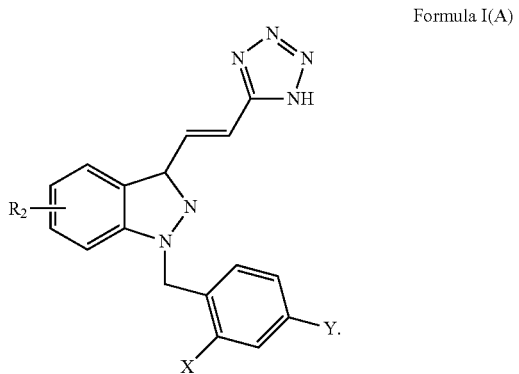

Formula I(A)

Examples of Formula I(A) derivatives include: 1-(2,4-difluoro-benzyl)-3-[2-(1H-tetrazol-5-yl)-vinyl]-6-trifluoromethyl-1H-indazole; 1-(2-chloro-4-fluorobenzyl)-3-[2-(1H-tetrazol-5-yl)-vinyl]-6-trifluoromethyl-1H-indazole; and 1-(2-fluoro-4-chlorobenzyl)-3-[2-(1H-tetrazol-5-yl)-vinyl]-6-trifluoromethyl-1H-indazole.

In addition to the foregoing, the derivatives in accordance with Formula I can include $R_1$ according to the Formula I(B):

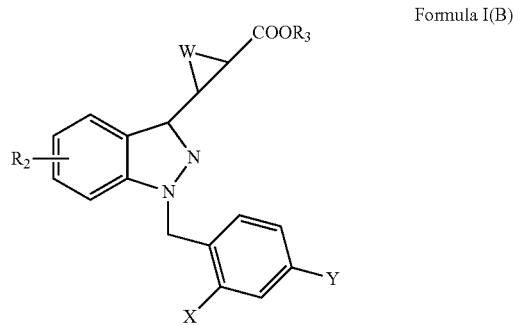

Formula I(B)

wherein $R_3$ is hydrogen, alkyl, aralkyl, or cycloalkyl;
and wherein W is carbon or oxygen;
X and Y are independently halogen; and/or
$R_2$ is trihaloalkyl.

Examples of Formula I(B) derivatives include: 3-[1-(2,4-fluorobenzyl)-6-trifluoromethyl-1H-indazol-3-yl]-oxirane-2-carboxylic acid; 3-[1-(2-chloro-4-fluorobenzyl)-6-trifluoromethyl-1H-indazol-3-yl]-oxirane-2-carboxylic acid; 3-[1-(2-fluoro-4-chlorobenzyl)-6-trifluoromethyl-1H-indazol-3-yl]-oxirane-2-carboxylic acid; 2-[1-(2,4-difluorobenzyl)-6-trifluoromethyl-1H-indazol-3-yl]-cyclopropanecarboxylic acid; 2-[1-(2-chloro-4-fluorobenzyl)-6-trifluoromethyl-1H-indazol-3-yl]-cyclopropanecarboxylic acid; 2-[1-(2-fluoro-4-chlorobenzyl)-6-trifluoromethyl-1H-indazol-3-yl]-cyclopropanecarboxylic acid; 3-[1-(2,4-dichlorobenzyl)-6-halo-1H-indazol-3-yl]-oxirane-2-carboxylic acid; 3-[1-(2,4-fluorobenzyl)-6-halo-1H-indazol-3-yl]-oxirane-2-carboxylic acid; 3-[1-(2-chloro-4-fluorobenzyl)-6-halo-1H-indazol-3-yl]-oxirane-2-carboxylic acid; 3-[1-(2-fluoro-4-chlorobenzyl)-6-halo-1H-indazol-3-yl]-oxirane-2-carboxylic acid; 2-[1-(2,4-dichlorobenzyl)-6-halo-1H-indazol-3-yl]-cyclopropanecarboxylic acid; 2-[1-(2,4-difluorobenzyl)-6-halo-1H-indazol-3-yl]-cyclopropanecarboxylic acid; 2-[1-(2-chloro-4-fluorobenzyl)-6-halo-1H-indazol-3-yl]-cyclopropanecarboxylic acid; and 2-[1-(2-fluoro-4-chlorobenzyl)-6-halo-1H-indazol-3-yl]-cyclopropanecarboxylic acid.

In addition to the foregoing, the derivatives in accordance with Formula I can include $R_1$ as a carboxylic acid ester and $R_2$ as hydrogen: 1-(2,4-difluorobenzyl)indazole-3-carboxylic acid methyl ester; 1-(2-chloro-4-fluorobenzyl)indazole-3-carboxylic acid methyl ester; 1-(2-fluoro-4-chlorobenzyl)indazole-3-carboxylic acid methyl ester; 1-[(2,4-difluorobenzyl)-1H-indazole]-3-carboxylic acid ethyl ester; 1-[(2-chloro-4-fluorobenzyl)-1H-indazole]-3-carboxylic acid ethyl ester; 1-[(2-fluoro-4-chlorobenzyl)-1H-indazole]-3-carboxylic acid ethyl ester; 1-[(2,4-difluorobenzyl)-1H-indazole]-3-carboxylic acid propyl ester; 1-[(2-chloro-4-fluorobenzyl)-1H-indazole]-3-carboxylic acid propyl ester; and 1-[(2-fluoro-4-chlorobenzyl)-1H-indazole]-3-carboxylic acid propyl ester.

In addition to the foregoing, the derivatives in accordance with Formula I can include $R_1$ as a carboxylic acid and $R_2$ as hydrogen, alkoxy, or carboxylic acid: 1-(2-fluoro-4-chlorobenzyl)-6-chloro-1H-indazole-3-carboxylic acid; 1-(2,4-difluorobenzyl)-6-fluoro-1H-indazole-3-carboxylic acid; 1-(2-chloro-4-fluorobenzyl)-6-fluoro-1H-indazole-3-carboxylic acid; 1-(2-fluoro-4-chlorobenzyl)-6-fluoro-1H-indazole-3-carboxylic acid; 1-(2,4-difluorobenzyl)-6-methoxy-1H-indazole-3-carboxylic acid; 1-(2-chloro-4-fluorobenzyl)-6-methoxy-1H-indazole-3-carboxylic acid; 1-(2-fluoro-4-chlorobenzyl)-6-methoxy-1H-indazole-3-carboxylic acid; 1-(2,4-difluoro-benzyl)-1H-indazole-3,6-dicarboxylic acid; 1-(2-chloro-4-fluoro-benzyl)-1H-indazole-3,6-dicarboxylic acid; and 1-(2-fluoro-4-chloro-benzyl)-1H-indazole-3,6-dicarboxylic acid.

In addition to the foregoing, the derivatives in accordance with Formula I can include $R_1$ as a carboxylic acid and $R_2$ as a trihaloalkyl: 1-(2-fluoro-4-chlorobenzyl)-6-trifluoromethyl-1H-indazole-3-carboxylic acid; 1-(4-fluoro-2-methylbenzyl)-6-trifluoromethyl-1H-indazole-3-carboxylic acid; 1-(4-methyl-2-chloro-benzyl)-6-trifluoromethyl-1H-indazole-3-carboxylic acid; 1-(4-methyl-2-fluoro-benzyl)-6-trifluoromethyl-1H-indazole-3-carboxylic acid; 3-[1-(2,4-difluorobenzyl)-6-trifluoromethyl-1H-indazol-3-yl]-propionic acid; 3-[1-(2-chloro-4-fluorobenzyl)-6-trifluoromethyl-1H-indazol-3-yl]-propionic acid; 3-[1-(2-fluoro-4-chlorobenzyl)-6-trifluoromethyl-1H-indazol-3-yl]-propionic acid; 3-[1-(2,4-dichlorobenzyl)-6-trifluoromethyl-1H-indazol-3-yl]-2-methylpropionic acid; 3-[1-(2,4-fluorobenzyl)-6-trifluoromethyl-1H-indazol-3-yl]-2-methylpropionic acid; 3-[1-(2-chloro-4-fluorobenzyl)-6-trifluoromethyl-1H-indazol-3-yl]-2-methylpropionic acid; 3-[1-(2-fluoro-4-chlorobenzyl)-6-trifluoromethyl-1H-indazol-3-yl]-2-methylpropionic acid; 3-[1-(2,4-dichlorobenzyl)-6-trifluoromethyl-1H-indazol-3-yl]-oxirane-2-carboxylic acid; 3-[1-(2,4-fluorobenzyl)-6-trifluoromethyl-1H-indazol-3-yl]oxirane-2-carboxylic acid; 3-[1-(2-chloro-4-fluorobenzyl)-6-trifluoromethyl-1H-indazol-3-yl]-oxirane-2-carboxylic acid; 3-[1-(2-fluoro-4-chlorobenzyl)-6-trifluoromethyl-1H-indazol-3-yl]-oxirane-2-carboxylic acid; 2-[1-(2,4-dichlorobenzyl)-6-trifluoromethyl-1H-indazol-3-yl]-cyclopropanecarboxylic acid; 2-[1-(2,4-difluorobenzyl)-6-trifluoromethyl-1H-indazol-3-yl]-cyclopropanecarboxylic acid; 2-[1-(2-chloro-4-fluorobenzyl)-6-trifluoromethyl-1H-indazol-3-yl]-cyclopropanecarboxylic acid; 2-[1-(2-fluoro-4-chlorobenzyl)-6-trifluoromethyl-1H-indazol-3-yl]-cyclopropanecarboxylic acid; 1-(2-chloro-4-fluorobenzyl)-5-trifluoromethyl-1H-indazole-3-carboxylic acid; 1-(2-fluoro-4-chlorobenzyl)-5-trifluoromethyl-1H-indazole-3-carboxylic acid; 3-[1-(2,4-dichlorobenzyl)-5-trifluoromethyl-1H-indazol-3-yl]-propionic acid; 3-[1-(2,4-difluorobenzyl)-5-trifluoromethyl-1H-indazol-3-yl]-propionic acid; 3-[1-(2-chloro-4-fluorobenzyl)-5-trifluoromethyl-1H-indazol-3-yl]-propionic acid; 3-[1-(2-fluoro-4-chlorobenzyl)-5-trifluoromethyl-1H-indazol-3-yl]-propionic acid; 3-[1-(2,4-dichlorobenzyl)-5-trifluoromethyl-1H-indazol-3-yl]-2-methylpropionic acid; 3-[1-(2,4-fluorobenzyl)-5-trifluoromethyl-1H-indazol-3-yl]-2-methylpropionic acid; 3-[1-(2-chloro-4-fluorobenzyl)-5-trifluoromethyl-1H-indazol-3-yl]-2-methylpropionic acid; 3-[1-(2-fluoro-4-chlorobenzyl)-5-trifluoromethyl-1H-indazol-3-yl]-2-methylpropionic acid; 3-[1-(2,4-dichlorobenzyl)-5-trifluoromethyl-1H-indazol-3-yl]-oxirane-2-carboxylic acid; 3-[1-(2,4-fluorobenzyl)-5-trifluoromethyl-1H-indazol-3-yl]-oxirane-2-carboxylic acid; 3-[1-(2-chloro-4-fluorobenzyl)-5-trifluoromethyl-1H-indazol-3-yl]-oxirane-2-carboxylic acid; 3-[1-(2-fluoro-4-chlorobenzyl)-5-trifluoromethyl-1H-indazol-3-yl]-oxirane-2-carboxylic acid; 2-[1-(2,4-dichlorobenzyl)-5-trifluoromethyl-1H-indazol-3-yl]-cyclopropanecarboxylic; 2-[1-(2,4-difluorobenzyl)-5-trifluoromethyl-1H-indazol-3-yl]-cyclopropanecarboxylic; 2-[1-(2-chloro-4-fluorobenzyl)-5-trifluoromethyl-1H-indazol-3-yl]-cyclopropanecarboxylic; and 2-[1-(2-fluoro-4-chlorobenzyl)-5-trifluoromethyl-1H-indazol-3-yl]-cyclopropanecarboxylic.

In addition to the foregoing, the derivatives in accordance with Formula I can include $R_1$ as a carboxylic acid and $R_2$ as a dihaloalkyl: 1-(2,4-difluorobenzyl)-6-difluoromethyl-1H-indazole-3-carboxylic acid; 1-(2-chloro-4-fluorobenzyl)-6-difluoromethyl-1H-indazole-3-carboxylic acid; 1-(2-fluoro-4-chlorobenzyl)-6-difluoromethyl-1H-indazole-3-carboxylic acid; 1-(2,4-dichlorobenzyl)-5-difluoromethyl-1H-indazole-3-carboxylic acid; 1-(2,4-difluorobenzyl)-5-difluoromethyl-1H-indazole-3-carboxylic acid; 1-(2-chloro-4-fluorobenzyl)-5-difluoromethyl-1H-indazole-3-carboxylic acid; and 1-(2-fluoro-4-chlorobenzyl)-5-difluoromethyl-1H-indazole-3-carboxylic acid.

In addition to the foregoing, the derivatives in accordance with Formula I can include $R_1$ as a carboxylic acid and $R_2$ as a monohaloalkyl: 1-(2,4-dichlorobenzyl)-6-fluoromethyl-1H-indazole-3-carboxylic acid; 1-(2,4-difluorobenzyl)-6-fluoromethyl-1H-indazole-3-carboxylic acid; 1-(2-chloro-4-fluorobenzyl)-6-fluoromethyl-1H-indazole-3-carboxylic acid; 1-(2-fluoro-4-chlorobenzyl)-6-fluoromethyl-1H-indazole-3-carboxylic acid; 1-(2,4-dichlorobenzyl)-5-fluoromethyl-1H-indazole-3-carboxylic acid; 1-(2,4-difluorobenzyl)-5-fluoromethyl-1H-indazole-3-carboxylic acid; 1-(2-chloro-4-fluorobenzyl)-5-fluoromethyl-1H-indazole-3-carboxylic acid; and 1-(2-fluoro-4-chlorobenzyl)-5-fluoromethyl-1H-indazole-3-carboxylic acid.

In addition to the foregoing, the derivatives in accordance with Formula I can include $R_1$ as a carboxylic acid and $R_2$ as a trihaloalkoxy: 1-(2,4-difluorobenzyl)-6-trifluoromethoxy-1H-indazole-3-carboxylic acid; 1-(2-chloro-4-fluorobenzyl)-6-trifluoromethoxy-1H-indazole-3-carboxylic acid; 1-(2-fluoro-4-chlorobenzyl)-6-trifluoromethoxy-1H-indazole-3-carboxylic acid; 1-(4-fluoro-2-methyl-benzyl)-6-trifluoromethoxy-1H-indazole-3-carboxylic acid; 1-(4-methyl-2-chloro-benzyl)-6-trifluoromethoxy-1H-indazole-3-carboxylic acid; 1-(4-methyl-2-fluoro-benzyl)-6-trifluoromethoxy-1H-indazole-3-carboxylic acid; 1-(2,4-dichlorobenzyl)-5-trifluoromethoxy-1H-indazole-3-carboxylic acid; 1-(2,4-difluorobenzyl)-5-trifluoromethoxy-1H-indazole-3-carboxylic acid; 1-(2-chloro-4-fluorobenzyl)-5-trifluoromethoxy-1H-indazole-3-carboxylic acid; and 1-(2-fluoro-4-chlorobenzyl)-5-trifluoromethoxy-1H-indazole-3-carboxylic acid.

In addition to the foregoing, the derivatives in accordance with Formula I can include $R_1$ as a carboxylic acid and $R_2$ as an amino: 1-(2,4-difluorobenzyl)-6-dimethylamino-1H-indazole-3-carboxylic acid; 1-(2-chloro-4-fluorobenzyl)-6-dimethylamino-1H-indazole-3-carboxylic acid; 1-(2-fluoro-4-chlorobenzyl)-6-dimethylamino-1H-indazole-3-carboxylic acid; 1-(2,4-dichlorobenzyl)-5-dimethylamino-1H-indazole-3-carboxylic acid; 1-(2,4-difluorobenzyl)-5-dimethylamino-1H-indazole-3-carboxylic acid; 1-(2-chloro-4-fluorobenzyl)-5-dimethylamino-1H-indazole-3-carboxylic acid; 1-(2-fluoro-4-chlorobenzyl)-5-dimethylamino-1H-indazole-3-carboxylic acid; 1-(2,4-dichlorobenzyl)-4-dimethylamino-1H-indazole-3-carboxylic acid; 1-(2,4-difluorobenzyl)-4-dimethylamino-1H-indazole-3-carboxylic acid; 1-(2-chloro-4-fluorobenzyl)-4-dimethylamino-1H-indazole-3-carboxylic acid; and 1-(2-fluoro-4-chlorobenzyl)-4-dimethylamino-1H-indazole-3-carboxylic acid.

In addition to the foregoing, the derivatives in accordance with Formula I can include $R_1$ as a carboxylic acid and $R_2$ as a lower alkyl: 1-(2,4-difluorobenzyl)-6-methyl-1H-indazole-3-carboxylic acid; 1-(2-chloro-4-fluorobenzyl)-6-methyl-1H-indazole-3-carboxylic acid; 1-(2-fluoro-4-chlorobenzyl)-6-methyl-1H-indazole-3-carboxylic acid; 1-(2,4-dichlorobenzyl)-5-methyl-1H-indazole-3-carboxylic acid; 1-(2,4-difluorobenzyl)-5-methyl-1H-indazole-3-carboxylic acid; 1-(2-chloro-4-fluorobenzyl)-5-methyl-1H-indazole-3-carboxylic acid; 1-(2-fluoro-4-chlorobenzyl)-5-methyl-1H-indazole-3-carboxylic acid; 1-(2,4-difluorobenzyl)-4-methyl-1H-indazole-3-carboxylic acid; 1-(2-chloro-4-fluorobenzyl)-4-methyl-1H-indazole-3-carboxylic acid; and 1-(2-fluoro-4-chlorobenzyl)-4-methyl-1H-indazole-3-carboxylic acid.

In addition to the foregoing, the derivatives in accordance with Formula I can include $R_1$ as a carboxylic acid and $R_2$ as an alcohol: 1-(2,4-difluorobenzyl)-6-hydroxymethyl-1H-indazole-3-carboxylic acid; 1-(2-chloro-4-fluorobenzyl)-6-hydroxymethyl-1H-indazole-3-carboxylic acid; 1-(2-fluoro-4-chlorobenzyl)-5-hydroxymethyl-1H-indazole-3-carboxylic acid; 1-(2,4-dichlorobenzyl)-5-hydroxymethyl-1H-indazole-3-carboxylic acid; 1-(2,4-difluorobenzyl)-5-hydroxymethyl-1H-indazole-3-carboxylic acid; 1-(2-chloro-4-fluorobenzyl)-5-hydroxymethyl-1H-indazole-3-carboxylic acid; and 1-(2-fluoro-4-chlorobenzyl)-5-hydroxymethyl-1H-indazole-3-carboxylic acid.

Modulating Fertility

The compounds described herein can be used in managing male and female fertility. The compounds can be administered in one or more doses to inhibit fertility for a period or time or to sterilize the male or female.

Gamendazole as used herein also refers to H2-gamendazole (i.e., JWS-2-72 or GMZ), which is a novel indazole carboxylic acid derivative has been shown to be a reversible inhibitor of male spermatogenesis. Gamendazole is well-tolerated in animal studies with no apparent histopathology in any organ at 25 mg/kg of IP dosage. In rats administered Gamendazole, there was no evidence of behavioral or body weight changes in the five days post-treatment. Recent studies have found that Gamendazole acts as an HSP90 inhibitor in rat sertoli cells. GMZ binds directly to HSP90-beta, HSP90AB1, and eukaryotic elongation factor EEF1A1 as shown by affinity chromatography and direct binding studies.

It was found that 100% infertility was achieved in seven out of seven proven fertile male rats three weeks following a single oral dose of 6 mg/kg gamendazole. Fertility returned by nine weeks in four of seven animals, with typical numbers of normal-appearing conceptuses. 100% fertility returned in the four of six animals that became infertile at a single oral dose of 3 mg/kg gamendazole. No differences in mating behavior were observed in either of the gamendazole-treated groups versus control (vehicle only) animals. In the animals that showed reversible infertility, a transient increase in circulating FSH levels coincided with an initial decline in inhibin B levels following administration of gamendazole, but no other significant changes in circulating reproductive hormones were observed. Gamendazole inhibited production of inhibin B by primary Sertoli cells in vitro with an $IC_{50}$ of $6.8 \pm 3.0 \times 10^{-10}$ M, suggesting that Sertoli cells are a primary target. A biotinylated gamendazole analogue revealed cytoplasmic and perinuclear binding of gamendazole in primary Sertoli cells. Gamendazole represents the most potent new oral anti-spermatogenic indazole carboxylic acid to date. However, our results demonstrate that additional dose finding studies are required to improve reversibility and widen the therapeutic window before more detailed drug development of this potential non-hormonal male contraceptive agent can occur.

This study presents initial dose ranging results that suggest gamendazole should continue on the preclinical pathway as a small molecule male contraceptive drug candidate. In support of this goal, we report that gamendazole is the most potent analogue of LND synthesized thus far, producing 100% infertility in rats after a single oral dose of only 6 mg/kg and 67% infertility after a single oral dose of 3 mg/kg. Furthermore, the recovery of fertility in the animals rendered infertile was 100% at 3 mg/kg and 57% at the 6 mg/kg dose. It is also important to note that the number and proportion of normal-appearing conceptuses in the animals that regained fertility was identical to control animals. By comparison, prior analogues of LND, required multiple doses at 25-50 mg/kg to induce complete infertility in the rat. Thus, gamendazole appears to be an improvement over other LND analogues; however, the single oral dose results reported here, while promising also suggest that lower multiple dose-ranging experiments are necessary to determine if a wider therapeutic window exists which can produce the ideal 100% infertility and yield 100% recovery of fertility once the dosing regimen is terminated. It must also be emphasized that a near 100% return to fertility will likely be required for a male contraceptive drug intended for marketing to men who have not yet had their families. In order to properly approach these goals additional dose-ranging experiments are planned as well as formulation, pharmacokinetics, pharmacodynamics, etc. studies of the compounds. In general, an oral nonhormonal male contraceptive offers advantages over current hormone-based contraceptives in that the latter generally require combinations of hormones and multiple routes of administration including repeated oral doses plus injection of additional agents, a long period of administration before the onset of infertility, and a long lag period for the return of fertility. Immunocontraceptive approaches also require injection and show significant variability including a lack of immune response in a significant subset of individuals.

Another key aspect of gamendazole is the lack of side-effects noted with previous LND analogues. In the studies reported here, LND and similar analogues produced lethargy, temporary declines in weight gain, and histopathology of liver and pancreas following administration in rats. However, none of these observed side-effects were noted in this study following gamendazole administration at doses sufficient to cause infertility. Mortality was observed at 200 mg/kg of gamendazole.

It should be noted that the level of reversibility following a single oral dose of gamendazole at 6 mg/kg was 57%. Our finding that a single lower oral dose of gamendazole (3 mg/kg) produced a 67% reduction in fertility with a 100% recovery of fertility is promising. Efficacy combined with reversibility may be improved by using a lower dose but at a repeated interval. Given the duration of the spermatogenic cycle, the multiple low dose option is also attractive in that it is conceivable that a once a week or once a month oral male contraceptive pill could selectively block the spermatid stage of spermatogenesis, also allowing for eventual repopulation of testis after terminating compound administration.

HSP90AB1 (previously known as HSP90beta [heat shock 90 kDa protein 1, beta]) and EEF1A1 (previously known as eEF1A [eukaryotic translation elongation factor 1 alpha 1]) were identified as binding targets by biotinylated gamendazole (BT-GMZ) affinity purification from testis, Sertoli cells, and ID8 ovarian cancer cells, and confirmed by MALDI-TOF MS and western analysis. BT-GMZ bound to purified yeast HSP82 (homologue to mammalian HSP90AB1) and EEF1A1, but not TEF3 nor HBS1, and was competed by unlabeled gamendazole. However, gamendazole did not inhibit nucleotide binding by EEF1A1. Gamendazole binding to purified *Saccharomyces cerevisiae* HSP82 inhibited luciferase refolding, and was not competed by HSP90 drugs geldanamycin or novobiocin analogue, KU-1. Gamendazole elicited degradation of HSP90-dependent client proteins AKT1 and ERBB2 and had an antiproliferative effect in MCF-7 cells without inducing HSP90. These data suggested that gamendazole may represent a new class of selective HSP90AB1 and EEF1A1 inhibitors. Testis gene microarray analysis from gamendazole-treated rats showed a marked rapid increase in three interleukin 1 genes and Nfkbia (NF-kappaB inhibitor alpha) 4 hrs after oral administration. A spike in IL1A transcription was confirmed by rt-PCR in primary Sertoli cells 60 min after exposure to 100 nM gamendazole, demonstrating Sertoli cells are a target. AKT1, NFKB, and interleukin 1 are known regulators of the Sertoli cell spermatid junctional complexes. A current model for gamendazole action posits this pathway links interaction with HSP90AB1 and EEF1A1 to the loss of spermatids and resulting infertility.

DEFINITIONS

The term "micro" can be represented by the symbol "μ" and the letter "u." As such, uL refers to microliters.

The term "amino" signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidino, piperidino, piperazino, morpholino, etc.

The term "alcohol" indicates an optionally substituted hydrocarbon group having one or more hydroxy substituents. At the 6-position or 5-position, primary, secondary, and tertiary alcohols are contemplated, such as mono-alcohols as well as polyhydroxy variants—e.g., alkandiols, alkantriols, alkantetrols, etc. Preferred alkanols are those containing from about one up to twelve carbon atoms, with alkanols having one to up to six carbon atoms being most preferred. Exemplary of preferred aliphatic alcohols are: methanol, ethanol, 1-propanol, 2-propanol, 1-propen-2-ol, 1-butanol, 2-butanol, 2-methyl-2-propanol, 1-pentanol, 2-pentanol, 3-pentanol, 3-methyl-1-butanol, 1,2-ethandiol (ethylene glycol), 1,2,3-propanetriol (glycerol), i-1,2,3,4-butanetetrol (1-erythritol), and 2,2-dihydroxymethyl-1,3-propandiol (pentaerythritol).

The term "alkyl" refers to a branched or unbranched saturated hydrocarbon group of one to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain one to twelve carbon atoms. "Lower alkyl" refers to an alkyl group of one to six, more preferably one to four, carbon atoms.

The term "alkoxy" denotes oxy-containing groups substituted with an alkyl group. Examples include, without limitation, methoxy, ethoxy, and tert-butoxy. Most preferred are "lower alkoxy" groups having one to six carbon atoms. Examples of such groups include methoxy, ethoxy, propoxy, butoxy, isopropoxy, and tert-butoxy alkyls.

The term "aryl" means a carbocyclic aromatic group containing one, two or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed". The term "aryl" embraces aromatic groups such as phenyl, naphthyl, tetrahydronaphthyl, indane and biphenyl.

The term "aralkyl" embraces aryl-substituted alkyl group. Preferable aralkyl groups are "lower aralkyl" groups having aryl groups attached to alkyl groups having one to six carbon atoms. Examples of such groups include benzyl, diphenylmethyl, triphenylmethyl, phenylethyl and diphenylethyl. The terms benzyl and phenylmethyl are interchangeable.

The term "carbocyclic" refers to an alkyl group that contains one or more covalently closed ring structures, and that the atoms forming the backbone of the ring are all carbon atoms. The term thus distinguishes carbocyclic from heterocyclic rings in which the ring backbone contains at least one non-carbon atom.

The term "heterocyclic" or "heterocycle" means a saturated or unsaturated cyclic hydrocarbon group with three to about 12 carbon atoms, preferably about five to about six, wherein one to about four carbon atoms are replaced by nitrogen, oxygen or sulfur. The preferred heterocycles are selected from the group consisting of benzimidazole, dihydrothiophene, dioxin, dioxane, dioxolane, dithiane, dithiazine, dithiazole, dithiolane, furan, epoxide, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole.

The term "carboxyl" refers to —$R_1C(=O)O—R_2$, wherein $R_1$ is substituted or unsubstituted alkyl, cycloalkyl, heterocyclic, or aryl or $R_1$ can additionally be a covalent bond and wherein $R_2$ is hydrogen, alkyl, cycloalkyl, heterocyclic, aryl, aralkyl, and wherein $R_2$ may optionally be substituted with a hydroxyl or amino group.

The term "carboxylic acid" refers to a carboxyl group in which $R_2$ is hydrogen. Such acids include formic, acetic, propionic, butyric, valeric acid, 2-methyl propionic acid, oxirane-carboxylic acid, and cyclopropane carboxylic acid.

The term "carboxylic acid ester" or "ester" refers to a carboxyl group in which $R_2$ is alkyl, cycloalkyl, aryl, aralkyl, and wherein $R_2$ may optionally be substituted with a hydroxyl or amino group.

The term "cycloalkane" or "cyclic alkane" or "cycloalkyl" is a carbocyclic group in which the ring is an optionally substituted cyclic aliphatic hydrocarbon, for example, a cyclic alkyl group preferably with three to 12 ring carbons. "Cycloalkyl" includes, by way of example, cyclopropyl, cyclobutyl, cyclopentyl, cyclohexyl, cycloheptyl, or cyclooctyl, and the like. Most preferred are cyclopropyl.

The term "halo" or "halogen" refers to fluoro, chloro, bromo or iodo, usually regarding halo substitution for a hydrogen atom in an organic compound. Of the halos, chloro and bromo are generally preferred with fluoro generally being the more preferred.

The term "hydroxyl" means —OH.

The term "haloalkyl" refers to an alkyl or cycloalkyl group having at least one halogen thereon. The term includes monohaloalkyl, dihaloalkyl, and trihaloalkyl groups. Examples of haloalkyl groups include fluoromethyl, difluoromethyl, trifluoromethyl, fluoroethyl, pentafluoroethyl, 2,2,2-trifluoroethyl, and 2,2,3,3,3-pentafluoropropyl. Preferably, the haloalkyl comprises one to three halo groups, such as a hydrocarbon comprising a dichloromethyl group, or a monohalosubstituted hydrocarbon.

The term "haloalkoxy" refers to an alkoxy or cycloalkoxy group having at least one halogen thereon. The term includes monohaloalkoxy, dihaloalkoxy, and trihaloalkoxy groups. Examples of haloalkoxy groups include fluoromethoxy, difluoromethoxy, trifluoromethoxy, and fluoroethoxy. Preferably, the haloalkyl comprises 1 to 3 halo groups, such as a hydrocarbon comprising a dichloromethyl group, or a monohalosubstituted hydrocarbon.

The term "acryl" includes where one of four hydrogen atoms in which ethene is replaced with a different functional group. The term includes substituted and unsubstituted acrylic acids and acrylic acid esters, as well as acrylic acid hydrazides. Non-limiting examples include alkyl (meth)acrylates, hydroxyalkyl (meth)acrylates, alkyl (meth)acrylamides, alkyl di(meth)acrylates, ethylenically unsaturated carboxylic acids, epoxy (meth)acrylates (e.g., glycidyl (meth)acrylate), cyclopropyl(methy)acrylates, ethoxylated (meth)acrylates, cyanoacrylates, etc. Also included are acrylic-, (meth)acrylamido-, and (meth)acrylonitrile. Carbocylic and heterocyclic (especially aryl and aralkyl)acrylates and meth-acrylates, e.g., cyclohexyl acrylate, isobornyl acrylate, are also included. Exemplary acryl groups are methylacrylate, ethylacrylate, butylacrylate, isobutylacrylate, tert-butylacrylate, di(meth)acrylate, hydroxyethylacrylate ("HEA"), hydroxypropylacrylate, dimethylaminoethylacrylate, glycidylacrylates, ethyl(meth)acrylate, butyl(meth)acrylate, hydroxyethyl(meth)acrylate, hydroxypropyl(meth)acrylate ("HEMA"), dimethylaminoethyl(meth)acrylate, glycidyl (meth)acrylates, acrylonitrile, (meth)acrylonitrile, acrylamide or methacrylamide, N-methylol (meth)acrylamide, N-ethanol acrylamide, N,N-dimethyl (meth)acrylamide, N-t-butyl acrylamide, octyl-acrylamide, etc. In one embodiment, the acryl group comprise an ethene substituted with a tetrazole group. In another aspect, the acryl group comprises and ethene substituted with an oxadiazolone, sulfonamine, sulfonate, or phosphate group.

"Acrylic acid" means the group —$(CR_1=CR_2)_n$—COOH, wherein $R_1$ and $R_2$ are independently hydrogen, alkyl, cycloalkyl, aryl, or aralkyl, and n is between an integer, e.g., 1, 2, 3, 4, and is preferably less than 10.

"Acrylic acid ester" means the group —$(CR_1=CR_2)_n$—COOR$_3$ where $R_1$ and $R_2$ are independently hydrogen, alkyl, cycloalkyl, aryl, or aralkyl, and $R_3$ is alkyl or cycloalkyl. Examples of acrylic acid esters include methyl acrylate, ethyl acrylate, n-butyl acrylate, 2-methyl acrylate, and 2-ethylhexyl acrylate, and the like, and n is between an integer, e.g., 1, 2, 3, 4, and is preferably less than 10.

"Acrylic acid hydrazide" refers to the group —$(CR_1=CR_2)_n$—CONR$_3$NR$_4$R$_5$, wherein $R_1$, $R_2$, $R_3$, $R_4$, and $R_5$ are independently hydrogen, alkyl, cycloalkyl, aryl, or aralkyl hydrogen or alkyl, and n is between an integer, e.g., 1, 2, 3, 4, and is preferably less than 10.

"Carboxylic acid hydrazide" refers to the group —C(O)NR$_1$NR$_2$R$_3$ wherein $R_1$, $R_2$, and $R_3$ are independently hydrogen, alkyl, cycloalkyl, aryl, or aralkyl.

The term "epoxide" is understood as meaning and optionally substituted saturated or unsaturated aliphatic compounds containing at least one ether in which the oxygen atom is part of a ring of three atoms. Exemplary epoxides according to the invention include oxirane (ethylene oxide), oxirane carboxylic acids, epoxypropane, epoxybutane, 2-methylepoxypropane, 2-methylepoxybutanes, glycidol and epichlorohydrin, 2-methyl-2,3-epoxybutane.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. The term also includes one or more heteroatoms in the phenyl ring. "Optionally" is inclusive of embodiments in which the described conditions is present and embodiments in which the described condition is not present.

The "patient" to be treated with the compounds of the present invention can be any animal, and is preferably a mammal, such as a wild or domesticated animal (e.g., cats or dogs) or a livestock animal (e.g., horses, cows, pigs, sheep, etc.) or human.

The term "treatment" as used herein refers to a patient receiving treatment with a compound of the present invention such that the patient has temporarily or permanently inhibited fertility or has inhibited reproduction potential. Such treatment can be a single treatment that results in inhibited fertility and inhibited reproduction potential or regular treatments as with any common prescription. The treatment of the patient, such as a mammal (particularly a human), can include: (a) inhibiting or preventing the patient from producing sperm or eggs that are capable of participating in reproduction, i.e., prophylactic treatment of a patient; (b) ameliorating the ability to produce sperm or eggs that are capable of participating in reproduction, i.e., eliminating or causing regression of the patient's ability to produce sperm or eggs or to procreate; or (c) suppressing the ability to produce sperm or eggs that are capable of participating in reproduction, i.e., inhibiting, slowing or arresting the development of sperm or eggs in a patient.

The term "inhibit" or "inhibiting" refers to a statistically significant and measurable reduction in activity, preferably a reduction of at least about 10% versus control, more preferably a reduction of about 50% or more, still more preferably a reduction of about 80% or more. In the case of inhibiting spermatogenesis, the ability to produce sperm can be reduced by at least about 10%, more preferably about 50%, and most preferably 75% or more. Similarly, ovarian follicles can be inhibited.

According to another aspect, the present invention provides a pharmaceutical composition, which comprises an effective amount of one or more compounds of the present invention or a pharmaceutically-acceptable salt, ester or prodrug thereof, together with a pharmaceutically-acceptable diluent or carrier. The effective amount is sufficient for inhibiting fertility.

The compositions may be formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject lonidamine analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the present invention may be administered in free form or in pharmaceutically acceptable salt form.

Such salts may be prepared in conventional manner and exhibit the same order of activity as the free compounds. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein.

An "effective amount" is an amount of a compound of the present invention or a combination of two or more such compounds, which inhibits, totally or partially, the fertility potential of the subject, either male or female. An effective amount can also be an amount that is prophylactically effective. The amount that is effective will depend upon the patient's size and gender, the condition to be treated, the severity of the condition and the result sought. For a given patient, an effective amount can be determined by methods known to those of skill in the art. With regard to reducing fertility, a compound of the present invention can be administered in an effective amount so as to inhibit the formation of viable sperm and/or eggs that can participate in reproduction. The effective amount can be sufficient to temporarily or permanently inhibit fertility the male or female patient.

In the context of the present invention, an effective amount will be that concentration which is effective to inhibit the formation of viable sperm or eggs that can participate in reproduction. For example, for RC-MC-110, JSW-2-72, and JSW-1-190, it is currently thought that a formulation containing between about 25.0 mg/kg of body weight and about 0.3 mg/kg, preferably less than 6.0 mg/kg, of body weight will constitute an effective amount for intravenous or oral application, with routine experimentation providing adjustments to these concentrations for other routes of administration if necessary. Specific examples of the effective amount for inhibiting male fertility can include from about 0.05 mg/kg to less than 200 mg/kg or less than 150 mg/kg or less than 100 mg/kg, more preferably from about 0.5 mg/kg to about 75 mg/kg, even more preferably from about 1 mg/kg to about 50 mg/kg, or most preferably from about 2 mg/kg to about 25 mg/kg. Specific examples of the effective amount for inhibiting female fertility can include from about 0.5 mg/kg to less than 200 mg/kg or less than 150 mg/kg, more preferably from about 1 mg/kg to about 125 mg/kg, even more preferably from about 2 mg/kg to about 100 mg/kg, more preferably from about 4 mg/kg to about 50 mg/kg, or most preferably from about 6 mg/kg to about 25 mg/kg.

An exemplary synthesis of the compounds of the present invention is generally set forth in the scheme below. Although the exemplary scheme is for the carboxylic acid and carboxylic acid ester derivatives of the present invention, it will be appreciated by those skilled in the art that a similar scheme can be used to produce the ester, hydrazide, or carboxylic acid hydrazide, etc. derivatives of the present invention.

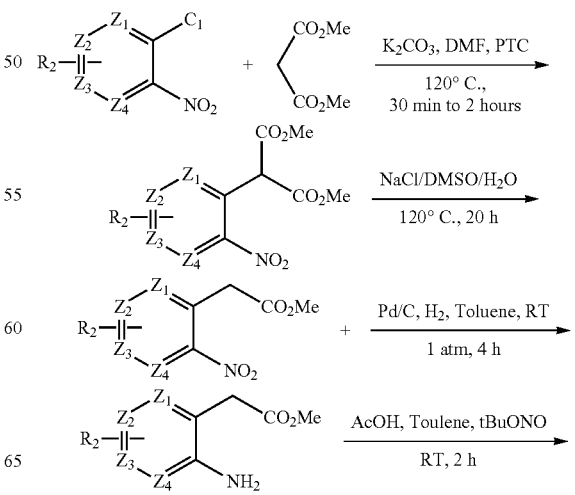

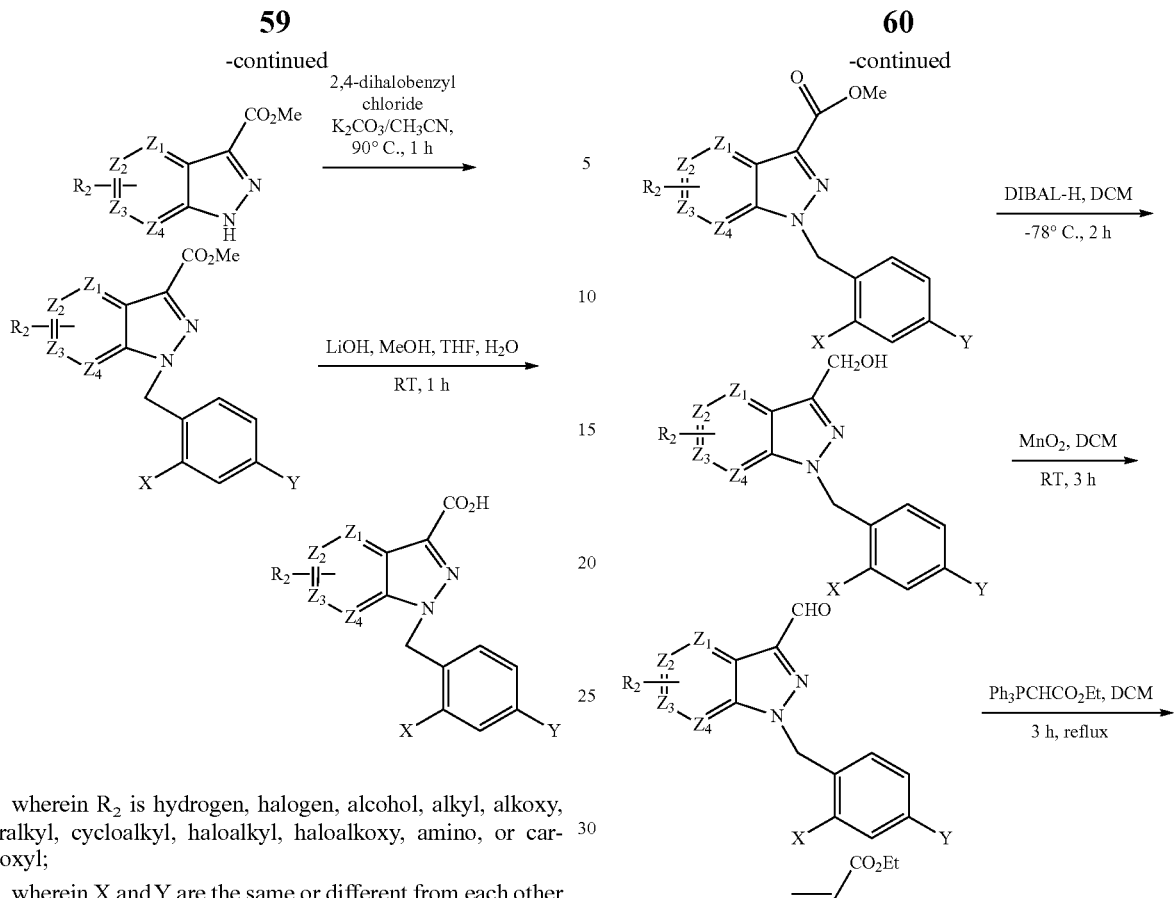

wherein $R_2$ is hydrogen, halogen, alcohol, alkyl, alkoxy, aralkyl, cycloalkyl, haloalkyl, haloalkoxy, amino, or carboxyl;

wherein X and Y are the same or different from each other and are halogen or lower alkyl; and wherein $Z_1$, $Z_2$, $Z_3$, and $Z_4$ are independently nitrogen or carbon.

In a similar manner, the compounds of the present invention having an acryl derivatives.

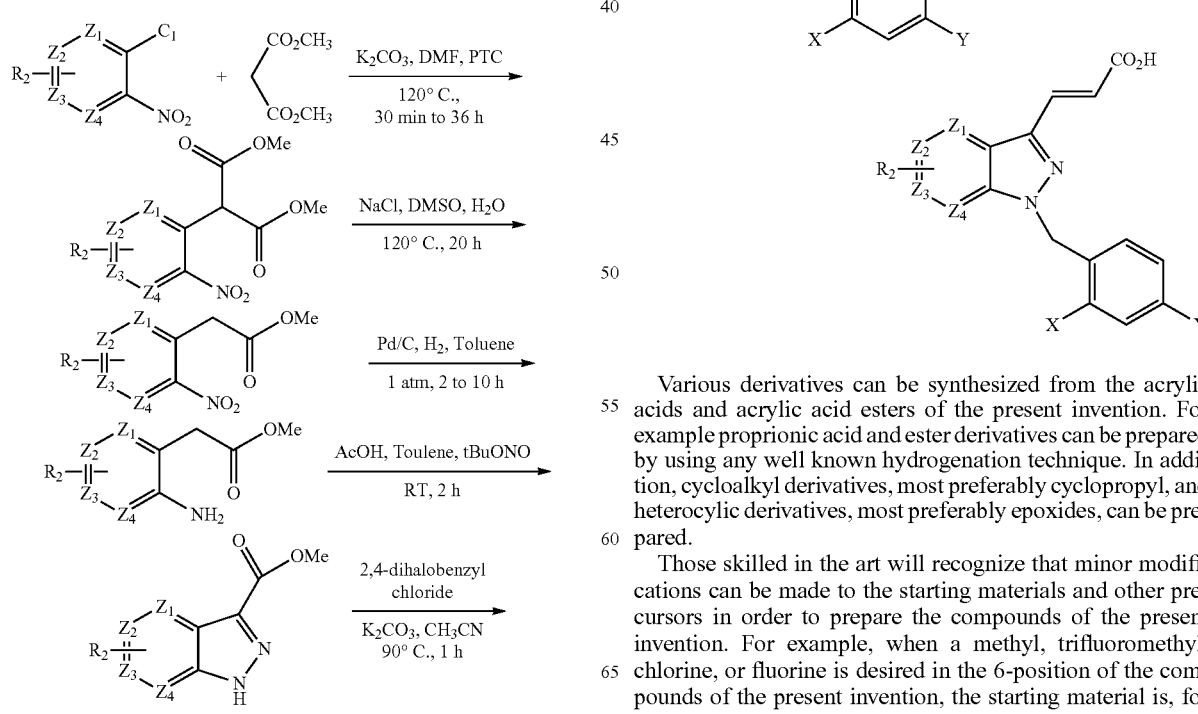

Various derivatives can be synthesized from the acrylic acids and acrylic acid esters of the present invention. For example proprionic acid and ester derivatives can be prepared by using any well known hydrogenation technique. In addition, cycloalkyl derivatives, most preferably cyclopropyl, and heterocylic derivatives, most preferably epoxides, can be prepared.

Those skilled in the art will recognize that minor modifications can be made to the starting materials and other precursors in order to prepare the compounds of the present invention. For example, when a methyl, trifluoromethyl, chlorine, or fluorine is desired in the 6-position of the compounds of the present invention, the starting material is, for example, 4-chloro-3-nitro-methylbenzene, 1-chloro-2-nitro- 4-trifluoromethyl-benzene, 1,4-dichloro-2-nitro-benzene, 1-chloro-4-fluoro-2-nitrobenzene, respectively. Likewise, when a trifluoromethyl is desired to be in the 5-position, the starting material is 1-chloro-2-nitro-5-trifluoromethyl-benzene. All of these starting materials are commercially available from Marshallton Research Lab (King, N.C.).

Further, synthesis of the halogenated alkoxy substituents can be performed using by starting with commercially available 1-chloro-4-fluoromethoxybenzene. This on nitration with $HNO_3$ and $H_2SO_4$ at 50° C. about 3 h. The yield (2 isomers) obtained in 98% (scheme-1). 2-Chloro-4-trifluoromethoxy nitrobenzene is readily synthesized according to the following scheme from Michel Dury, U.S. Pat. No. 6,121,492, which is incorporated by reference.

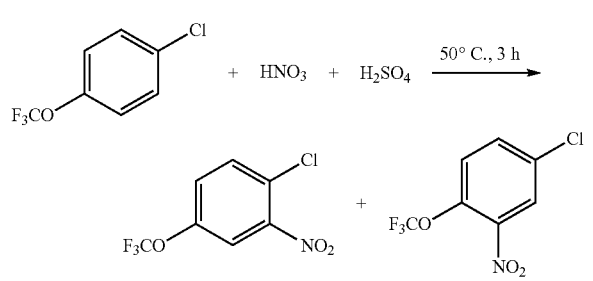

The above two isomers were condensed with dimethylmalonate in DMF in the presence of $K_2CO_3$ at 120° C. for about 8 h. The required product obtained by recrystallization in methanol. The yield was about 55%.

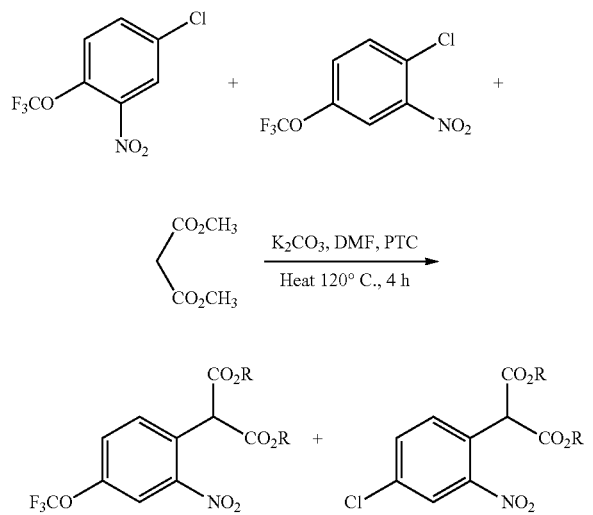

When it is desirable to have one or more nitrogens in the six-membered ring, suitable starting materials include, for example, 2-chloro-3-nitropyridine, 4-hydroxy-3-nitropyridine, 2-chloro-6-methoxy-3-nitro-pyridine, 5-trifluoromethyl-2-pyridonol, 2,3-dichloropyrazine, 4-chloro-3-nitroaniline, and 2-chloro-pyridine. All of these compounds are commercially available from Sigma Aldrich or can be readily synthesized.

It will be appreciated that 4-chloro-3-nitropyridine is readily synthesized according to the following scheme from Reich et al., J. Med. Chem. 1989, 32, 2474-2485.

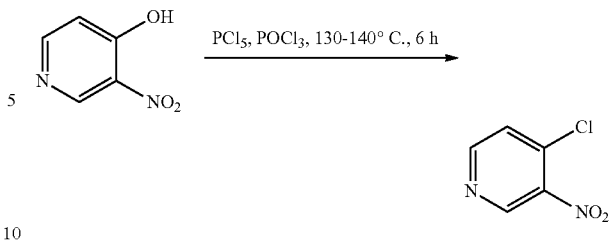

It will be appreciated that 2-chloro-3-nitro-5-trifluoromethyl-pyridine can be synthesized according to the following scheme according to European Patent Application 0272824:

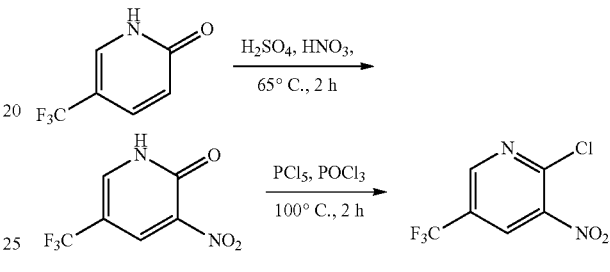

Suitable pyrazine precursors can also be readily synthesized. For example 2-amino-3-chloropyrazineis is readily synthesized according to the following scheme from A. P. Komin et al., J. Het. Chem., Vol., 13, 13-22 (1976), which is incorporated by reference.

The S,S-dimethyl-N-(3-chloropyrazin-2-yl)sulfilimine is readily synthesized according to the following scheme from Hartman, U.S. Pat. No. 4,609,659, which is incorporated by reference. Oxidation of the sulfilimine with MCPBA furnishes the nitro derivative.

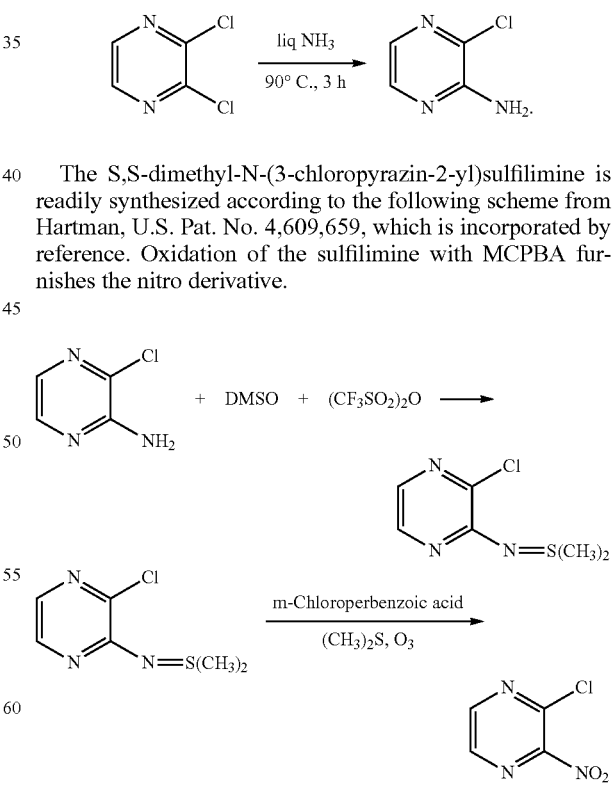

The pyrimidine series can also be synthesized using commercially available 5-nitro-4-chloro pyrimidine (Magical Scientific).

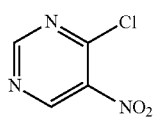

The 4-chloro-2-methyl-benzyl chloride is readily synthesized according to the following scheme from T. S Osdene and et al, Journal of Medicinal Chemistry., 10, 431-434 (1967).

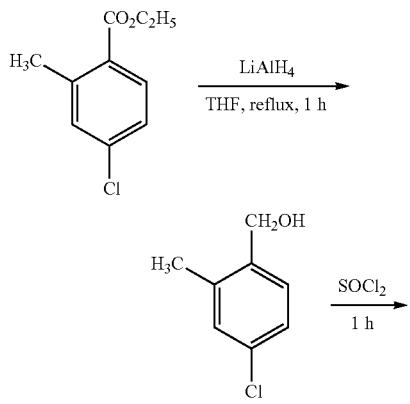

The following synthetic examples are offered to illustrate the invention, and are not to be construed in any way as limiting the scope of the invention.

Example 1

Synthesis of 1-(2,4-dichlorobenzyl)-1H-indazole-3-carboxylic acid methyl ester (RC-MC-30)

For the synthesis of RC-MC-30, methyl indazole-3-carboxylate was first formed. Acetyl chloride (7 mL, excess) was added dropwise to ice-cooled methanol (20 mL) and the solution was stirred at the same temperature for 10 minutes. Commercially available indazole-3-carboxylic acid (2.3 g, 14 mmol) was then added to the solution in one lot and the mixture was allowed to warm to room temperature and stirred overnight. The solvent was removed under vacuum, then the residual solid was dissolved in CHCl₃ (100 mL), and washed with std. NaHCO₃ solution. The aqueous layer was extracted with CHCl₃ and the combined organic extract was washed with brine and dried over anhydrous Na₂SO₄. Removal of solvent left the product as a light yellow solid. Yield=2.05 g (85%); m.p.=168°-170° C.; ¹H NMR (400 MHz, CDCl₃) □8.25 (d, J=8.8 Hz, 1H), 7.89 (d, J=8.8 Hz, 1H), 7.50 (t, J=7.8 Hz, 1H), 7.37 (t, J=7.8 Hz, 1H), 4.10 (s, 3H).

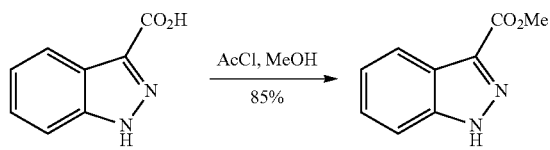 [SMILES: O=C(O)c1n[nH]c2ccccc12 ; COC(=O)c1n[nH]c2ccccc12]

Methyl indazole-3-carboxylate

Next, a mixture of methyl indazole-3-carboxylate (2.05 g, 11.4 mmol), 2,4-dichlorobenzyl chloride (3.35 mL, 12.54 mml), and K₂CO₃ (7.0 g, 50 mmol) in acetone (22 mL) was refluxed overnight at a temperature of 70° C. The reaction mixture was cooled to room temperature, filtered, and the residue was washed with acetone. The combined filtrate was concentrated under vacuum (rotovapor). The solid thus obtained was dissolved in CH₂Cl₂ and filtered to remove any undissolved solid. The solution was then concentrated, diluted with hexane and left in the refrigerator overnight. The precipitated solid was then filtered, washed with a mixture of hexane/ethyl acetate (9:1) to yield the pure product as a white solid. Yield=3.5 g (89%); m.p.=144°-146° C.; ¹H NMR (400 MHz, CDCl₃) □8.31 (d, J=8.8 Hz, 1H), 7.39-7.47 (m, 4H), 7.12 (d, J=8.8 Hz, 1H), 6.71 (d, J=8.8 Hz, 1H), 5.81 (s, 2H), 4.11 (s, 3H).

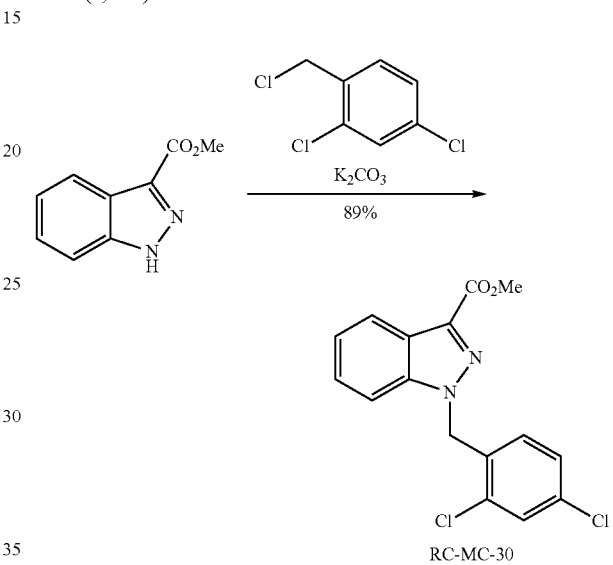

Methyl 1-(2,4-dichlorobenzyl)indazole-3-carboxylate

Example 2

Synthesis of 3-[1-(2,4-dichlorobenzyl)-6-trifluoromethyl-1H-indazol-3-yl]-acrylic acid (RC-MC-110)

Step 1: 2-(2-nitro-4-trifluoromethylphenyl)-malonic Acid dimethyl ester

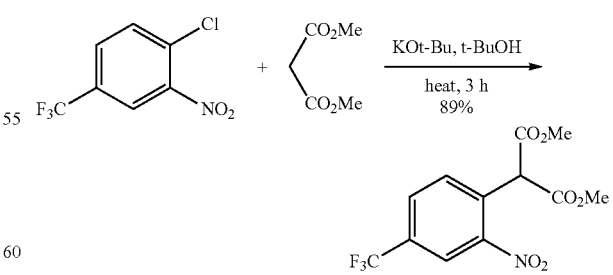

Dimethyl malonate (59.7 g, 0.44 mol) was added dropwise to a stirred solution of potassium tert-butoxide (51 g, 0.44 mol) in dry t-butanol (500 mL). To the resultant suspension, a warm solution of 2-chloro-5-trifluoromethylnitrobenzene (50 g, 0.22 mol) in t-butanol (100 mL) was added and the mixture was refluxed for 6 h (reaction monitored by TLC). After completion of the reaction, most of the t-butanol was distilled off under vacuum, and chilled water was then added to the reaction mixture. The pH was adjusted to neutral with dilute hydrochloric acid, which resulted in the precipitation of the product. The mixture was stirred for 30 minutes and the product was filtered off (68 g, 95%). This material was used without further purification in the next step. A small amount was crystallized (EtOAc/hexane, 4:6) for analysis, to yield a yellow crystalline material, mp 65-67° C. $^1$H NMR (CDCl$_3$) 8.30 (s, 1H), 7.92 (d, J=8.4 Hz, 1H), 7.69 (d, J=8.4 Hz, 1H), 5.37 (s, 1H), 3.80 (s, 6H). MS (FAB) m/z: 322.1 (M$^+$+1).

Step 2: (2-nitro-4-trifluoromethylphenyl)-acetic acid methyl ester

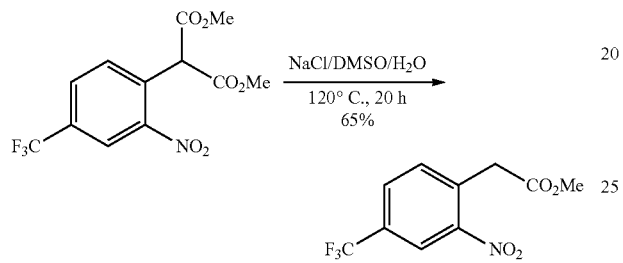

2-(2-Nitro-4-trifluoromethylphenyl)-malonic acid dimethyl ester (68 g, 0.21 mol) was dissolved in dimethyl sulfoxide (200 mL). Sodium chloride (34 g, 0.58 mol) and water (60 mL) were added and the mixture was stirred for 16-20 h at 120° C. (reaction monitored by TLC). The reaction mixture was then cooled to room temperature and quenched into water, which caused precipitation of the product. After stirring for 30 minutes, the product. (45 g, 80%) was isolated by filtration. The product was used without further purification in the next reaction. A small sample was crystallized (EtOAc/hexane, 2:8) for analysis, to yield yellow crystals, mp 104-105° C. $^1$H NMR (CDCl$_3$) 8.3 (s, 1H), 7.88 (d, J=8.4 Hz, 1H), 7.50 (d, J=8.4 Hz, 1H), 4.12 (s, 2H), 3.60 (s, 3H). MS (FAB) m/z: 275.2 (M$^+$+1).

Step 3: (2-Acetylamino-4-trifluoromethylphenyl)-acetic acid methyl ester

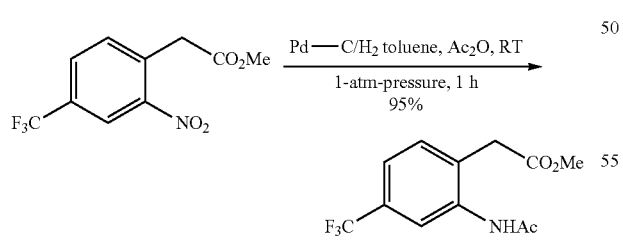

Hydrogenation and acetylation of (2-nitro-4-trifluoromethylphenyl)-acetic acid methyl ester (25 g, 0.095 mol) in the presence of 5% Pd—C (2.5 g, 50% wet) and acetic anhydride (38 g, 0.37 mol) in toluene (200 mL) was carried out under vigorous stirring at room temperature and atmospheric pressure for about 4-5 h (reaction monitored by TLC). The catalyst was removed by filtration and washed with toluene two times. The combined organics were evaporated in vacuo to yield the product (24.8 g, 95%), which was used without further purification in the next step. A small sample was crystallized from hexane to yield the product as a yellow solid, mp 92-94° C. $^1$H NMR (CDCl$_3$) 8.86 (s, 1H), 8.21 (s, 1H), 7.36 (d, J=8.1 Hz, 1H), 7.31 (d, J=8.1 Hz, 1H), 3.74 (s, 3H), 3.68 (s, 2H), 2.23 (s, 3H).

Step 4: 6-Trifluoromethyl-1H-indazole-3-carboxylic acid methyl ester

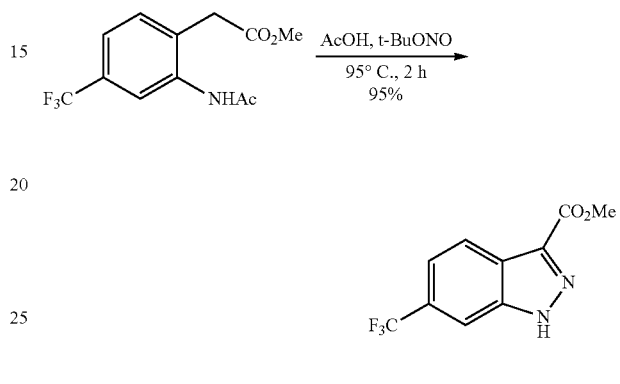

To a solution of (2-acetylamino-4-trifluoromethylphenyl)-acetic acid methyl ester (16 g, 0.058 mol) in acetic acid (50 mL) was added dropwise t-butyl nitrite (90%) (7.35 g, 0.063 mol) over a period of 20 min. at 90-95° C. The mixture was then stirred for 0.5 h at 95° C., poured into cold water and stirred for 1 h. The precipitates were collected by filtration and washed with water. The crude material was dissolved in ethyl acetate and dried over sodium sulfate. The solvent was removed in vacuo. This material (13.4 g, 95%) was used without further purification in the next step. A small sample was crystallized from ethyl acetate to yield a white solid, mp 240-242° C. $^1$H NMR (DMSO-d-6) 8.25 (d, J=8.5 Hz, 1H), 8.04 (s, 1H), 7.58 (d, J=8.5 Hz, 1H), 3.95 (s, 3H). MS (FAB) m/z: 245.1 (M$^+$+1).

Step 5: 1-(2,4-Dichlorobenzyl)-6-trifluoromethyl-1H-indazole-3-carboxylic Acid methyl ester

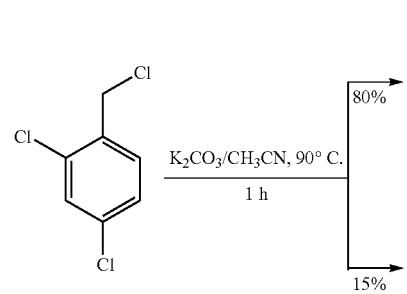

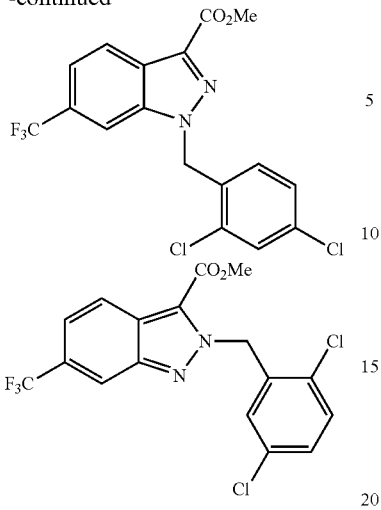

6-Trifluoromethyl-1H-indazole-3-carboxylic acid methyl ester (2.75 g, 0.0112 mol) was dissolved in acetonitrile (50 mL), and potassium carbonate (10 g, 0.07 mol), 2,4-dichlorobenzyl chloride (2.42 g, 0.01239 mol) and tetrabutylammonium iodide (catalytic) were added. The reaction mixture was heated to reflux and refluxed for 2 h under good stirring. The progress of the reaction was monitored by TLC. After completion of the reaction, potassium carbonate was filtered while hot and then washed with acetone. The combined solvents were distilled off under reduced pressure to afford the crude mixture of N1 and N2 benzylated products. The isomers were separated by column chromatography (silica gel, eluent started with hexane then changed to 8:2 hexane, ethyl acetate).

1-(2,4-Dichlorobenzyl)-6-trifluoromethyl-1H-indazole-3-carboxylic acid methyl ester. Yield: 3.62 g (80%), white crystals mp 118-120° C. $^1$H NMR (CDCl$_3$) 8.39 (d, J=8.4 Hz, 1H) 7.74 (s, 1H), 7.57 (d, J=8.4 Hz, 1H), 7.45 (d, J=2.1 Hz, 1H), 7.12 (dd, J=8.4 and 2.1 Hz, 1H), 6.78 (d, J=8.4 Hz, 1H), 5.82 (s, 2H), 4.07 (s, 3H). MS (FAB) m/z: 403 (M$^+$+1).

2-(2,4-Dichlorobenzyl)-6-trifluoromethyl-2H-indazole-3-carboxylic acid methyl ester. Yield: 680 mg (15%), white crystals mp 132-134° C. $^1$H NMR (DMSO-d-6) 8.27 (s, 1H), 8.20 (d, J=8.7 Hz, 1H), 7.76 (d, J=1.8 Hz, 1H), 7.57 (d, J=8.7 Hz, 1H), 7.30 (dd, J=8.3 and 1.8 Hz, 1H), 6.78 (d, J=8.3 Hz, 1H), 6.17 (s, 2H), 3.96 (s, 3H).

Step 6: [1-(2,4-Difluorobenzyl)-6-trifluoromethyl-1H-indazol-3-yl]-methanol

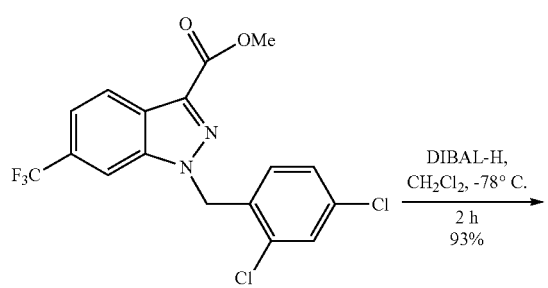

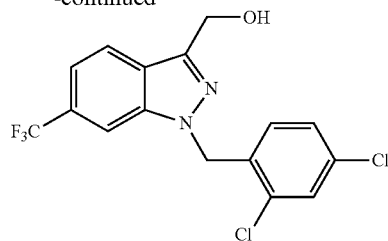

1-(2,4-Dichlorobenzyl)-6-trifluoromethyl-1H-indazole-3-carboxylic acid methyl ester (3.0 g, 0.0075 mol) dissolved in CH$_2$Cl$_2$ (50 mL) was cooled to −78° C. DIBAL-H (8.18 mL, 0.00818 mol) was added slowly dropwise via a syringe under an argon blanket over a period of 15 minutes. After the complete addition of DIBAL-H, the reaction mixture was stirred at −78° C. for another 2 h (reaction monitored by TLC). The reaction was quenched carefully with methanol at −78° C. The reaction mixture was then carefully poured into water and the layers were separated. The organic layer was washed with water and dried over sodium sulfate. Removal of the solvent yielded the crude alcohol (2.6 g, 93%), which was used without purification in the next step. The alcohol was a white solid, mp 137-139° C. $^1$H NMR (CDCl$_3$) 7.97 (d, J=8.4 Hz, 1H), 7.66 (s, 1H), 7.44 (d, J=2.0 Hz, 1H), 7.42 (d, J=8.5 Hz, 1H), 7.12 (dd, J=8.3 and 2.0 Hz, 1H), 6.93 (d, J=8.3 Hz, 1H), 5.65 (s, 2H), 5.09 (s, 2H). MS (FAB) m/z: 375 (M$^+$+1).

Step 7: 1-(2,4-Dichlorobenzyl)-6-trifluoromethyl-1H-indazole-3-carbaldehyde

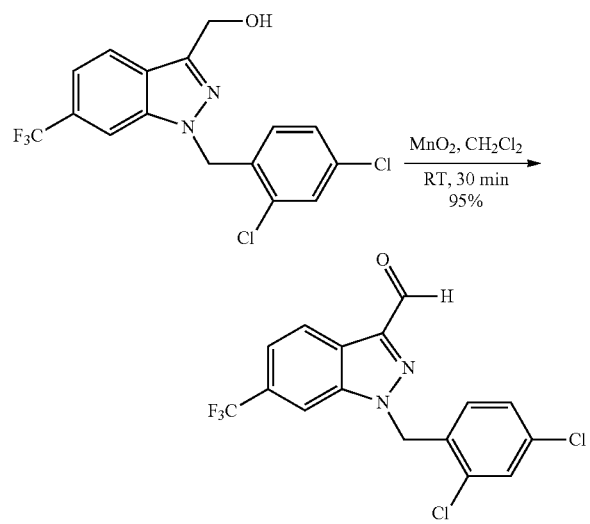

[1-(2,4-Difluorobenzyl)-6-trifluoromethyl-1H-indazol-3-yl]-methanol (3.75 g, 0.01 mol) was dissolved in CH$_2$Cl$_2$ (100 mL) and manganese(IV) oxide (8.7 g, 0.1 mol) was added and stirred for 2-3 h at room temperature (reaction monitored by TLC). The solids were removed by filtration and the removal of the CH$_2$Cl$_2$ in vacuo yielded the crude aldehyde. The aldehyde was used without further purification in the next step. The aldehyde (3.54 g, 95%) was a white solid, mp 97-98° C. $^1$H NMR (CDCl$_3$) 10.25 (s, 1H), 8.45 (d, J=8.5 Hz, 1H), 7.79 (s, 1H), 7.60 (d, J=8.5 Hz, 1H), 7.48 (d, J=2.0 Hz, 1H), 7.20 (dd, J=8.3 Hz and 2.0 Hz, 1H), 6.93 (d, J=8.3 Hz, 1H), 5.79 (s, 2H). MS (FAB) m/z: 373 (M$^+$+1).

Step 8: 3-[1-(2,4-Dichlorobenzyl)-6-trifluoromethyl-1H-indazol-3-yl]-acrylic acid ethyl ester

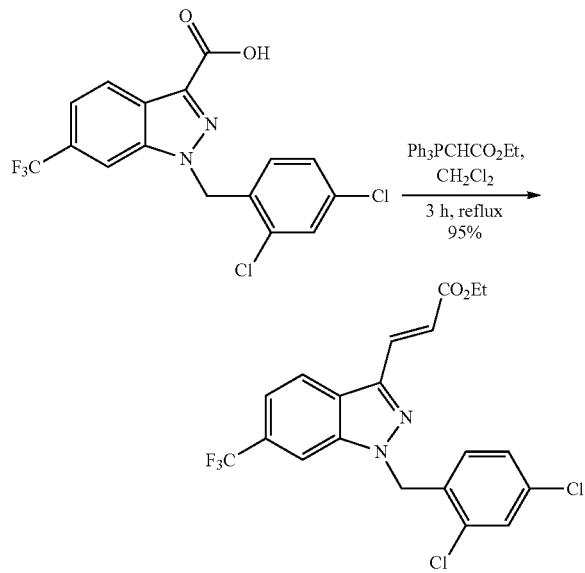

1-(2,4-Dichlorobenzyl)-6-trifluoromethyl-1H-indazole-3-carbaldehyde (2.0 g, 0.00536 mol) was dissolved in CH$_2$Cl$_2$ (50 mL) and Wittig reagent (carbethoxymethylene)triphenylphosphorane (1.06 g, 0.0536 mol) was added to the solution. The homogeneous reaction mixture was heated to reflux in an oil bath for 12 h. The reaction progress was monitored by TLC. The reaction mixture was cooled to room temperature and worked up by quenching into water and separating the organic layer. Removal of the CH$_2$Cl$_2$ yielded the crude product, which was purified by column chromatography to yield the pure product (2.25 g, 95%) as a white solid, mp 186-188° C. $^1$H NMR (CDCl$_3$) 8.08 (d, J=8.5 Hz, 1H), 7.99 (d, J=16.2 Hz, 1H), 7.74 (s, 1H), 7.52 (d, J=8.5 Hz, 1H), 7.47 (d, J=2.0 Hz, 1H), 7.16 (dd, J=8.3 and 2.0 Hz, 1H), 6.84 (d, J=8.3 Hz, 1H), 6.82 (d, J=16.2 Hz, 1H), 5.72 (s, 2H), 4.32 (q, J=7.1 Hz, 2H), 1.38 (t, J=7.1 Hz, 3H). MS (FAB) m/z: 443 (M$^+$+1).

It will be appreciated that the acrylic acid ethyl ester can be hydrogenated using 5% Pd—C in the presence of methanol, DCM at RT and 1 atm-pressure to give the propionic acid ester derivative. For example, treatment under such conditions yields 3-[1-(2,4-dichlorobenzyl)-6-trifluoromethyl-1H-indazol-3-yl]-propionic acid ethyl ester (JWS-2-70).

Step 9: 1-(2,4-Dichlorobenzyl)-3-[6-trifluoromethyl-1H-indazol-3-yl]-acrylic acid

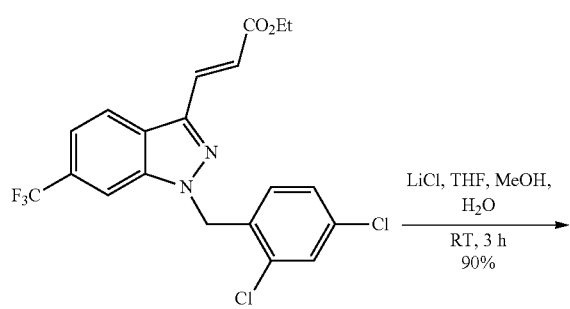

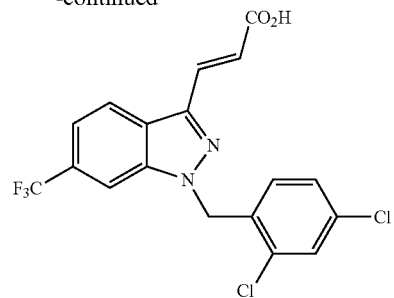

1-(2,4-Dichlorobenzyl)-3-[6-trifluoromethyl-1H-indazol-3-yl]-acrylic acid ethyl ester (2.0 g, 0.0045 mol) was dissolved in a mixture of tetrahydrofuran (50 mL) and methanol (25 mL). A lithium hydroxide solution (0.33 g, 0.013 mol lithium hydroxide in 7.5 mL water) was added slowly at room temperature under good stirring. The reaction mixture was then warmed to 40° C. and held at that temperature for 2 h. The reaction mixture was diluted with water and extracted with ethyl acetate in order to remove neutral impurities. The layers were separated and the aqueous layer was cooled to 0° C. and then acidified with 20% sulfuric acid to pH 2. White solids precipitated and were filtered and dried to constant weight. The crude product was recrystallized from ethyl acetate and hexane (1:1) to afford the pure product (1.68 g, 90%) as a white solid, mp 186-188° C. $^1$H NMR (DMSO-d-6) 8.39 (s, 1H), 8.36 (d, J=8.5 Hz, 1H), 7.79 (d, J=16.2 Hz, 1H), 7.66 (d, J=1.6 Hz, 1H), 7.55 (d, J=8.5 Hz, 1H), 7.35 (dd, J=8.3 and 1.6 Hz, 1H), 6.93 (d, J=8.3 Hz, 1H), 6.76 (d, J=16.2 Hz, 1H), 5.89 (s, 2H). Anal. calcd. for C$_{18}$H$_{11}$Cl$_2$F$_3$N$_2$O$_2$: C, 52.02; H, 2.65; N, 6.74. Found: C, 50.63; H, 2.63; N, 6.63. HRMS (FAB+) m/z calcd. for C$_{18}$H$_{11}$O$_2$F$_3$N$_2$O$_2$ 415.01. found 415.0233. MS (FAB) m/z: 415 (M$^+$+1).

It will be appreciated that proprionic derivatives of the acrylic acid derivatives of the, such as RC-MC-110, present invention can be prepared by was hydrogenated using 5% Pd—C in the presence of methanol, DCM at RT and 1 atm-pressure to give desired product. For example, treatment of RC-MC-110 under such conditions yields 3-[1-(2,4-dichlorobenzyl)-6-trifluoromethyl-1H-indazol-3-yl]-propionic acid (JWS-2-72).

Similarly, three-membered cycloalkyl heterocyclic ring systems can be prepared from the acrylic acid and ester compounds of the present invention. For example, compounds comprising cis- and trans-3-[1-(2,4-dichlorobenzyl)-6-trifluoromethyl-1H-indazol-3-yl]-oxirane-2-carboxylic acid were prepared by treating RC-MC-110 or its cis isomer with 30% hydrogen peroxide in the presence of sodium hydroxide, methanol and water at room temperature for 6 hours. Similarly, compounds comprising cis- and trans-2-[1-(2,4-dichloro-benzyl)-6-trifluoromethyl-1H-indazol-3-yl]-cyclopropanecarboxylic acid were prepared by refluxing RC-MC-110 and its cis analogue with methylene iodide and zinc-copper couple in anhydrous ethyl ether for 48 hours.

Example 3

Synthesis of 1-(2,4-dichlorobenzyl)-1H-pyrazolo[3,4-b]pyridine-3-carboxylic acid (RC-MC-86)

Step 1: 1-(2-Chloropyridin-3-yl)ethanol

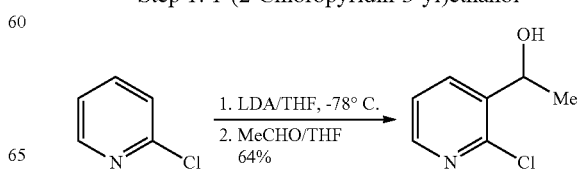

Dry THF (400 mL) and n-butyllithium (1.6 M in hexane, 63 mL, 0.1 mol) were introduced into a 1 L flask under nitrogen at −70° C. A solution of dry diisopropylamine (10.1 g, 0.1 mol) in THF (25 mL) was added dropwise to the mixture at −70° C. The mixture was then kept for 1 h at 0° C. and then cooled to −70° C. A solution of 2-chloropyridine (11.3 g, 0.1 mol) in THF (25 mL) was added dropwise to the mixture at −70° C. and the mixture was stirred for 3 h at this temperature. A solution of acetaldehyde (4.85 g, 0.11 mol) in dry THF (50 mL) was then added dropwise and the mixture was kept for 3 h at −70° C. A solution of water (4 mL) in THF (40 mL), acidified by a few drops of concentrated hydrochloric acid, was added to the mixture at −40° C. and then water (200 mL) was introduced at −10° C. Extraction with diethyl ether (3×150 mL), drying over anhydrous sodium sulfate, and evaporation gave a crude product, which was purified by column chromatography to yield an oil (10 g, 64%). *$^1$H NMR (CDCl$_3$) 8.15 (dd, J=5 and 2 Hz, 1H), 7.95 (dd, J=8 and 2 Hz, 1H), 7.20 (dd, J=8 and 5 Hz, 1H), 5.15 (d, J=7 Hz, 1H), 3.90 (s, 1H), 1.45 (d, J=7 Hz, 3H).

* NMR values reported in Journal of Chemical Society Perkin Trans 1: Organic and Bio-organic Chemistry, 1990, 9, 2409-2415.

Step 2: 1-(2-Chloropyridin-3-yl)ethanone

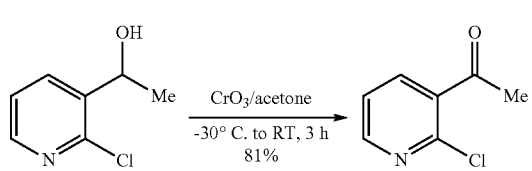 [SMILES: CC(O)c1cccnc1Cl ; CC(=O)c1cccnc1Cl]

A solution of 1-(2-chloropyridin-3-yl)ethanone (10 g, 0.0635 mol) in dry acetone (200 mL) was introduced under argon into a 1 L flask. The mixture was cooled to −30° C. and pure, pulverized chromic anhydride (19 g, 0.19 mol) was added. The reaction mixture was kept at room temperature for 3 h. 2-Propanol (100 mL) was added, followed by aqueous sodium hydrogen carbonate to pH 8. After filtration, solids were washed with chloroform. The organic and aqueous layers were then separated and the aqueous layer was extracted with chloroform (2×100 mL). The combined organics were dried over anhydrous sodium sulfate and evaporated to yield the crude pyridyl ketone as an oil. This product was purified by column chromatography (8 g, 81%). *$^1$H NMR (CDCl$_3$) 8.44 (dd, J=5 and 2 Hz, 1H) 7.91 (dd, J=7.5 and 2 Hz, 1H), 7.34 (dd, J=7.5 and 5 Hz, 1H), 2.68 (s, 3H).

* NMR values reported in Journal of Chemical Society Perkin Trans 1: Organic and Bio-organic Chemistry, 1990, 9, 2409-2415.

Step 3: 3-Methyl-1H-pyrazolo[3,4b]pyridine

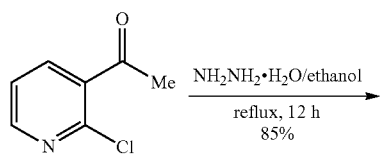

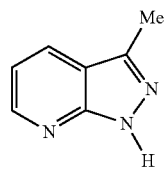

A solution of 1-(2-chloropyridin-3-yl)ethanone (22 g, 0.1415 mol) and hydrazine hydrate 98% (113 g, 2.21 mol) in ethanol (300 mL) was refluxed for 12 h. About 80% of the ethanol was distilled off under reduced pressure using a rotary evaporator. The residue was allowed to come to room temperature. The precipitated solid was filtered and washed with water. The product was dried at 90° C. to constant weight (16 g, 85%) mp 152-154° C. $^1$H NMR (CDCl$_3$) 8.62 (dd, J=4.5 and 1.4 Hz, 1H), 8.08 (dd, J=8.0 and 1.4 Hz, 1H), 7.15 (dd J=8.0 and 4.5 Hz, 1H), 2.64 (s, 3H). MS (FAB) m/z: 133 (M$^+$+1).

Step 4: 1H-Pyrazolo[3,4-b]pyridine-3-carboxylic Acid

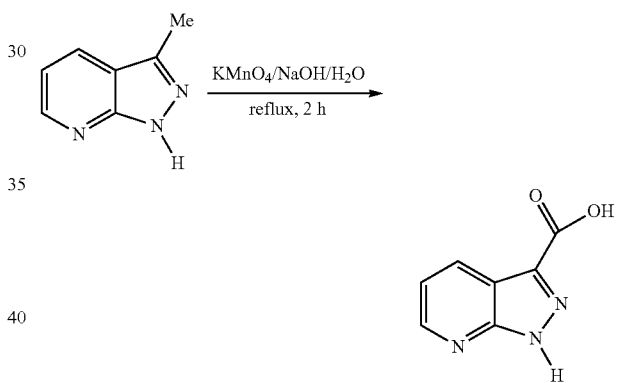

Sodium hydroxide (35 g, 0.88 mol) was dissolved in water (800 mL), then 3-methyl-1H-pyrazolo[3,4b]pyridine (16 g, 0.12 mol) was added to a solution of sodium hydroxide and stirred at room temperature for 10 minutes. The reaction mixture was heated to 80° C. Under good stirring potassium permanganate solution (68.5 g, 0.433 mol of KMnO$_4$ in 300 mL water) was slowly added dropwise over a period of 2 h, keeping the oil bath temperature at 100° C. After completing the addition of potassium permanganate, the reaction mixture was further heated for 1 hr. The progress of the reaction was monitored by TLC. The reaction mixture was cooled to 70-80° C. and the byproduct manganese dioxide was filtered off. The manganese dioxide cake was washed with hot water. The main filtrate and the washings were combined and acidified to pH 2 with concentrated sulfuric acid. The water was then distilled off under reduced pressure using a rotary evaporator. The yellow solid obtained was a mixture of the desired 1H-pyrazolo[3,4b]pyridine-3-carboxylic acid, sodium sulfate and potassium sulfate (95 g). This mixture of solids was taken without purification to the next step. A small sample was purified by column chromatography for analytical purposes to afford white crystals mp 175-176° C. $^1$H NMR (CDCl₃) 8.28 (dd, J=4.9 and 1.6 Hz, 1H), 7.82 (dd, J=7.5 and 1.6 Hz, 1H), 7.39 (dd J=7.5 and 4.9 Hz, 1H). MS 9FAB) m/z: 147 (M⁺+1).

Step 5: 1H-Pyrazolo[3,4b]pyridine-3-carboxylic Acid Methyl Ester

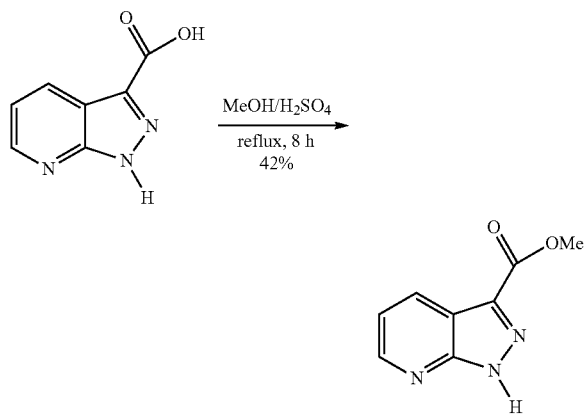

The mixture of solids from the preceding step 4 (95 g) was suspended in methanol (500 mL) and sulfuric acid (5 mL) was added carefully. The reaction mixture was then heated to reflux for 6-8 h, and the reaction was monitored using TLC. After completion of the reaction, inorganic solids were filtered off from the reaction mixture and the solid cake was washed with hot methanol. The main filtrate and the washings were combined, then methanol was distilled off under reduced pressure on the rotary evaporator. The resulting solids were suspended in 5% sodium bicarbonate solution (300 mL) and stirred for 5 min. at room temperature. The white solids were filtered off and dried in an oven at 90-95° C. to constant weight (8.07 g, 42% based on 3-methyl-1H-pyrazolo[3,4b]pyridine), mp 201-203° C. ¹H NMR: (CDCl₃) 14.4 (brs, 1H), 8.74 (dd, J=4.6 and 1.5 Hz, 1H), 8.64 (dd, J=8.1 and 1.5 Hz, 1H), 7.39 (dd J=8.1 and 4.6 Hz, 1H), 4.10 (s, 3H).

Step 6: 1-(2,4-Dichlorobenzyl)-1H-pyrazolo[3,4b]pyridine-3-carboxylic Acid Methyl Ester

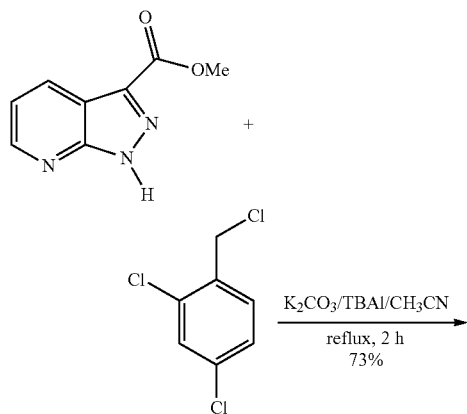

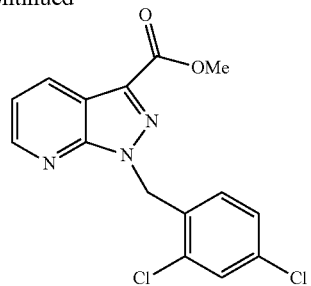

1H-Pyrazolo[3,4b]pyridine-3-carboxylic acid methyl ester (8 g, 0.0452 mol) was suspended in acetonitrile (200 mL) and the resulting suspension was stirred under heating for 10 min. in order to homogenize the solution. Potassium carbonate (31.2 g, 0.226 mol) was then added in one lot, followed by the addition of the tetrabutylammonium iodide (0.08 g, catalytic) and 2,4-dichlorobenzyl chloride (10.6 g, 0.0543 mol). The reaction mixture was heated to reflux for 2 h under good stirring. The reaction progress was monitored by TLC. After completion of the reaction, the mixture was cooled to room temperature and potassium carbonate was filtered off. Acetonitrile was distilled off under reduced pressure to afford the crude benzylated product. The crude product was purified using column chromatography (silica gel, eluent started with hexane then 8:2 hexane/ethyl acetate) to yield the pure product as white crystals (11 g, 73%) mp 135-136° C. ¹H NMR (CDCl₃) 8.04 (dd, J=4.5 and 1.6 Hz, 1H), 8.58 (dd, J=8.1 and 1.6 Hz, 1H), 7.45 (d, J=2.0 Hz, 1H), 7.36 (dd, J=8.1 and 4.5 Hz, 1H), 7.10 (dd, J=8.3 and 2.0 Hz, 1H), 6.72 (d, J=8.3 Hz, 1H), 5.92 (s, 2H), 4.06 (s, 3H). MS (FAB) m/z: 336 (M⁺+1).

Step 7: 1-(2,4-Dichlorobenzyl)-1H-pyrazolo[3,4b]pyridine-3-carboxylic Acid

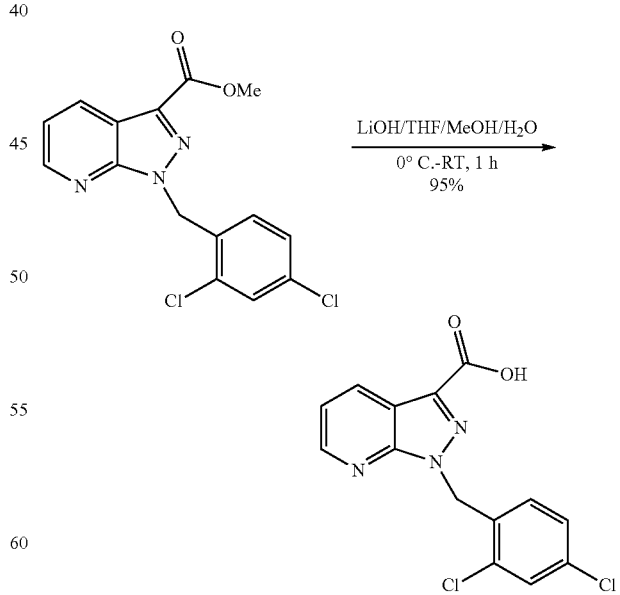

The benzylated methyl ester (4 g, 0.012 mol) was dissolved in a mixture of tetrahydrofuran (60 mL) and methanol (30 mL). A lithium hydroxide solution (1 g, 0.040 mol, lithium hydroxide in 15 mL water) was added slowly at room temperature under good stirring. The reaction was completed (monitored by TLC) after stirring for 1 h. The reaction mixture was diluted with water and extracted with ethyl acetate in order to remove neutral impurities. The layers were separated and the aqueous layer was cooled to 0° C. and acidified with 20% sulfuric acid to pH 2. The white solids that precipitated were filtered and dried to constant weight. The crude product was recrystallized from ethyl acetate and hexane (6:4) to afford the pure product (3.48 g, 95%), mp 233-235° C. HPLC purity 99.98%. $^1$H NMR (CDCl$_3$) 9.12 (dd, J=4.5 and 1.5 Hz, 1H), 9.00 (dd, J=8.1 and 1.5 Hz, 1H), 8.06 (d, J=2.1 Hz, 1H), 7.90 (dd J=8.1 and 4.5 Hz, 1H), 7.81 (d, J=8.3 Hz, 1H), 7.57 (d, J=8.3 Hz, 1H), 6.41 (2H, s). $^{13}$C NMR (DMSO/acetone-d-6) δ 169.9, 152.0, 150.7, 136.6, 134.7, 134.5, 134.3, 132.4, 132.2, 130.0, 128.6, 120.4, 116.1, 48.8. Anal. calcd. for $C_{14}H_{10}ClNO_2$: C, 52.17; H, 2.79; N, 13.04. Found: C, 51.94; H, 2.51; N, 13.06. HRMS (FAB) m/z calcd. for $C_{14}H_{10}ClNO_2$ 322.0150. found 322.0159.

Example 4

Ames Test for Mutigenicity

The Ames test was performed on the compounds of the present invention. The procedure involved the following steps:

1. Bacteria Culture (Strain *Salmonella Typhimurium* TA 100)

A lyophilized disc of *S. typhimurium* TA 100 left over from the Muta-Chromoplate Kit Version 3.0 (obtained from Environmental Bio-Detection Products, inc. (EBIP), 14 Abacus Road, Brampton, Ontario, Canada, L6T 5B7) was placed in 5.0 ml of Difco Nutrient Broth (2 g/L, pH 7.40) or Oxoid broth No. 2 in a 13×100 mm sterile culture tube. The material was incubated for 24 hours at 37° C. with the cap slightly loosened. Turbidity was evaluated the next day.

Following the above initial preparation, the bacteria were mixed with DMSO (0.09 ml of DMSO per 1.0 ml of bacteria culture) and divided into 500 μl aliquots in sterile centrifuge tubes and stored at −80° C. For this assay, one tube was thawed and placed into 5.0 ml of Oxoid broth the night before the assay was run. On the following day, checks for the rfa mutation were performed.

2. Rfa Mutation Test

Two nutrient agar plates were placed in a 37° C. incubator 30 minutes to an hour before preparing the top agar. The plates were removed just before adding the culture in step 3.

A bottle of the top agar was melted and 2 ml was placed in a 13×100 mm sterile culture tube. The tube was placed in a heating block at 45° C. About 0.1 ml of a bacteria culture was grown overnight in the 2 ml of agar. As soon as possible after adding the culture, the tube was vortexed and the material was poured onto the nutrient agar plate. The plates were placed on a level surface for several minutes to allow the top agar to become firm.

About 10 μl of sterile Crystal Violet (0.1 g/100 ml) was placed onto a sterile ¼ inch round disk made from Whitman 1 filter paper. The disc was gently pressed into the top agar. The plates were placed into a humidified 37° C. degree incubator. The plates were checked every 12 hours to 16 hours for a zone of inhibition around the disks.

For this test, a zone of inhibition of 12 mm was noted in the first plate and 12 mm in the second indicating the rfa mutation was intact.

3. Histidine Requirement

This test ensures that the His$^-$ mutation is still functional. Using a broth culture grown overnight from a frozen aliquot from, a small sample of the culture was spread over a histidine/biotin plate using a platinum 20 μl loop. The plate was inverted and placed in a 37° C. incubator overnight.

At the same time, a small amount of the culture broth was removed and placed in a sterile 500 μl centrifuge tube. The tube was spun for 10 minutes at 3000 rpm on a Fisher Marathon 13K microcentrifuge. The broth was removed and the bacteria was re-suspended in sterile 10 mM Tris, pH 7.40. The bacteria was placed on a biotin plate and incubate overnight.

The histidine/biotin plates should show growth along the streaked areas while the biotin only plates should show no growth. The colonies from the Histidine/Biotin plates can be used as master plates to make new cultures, including those to be frozen and stored at −80° C.

4. Bacteria Cultures for Mutagenicity Assay

About 600 μl of the culture was placed into 7.0 ml of nutrient broth (Oxoid Broth No. 2) in a 13×100 mm culture tube. The tube was incubated at 37° C. for approximately 12 hours. About 600 μl of the culture was placed into another 7.0 ml of nutrient broth in a 13×100 mm culture tube and incubated at 37° C. for approximately 12 hours. Both tubes were combined in a sterile 15 ml conical immediately prior to use. This is the test culture used for inoculating plates and making the dilutions used for determining culture density.

The tubes were rechecked for the His$^-$ mutation using the procedure listed above.

5. Bacterial Culture Density Check

The cultures contained around 2×10$^8$ bacteria/plate for optimal results. The best means of testing was with a turbidometer at 650 nm. Concentration was determined by making serial dilutions and plating them out in duplicate at the time of the mutagenicity assay.

6. Mutagenicity Assay

About 10 ml of the 0.5 mM histidine/biotin solution was added to 100 ml of top agar. The agar was melted in a water bath at 60-70° C. The minimal glucose plates were placed in a 37° C. incubator 30-45 minutes prior to starting the assay.

The test compound was dissolved in DMSO (Fisher D128-500) and made a 1 to 10 and 1 to 100 dilution. For example:

| Compound | wt. of compound (g) | ml of DMSO |
| --- | --- | --- |
| RC-MC-110 | 0.1001 | 1.0 ml |
| RC-MC-86 | 0.1001 | 1.0 ml |

The solution was sterilized with a 0.22 μM Nylon syringe filter. (Fisher, 09-719C). Then, about 80 ml of the above 100 mg/ml solution was pipetted into 720 ul of sterile DMSO to obtain a 10 mg/ml solution.

The positive mutagens were prepared as follows:

Sodium azide (15 μg/ml). About 3 mg (Actual wt.=0.0030 g, FisherBiotech BP922-500) was dissolved in 2 ml of sterile water and then diluted by placing 1 ml of the above 1500 μg/ml solution in 9 ml of sterile water. About 1 ml of the 150 μg/ml solution was placed in 9 ml of sterile water to yield the final 15 μg/ml solution. This solution was sterilized by placing it in a 10 ml syringe and passing it through a 0.20 μm nylon filter (Fisherbrand 09-719C).

Amino anthracene (25 μg/ml). About 5 mg of amino anthracene (Actual wt.=0.0050 g, 2-Anthramine, Sigma A-1381) was dissolved in 2 ml of ethanol (Fisher A-405-20) to obtain a 2500 μg/ml solution. About 0.5 ml of the 2500 μg/ml solution was placed in 4.5 ml of ethanol to obtain a 250 μg/ml solution. About 0.5 ml of the 250 μg/ml solution was placed in 4.5 ml of ethanol to obtain a 25 μg/ml solution. This solution was sterilized by placing it in a 10 ml syringe and passing it through a 0.20 μm nylon filter (Fisherbrand 09-719C).

The S9 solutions were prepared as follows:

| Ingredient | (+) S9 mix | (−) S9 mix |
|---|---|---|
| Sterile H$_2$O | 9.88 ml | 10.88 ml |
| 0.2 M phosphate buffer (pH 7.4) | 12.5 ml | 12.5 ml |
| 0.1 M NADP | 1.0 ml | 1.0 ml |
| 1 M glucose-6-phosphate | 0.125 ml | 0.125 ml |
| MgCl$_2$—KCl salt solution | 0.5 ml | 0.5 ml |
| S9 enzyme preparation | 1.0 ml | 0 ml |

The S9 was obtained from Moltox (Sprague-Dawley, Phenobarbital-5,6-Benzoflavone). The solutions were added in the order indicated and kept on ice even during the assay until added to the top agar solution.

Six 13×100 mm culture tubes were placed in a heating block at 45° C. for a few minutes prior to use. About 2 ml of the molten top agar containing the 0.5 mM histidine/biotin solution was pipetted into each tube. The bacterial broth culture was removed placed on a minimal glucose plate for each tube from the incubator. Then, 0.1 ml of the drug, buffer or solvent was added to the top agar.

About 0.1 ml of the bacteria culture was then added. Then, the appropriate S9 solution was added to the tube and immediately vortexed. The top agar was placed onto the pre-warmed minimal glucose plate and swirled to get uniform distribution.

Each test compound was run with both the (+)S9 mix and (−)S9 mix with the following exceptions: (1) sodium azide-(−)S9 only (positive control for bacterial mutation; and (2) amino anthracene-(+)S9 only (positive control for S9 activation).

All plates were incubated for 48 hours at 37° C. The plates were removed and inspected for colony count.

The following Table 1 summarizes the results of the Ames test with respect to the compounds of the present invention.

TABLE 1

| Compound | (+)S9 10 mg/pl. | (+)S9 1 mg/pl. | (+)S9 0.1 mg/pl. | (−)S9 10 mg/pl. | (−)S9 1 mg/pl. | (−)S9 0.1 mg/pl. |
|---|---|---|---|---|---|---|
| RC-MC-30 | Pass | Pass | Pass | Pass | Pass | Pass |
| RC-MC-60* | Pass | Pass | Pass | Pass | Pass | Pass |
| RC-MC-65 | Fail | Fail | Pass | Fail | Fail | Pass |
| RC-MC-86 | Pass | Pass | Pass | Pass | Pass | Pass |
| RC-MC-100 | Pass | Pass | Pass | Pass | Pass | Pass |
| RC-MC-101 | Pass | Pass | Pass | Pass | Pass | Pass |
| TH-2-178 | Pass | Pass | Pass | Pass | Pass | Pass |
| TH-2-179 | Pass | Pass | Pass | Pass | Pass | Pass |
| RC-MC-110 | Pass | Pass | Pass | Pass | Pass | Pass |
| DD-MC-1 | Pass | Pass | Pass | Pass | Pass | Pass |
| DD-MC-II | Pass | Pass | Pass | Pass | Pass | Pass |
| AD-1-115-21 | Pass | Pass | Pass | Pass | Pass | Pass |
| AD-1-117-19 | Pass | Pass | Pass | Pass | Pass | Pass |
| AD-1-131-14 | Pass | Pass | Pass | Pass | Pass | Pass |
| AG-2-51* | Pass | Pass | Pass | Pass | Pass | Pass |
| JWS-1-110 | Pass | Pass | Pass | Pass | Pass | Pass |
| JWS-1-112* | Pass | Pass | Pass | Fail | Fail | Pass |
| JWS-1-114 | Pass | Pass | Pass | Pass | Pass | Pass |
| JWS-1-130 | Pass | Pass | Pass | Pass | Pass | Pass |
| JWS-1-132 | Pass | Pass | Pass | Pass | Pass | Pass |
| JWS-1-140 | Pass | Pass | Pass | Pass | Pass | Pass |
| JWS-1-142 | Pass | Pass | Pass | Pass | Pass | Pass |
| JWS-1-144 | Pass | Pass | Pass | Pass | Pass | Pass |
| JWS-1-146* | Pass | Pass | Pass | Pass | Pass | Pass |
| JWS-1-158 | Pass | Pass | Pass | Pass | Pass | Pass |
| JWS-1-160 | Pass | Pass | Pass | Pass | Pass | Pass |
| JWS-1-162 | Pass | Pass | Pass | Pass | Pass | Pass |
| JWS-1-170 | Pass | Pass | Pass | Pass | Pass | Pass |
| JWS-1-190 | Pass | Pass | Pass | Pass | Pass | Pass |
| JWS-1-228 | Pass | Pass | Pass | Pass | Pass | Pass |
| JWS-1-230 | Pass | Pass | Pass | Pass | Pass | Pass |
| JWS-1-232 | Pass | Pass | Pass | Pass | Pass | Pass |
| JWS-1-254 | Pass | Pass | Pass | Pass | Pass | Pass |
| JWS-1-258 | Pass | Pass | Pass | Pass | Pass | Pass |
| JWS-1-260 | Pass | Pass | Pass | Pass | Pass | Pass |
| JWS-1-268 | Pass | Pass | Pass | Pass | Pass | Pass |
| JWS-1-270 | Pass | Pass | Pass | Pass | Pass | Pass |
| JWS-1-274 | Pass | Pass | Pass | Pass | Pass | Pass |
| JWS-1-276 | Pass | Pass | Pass | Pass | Pass | Pass |
| JWS-1-280 | Pass | Pass | Pass | Pass | Pass | Pass |
| JWS-1-282 | Fail | Pass | Pass | Pass | Pass | Pass |
| JWS-1-284 | Fail | Fail | Pass | Fail | Fail | Pass |
| JWS-1-294 | Pass | Pass | Pass | Pass | Pass | Pass |
| JWS-1-298 | Fail | Fail | Pass | Fail | Fail | Pass |
| JWS-1-300 | Fail | Fail | Pass | Fail | Fail | Pass |
| JWS-1-302 | Fail | Pass | Pass | Pass | Pass | Pass |
| JWS-2-1 | Pass | Pass | Pass | Fail | Marginal | Pass |
| JWS-2-10 | Pass | Pass | Pass | Pass | Pass | Pass |
| JWS-2-12 | Pass | Pass | Pass | Pass | Pass | Pass |
| JWS-2-14 | Fail | Pass | Pass | Fail | Fail | Pass |

TABLE 1-continued

| Compound | (+)S9 10 mg/pl. | (+)S9 1 mg/pl. | (+)S9 0.1 mg/pl. | (−)S9 10 mg/pl. | (−)S9 1 mg/pl. | (−)S9 0.1 mg/pl. |
| --- | --- | --- | --- | --- | --- | --- |
| JWS-2-18 | Fail | Fail | Pass | Marginal | Pass | Pass |
| JWS-2-20 | Fail | Fail | Pass | Fail | Fail | Marginal |
| JWS-2-22 | Pass | Pass | Pass | Pass | Pass | Pass |
| JWS-2-36 | Pass | Pass | Pass | Pass | Fail | Pass |
| JWS-2-40 | Pass | Pass | Pass | Marginal | Pass | Pass |
| RC-MC-156 | Pass | Pass | Pass | Pass | Pass | Pass |
| RC-MC-158 | Pass | Pass | Marginal | Pass | Pass | Pass |
| RC-MC-200 | Fail | Fail | Pass | Pass | Pass | Pass |
| RC-MC-205 | Fail | Fail | Pass | Marginal | Fail | Pass |
| TH-2-192 | Pass | Pass | Pass | Pass | Pass | Pass |

*Compounds indicated showed bactericidal activity at 1 or more high doses.

In Table 1, "Pass" indicates compounds that were not significantly above the control with respect to colony count (p<0.05).

7. Colormetric Ames Test Procedure

The following procedures were performed aseptically. First, the day before the assay, as late as possible in the day, the vial labeled "G" Nutrient Broth was dispensed into the vial labeled *S. typhimurium* TA100 (lyophilized). The mixture was incubated over night at 37° C. for about 16-18 hours.

In appropriate vial, about 50 mg of the test compound was weighed out. About 1 mL of DMSO was added, and the mixture was filter sterilized with 25 mm syringe filter into a sterile tube. The concentration of DMSO was noted.

In a sterile 50 mL tube, about 15 mL of sterile Davis Mingioli Salt (see Davis & Mingioli, Aromatic biosynthesis, VII. Accumulation of two derivatives of shikimic acid by bacterial mutants, J. Bacteriol. 1953. August; 66(2): 129-36) was pipetted. This salt solution (Muta Component "A") was comprised of (1) Milli-Q, 600 mL; (2) dipotassium phosphate, anhyd., 38.5 g; (3) monopotassium phosphate, anhyd. 11.0 g; (4) ammonium sulfate, 5.5 g; (5) trisodium citrate, 1.375 g; and (6) magnesium sulfate, 0.55 g. Appropriate volume of Milli-Q water was added to bring total volume to 1 L. Each component was dissolved one at a time in the above order. The solution was filtered through a 0.22 µm filter to remove sediment at a pH of about 7.3.

To the salt solution, small amounts of DMSO diluted compound was added, not to exceed 500 µl of DMSO. For example, about 100 µl aliquots of the DMSO diluted compound was added until the highest concentration is reached with compound still in solution. It was found that this may need to be repeated with a lower volume of DMSO diluted compound, if the compound falls out of solution and does not go back into solution with the addition of sterile DMSO and/or sonication for twenty minutes to an hour. The volume of DMSO diluted compound was noted in the total solution. When the highest concentration of compound was determined, an appropriate volume of sterile Davis Mingioli salts was added to bring the total volume of solution to 17.5 mL. The concentration of compound and DMSO in the test solution was then noted.

The components were then mixed in a 50 mL sterile tube labeled Reaction Mixture as follows: 21.62 mL of A+4.75 ml of B (D-glucose, 40% w/v)+2.38 mL of C (bromocresol purple, 5 mg/ml)+1.19 ml of D (D-biotin, 0.1 mg/ml)+0.060 ml (60 µl) of E (L-histidine, 0.1 mg/ml). The vial was vortexed and then set aside.

The S9 Mixture was prepared by reconstituting the S9 enzymes with 2.1 mL of sterile water. This was labeled "S9F." In a 50 mL tube labeled S9 Mixture, the following were mixed together (all available from EBIP): 0.4 mL of S9A (MgCl$_2$, 0.4 M and KCl, 1.65 M)+0.09 mL of S9B (glucose-6-phosphate, 1.0 M)+0.81 mL of S9C (nicotine amide di-nucleotide phosphate, 0.1 M)+9.98 mL of S9D (phosphate buffer, pH 7.4)+6.72 mL of S9E (sterile distilled water)+2 mL of S9F (Rate liver extract). The vial was vortexed and then set aside.

Sterile tubes were labeled as follows: Blank, Background I, Background II, Standard Mutagen, Compound 1 (−), Compound 1 (S9+), Compound 2 (−), Compound 2 (S9+), Compound 3 (−), Compound 3 (S9+). Next, about 2.5 mL of the reaction mix was added to each tube. Then, about 2 mL of the S9 mix was added to the Background II and the S9+ compounds. Next, to each of the compound vials, about 8 mL of the prepared compounds was added. The concentration of the compound in the final solution was noted. Then, about 100 µl of the standard mutagen was added to the Standard mutagen vial. (NaN$_3$ for non S9 activation and 2-aminoanthracene with S9 activation). The appropriate volume of sterile water was next added for a final volume of 17.5 mL. Then, about 5 µl of bacteria was added to each tube except the Blank. Each vial was vortexed and poured into a sterile multi-channel pipette boat, and pipette 200 µl per well into the 96 well plate with a multi channel pipetter. The plates were labeled, covered, placed in zip lock bag, and then incubated for 5 days at 37° C.

On day five of the incubation, the plates were removed from the incubator and placed in a laminar flow hood. The Blank was analyzed first. If there were any wells that were yellow, the test was considered contaminated and the results invalid. The plates were then scored visually in the following manner: (1) all yellow, partially yellow or turbid wells are scored as positives or (2) all purple wells are scored as negative (compare to negative control plates). The number of positive wells for each plate was recorded. The Background plates showed the level of spontaneous or background mutation of the assay organism. The results of each treatment plate were scored against the background mutations. For each treatment-plate, the statistical significance of the difference using the Table 4.1 provided with the kit was determined. See Gilbert, R. I., *The Analysis of Fluctuation Tests, Mutation Research*, at 283-289 (1980), which is incorporated by reference. If a treatment plate contained all purple wells, acute toxicity of the sample to the tester strain may have resulted.

Other references, which are incorporated by reference, with respect to the aforementioned Ames Tests protocols, are as follows: Ames, B., F. Lee, and W. Durston. 1973. *An improved bacterial test system for the detection and classification of mutagens and carcinogens*. Proc. Natl. Acad. Sci. USA 70: 782-786; McCann, J., N. Spingarn, J. Kobori, and B. Ames. 1975a. *Detection of carcinogens as mutagens: Bacterial tester strains with R Factor plasmids*. Proc. Natl. Acad. Sci. USA 72 979-983; McCann, J., E. Choi, E. Yamasaki, and B. Ames. 1975b. *Detection of carcinogens as mutagens in the Salmonella/microsome test: Assay of 300 chemicals.* Proc. Natl. Acad. Sci. USA 72: 5135-5139; and Mortelmans K, and E. Zeiger. 2000. *The Ames Salmonella/microsome mutagenicity assay.* Mutat Res. 455: 29-60.

The results of the assay was as follows:

| Compound | Concentration | without S9 | with S9 |
|---|---|---|---|
| JWS-2-132 | 360.1 μM | Pass* | Pass* |
| TH-3-130 | 182.3 μM | Pass* | Pass* |
| JWS-2-92 | 3.40 μM | Pass* | Pass* |
| JWS-2-100 | 246 μM | Pass* | Pass* |
| JWS-2-102 | 3.28 μM | Pass* | Pass* |
| JWS-2-104 | 6.12 μM | Pass* | Pass* |
| JWS-2-110 | 5.77 μM | Pass* | Pass* |
| JWS-2-120 | 11.48 μM | Pass* | Pass* |
| JWS-2-122 | 2.57 μM | Pass* | Pass* |
| LN-2-4 | 11.9 μM | Pass* | Pass* |
| JWS-2-112 | 1.39 μM | Pass* | Pass* |

Example 5

In Vivo Antispermatogenic Testing in Long Evans Rats

Male Long Evans rats were ordered in at day 55 and allowed a quarantine period of 5 days prior to inoculation. Water and food were given ad libitum. The day prior to testing all animals are weighed.

When the rats were 60 days old, the test compound was taken out of the refrigerator, and 480 mg of material was weighed. The material was then dissolved in 6.00 ml of dimethyl sulfoxide ("DMSO") (Fisher, Certified ACS, D128-500) to yield an 80 mg/ml solution. This solution was used for injecting the rats in the 200 mg/kg range.

In the case of lonidamine, it was necessary to add 1% concentrated HCl and sonicate for approximately 15 minutes to solubilize and suspend the material. Ice was placed in the sonicator to prevent overheating during this time.

About 1.00 ml of the 80 mg/ml solution was then added to 7 ml of DMSO to yield a final concentration of 10 mg/ml. This solution was used for injecting the rats in the 25 mg/kg range.

Both the 80 mg/kg and 10 mg/kg solutions were kept wrapped in foil until immediately prior to use. For controls, the animals were injected with DMSO only (or DMSO+1% HCl in the case of lonidamine). The rats were then weighed immediately prior to injection. The weight was converted to kilograms, multiplied by the treatment concentration and then divided by the concentration of the solution for that group. As an example, 250 g in the 200 mg/kg treatment group would be calculated as follows:

(a.) (0.250 kg)(200 mg/kg)/(80 mg/ml)=0.625 or 0.63 ml (b) The injections for the controls were done in the same manner by calculating the amount they would receive if they were in one of the treatment groups. That is, a 250 g control rat would also receive 0.63 ml (c) The amount of solution calculated for each rat was then drawn up in a sterile 1 cc tuberculin syringe capped with a 21 gauge needle and injected i.p. into the upper part of the left lower quadrant of the animal. The syringe was pulled back prior to injection to insure that the needle was not in a blood vessel or organ.

The animal was placed back in its cage and observed closely for the next few hours, and thereafter were checked at least once a day. All surviving animal were re-weighed on the second day post-injection. Five days following injection, the animals were re-weighed for the final time and then euthanized by carbon dioxide asphyxiation. Immediately following asphyxiation the animal was opened with a mid-sagittal abdominal incision and both the left and right testes were removed. The testes were trimmed of any extraneous tissue and weighed.

Following weighing, about 7-10 puncture holes were placed in the tunica albuginea using a number 11 scalpel blade, and the testes was then placed into 6 ml of Bouin's fixative for at least 48 hours at 4° C. The Bouin's fixative was prepared by mixing together: 125 ml of saturated picric acid (Sigma), 25 ml of glacial acetic acid (Fisher, A38-500), 375 ml of 37% Formaldehyde (Fisher F79-500). Alternatively, the testes were fixed in 10% formalin.

In at least two of the animals in each group, the pancreas, right kidney and part of the liver, heart, spleen, and lung were removed and evaluated for toxic effects. See Example 6 below.

After 48 hours, the testes were removed and cut in half in the mid-coronal region, then placed back in Bouin's for an additional 48 hours. A similar process was performed with the 10% formalin for testes fixed in formalin. Following the second 48 hours, the tissues were removed, placed in embedding cassettes, and then in two washes of 70% Ethanol to attempt to remove some of the fixative. The tissues were then embedded in paraffin using the following protocol. (a) 70% Ethanol, 1 hour, (b) 80% Ethanol, 1 hour, (c) 95% Ethanol, 40 min, (d) 95% Ethanol, 40 min, (e) 95% Ethanol, 40 min, (f) 100% Ethanol, 40 min, (g) 100% Ethanol, 40 min, (h) 100% Ethanol, 40 min, (i) Xylene subst., 1 hour, (j) Xylene subst., 1 hour, (k) Paraffin, 1.5 hour, (l) Paraffin, 1.5 hour. Then sections at 5 μm were cut and stained with H&E.

FIGS. 1A, 1B, 1C, 1D, 1E, 2A, 2B (RC-MC-30), 3A, 3B, 3C, 3D, 3E, 4A, 4B (RC-MC-86), 5A, 5B, 5C, 5D, 5E, 6A, 6B, 6C, 6D, 6E, 6G (RC-MC-110) show the change in body weight, left and/or right testes weight, staging, tubular development, and histologic testes effects for some of the compounds in accordance with the present invention. These results show that spermatogenesis was inhibited using the compounds of the present invention without adversely affecting the body weight of the subject. See J. M. Whitsett et al., *Effect of Transitional Photoperiods on Testicular Development and Puberty in Male Deer Mice, J. Reprod. Fertil.* 72 (2):277-286 (1984).

The dose response for the compounds of the present invention is shown in the following Table 2:

| Compound | Response 25 mg/kg | Mortality | Response 200 mg/kg | Mortality | Staging 25 mg/kg | Staging 200 mg/kg |
|---|---|---|---|---|---|---|
| Lonidamine | 2/5 | 0/5 | 5/5 | 0/5 | 4.7 | 1.8 |
| AF2785 | 1/5 | 0/5 | 3/4 | 2/6 | 5.5 | 3.4 |
| AF2364 | 3/5 | 0/5 | 5/5 | 0/5 | 3.5 | 2.1 |
| RC-MC-30 | 3/5 | 0/5 | 4/5 | 0/5 | 4.1 | 3.1 |
| RC-MC-60 | 0/5 | 0/5 | 0/5 | 0/5 | NA | NA |

-continued

| Compound | Response 25 mg/kg | Mortality | Response 200 mg/kg | Mortality | Staging 25 mg/kg | Staging 200 mg/kg |
|---|---|---|---|---|---|---|
| RC-MC-86 | 0/5 | 0/5 | 5/5 | 0/5 | 5.9 | 2.4 |
| RC-MC-101 | 0/5 | 0/5 | 0/5 | 0/5 | NA | NA |
| RC-MC-100 | 0/5 | 0/5 | 0/5 | 0/5 | 5.9 | 5.9~ |
| TH-2-192 | 0/5 | 0/5 | 0/4 | 4/5 | 5.9 | 5.8 |
| RC-MC-110 | 5/5 | 0/5 | 2/2 | 3/5 | NA | NA |
| DD-MC-1 | 0/5 | 0/5 | 2/5 | 0/5 | NA | NA |
| JWS-1-254 | 0/5 | 0/5 | 0/5 | 0/5 | NA | NA |
| JWS-1-270 | 0/5 | 0/5 | 0/5 | 0/5 | NA | NA |
| JWS-1-274 | 0/5 | 0/5 | 0/5 | 0/5 | NA | NA |
| JWS-1-276 | 0/5 | 0/5 | 0/5 | 0/5 | NA | NA |
| JWS-1-280 | 0/5 | 0/5 | 0/5 | 0/5 | NA | NA |
| JWS-2-12 | 0/5 | 0/5 | 0/5 | 0/5 | NA | NA |
| DD-MC-I | 0/5 | 0/5 | 2/5 | 0/5 | 5.9 | 4.5 |
| JWS-1-110 | 0/5 | 0/5 | 0/5 | 0/5 | NA | NA |
| JWS-1-114 | 1/5 | 0/5 | 0/5 | 0/5 | NA | NA |
| JWS-130 | 0/5 | 0/5 | 0/5 | 0/5 | NA | NA |
| JWS-1-142 | 0/5 | 0/5 | 0/5 | 0/5 | NA | NA |
| JWS-1-144 | 0/5 | 0/5 | Not tested due to insolubility | N/A | NA | NA |
| JWS-1-146 | 0/5 | 0/5 | Not tested due to insolubility | N/A | NA | NA |
| JWS-1-158 | 4/5 | 0/5 | 5/5 | 0/5 | NA | NA |
| JWS-1-160 | 3/5 | 0/5 | 3/3 | 2/5 | NA | NA |
| JWS-1-170 | 3/5 | 0/5 | 3/3 | 0/5 | 3.7 | 2.8 |
| JWS-1-190 | 5/5 | 0/5 | 0/0 | 5/5 | NA | |
| RC-MC-156 | 2/5 | 0/5 | 4/5 | 0/5 | NA | |
| RC-MC-158 | 2/5 | 0/5 | 5/5 | 0/5 | NA | |
| TH-2-178 remake TH-2-193 | 0/5 | 0/5 | 4/5 | 0/5 | 5.4 | 2.9 |
| TH-2-179 remake TH-2-194 | 2/5 | 0/5 | 5/5 | 0/5 | 4.7 | 2.0 |
| JWS-1-190 | 4/5 | 0/5 | 2/5 | 0/5 | 5/5 | 0/5 |

For dose response, the fraction represents the number of animals responding out of five and the animals surviving out of five. For the mortality, the fraction represents the number of animals dead out of five injected.

Example 6

The toxicology of animals receiving some of the compounds of the present invention IP and/or oral was examined. At the time of sacrifice samples of liver, pancreas, heart, lung, spleen and kidney were removed, visually inspected, and immersion fixed in Bouin's solution for a minimum of 48 hours. All organs were then sectioned and examined for evidence of necrosis, inflammation, hemorrhage, and possible tumors. The major veins in each tissue were also examined for distention, especially in the liver and pancreas, and any other abnormalities are compared to known histopathological states. In addition to the above, the heart was examined for evidence of fibrosis in the muscular walls, and to compare the thickness of the ventricular walls. The pancreas was examined mainly for calcium deposits, while the lung was checked for signs of any exudates or hemorrhage, especially in the alveolar spaces. Finally, the kidney was examined mainly for microscopic hemorrhages, tubular necrosis or alterations in the glomeruli in the cortex.

Example 6A

Toxicology Comparison RC-MC-30 Versus Lonidamine

In this example, the effects of RC-MC-30 were compared with those of lonidamine in sexually mature rats. As discussed above, each of the rats (8 total) received a single injection and were sacrificed five days after injection and examined. The following tables (Table 3A-3B) illustrates the findings

TABLE 3A

| | Lonidamine | | |
|---|---|---|---|
| | Liver and Pancreas | Kidney | Dosage mg/kg |
| Animal 101 | Non-remarkable, no evidence of inflammation, necrosis, hemorrhage or tumor | Non-remarkable, no evidence of inflammation, necrosis, hemorrhage or tumor | 25 |
| Animal 104 | Non-remarkable, no evidence of inflammation, necrosis, hemorrhage or tumor | Non-remarkable, no evidence of inflammation, necrosis, hemorrhage or tumor | 25 |

TABLE 3A-continued

Lonidamine

| | Liver and Pancreas | Kidney | Dosage mg/kg |
|---|---|---|---|
| Animal 37 | Some areas of the liver contained arteries and veins engorged with blood, while other areas did not appear to be congested. Otherwise, no evidence of inflammation, necrosis, hemorrhage or tumor. | Some engorgement of arteries, otherwise non-remarkable with no evidence of inflammation, necrosis, hemorrhage or tumor | 200 |
| Animal 40 | Same as for Animal 37 except that the Pancreas also had engorged arteries and veins | Swollen arterioles, large amounts of blood mainly between the proximal tubules | 200 |

TABLE 3B

RC-MC-30

| | Liver and Pancreas | Kidney | Dosage mg/kg |
|---|---|---|---|
| Animal 126 | Non-remarkable, no evidence of inflammation, necrosis, hemorrhage or tumor | Small areas with blood between the tubules, may have been due to the way it was cut. Otherwise no evidence of inflammation, necrosis, hemorrhage or tumor | 25 |
| Animal 127 | Non-remarkable, no evidence of inflammation, necrosis, hemorrhage or tumor | Same as for animal 126, a few more areas of possible hemorrhage | 25 |
| Animal 131 | Non-remarkable, no evidence of inflammation, necrosis, hemorrhage or tumor | Patchy hemorrhagic areas, some showing evidence of hemosiderin. Again could be due to cutting. Otherwise, no evidence of inflammation, necrosis, hemorrhage or tumor | 200 |
| Animal 132 | Non-remarkable, no evidence of inflammation, necrosis, hemorrhage or tumor | Patchy hemorrhagic areas, some showing evidence of hemosiderin. Again could be due to cutting. Otherwise, no evidence of inflammation, necrosis, hemorrhage or tumor | 200 |

Example 6B

Toxicology Results for RC-MC-110

In this example, the toxicology results of RC-MC-110 were investigated compared to controls. Two controls and four animals receiving RC-MC-110 were investigated.

In the two controls (Animal 261 and 262), the liver, lung, pancreas, spleen, heart and kidney all appeared within normal limits. No sign of necrosis or hemorrhage were apparent in any of the tissues. The heart showed no signs of dilation or hypertrophy in the ventricular walls.

Animals receiving 25 mg/kg and 200 mg/kg of RC-MC-110 were also investigated. The liver, lung, pancreas, spleen, heart and kidney all appear within normal limits in the two animals receiving 25 mg/kg (animal 266 and 267) and those receiving 200 mg/kg (animal 271 and 274). No sign of necrosis or hemorrhage in any of the tissues were revealed. The heart showed no signs of dilation or hypertrophy in the ventricular walls.

In a separate experiment, five animals were given 200 mg/kg of RC-MC-100. Approximately 10 minutes after IP injection, all 5 animals tested became lethargic and ceased moving. At 15 to 20 minutes post-injection, all of the animals in this group began to have minor tremors in both hindlimbs which lasted approximately 30 minutes. Two of the animals also had wet rates with their breathing being audible within 5 feet of their cage. Three of the animals died 2-3 hours later, while the other two recovered and did not show any other symptoms.

In a follow-up experiment, the toxicology of animals receiving 6 mg/kg and 12 mg/kg of RC-MC-110 were investigated. For Animal 286 (6 mg/kg), the lung, pancreas, spleen, heart and kidney all appeared within normal limits. There was no evidence of necrosis, tumor or hemorrhage in any of the tissues. The heart showed no sign of dilatation or hypertrophy in the ventricular walls. The liver did have isolated, scattered, small necrotic patches. For Animal 287 (6 mg/kg), the lung, pancreas, spleen, heart and kidney all appeared within normal limits. There was no evidence of necrosis, tumor or hemorrhage in any of the tissues. The heart showed no sign of dilatation or hypertrophy in the ventricular walls. The liver did have isolated, scattered, small necrotic patches, resembling what is often found in subacute hepatic necrosis.

For Animal 291 (12 mg/kg), the lung, pancreas, spleen, heart and kidney all appeared within normal limits. There was no evidence of necrosis, tumor or hemorrhage in any of the tissues. The heart showed no sign of dilatation or hypertrophy in the ventricular walls. The liver did have isolated, scattered, small necrotic patches, resembling what is often found in subacute hepatic necrosis. For Animal 292 (12 mg/kg), the pancreas, spleen, heart and kidney all appeared within normal limits. There was no evidence of necrosis, tumor or hemorrhage in any of the tissues. The heart did not show any signs of dilatation or hypertrophy in the ventricular walls. The liver contained small, patchy areas of necrosis resembling what is often described for subacute hepatic necrosis. The lungs also had multiple, small hemorrhagic areas around the respiratory and terminal bronchioles.

Example 6C

Toxicology Results for RC-MC-110 Compared to Lonidamine

In this example, the toxicology of animals receiving varying amounts of RC-MC-110 and 25 mg/kg of lonidamine were investigated. Controls were corn oil only.

In the two controls using corn oil (Animals 326 and 327) and those receiving 25 mg/kg of lonidamine (Animals 356 and 357), the liver, lung, pancreas, spleen, heart and kidney all appeared normal. There was no evidence of necrosis, tumor or hemorrhage in any of the tissues. The heart showed no sign of dilatation or hypertrophy in the ventricular walls.

In two animals from each of the four dose levels of oral 6 mg/kg, 3 mg/kg, 1 mg/kg and 0.5 mg/kg of RC-MC-110 (Animal 331 and 332), the liver, lung, pancreas, spleen, heart and kidney all appeared within normal limits. There was no evidence of necrosis, tumor or hemorrhage in any of the tissues. In one animal receiving 1.5 mg/kg of RC-MC-110 (Animal 341), the liver showed a small number of randomly scattered, small necrotic patches, but was otherwise normal. The other animal receiving 1.5 mg/kg appeared normal.

Example 6D

Toxicology Results for JWS-1-110

In this example, the toxicology of animals receiving 25 mg/kg and 200 mg/kg of JWS-1-110 were investigated. Controls were DMSO only. For Animal 306 (25 mg/kg), the liver, lung, pancreas, heart and kidney all appeared within normal limits. There was no sign of necrosis, tumor or hemorrhage in any of the tissues. The heart did not have any signs of dilatation or hypertrophy in the ventricular walls. The spleen had distended veins and necrosis in the white pulp, often early indicators of portal hypertension. The pancreas, heart and kidney of Animal 307 (25 mg/kg) all appeared within normal limits. There was no sign of necrosis, tumor, or hemorrhage in any of the tissues. The heart did not have any signs of dilatation or hypertrophy in the ventricular walls. The liver had distended portal veins with surrounding small patches of hepatic necrosis. The lung contained scattered hemorrhagic areas around the alveoli and terminal bronchioles. Also, the spleen had distended veins and diminished amounts of white pulp containing necrotic cells.

For Animal 311 (200 mg/kg), the kidney, heart and pancreas appeared to be within normal limits with no signs of necrosis, tumor or hemorrhage. The heart did not have any signs of dilatation or hypertrophy in the ventricular walls. The liver showed distended portal veins with scattered, small patches of necrosis. The lung contained multiple hemorrhagic areas throughout the alveoli, and terminal and respiratory bronchioles. Some of these hemorrhagic patches were causing distention between adjacent compartments. Finally, the spleen demonstrated distended veins, and diminished white pulp with necrotic cells. For Animal 312 (200 mg/kg), the kidney, heart, and lung appeared to be within normal limits with no signs of necrosis, tumor or hemorrhage. The heart was split so it was not possible to determine if ventricular dilatation is present, but there did not appear to be any hypertrophy of the ventricular walls. The liver had distended veins, with scattered, small patches of necrosis throughout. The pancreas had distended veins, but no other noticeable abnormalities. Finally, the spleen demonstrated distended veins, and diminished white pulp with necrotic cells.

Example 6E

Toxicology Results for JWS-1-114

In this example, the toxicology of animals receiving 25 mg/kg and 200 mg/kg of JWS-1-114 were investigated. Controls were DMSO only. Animals 316 and 317 (25-mg/kg) had a liver, lung, pancreas, spleen, heart and kidney that appeared within normal limits. There was no sign of necrosis, tumor or hemorrhage in any of the tissues. The heart did not have any signs of dilatation or hypertrophy in the ventricular walls.

Animal 321 (200 mg/kg) had a pancreas, heart, and kidney that appeared within normal limits. There was no sign of necrosis, tumor or hemorrhage in any of the tissues. The heart did not have any signs of dilatation or hypertrophy in the ventricular walls. The lung had massive pulmonary hemorrhaging around the bronchioles, with congested, distended regions between the alveolar clusters. The liver had moderate sized (5-10 cell in diameter) necrotic patches generally in the periportal areas, however, there was no evidence of venous distension. There was no spleen sample for this animal. Animal 322 (200 mg/kg) exhibited a liver, lung, pancreas, spleen, heart and kidney that appeared within normal limits. There was no sign of necrosis, tumor or hemorrhage in any of the tissues. The heart did not have any signs of dilatation or hypertrophy in the ventricular walls.

Example 6F

Toxicology Results for JWS-1-130

In this example, the toxicology of animals receiving 25 mg/kg and 200 mg/kg of JWS-1-130 were investigated. Controls were corn oil only. For Animal 366 (25 mg/kg), the lung, pancreas, spleen, heart and kidney all appeared within normal limits. There was no sign of necrosis, tumor or hemorrhage, although the heart did have some artificial tears from cutting the section out from the ventricles. The heart showed no evidence of hypertrophy or dilation in the ventricular walls. The liver appeared to have distended veins throughout, but no other abnormalities were noted. For Animal 367 (25 mg/kg), the lung, pancreas, spleen, heart and kidney all appeared within normal limits. There was no sign of necrosis, tumor or hemorrhage in any of the tissues. The heart did not have any signs indicating dilation or hypertrophy in the ventricular walls. The liver did have distended veins throughout, with small scattered patches of necrosis, usually located around the periportal areas.

For Animal 371 (200 mg/kg), the liver, lung, pancreas, spleen, heart and kidney all appeared within normal limits. There was no sign of necrosis, tumor or hemorrhage in any of the tissues. The heart did not have any signs indicating dilation or hypertrophy in the ventricular walls. For Animal 372, the lung, pancreas, spleen, heart and kidney all appeared within normal limits. There was no sign of necrosis, tumor or hemorrhage in any of the tissues. The heart did not have any signs indicating dilation or hypertrophy in the ventricular walls. The liver did have distended veins throughout, with small scattered patches of necrosis, usually located around the periportal areas.

Example 6G

Toxicology Results for JWS-1-142

In this example, the toxicology of animals receiving 25 mg/kg and 200 mg/kg of JWS-1-142 were investigated. Controls were corn oil only. For both Animal 376 and 377 (25 mg/kg), the liver, lung, pancreas, spleen, heart and kidney all appeared within normal limits. There was no sign of necrosis, tumor or hemorrhage in any of the tissues. The heart did not have any signs indicating dilation or hypertrophy in the ventricular walls.

For Animal 381 (200 mg/kg), the lung, pancreas, spleen, heart and kidney all appeared within normal limits. There was no sign of necrosis, tumor or hemorrhage in any of the tissues. The heart did not have any signs indicating dilation or hypertrophy in the ventricular walls. The liver contained a small, confined cluster of lymphocytes in the parenchyma. For Animal 382 (200 mg/kg), the liver, lung, pancreas, spleen, heart and kidney all appeared within normal limits. There was no sign of necrosis, tumor or hemorrhage in any of the tissues. The heart did not have any signs indicating dilation or hypertrophy in the ventricular walls.

Example 6H

Toxicology Results for JWS-1-146

In this example, the toxicology of animals receiving 25 mg/kg of JWS-1-146 were investigated. Controls were corn oil only. Animal 396 and 397 (25 mg/kg) had a liver, lung, pancreas, spleen, heart and kidney that appeared within normal limits. There was no sign of necrosis, tumor or hemorrhage in any of the tissues. The heart did not have any signs indicating dilation or hypertrophy in the ventricular walls.

Example 6I

Toxicology Results for JWS-1-144

In this example, the toxicology of animals receiving 25 mg/kg of JWS-1-144 were investigated. Controls were DMSO only. Animal 441 and 442 (25 mg/kg) had a liver, lung, pancreas, spleen, heart and kidney that appeared within normal limits. There was no sign of necrosis, tumor or hemorrhage in any of the tissues. The heart did not have any signs indicating dilation or hypertrophy in the ventricular walls.

Example 6J

Toxicology Results for JWS-1-170

In this example, the toxicology of animals receiving 25 mg/kg and 200 mg/kg of JWS-1-170 were investigated. Controls were DMSO only. Animal 456 and 457 (25 mg/kg) had a liver, lung, pancreas, spleen, heart and kidney that appeared within normal limits. There was no sign of necrosis, tumor or hemorrhage in any of the tissues. The heart did not have any signs indicating dilation or hypertrophy in the ventricular walls For Animal 462 (200 mg/kg), the liver, lung, pancreas, spleen, heart and kidney all appeared within normal limits. There was no evidence of necrosis, tumor, or hemorrhage in any of the tissues. The heart showed no sign of dilatation or hypertrophy in the ventricular walls. For Animal 463 (200 mg/kg), the lung, pancreas, spleen, heart and kidney all appeared within normal limits. There was no evidence of necrosis, tumor, or hemorrhage in any of the tissues. The heart showed no sign of dilatation or hypertrophy in the ventricular walls. The liver did have moderate patches (5-10 cells in diameter) of necrosis mainly in the periportal areas.

Example 6K

Toxicology Results for JWS-1-190

In this example, the toxicology of animals receiving 25 mg/kg of JWS-1-190 were investigated. Controls were DMSO only. For Animal 466, the liver, pancreas, spleen, heart and kidney all appeared within normal limits. There is no evidence of necrosis, tumor, or hemorrhage in any of the tissues. The heart did not show any sign of dilatation or hypertrophy in the ventricular walls. The lung did have multiple, scattered hemorrhagic patches in the alveolar clusters, and many of the alveoli were filled with a clear exudates that appeared to stain lightly with eosin. For Animal 467, the liver, lung, pancreas, spleen, heart and kidney all appeared within normal limits. There was no evidence of necrosis, tumor, or hemorrhage in any of the tissues. The heart showed no sign of dilatation or hypertrophy in the ventricular walls.

Example 6L

Toxicology Results for RC-MC-156

In this example, the toxicology of animals receiving 25 mg/kg and 200 mg/kg of RC-MC-156 were investigated. Controls were DMSO only. For Animal 476 (25 mg/kg), the liver, pancreas, spleen, heart and kidney all appeared within normal limits. There was no evidence of necrosis, tumor, or hemorrhage in any of the tissues. The heart did not show any signs of dilatation or hypertrophy in the ventricular walls. The lung did have scattered small, hemorrhagic patches, mainly in the alveolar and terminal bronchiole regions. For Animal 477 (25 mg/kg), the liver, pancreas, spleen, heart and kidney all appear within normal limits. There was no evidence of necrosis, tumor, or hemorrhage in any of the tissues. The heart did not show any signs of dilatation or hypertrophy in the ventricular walls. The lung showed widespread hemorrhagic regions throughout the alveoli and terminal bronchioles with small hemosiderin deposits around a few smaller bronchioles.

For Animal 481 (200 mg/kg), the liver, lung, pancreas, spleen, heart and kidney all appeared within normal limits. There was no evidence of necrosis, tumor, or hemorrhage in any of the tissues. The heart shows no sign of dilatation or hypertrophy in the ventricular walls. For Animal 482 (200 mg/kg), the pancreas, spleen, heart and kidney all appear within normal limits. There was no evidence of necrosis, tumor, or hemorrhage in any of the tissues. The heart showed no sign of dilatation or hypertrophy in the ventricular walls. The lung had small, scattered areas of hemorrhage mainly around the alveoli and small bronchioles. The liver had small (4-5 cells in diameter) patches of necrosis scattered throughout the parenchyma which resembles what is normally found in subacute necrosis.

Example 6M

Toxicology Results for RC-MC-158

In this example, the toxicology of animals receiving 25 mg/kg and 200 mg/kg of RC-MC-158 were investigated. Controls were DMSO only. For Animal 486 (25 mg/kg), the liver, lung, pancreas, spleen, heart and kidney all appeared within normal limits. There was no evidence of necrosis, tumor, or hemorrhage in any of the tissues. The heart shows no sign of dilatation or hypertrophy in the ventricular walls. For Animal 487 (25 mg/kg), the liver, pancreas, spleen, heart and kidney all appeared within normal limits. The lung did have small scattered hemorrhagic areas, mainly around the alveoli and terminal bronchioles.

For Animal 491 (200 mg/kg), the liver, pancreas, spleen, heart and kidney all appeared within normal limits. There was no evidence of necrosis, tumor or hemorrhage in any of the tissues. The heart showed no sign of dilatation or hypertrophy in the ventricular walls. The lung had multiple, large hemorrhagic areas, mainly in the alveolar regions with some hemosiderin deposits. For Animal 492, the pancreas, spleen, heart and kidney all appeared within normal limits. There was no evidence of necrosis, tumor or hemorrhage in any of the tissues. The heart showed no sign of dilatation or hypertrophy. The lung contained multiple large hemorrhagic areas, mainly in the alveoli. The liver contained small, scattered necrotic areas, generally around the portal veins.

Example 6N

Toxicology Results for JSW-1-158

In this example, the toxicology of animals receiving 25 mg/kg and 200 mg/kg of JSW-1-158 were investigated. Controls were DMSO only. Both controls had moderate areas of necrosis between the periportal areas, and the cytoplasm appeared to be washed out in many areas. For Animal 406 (25 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles. For Animal 407, the liver, pancreas, spleen, heart and kidney all appeared within normal limits. There was no sign of necrosis, tumor or hemorrhage in any of the tissues. The heart showed no signs of dilatation or hypertrophy in the ventricles. The lung had thickening of the alveolar and bronchiole walls, and scattered areas of moderate sized hemorrhaging covering several adjacent alveoli.

For Animal 411 (200 mg/kg), the liver, lung, spleen, heart and kidney all appeared within normal limits. There was no sign of necrosis, tumor or hemorrhage in any of the tissues. The heart shows no signs of dilatation or hypertrophy in the ventricles. The pancreas had areas of lymphocytic infiltrates extending from the periphery inwards between the acinar cells. For Animal 412 (200 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles.

Example 6O

Toxicology Results for JSW-1-160

In this example, the toxicology of animals receiving 25 mg/kg and 200 mg/kg of JSW-1-160 were investigated. Controls were DMSO only. Both controls had moderate areas of necrosis between the periportal areas, and the cytoplasm appeared to be washed out in many areas. For Animal 416 (25 mg/kg), the lung, pancreas, spleen and heart all appeared within normal limits. There was no sign of necrosis, tumor, or hemorrhage in any of the tissues. The heart showed no signs of dilatation or hypertrophy in the ventricles. The kidney does have scattered, small patches of tubular necrosis in the inner cortex, closer to the medullary-cortical border than the periphery. The liver had several distended veins, but no other abnormalities were noted. For Animal 417 (25 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles.

For Animal 421 (200 mg/kg), the liver, lung, pancreas, spleen, and heart all appeared within normal limits. There was no sign of necrosis, tumor or hemorrhage in any of the tissues. The heart showed no signs of dilatation or hypertrophy in the ventricles. The kidney did have scattered, small patches of tubular necrosis in the inner cortex. For Animal 422, the liver, lung, pancreas, spleen, heart and kidney all appeared within normal limits. There was no sign of necrosis, tumor or hemorrhage in any of the tissues. The heart showed no signs of dilatation or hypertrophy in the ventricles.

Example 6P

Toxicology Results for JSW-1-162

In this example, the toxicology of animals receiving 25 mg/kg and 200 mg/kg of JSW-1-162 were investigated. Controls were DMSO only. Both controls had moderate areas of necrosis between the periportal areas, and the cytoplasm appeared to be washed out in many areas. For Animals 426 and 427 (25 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles For Animal 431 (200 mg/kg), the liver, pancreas, spleen, heart and kidney all appeared within normal limits. There was no sign of necrosis, tumor or hemorrhage in any of the tissues. The heart showed no signs of dilatation or hypertrophy in the ventricles. The lung had scattered hemorrhagic patches surrounding many of the small bronchioles, generally with thickening of the alveolar walls in the immediate vicinity. For Animal 432 (200 mg/kg), the liver, pancreas, spleen, heart and kidney all appeared within normal limits. There was no sign of necrosis, tumor or hemorrhage in any of the tissues. The heart showed no signs of dilatation or hypertrophy in the ventricles. The lung had moderate regions showing thickening of the alveolar walls, with a clear exudates slightly stained by eosin filling the alveoli.

Example 7

Fertility Trials Following Oral Administration of Compounds

The following table (Table 4A) illustrates the results of a single oral dose of 6 mg/kg of RC-MC-110 orally to male rats. The compounds were dissolved in a minimum amount of 10% ethyl alcohol and mixed with corn oil. The ethyl alcohol was evaporated 10% prior to administration. The "embryos normal" and "embryos abnormal" represents the mean number of embryos per pregnant female.

TABLE 4A

Fertility of Male Rats Following
Seven Consecutive Daily Oral Doses of 6 mg/day of RC-MC-110

| | CONTROLS | | | | EXPERIMENTAL | | | |
|---|---|---|---|---|---|---|---|---|
| WEEK | Males mated | Males fertile | Embryos normal[1] | Embryos abnormal[1] | Males mated | Males fertile | Embryos normal[1] | Embryos abnormal[1] |
| 1 | 7 | 7 | 15 | 0.1 | 7 | 7 | 15 | 0.2 |
| 2 | 7 | 7 | 14 | 0.6 | 7 | 7 | 13 | 0.3 |
| 3 | 7 | 7 | 14 | 0.2 | 7 | 2 | 7 | 0 |
| 4 | 7 | 7 | 14 | 0.1 | 7 | 3 | 7 | 0.5 |
| 5 | 7 | 7 | 14 | 0.6 | 7 | 0 | 0 | 0 |
| 6 | 7 | 7 | 15 | 0.3 | 7 | 0 | 0 | 0 |
| 7 | 7 | 7 | 14 | 0.3 | 7 | 0 | 0 | 0 |
| 8 | 7 | 7 | 14 | 0.3 | 6 | 0 | 0 | 0 |
| 9 | 7 | 7 | 14 | 0.5 | 7 | 1 | 9 | 1 |
| 10 | 7 | 7 | 14 | 0.5 | 7 | 1 | 2 | 0 |
| 12 | 7 | 7 | 14 | 0.4 | 7 | 2 | 14 | 0.3 |
| 13 | 7 | 7 | 13 | 0.3 | 7 | 2 | 15 | 0.3 |
| 14 | 7 | 7 | 15 | 0.3 | 7 | 2 | 14 | 0 |
| 18 | 7 | 7 | 15 | 0.4 | 7 | 2 | 14 | 0 |

The following table (Table 4B) illustrates the results of a single oral dose of 6 mg/kg/day of RC-MC-110 orally to male rats.

TABLE 4B

Fertility of Male Rats Following a Single Oral Dose of 6 mg/kg of RC-MC-110.

| | CONTROLS | | | | EXPERIMENTAL | | | |
|---|---|---|---|---|---|---|---|---|
| WEEK | Males mated | Males fertile | Embryos normal[2] | Embryos abnormal[1] | Males mated | Males fertile | Embryos normal[1] | Embryos abnormal[1] |
| 1 | 7 | 7 | 15 | 0.1 | 7 | 7 | 15 | 0.2 |
| 2 | 7 | 7 | 14 | 0.6 | 7 | 7 | 12 | 0.3 |
| 3 | 7 | 7 | 14 | 0.2 | 7 | 2 | 6 | 2 |
| 4 | 7 | 7 | 14 | 0.1 | 7 | 0 | 0 | 0 |
| 5 | 7 | 7 | 14 | 0.6 | 7 | 0 | 0 | 0 |
| 6 | 7 | 7 | 15 | 0.3 | 7 | 1 | 10 | 1 |
| 7 | 7 | 7 | 14 | 0.3 | 7 | 2 | 13 | 0 |
| 8 | 7 | 7 | 14 | 0.3 | 7 | 3 | 12 | 1 |
| 9 | 7 | 7 | 14 | 0.5 | 7 | 4 | 12 | 0.4 |
| 10 | 7 | 7 | 14 | 0.5 | 7 | 3 | 11 | 1 |
| 12 | 7 | 7 | 14 | 0.4 | 7 | 4 | 14 | 0.1 |
| 13 | 7 | 7 | 13 | 0.3 | 7 | 3 | 14 | 1.0 |
| 14 | 7 | 7 | 15 | 0.3 | 7 | 4 | 11 | 0.7 |
| 18 | 7 | 7 | 15 | 0.4 | 7 | 4 | 14 | 0.7 |
| 26 | 7 | 7 | 15 | 0.6 | 7 | 3 | 13 | 0.6 |

[1]Mean number of normal or abnormal embryos per pregnant female
[2]Mean number of normal or abnormal embryos per pregnant female The following table (Table 4C) illustrates the results of a single oral dose of four different doses of RC-MC-110 orally to male rats.

TABLE 4C

Challenge Mating Studies Following a Single Oral Dose of RC-MC-110 in 10% Ethyl Alcohol and Sesame Oil

| | MALES MATED/MALES FERTILE | | | |
|---|---|---|---|---|
| WEEK | 0.75 MG/KG | 1.5 MG/KG | 3.0 MG/KG | 6.0 MG/KG |
| 1 | 6/6 | 6/5 | 6/6 | 7/7 |
| 2 | 8/8 | 6/6 | 6/6 | 7/7 |
| 3 | 6/6 | 6/5 | 6/3 | 7/2 |
| 4 | 6/6 | 6/5 | 6/2 | 7/0 |
| 5 | 6/6 | 6/6 | 6/6 | 7/0 |
| 6 | 6/6 | 6/6 | 6/6 | 7/1 |
| 7 | 6/6 | 6/6 | 6/6 | 7/2 |
| 8 | 6/6 | 6/6 | 6/6 | 7/3 |
| 9 | | 6/6 | 6/6 | 7/4 |
| 10 | | | | 7/3 |
| 12 | | | | 7/4 |
| 13 | | | | 7/3 |
| 14 | | | | 7/4 |

Example 8

Compounds that Inhibit Spermatogenesis

As discussed above, it has been shown that some of the compounds of the present invention bind to Hsp90 and EF1-alpha and function to inhibit spermatogenesis. It is thus contemplated that other compounds that bind to one of both of these proteins may inhibit spermatogenesis. Thus, the present invention is broadly directed to a method of inhibiting spermatogenesis by administering a therapeutically effective amount of a compound that inhibits the action of Hsp90 and/or EF1-alpha.

Several known Hsp90 inhibitors are listed above. With regard to HSP90, RC-MC-110 likely a novel inhibitor of the N-terminal ATP binding site or a novel site on Hsp90. It should be noted that mutants of Hsp90 in *Drosophila* (fruitfly) produce sterile males and females. See Yue L, Karr T L, Nathan D F, Swift H, Srinivasan S, Lindquist S. *Genetic analysis of viable Hsp90 alleles reveals a critical role in Drosophila spermatogenesis*. Genetics. 1999 March; 151(3): 1065-79. When lonidamine and RC-MC-110 were provided to a fruitfly, both inhibited reproduction. However, RC-MC-110 was more potent than lonidamine.

In addition, since elongation factor 1-alpha (EF1a) is a GTP binding protein, it is contemplated that certain nucleotide analogues or certain inhibitors of GTP binding pockets should work as contraceptives. Ubiquitin-aldehyde, an inhibitor of certain peptidases may also inhibit EF1a. See Gonen H, Smith C E, Siegel N R, Kahana C, Merrick W C, Chakraburtty K, Schwartz A L, Ciechanover A. *Protein synthesis elongation factor EF-1 alpha is essential for ubiquitin-dependent degradation of certain N alpha-acetylated proteins and may be substituted for by the bacterial elongation factor EF-Tu*. Proc Natl Acad Sci USA. 1994 Aug. 2; 91(16): 7648-52.

Example 9

For initial screening and characterization of anti-spermatogenic activity, control and test groups each contained five male Long-Evans rats 65-70 days old (250-274 g). Initial screening was performed in three groups of animals receiving single IP injection of 25 mg/kg, 200 mg/kg, or equivalent volume of vehicle control (at 2.5 ml/kg). Compounds that were more potent than LND by IP administration at the 25 mg/kg dose were then tested by oral administration (single oral gavage) and included in mating trials. For oral administration, gamendazole was formulated in 10% ethanol/sesame oil. For the mating trials, one group of rats (seven per group) was treated with vehicle (5 ml/kg), and the remaining groups were treated with gamendazole at 0.75, 1.5, 3.0, or 6.0 mg/kg, as a single dose, or 6.0 mg/kg/day for 7 days.

Tissues were processed for histology. In experiments using lonidamine as a standard, disruption of the germinal epithelium was noted 48 hrs after single IP injection. However, the lumens of the seminiferous tubules were filled with released cells making it impossible to assess spermatogenic index. Between 5 and 7 days after a single administration, clearance of shed cells and debris from the lumens had stabilized making it possible to quantify spermatogenic index. Early experiments used euthanasia on day 7, but later 5 days was chosen to reduce costs with no effect on the resulting data. Animals were euthanized and the testes removed and weighed. Testes were processed for histology as described previously [20] except that the tissue was stained with Hematoxylin & Eosin. The post-mating trial testes sections were stained with PAS-hematoxylin. In the initial screening experiments described above, at euthanasia two animals from each group were randomly selected for tissue necropsy examination (including brain, lung, stomach, heart, liver, spleen, kidneys, and gut). In cases where animals died or were euthanized prior to the 5 day post-treatment schedule (for AF2785 this was 2 of 6 animals at 200 mg/kg IP, and for gamendazole this was 3 of 5 animals at 200 mg/kg IP), these rats were also subjected to necropsy examination. The tissues from this screening experiment were evaluated by a veterinary pathologist to provide initial information on potential toxicity. More detailed and extensive toxicity studies are needed to further evaluate the toxicity of gamendazole.

AF2785 and AF2364 (FIG. 2) were synthesized and tested to compare with LND analogues already reported in the literature. Of previously published compounds, only AF2785 and AF2364 were chosen as reference standards to LND because all other previous indazole carboxylic acid analogues were less potent, more toxic, and or poorly reversible.

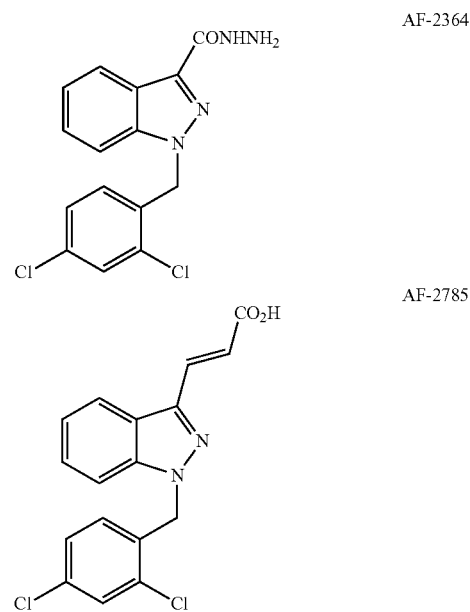

Figure 7:
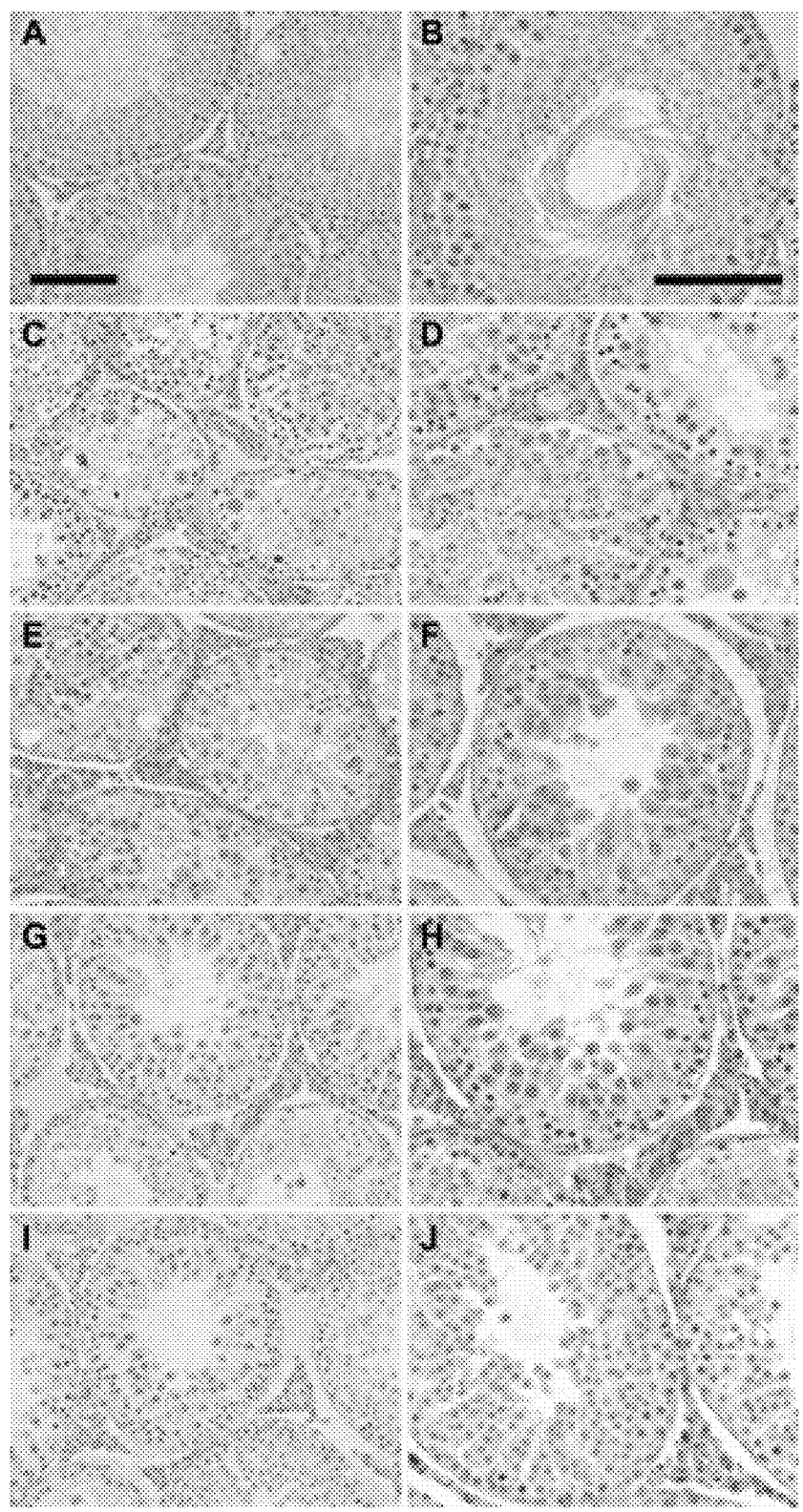
FIG. 7 includes images that provide a comparison of single doses of gamendazole or lonidamine (LND) on testicular histology: Panels A-B show testis from control animal administered vehicle alone; Panels C-D show testis from an animal that responded to IP 25 mg/kg LND; Panels E-F show testis from IP 25 mg/kg gamendazole-treated animal; Panels G-H show testis from oral 6 mg/kg gamendazole-treated animal; Panels I-J show testis from oral 3 mg/kg gamendazole-treated animal. Panels A, C, E, G, and I are all the same magnification, Bar=200 μm. Panels B, D, F, H, and J are all the same magnification, Bar=200 μm.

To rank AF2785, AF2364, and the newly designed compounds based on efficacy relative to lonidamine (LND), dose-response experiments were first conducted to identify a dose of LND that would give a response in ~50% of the animals tested as follows: A positive response in an animal was based on a reduction in testis weight greater than 30% five days after a single compound administration as well as a loss of spermatids (5 or less per tubule) in more than 50% of the tubules. For all compounds that elicited a response reductions in testis weight always matched loss of spermatids. Using these criteria, 25 mg/kg LND was found to give an average 50% response (i.e. >2 animals per group) in replicate groups of five animals. Using the same criteria, for AF2785, AF2364, and most of the new analogues that had an anti-spermatogenic effect, the response was usually "all or none". In other words, animals that did not respond were nearly identical in testis weight to controls, and testicular histology appeared near normal. In responding animals, the testes were routinely 30 to 50% lower in weight than controls, and histology revealed at least 75% of the tubules with five or fewer spermatids. Similar findings were observed in rats evaluated 7 days after oral administration of LND or gamendazole at 25 mg/kg. Testicular weights were decreased by 32% ($p<0.02$) and 54% ($p<0.0001$) in LND- and gamendazole-treated rats, respectively. In addition, the percentage of tubules exhibiting normal morphology were significantly decreased ($p<0.05$) by oral treatment with LND (32±10%) and gamendazole (1±1%) as compared to vehicle-treated rats (99±1%; mean±SE, n=6, based on Kruskal-Wallis ANOVA on ranks followed by SNK test). In the responding animals, the disrupted germinal epithelium appeared identical to what has been published previously (FIG. 7). LND at a dose of 400 mg/kg is near the reported $LD_{50}$ and caused 40% mortality, whereas no animal losses occurred at all of the lower doses of LND. Thus, for routine screening we used two doses to test new analogues. A low dose of 25 mg/kg was used so that potency relative to LND could be determined; and a high dose of 200 mg/kg was given to screen for toxicity and determine whether increased mortality resulted relative to LND and two other analogues, AF2785 and AF2364.

Table 5 summarizes the results for gamendazole, LND, AF2785, and AF2364. No mortality was observed with any LND analogue or gamendazole at the 25 mg/kg dose; however, gamendazole was the only analogue with 100% efficacy at this dose. In contrast, mortality was observed at the 200 mg/kg dose of AF2785 and gamendazole.

TABLE 5

Summary of Anti-spermatogenic Response and Mortality Data in Rats after Single IP Administration of LND and a selected group of analogues.

| Compound | *Response (Five days post-treatment with a single dose of 25 mg/kg IP) | Mortality at 25 mg/kg | *Response (Five days post-treatment with a single dose of 200 mg/kg IP) | Mortality** at 200 mg/kg |
| --- | --- | --- | --- | --- |
| Lonidamine (LND) | 2/5 (40%) | 0/5 | 5/5 (100%) | 0/5 |
| AF2785 | 3/5 (60%) | 0/5 | 3/4 (75%) | 2/6 |
| AF2364 | 3/5 (60%) | 0/5 | 4/5 (80%) | 0/5 |
| Gamendazole | 5/5 (100%) | 0/5 | 2/2 (100%) | 3/5 |

*For Response, the fraction represents the number of animals responding by a decline in testis weight >30%/the total number of animals tested in the group. For mortality, the fraction represents number of animals deceased/number of animals tested.
**For LND, mortality in 2 out of 5 animals was observed at a single oral dose of 400 mg/kg.

Figure 8:
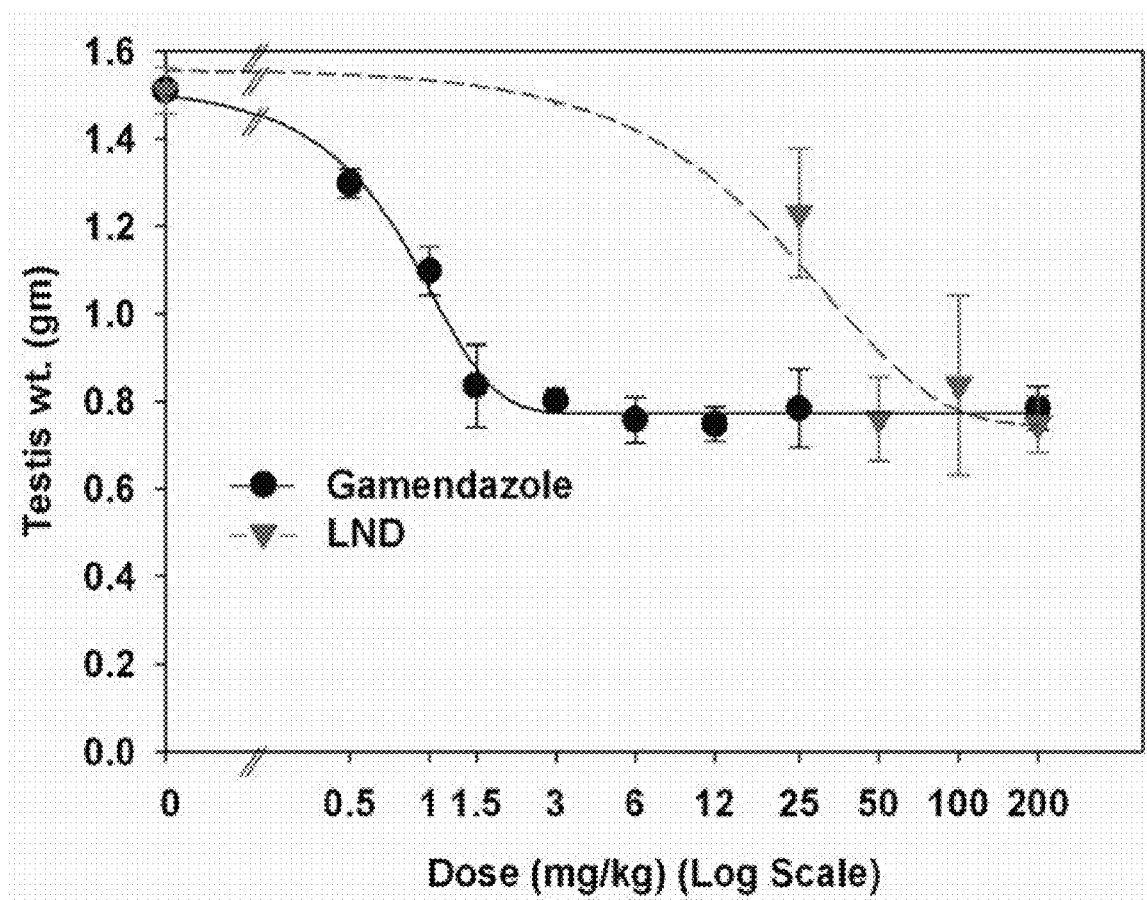
FIG. 8 includes a graph that shows the dose-dependent effect on testis weight five days following single oral administration of gamendazole or LND. The high variability observed in the LND-treated rats is due to the fact that two of five rats did not show a response to LND.

Since a minimum dose of 25 mg/kg produced a contraceptive effect and was 8 fold lower than the lethal dose (see below), detailed LD50 determinations were deferred to future more detailed dose-finding and toxicology studies. Additional dose ranging studies of compounds emerging from the first phase of testing were subsequently conducted. Experiments by oral administration were thus carried out and determined that gamendazole was also orally bioavailable and efficacious as a contraceptive at lower doses (FIG. 8).

It was found that gamendazole causes loss of late-stage spermatogenic cells. Gamendazole showed an anti-spermatogenic effect in 100% of the animals at the 25 mg/kg screening dose (FIG. 7 and Table 2), whereas LND inhibited spermatogenesis in 50% of the animals at this dose. The anti-spermatogenic effect of gamendazole at 25 mg/Kg (FIG. 7 panel C and panel D) was histologically similar to LND (FIG. 7 panel E and panel F). Compared with the control (FIG. 7 panel A and panel B), both LND and gamendazole cause a loss of the structured spermatogenic cell type layering, with loss of spermatozoa and spermatids from the germinal epithelium. The histologic patterns suggest that gamendazole produced more extensive loss of spermatids compared with LND. Spermatogenic index data support this observation (Table 6). Sloughing of the larger cells with dense chromatin pattern and high nuclear to cytoplasmic ratio (primary spermatocytes) and smaller less densely staining cells with less prominent chromatin pattern (secondary spermatocytes) was also seen with LND and gamendazole at this higher dose. Vacuolation of the different spermatogenic cell types and disruption of the spermatogonia layer on the basement membrane layer was also seen. At the lower oral doses of gamendazole which were used for the mating trial (3 and 6 mg/kg), similar loss of spermatids and spermatozoa were observed (FIG. 7 panels G-J). However there was a higher retention of seminiferous epithelium organization (96% normal tubules for 3 mg/kg and 85% normal tubules for 6 mg/kg) with less separation of cells and no vacuolation. Much less sloughing of the larger primary spermatocyte cells and smaller secondary spermatocytes was seen.

Example 10

Spermatogenic Index

The method utilized by Cook et al. (Cook C E, Wani M C, Jump J M, Lee Y W, Fail P A, Anderson S A, Gu Y Q, Petrow V. Structure-activity studies of 2,3,4,4a,5,9b-hexahydroindeno[1,2-c]pyridines as antispermatogenic agents for male contraception. J. Med. Chem. 1995; 38: 753-763) as modified from Whitsett et al. (Whitsett J M, Noden P F, Chemy J, Lawton A D. Effect of transitional photoperiods on testicular development and puberty in male deer mice (*Peromyscus maniculatus*). J. Reprod. Fertil. 1984; 72: 277-286) was used to score effects of test compounds on spermatogenesis. The assessment includes not only testicular weight, but also a spermatogenic index (SI). In one cross section through the middle of the testis all tubules are examined for the presence of spermatogonia, spermatocytes and spermatids. Based on the number of each cell type per tubule, a score is assigned as detailed in Table 6.

TABLE 6

Criteria for assessment of Spermatogenic Index based on testicular morphology

| Stage | Morphologic hallmarks |
| --- | --- |
| 1 | Only spermatogonia present |
| 2 | Spermatogonia and spermatocytes present |
| 3 | Spermatogonia, spermatocytes, and round (early) spermatids present with less than five late spermatids per tubule |
| 4 | Spermatogonia, spermatocytes, and round spermatids present; and up to 25 late spermatids per tubule |
| 5 | All cell types present and 50-75 late spermatids per tubule |
| 6 | All cell types present and >75 late spermatids per tubule |

The data from FIG. 7 were confirmed by quantitative spermatogenic index (Table 7). The enhanced potency of gamendazole versus LND was revealed by a dose-dependent decline in testis weight five days following single oral administration (FIG. 8): An ED50 of about 25 mg/kg was estimated for LND based on a 50% decline in testis weight from control to minimum resulting testis weight in the group treated with higher drug concentrations. An ED50 of 0.8 mg/kg was calculated for gamendazole based on the 0 to 3 mg/kg dosing study.

TABLE 7

Spermatogeneic Index (SI) in Seminiferous Tubules Five Days After a Single Dose of LND Analogues.

| Compound | SI at a ORAL dose of 3 mg/kg (mean ± SD) | SI at a ORAL dose of 6 mg/kg (mean ± SD) | SI at a IP dose of 25 mg/kg (mean ± SD) | SI at a IP dose of 200 mg/kg (mean ± SD) |
|---|---|---|---|---|
| Control* | 5.91 ± 0.12 | 5.91 ± 0.12 | 5.90 ± 0.30 | 5.90 ± 0.30 |
| Lonidamine | Not tested | Not tested | 4.66 ± 1.78 | 1.76 ± 0.50 |
| AF2364 | Not tested | Not tested | 3.53 ± 1.99 | 2.08 ± 0.77 |
| AF2785 | Not tested | Not tested | 5.45 ± 0.94 | 3.41 ± 1.78 |
| Gamendazole | 3.47 ± 0.40 | 2.72 ± 0.39 | 2.52 ± 0.78 | 2.05 ± 0.78 |

*Control animals were administered vehicle alone.

Example 11

Body Weight and Reproductive Organ Changes Following Treatment

Figure 9A:
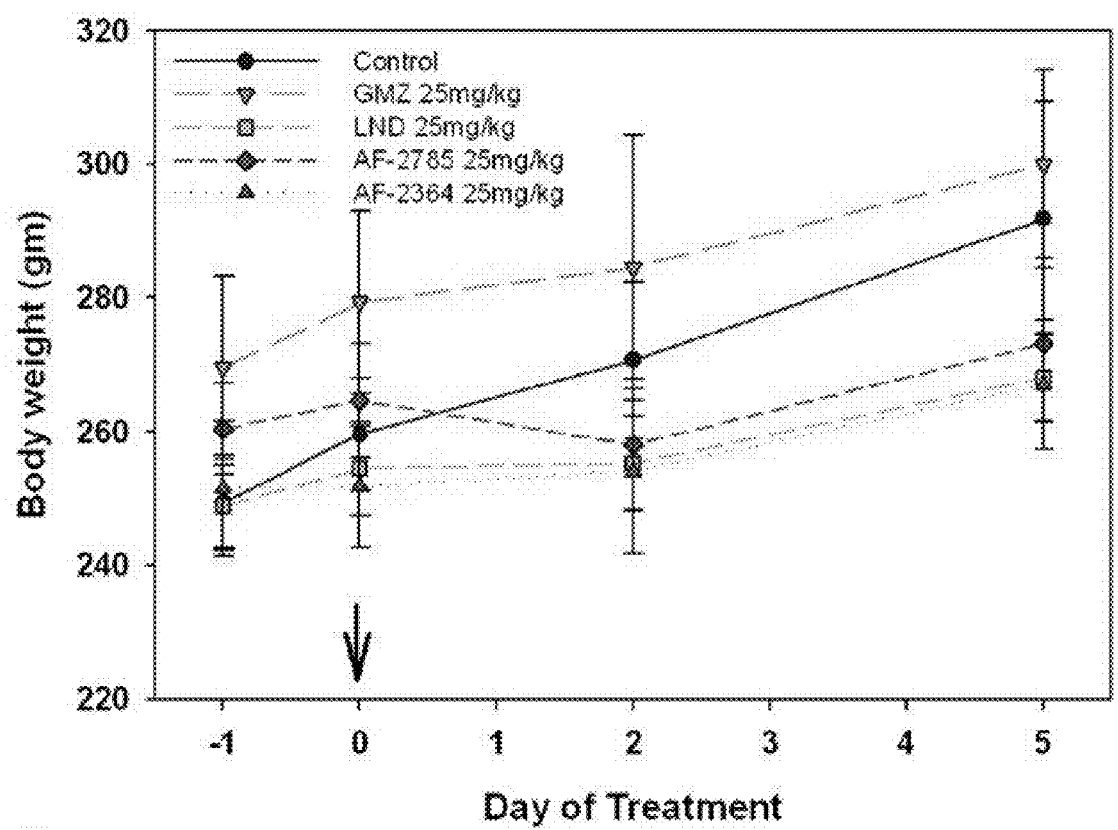
FIG. 9A-9B include graphs that show body weight changes following a single IP administration of LND, AF-2785, AF-2364, and gamendazole. Animals were 60 days of age at the start of the experiment, and weighed the day before compound administration, on the day of administration (day 0, arrow), and 2 and 5 days later.
Figure 9B:
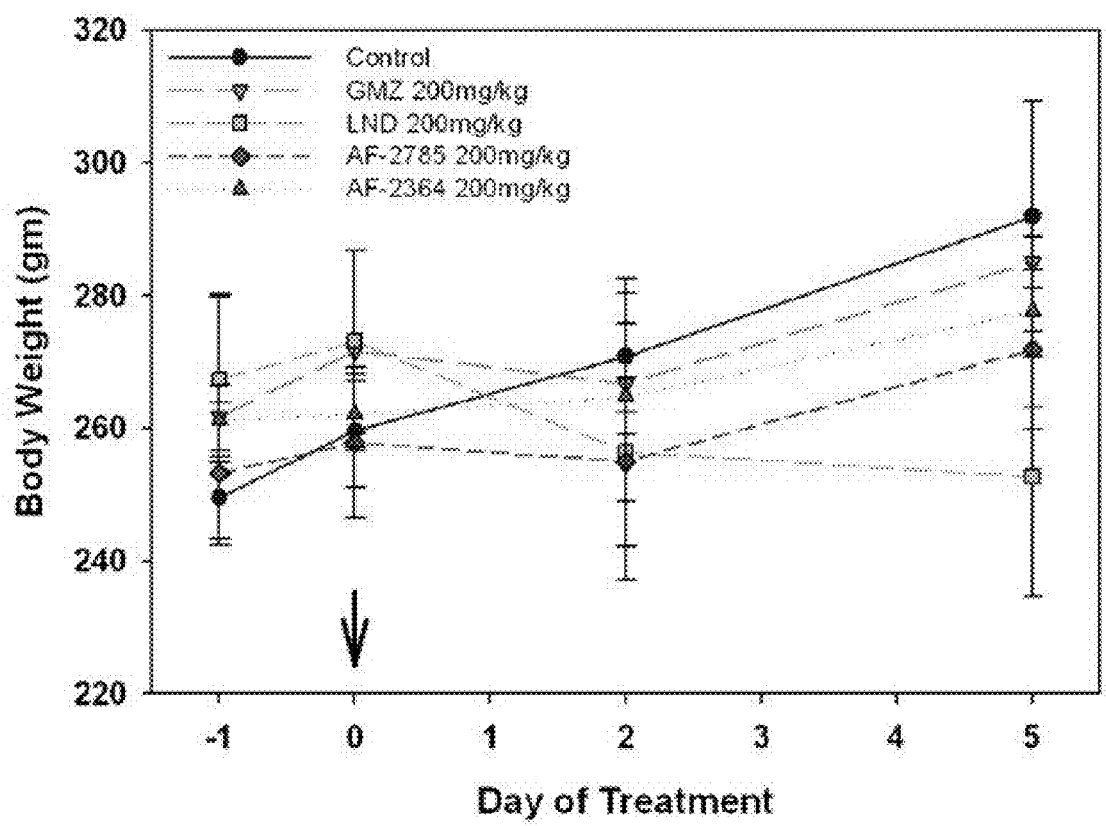

The animals used for anti-spermatogenic activity were 60 days of age, and vehicle-treated rats exhibited normal weight gain during the 5-day experiment (FIG. 9A-9B). At the 25 mg/kg of LND, AF-2785, and AF-2364, there was a delay in body weight gain for two days followed by an increase that paralleled the control group or a slight decline for two days followed by an increase that paralleled the control group. At 200 mg/kg of LND there was a larger decline in body weight for two days followed by maintenance of the same weight for the remaining three days. Animals dosed with AF-2785 and AF-2364 exhibited a delay in weight gain similar to that observed with the 25 mg/kg dose. There was no delay in body weight gain and the rate of weight gain in gamendazole-treated was parallel to that of the controls for the entire 5-day period. Although the 25 mg/kg gamendazole group started out at a slightly higher body weight it was not significantly different from controls at any point. At the 200 mg/kg dose, the surviving animals had a 2-day delay in weight gain followed by an increase that paralleled the control animals. In contrast to the IP administration experiments, above, in parallel single oral administration experiments at 25 mg/kg, the body weights of the rats were not different among treatment groups (p>0.05; data not shown).

The rats from the two mating trial studies (Tables 9 and 10) were subjected to necropsy at study termination (week 10 or 27) and the data on weights of reproductive organs and testicular endpoints were obtained. Data for only the 3 and 6 mg/kg single dose groups and their respective vehicle control group are presented in Table 8. In the 3 mg/kg treated group, all of the animals that were rendered infertile recovered fertility, and there was no significant difference in testicular or epididymal weight from those in control animals. There was a 10% reduction in spermatid counts and a 18% reduction in the proportion of normal seminiferous tubules 10 weeks after the treatment even though all of these animals were fertile. In the 6 mg/kg gamendazole group, data are presented for all the animals, as well as grouped by animals that recovered fertility versus those that remained infertile 27 weeks after treatment. For all treated animals, all of the male reproductive parameters were significantly lower in comparison to the control animals. However, when subgrouped by recovered fertile versus infertile, all of these parameters were still lower than those in vehicle-treated rats, but they were closer to control values.

TABLE 8

Body, Testis, and Epididymal Parameters after Single Oral Dose of Gamendazole

| Treatment Group (Necropsy week) | N† | Final Body Weight (g) | Paired Testes Weight‡ (g) | Spermatid Head Count‡ (#cells × $10^6$ per testis) | Tubules with Mature Spermatids (%)‡ | Mean Paired Epididymal Weight‡ (g) |
|---|---|---|---|---|---|---|
| Vehicle Control (week 10) | 6 | 589 ± 28 | 3.57 ± 0.25 | 108.48 ± 3.50 | 100 + 1 | 1.36 ± 0.07 |
| Gamendazole at 3.0 mg/kg on day 0 (week 10) | 6 | 596 ± 15 | 3.18 ± 0.13 | 96.92 ± 1.47* | 82 + 2* | 1.13 ± 0.04* |
| Vehicle Control (week 27) | 7 | 691 ± 21 | 3.82 ± 0.13 | 117.58 ± 4.22 | 100 ± 1 | 1.45 ± 0.06 |
| Gemendazole at 6.0 mg/kg on day 0 (week 27) | 7 | 746 ± 18 | 2.10 ± 0.30* (2.47 ± 0.43 vs 1.60 ± 0.23) | 40.59 ± 16.43* (66.56 ± 20.43 vs 5.97 ± 2.26) | 27 ± 11* (45 ± 13 vs 2 ± 1) | 0.96 ± 0.10* (1.05 ± 0.17 vs 0.85 ± 0.10) |

†N = number of males
‡For the 27 week study (6 mg/kg dose), the values in parenthesis represent mean ± SE for the recovered fertile vs. infertile males, respectively (n = 4 fertile; 3 infertile).
*Significantly different (p < 0.05) from respective vehicle control group based on Student's t test.

Five days after the single IP dose animals were euthanized and a gross necropsy was performed. Pathology was examined in at least one randomly chosen animal per gamendazole or LND analogue treatment group. Any animals that showed abnormal health or behavior effects were also examined in detail. All tissues were examined for histopathology; only affected tissues are reported. Following LND treatment at the 200 mg/kg dose, some areas of the liver contained arteries and veins that were engorged with blood, while other areas did not appear to be congested. For the kidney, some engorgement of arteries and swollen arterioles were observed with occasional large amounts of blood apparent between the proximal tubules. Engorged arteries and veins were also observed in the pancreas. These side effects were usually noted in at least one of the five animals at the 200 mg/kg dose of LND. These were not observed in animals dosed at 25 mg/kg; however it should be noted that at 25 mg/kg only about 50% of the animals exhibited an inhibition of spermatogenesis. Following treatment of AF-2785 at 25 mg/kg, scattered areas near the periphery of the liver and pancreas contained distended, blood filled sinuses. Evidence of necrosis, pyknotic nuclei and swelling of the remaining cells in the area, was observed. Following treatment with 25 mg/kg of AF-2364, small isolated necrotic nodules were observed near the periphery of the liver and pancreas. At 200 mg/kg, congestion and distension of most veins and some arteries in both the liver and pancreas were observed. Following 25 mg/kg of gamendazole, histopathological findings in all organs of treated animals were non-remarkable, with no evidence of inflammation, necrosis, hemorrhage or tumors. It should be noted that 100% of the 25 mg/kg gamendazole treated animals exhibited reduced spermatogenesis. At the higher dose of 200 mg/kg, gamendazole resulted in mortality in three of the five animals. However, in the two animals that survived, all of the organs were non-remarkable, with no evidence of inflammation, necrosis, hemorrhage or tumor. In subsequent testing at lower doses down to 6 mg/kg (oral) which gave 100% infertility, all organs were non-remarkable, with no evidence of inflammation, necrosis, hemorrhage or tumors.

Figure 10:
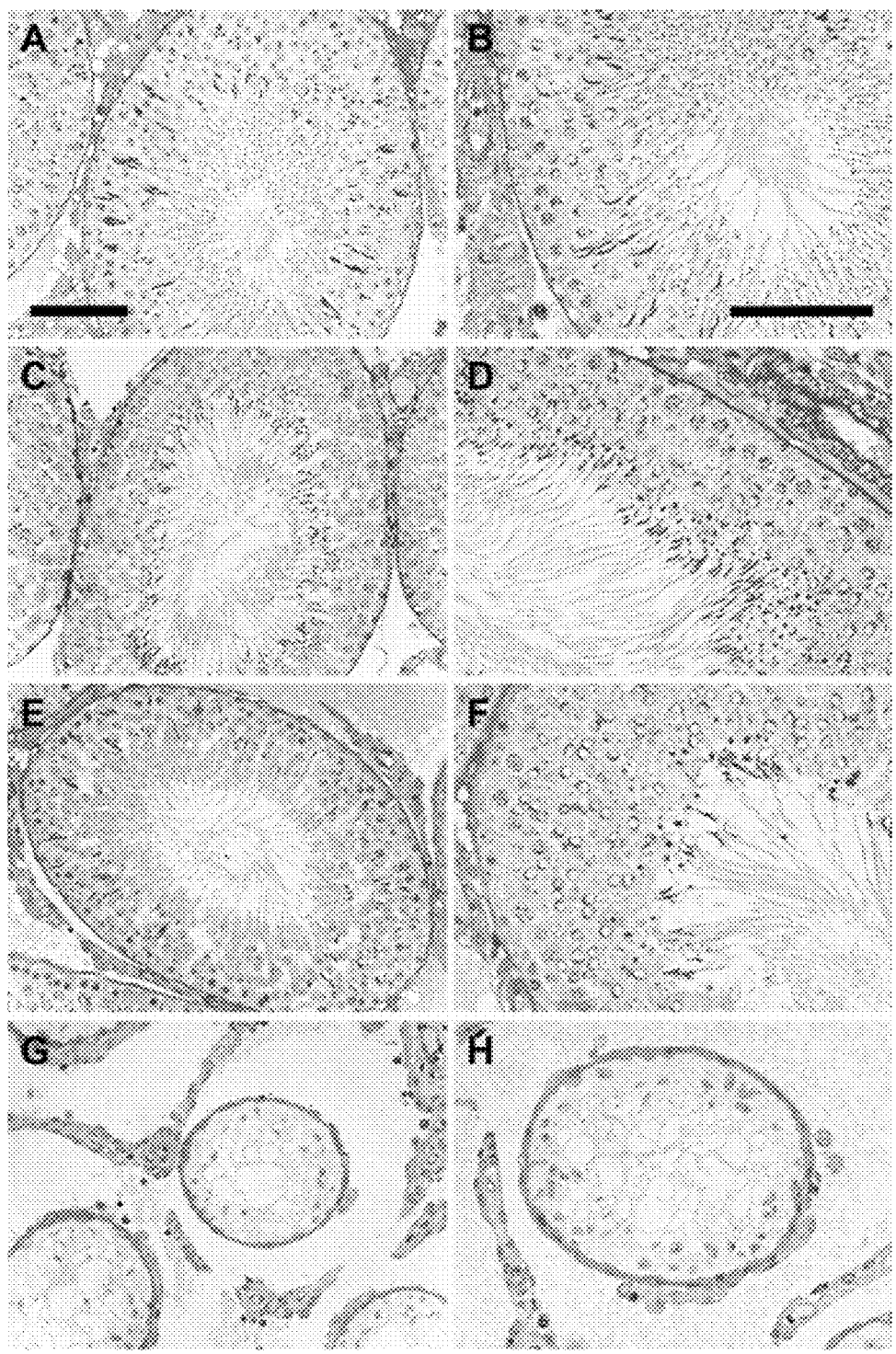
FIG. 10 includes images that show testis histology in gamendazole-treated animals following mating trials: Panels A-B show testis from control animal administered vehicle alone; Panels C-D show testis from an animal that was rendered infertile by 3 mg/kg gamendazole that recovered fertility; Panels E-F show testis from an animal that was rendered infertile by 6 mg/kg gamendazole that recovered fertility; Panels G-H show testis from an animal that was rendered infertile by 6 mg/kg gamendazole that remained infertile. Panels A, C, E, and G are all the same magnification, Bar=200 μm. Panels B, D, F, and H are all the same magnification, Bar=200 mm.

Histology of the testes from the animals used in the mating trials (FIG. 10) revealed that the recovery of fertility all of the 3 mg/kg treated animals was matched with restoration of normal spermatogenesis (FIG. 10 panels C-D) similar to paired control (vehicle) animals (FIG. 10 panels A-B). In the 6 mg/kg treated animals, those that recovered fertility also showed recovery of normal seminiferous tubule histology (FIG. 10 panels E-F). While the animals that failed to recovery fertility, showed not only a failure of repopulation of the germinal epithelium, but also loss of most of the remaining spermatogenic cells, with most tubules showing Sertoli cell only-like histopathology (FIG. 10 panels G-H).

Example 12

Mating Trials

Two mating trial assays were performed to evaluate the dose-dependent antifertility effects of gamendazole in rats. Adult male Crl:CD (SD) outbred rats ($\geq$300 g, $\geq$9 wks old; Charles River Laboratories, Kingston, N.Y.) were used for these mating trial assays. Fertility was established as known in the art. In the first assay, proven fertile male rats (6 per group) received a single oral dose of vehicle (5 ml/kg of 10% ethanol in sesame oil) or 0.75, 1.5, or 3.0 mg/kg of gamendazole (day of dosing=day 0 of week 0). Mating trials were performed as known in the art at weeks 1-9 and male rats were euthanized and a gross necropsy performed on week 10.

For the second study, proven fertile male rats (7 per group) were dosed orally as follows: vehicle control at 5 ml/kg/day for 7 days (days 0-6), gamendazole at 6 mg/kg on day 0 (single dose), or gamendazole at 6 mg/kg/day for 7 days (days 0-6). Mating trials were performed at weeks 1-10 (each week), and weeks 12, 14, 18, and 26. At week 27, the male rats were euthanized, and a gross necropsy performed. Blood samples were collected from the tail vein of the males throughout both studies to obtain serum samples for hormone assays. The number of conceptuses was determined after necropsy of the females and the conceptuses were grossly evaluated and classified as normal-appearing or resorbing. The number of normal conceptuses per pregnant female between the two groups was compared statistically by one-way analysis of variance (ANOVA). At necropsy, testes, ventral prostate and seminal vesicles were excised and weighed. Both epididymides and the right testis were excised, weighed, and preserved in Bouin's Solution. The left testis was homogenized and used to determine the number of mature spermatid heads.

The potent inhibition of spermatogenesis by gamendazole suggested that it may have antifertility activity. Dose ranging efficacy mating trials in proven fertile male rats demonstrated that single oral doses at 1.5, 3.0 and 6.0 mg/kg were effective at inducing infertility in rats (Tables 9 and 10). At a single oral dose of 1.5 mg/kg, gamendazole induced infertility in 2 of 6 rats for only one week (week 3 or 4) of the 9-week mating trial (Table 4). At a single oral dose of 3.0 mg/kg, 4 of 6 males were rendered infertile by week 4, and all 4 males recovered fertility by week 5 (Table 9). A single oral dose of 6.0 mg/kg of gamendazole produced 100% infertility four weeks after a single oral administration (Table 10). The 6 mg/kg dose was the lowest dose tested that gave 100% infertility after a single oral administration. The period of complete infertility lasted for two weeks followed by complete recovery of fertility in four of seven animals by six weeks. The remaining three animals in the group did not recover fertility. When administered at 6.0 mg/kg for 7 consecutive days, a similar onset of infertility was observed; however, only 2 of 7 animals recovered fertility during the 26 week mating trial interval. In all treatment groups, for the animals that recovered fertility, the number of conceptuses and the proportion of abnormal conceptuses were not significantly different from the vehicle control group.

TABLE 9

Gamendazole Induced Infertility in Adult Male Rats: Response to a Single Oral Dose

| Treatment Group | No. Males Infertile/ No. Males Treated | No. Males Recovering Fertility/ No. Males Rendered Infertile | No. Normal Implants/ Pregnant Rat |
|---|---|---|---|
| Vehicle Control | 0/6 | — | 16 ± 1 |
| Gamendazole at 0.75 mg/kg | 0/6 | — | 15 ± 1 |
| Gamendazole at 1.5 mg/kg | 2/6 | 2/2 | 15 ± 1 |
| Gamendazole at 3.0 mg/kg | 4/6 | 4/4 | 15 ± 1 |

[a]Mean ± SE for week 9 of the study. See Materials and Methods for details on the mating protocols and analysis of results. There were no significant differences (p = 0.86) in the number of normal implantation sites per pregnant female among the treatment groups (ANOVA).

TABLE 10

Gamendazole Induced Infertility in Adult Male Rats: Comparison of Single Dose Versus Seven Daily Doses

| Treatment Group | No. Males Infertile/ No. Males Treated | No. Males Recovering Fertility/No. Males Rendered Infertile | No. Normal Implants/ Pregnant Rat[a] |
|---|---|---|---|
| Vehicle Control 5 ml/kg/day for 7 days (days 0-6) | 0/7 | — | 15 ± 1 |
| Gamendazole at 6 mg/kg on day 0 (single dose) | 7/7 | 4/7 | 14 ± 1 |

TABLE 10-continued

Gamendazole Induced Infertility in Adult Male Rats: Comparison of Single Dose Versus Seven Daily Doses

| Treatment Group | No. Males Infertile/ No. Males Treated | No. Males Recovering Fertility/No. Males Rendered Infertile | No. Normal Implants/ Pregnant Rat[a] |
|---|---|---|---|
| Gamendazole at 6.0 mg/kg/day for 7 days (days 0-6) | 7/7 | 2/7 | 14 ± 1 |

[a]Mean ± SE for week 18 of the study. See Materials and Methods for details on the mating protocols and analysis of results. There were no significant differences (p = 0.80) in the number of normal implantation sites per pregnant female among the treatment groups (ANOVA).

Example 13

Behavior Following Administration

For 2-3 hr after injection of LND, AF-2785 and AF-2364 (25 mg/kg or 200 mg/kg dose), the animals became lethargic. For AF-2785, two of six animals died from seizures within 40 min. For gamendazole at the 200 mg/kg dose only, three animals were euthanized following initial spasms that ceased by 20 min, but were followed by labored breathing and a semiconscious state. In all of the 25 mg/kg and the remainder of the 200 mg/kg gamendazole groups, as well as all oral doses tested there was no evidence of lethargy (reduced alertness and awareness, lack of interest at cage opening, prolonged periods of inactivity relative to controls) at either the 25 mg/kg or 200 mg/kg dose. In the mating trials described in Tables 4 and 5, where gamendazole was administered orally, no differences in mating behavior were observed between control and gamendazole treated animals at any of the doses tested.

Example 14

Serum Hormone Assays

Serum samples collected throughout the study were analyzed for inhibin B by an ELISA kit (Oxford Bio-Innovation Ltd, Oxfordshire, UK). The RIA's for measuring testosterone and FSH in the rat were performed as known in the art. Briefly, testosterone was measured in unextracted serum samples using a kit (Coat-A-Count) from Diagnostic Products Corp. (Los Angeles, Calif.). Rat FSH was measured using NIDDK (National Institute of Diabetes and Digestive and Kidney Diseases) reagents supplied by Dr. A. Parlow (National Hormone and Peptide Program) following the procedures received with the reagents. The standard was NIDDK-rFSH-RP-2.

Isolated Sertoli cells were plated in black 96-well dishes and incubated for 72 hr at 33° C. Culture medium (serum-free supplemented DMEM/F-12) was removed and replaced with fresh medium containing various concentrations of gamendazole ($10^{-10}$ M to $2\times10^{-4}$ M) dissolved in ethanol or DMSO (final concentration in medium 0.1%). Cells were returned to 33° C. and incubated for 48 hr. ATP content of the cells was measured at 48 hr using the Perkin Elmer ATP-Lite M kit, containing mammalian lysis buffer, lyophilized substrate, and reconstitution buffer, according to the kit insert. Luminescence was measured in a scintillation counter (Perkin Elmer TopCount (Boston, Mass.); units were cps). The data were plotted and the $IC_{50}$'s estimated using GraphPad PRISM.

Isolated Sertoli cells were plated, incubated and treated with containing various concentrations of gamendazole ($10^{-11}$ M to $10^{-6}$ M) and incubated for 72 hr as described above. Medium was collected for measurement of inhibin B using a kit from Sertotec following the manufacturer's directions except that the boiling step was omitted, and the standard curve (recombinant human inhibin B) was prepared in Sertoli cell culture medium. The limit of detection (lowest standard) was 15.6 pg/ml.

Figure 11:
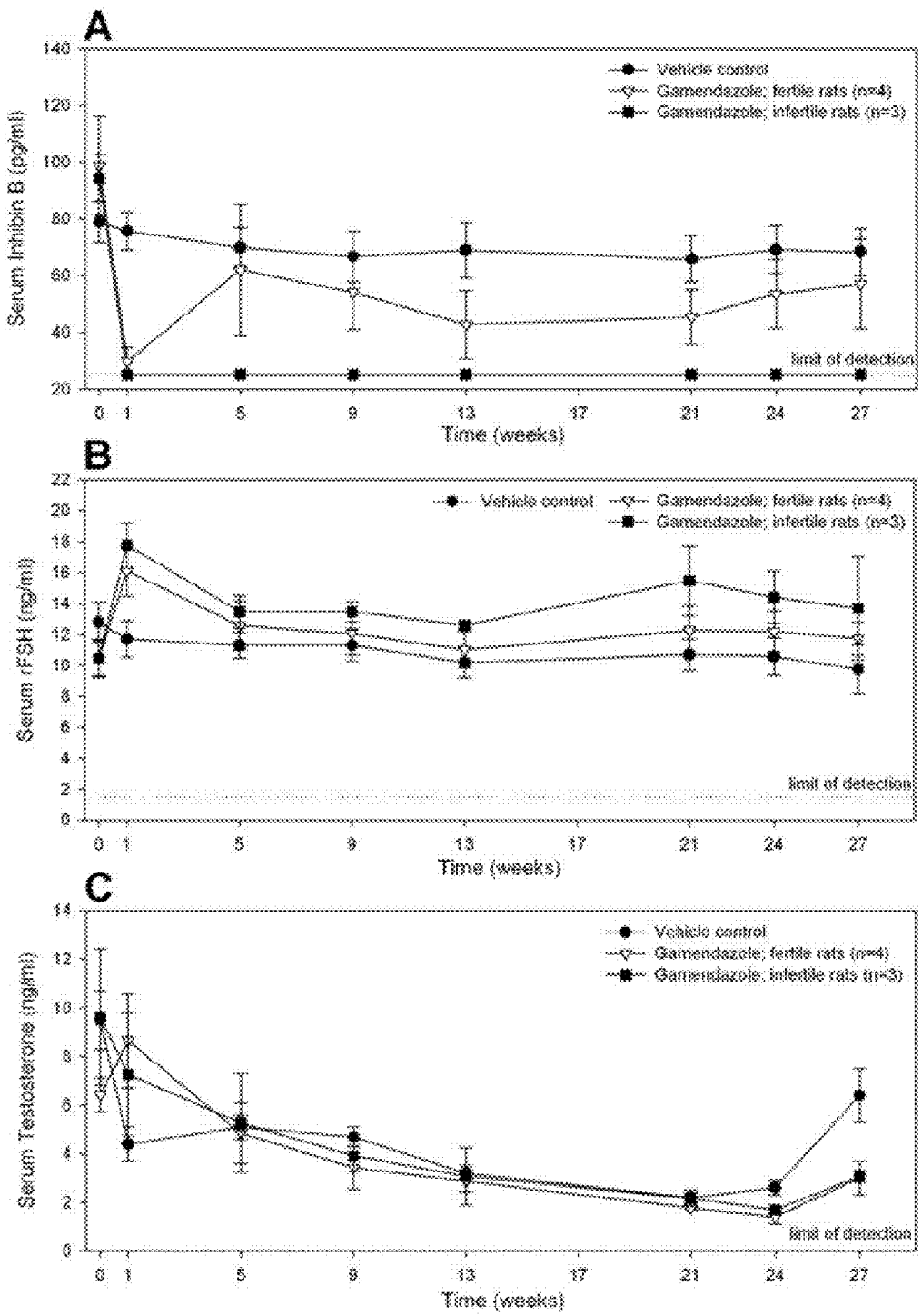
FIGS. 11A-11C are graphs that show a comparison of circulating inhibin B, FSH, and testosterone levels in proven fertile male rats treated with vehicle or gamendazole at 6 mg/kg. Gamendazole-treated rats were separated into animals that recovered fertility vs animals that remained infertile over a 27 week period.

It is important to note that no significant difference in circulating testosterone levels was observed between control and gamendazole treated animals (FIG. 11C). In addition, gamendazole produced no significant differences in weights of the seminal vesicles and ventral prostate, two androgen-dependent organs (data not shown). Previous studies on LND analogues demonstrated that Sertoli cells are the primary target of the drug leading to the loss of spermatids [33]. Analysis of additional serum hormone levels in the animals treated with 6 mg/kg gamendazole (FIG. 11A) demonstrated a temporary but significant decline in circulating inhibin B levels ($P<0.05$, ANOVA-RM followed by Holm-Sidak multiple comparison) matched with a transient but not significant increase in FSH levels (FIG. 11B). It should also be noted that inhibin B levels remained low in the animals that remained infertile after gamendazole treatment, but rebounded after the initial drop in animals that recovered fertility. Serum FSH levels were inversely related to inhibin B levels, but increases were not significant.

Figure 12A:
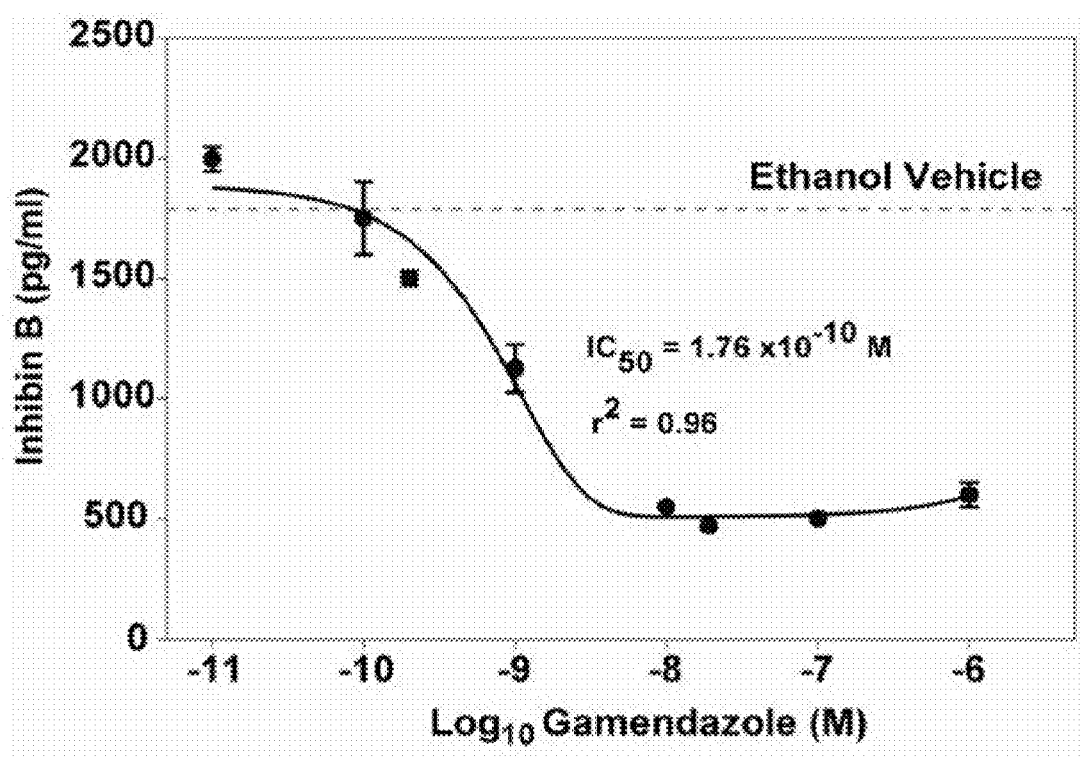
FIG. 12A-12B include graphs that show gamendazole responses and binding in primary Sertoli cells in vitro. Sertoli cells were incubated in the presence or absence of gamendazole at the concentrations indicated. The media were collected and assayed for inhibin B (FIG. 12 A) after 72 hr of treatment, and the cells for ATP content (FIG. 12 B) after 48 hr of treatment.
Figure 12B:
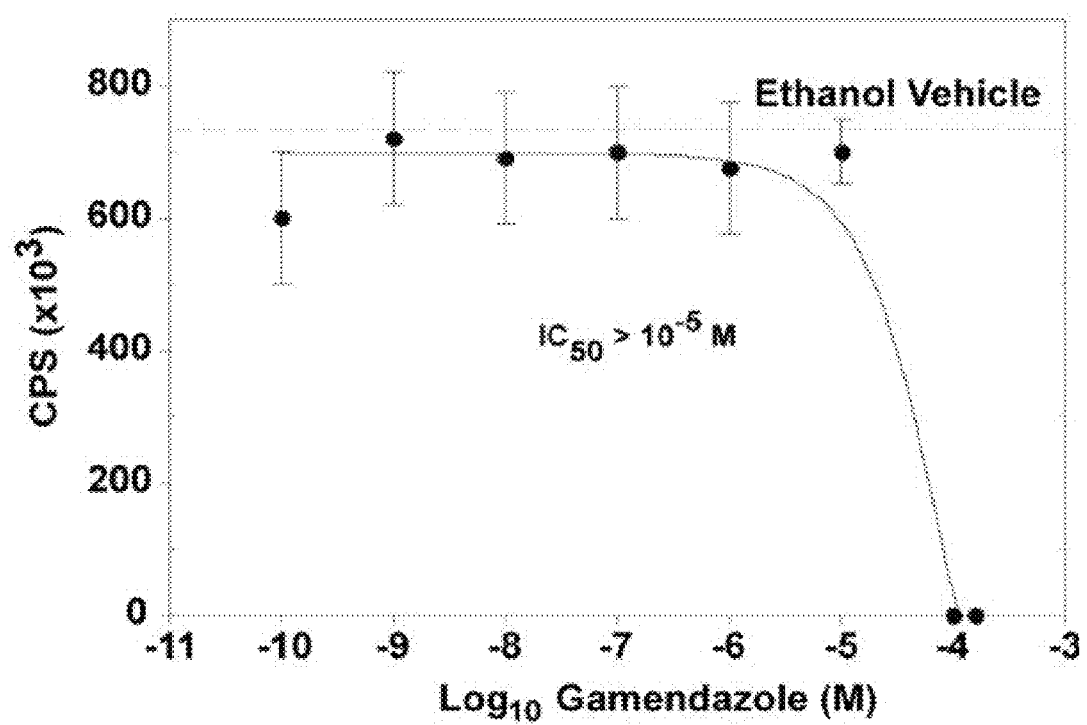

The effect of gamendazole on serum inhibin B levels suggests that gamendazole may also act in the testis via Sertoli cells [33] and this was confirmed by measuring inhibin B secretion in primary cultures of rat Sertoli cells incubated with varying concentrations of gamendazole (FIG. 12A). Indeed, Inhibin B production in Sertoli cells was remarkably sensitive to gamendazole with an $IC_{50}$ of only $6.8\pm3.0\times10^{-10}$ M. FIG. 12A presents the data from one of three replicate experiments used to determine the $IC_{50}$. By contrast, Sertoli cell ATP levels, a marker of cell viability, were not reduced until gamendazole concentrations were $10^{-5}$ M or greater (FIG. 12B). Thus, there is a five log difference between a physiologically significant biological marker of gamendazole action on Sertoli cells versus a toxic effect. Since gamendazole was derived from the cancer therapeutic agent, lonidamine, as an additional assessment of in vitro toxicity, gamendazole was also examined for an effect of growth of a variety of ovarian cancer cell lines using the MTT assay. Growth of ID8-T1, ID8, SKOV3, CAOV3 was inhibited by gamendazole with IC50's of $2.7\times10^{-5}$ M, $2.9\times10^{-5}$ M, $1.6\times10^{-4}$ M, and $7.2\times10^{-5}$ M, respectively. These IC50 values were comparable to the gamendazole concentrations that caused ATP leakage from the primary Sertoli cell. This difference in dose for a biologic versus toxic effect on cells in vitro is promising for further development of gamendazole.

Example 15

Binding of gamendazole to Primary Sertoli Cells In Vitro

Primary mouse Sertoli cells were isolated as described above and plated on pre-treated glass coverslips. The cells were washed with PBS to remove excess media, then fixed in 2% paraformaldehyde, followed by permeabilization with 1% NP-40. The cells were blocked with 5% BSA in buffer for 1 hr at room temperature, washed with buffer, then incubated with UV-crosslinked biotinylated gamendazole (BT-UV-GMZ) for 1 hr at 37° C. The cells were washed with buffer to remove unbound drug, followed by incubation in the dark for 20 min at room temperature with fluorescein-Avidin D (Vector Laboratories, Burlingame, Calif.). Crosslinking was accomplished with a UV mineral lamp at long wavelength for 20 min at 4° C. Coverslips were mounted with VectaShield™ mounting medium (Vector Laboratories, Burlingame, Calif.) suitable for fluorescence.

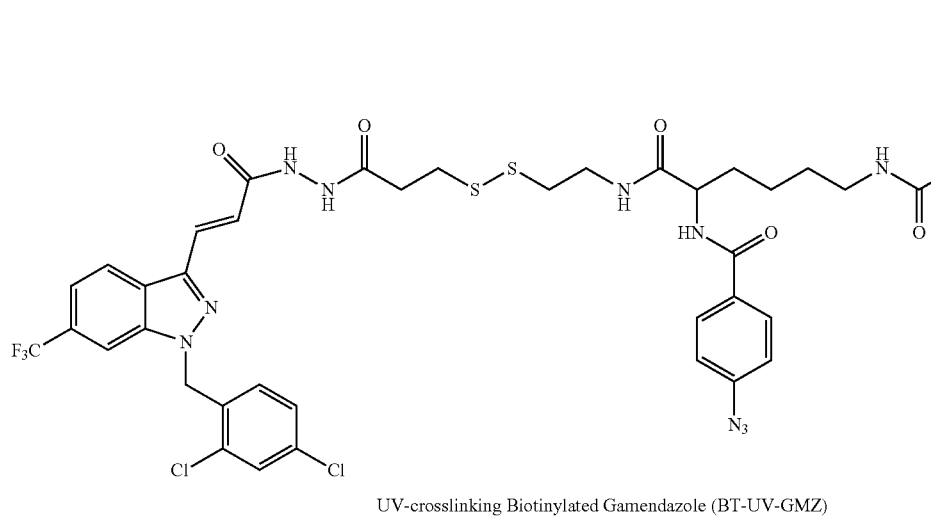

UV-crosslinking Biotinylated Gamendazole (BT-UV-GMZ)

Figure 13:
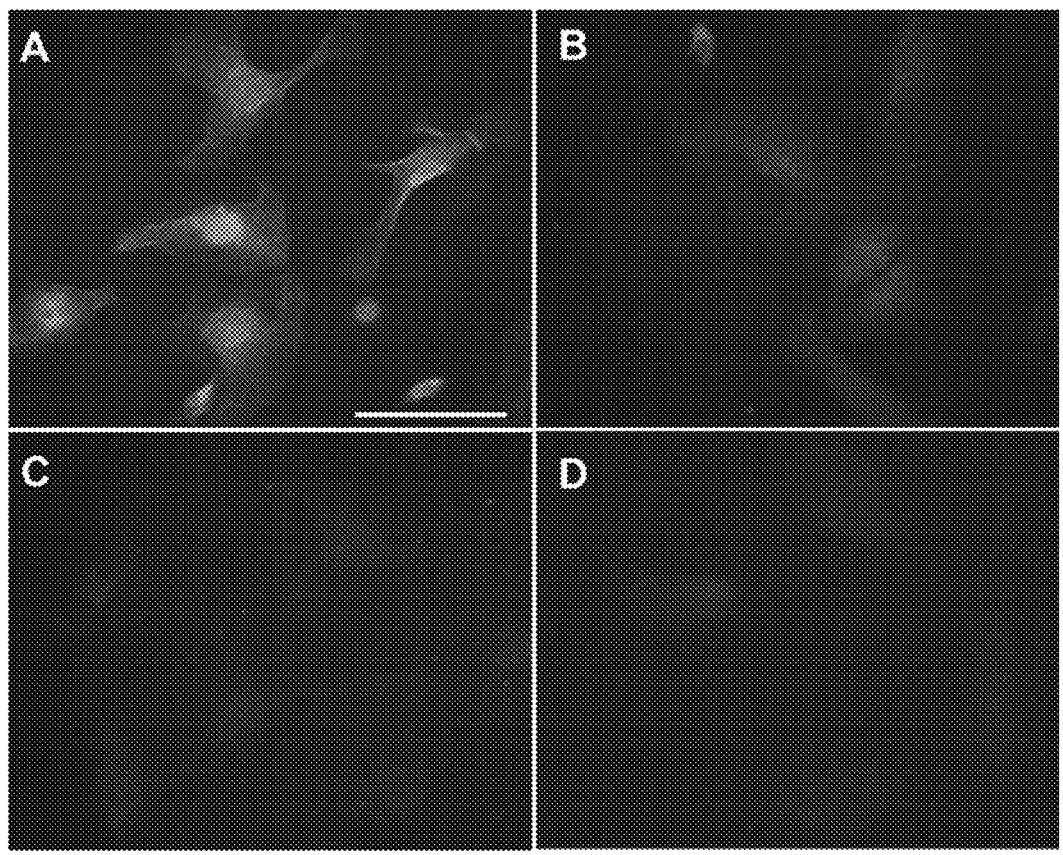
FIG. 13 includes images of the binding of gamendazole (GMZ-BT-UV) to mouse Sertoli cells in vitro. Panel A shows GMZ-BT-UV binding in formalin-fixed, detergent lysed Sertoli cells. Panel B shows binding in the presence of 10-fold excess gamendazole. Panel C shows binding in the presence of 10-fold excess LND. Panel D shows control incubation with FITC-avidin alone. Bar=50 μm.

The spatial binding of gamendazole was demonstrated in cultured primary mouse Sertoli cells using a UV-crosslinking biotinylated analogue of gamendazole (GMZ-BT-UV). Staining was predominantly perinuclear (punctate staining that could be nucleolar) with less pronounced cytoplasmic staining (FIG. 13 panel A). Control incubations with GMZ-BT-UV in the presence of 10-fold molar excess gamendazole (FIG. 13 panel B), or LND (FIG. 13 panel C) blocked the localization demonstrating that the pattern was compound specific. Non-specific binding with FITC-avidin alone was also very low (FIG. 13 panel D). These results suggest that Sertoli cells are a target of gamendazole action.

Example 15

Affinity Purification of gamendazole Binding Proteins

TM-4 Sertoli Cells and ID8 Ovarian Cancer Cells:

To ensure sufficient starting material for affinity purification, TM-4 Sertoli cells were used rather than primary Sertoli cells to provide sufficient protein for affinity purification and comparable quantities of protein as testis cytosol. TM-4 cells are a non-tumorigenic mouse cell line of Sertoli cell origin that retain FSH responsiveness. TM-4 cells were cultured in DMEM/F12 (50:50) with 5% horse serum and 2.5% FBS to confluency on two 150 mm plates. After washing once with PBS, cells were lysed with 3 ml per plate of lysis buffer comprising 50 mM Tris-HCl, pH 7.4, 0.05 M NaCl, 0.001% NP-40, 5 mM EDTA, 50 mM NaF, 1 mM sodium orthovanadate, 1 mM sodium pyrophosphate, 10 mM benzamidine, 0.05 mg/ml PMSF, 0.01 mg/ml TPCK, 0.3 µg/ml aprotinin, and 0.3 µg/ml soy bean trypsin inhibitor. The cells in lysis buffer were scraped and transferred into a Dounce glass homogenizer and homogenized with a tight pestle with 5-10 strokes to break the cells. After standing in ice for 30 min, the homogenate was centrifuged at 37,500×g for 10 min at 4° C. The supernatant lysate was applied to a 2 ml avidin-agarose (tetramer form) column (pre-equilibrated with 50 mM Tris-HCl/0.001% NP-40, pH 7.4) to remove native biotinylated compounds and obtain a pre-cleared lysate. The pre-cleared cell lysate (2.7 ml) was incubated with 60 µM biotinylated gamendazole (gamendazole-BT).

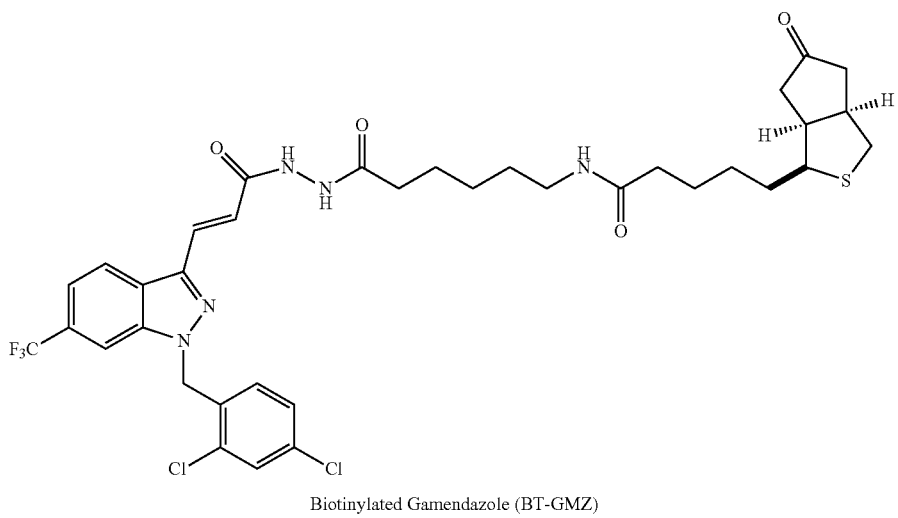

Biotinylated Gamendazole (BT-GMZ)

A parallel control 2.7 ml aliquot of pre-cleared lysate was incubated with 60 µM gamendazole-BT plus 10-fold molar excess gamendazole. After incubation overnight at 4° C. on a rocker platform, the samples were loaded on avidin-agarose columns pre-equilibrated with buffer (50 mM Tris-HCl pH 7.4, 0.1% NP-40=TD buffer) and washed with TD until background was reached. The columns were sequentially eluted with 2.5 ml of TD buffer containing 0.6 mg/ml gamendazole, then 250 mM NaCl, and finally 600 mM NaCl. Each 2.5 ml eluate was collected and concentrated in a Centricon Y-10 (Millipore, Billerica, Mass.) for 2 hr at 4° C. at 5000×g to a volume of 100-200 µl. Aliquots were removed for protein determination and SDS-PAGE electrophoresis sample buffer was added. Electrophoresis was performed on a 5-20% gradient gel. Gels were fixed and silver-stained using the MALDI-TOF compatible method.

Previously, it was noted that tumorigenic mouse ovarian surface epithelial cells (ID8) cells show growth inhibition in response to gamendazole. ID8 cells were developed following a spontaneous transformation event in vitro. Injection of ID8 cells into the peritoneal cavity of athymic and syngeneic mice resulted in formation of ascites fluid and multiple tumor implants throughout the peritoneum. Histopathologic analysis of tumors revealed a highly malignant neoplasm containing carcinomatous and sarcomatous components.

ID8 cells were cultured using standard procedures in complete medium [DMEM supplemented with 4% FBS, penicillin (100 U/ml), streptomycin (100 µg/ml), insulin (5 µg/ml), transferrin (5 µg/ml), and sodium selenite (5 ng/ml)] at 37° C. in a humidified atmosphere of 5% $CO_2$ and air. Cells were grown to near confluence in T75 flasks, were washed twice with cold phosphate buffered saline, place in lysis buffer as described above, and the cytosols were prepared and subjected to affinity binding and electrophoresis as described above for the TM-4 cells.

Rat Testis:

A testis cytosol from 60 day-old rats was prepared as follows: The detunicated testes from 2 rats (2.8 g total) were homogenized with a PowerGen homogenizer (Fisher, Pittsburgh, Pa.), with three bursts for 10 sec each on ice in 6 ml of lysis buffer (see above), then sonicated using a Sonic Dismembranator (Fisher, Pittsburgh, Pa.) for 5 sec at setting 5 on ice. The sample was placed on ice for 30 min, and then centrifuged at 37,500×g for 10 min at 4° C. The resulting cytosol was pre-cleared through an avidin-agarose column as described above, then split into two 2.7 ml aliquots and incubated overnight at 4° C. with either 60 µM gamendazole-BT or 60 µM gamendazole-BT plus 10-fold molar excess gamendazole, and then passed through an avidin-agarose column. Following methods similar to those described above, the columns were each first washed with buffer to achieve background, then eluted stepwise with 2.7 ml of 1.5 mM gamendazole, then 3.0 mM gamendazole, and finally with 600 mM NaCl to collect remaining proteins that were not eluted by gamendazole. Collected fractions were concentrated, and run on 5-20% SDS-PAGE gels as described above. The testis SDS-PAGE gels were fixed and stained with the MALDI-TOF compatible Coomassie blue method.

Figure 14:
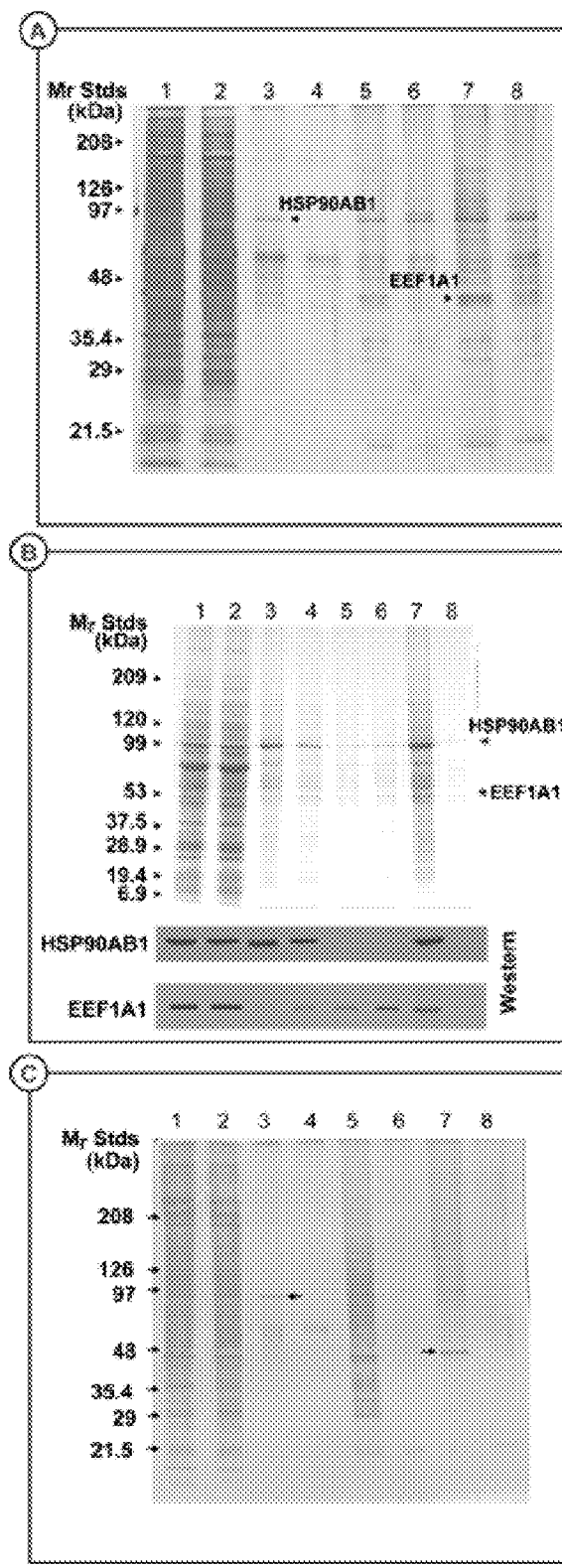
FIG. 14 panel A shows TM-4 Sertoli cell cytosol protein affinity binding using biotinylated gamendazole (gamendazole-BT): Lanes 1 and 2—silver-stained starting cytosol and pre-cleared avidin-agarose treated cytosol, respectively. Lanes 3 and 4—gamendazole eluates obtained from cytosols incubated with gamendazole-BT in the absence (Lane 3) and presence of 10-fold excess gamendazole (Lane 4). Lanes 5 and 7—250 and 600 mM NaCl eluates from the column to which cytosol incubated with gamendazole-BT alone was applied. Lanes 6 and 8—the 250 and 600 mM NaCl eluates from the column to which cytosol incubated with gamendazole-BT plus excess gamendazole was applied. Arrow in Lane 3—the band identified by MALDI-TOF MS as HSP90AB1. Arrow in Lane 7—the band that was identified by MALDI-TOF MS as EEF1A1.

It was shown that gamendazole elicits a dramatic decrease in circulating inhibin B levels in vivo, and that primary cultures of Sertoli cells show a decline in inhibin production in vitro by gamendazole with an IC50 of $6.8 \times 10^{-10}$ M. This suggests that testis, and Sertoli cells, in particular, contain a target, or targets, with high affinity for the compound. To test this hypothesis, a biotinylated gamendazole analogue, gamendazole-BT was employed as a ligand in avidin-affinity chromatography (FIG. 14) followed by MALDI-TOF MS to identify proteins contained in the excised affinity bands. As noted below, we focused attention on bands that were consistently pulled out of the cytosol from all tissues or cells that were studied previously and found to be affected by gamendazole treatment: Sertoli cells (TM4 cells, FIG. 14 panel A), rat testis (FIG. 14 panel B), and ID-8 ovarian cancer cells (FIG. 14 panel C).

Protein bands at 90 kDa and at 53 kDa band were consistently observed in the gamendazole and subsequent high salt eluate from all three cytosol sources, respectively. Furthermore, each 90 kDa and 53 kDa band, respectively, exhibited the same gamendazole and salt elution profile and comparable reduction in signal by excess gamendazole-competition from all three cytosol sources. The top ranked protein match for the 90 kDa band from TM-4 cells and testis were both heat shock protein HSP90AB1 (MW 83229, P34058) (scores 37 and 78 correspondingly). Although the score for testis band is below the significance level (score 50), provided by Mascot default at 5%, the additional evidence for the successful identification was that the proteins were excised from the 90 k gel bands. In addition, 7 peptide matches comprising 14% coverage of the entire HSP90AB1 sequence were made with the TM-4 90 kDa band, and 12 peptides comprising 18% of the entire sequence were matched for the testis 90 kDa band.

The top ranked protein match for the 53 kDa band from TM-4 cells and testis were both EEF1A1-1 (MW 50082, P62630) (scores 54 and 36 correspondingly). Confidence in identification of this protein comes from the expected molecular weight around 50,000 determined by gel electrophoresis. In addition, 4 peptide matches comprising 14% coverage of the entire sequence were made with the TM-4 53 kDa band, and 7 peptides comprising 17% of the entire EEF1A1 sequence were matched for the testis 53 kDa band.

The affinity purification and elution profiles for the HSP90AB1 and EEF1A1-containing bands were consistent with gamendazole binding directly to these proteins or gamendazole binding to a protein complex containing these proteins. Firstly, in the eluates before the high salt 'bumps', the bands containing these proteins bound to the avidin column in a gamendazole-dependent manner. Comparison of the gamendazole-eluted protein profiles from the cytosols initially incubated without and with excess gamendazole revealed the 90 kDa protein that was selectively eluted from the column by gamendazole (FIG. 14 panel A, lane 3), but absent in the gamendazole eluate that was pre-blocked by excess gamendazole (FIG. 14 panel A, lane 4). In the subsequent NaCl eluates, a 90 kDa was also present but did show gamendazole-dependent competition binding to the column (FIG. 14 panel A, lanes 6 and 8). The identity of this band is not known. A band at 53 kDa was also observed in the high salt eluates that was absent in the gamendazole pre-blocked eluates (FIG. 14 panel A, lane 5-8). This band was also identified as EEF1A1 by MALDI-TOF MS and sequence and resulting match of 7 of 36 resulting peptides with a minimum of 17% sequence coverage.

Figure 15:
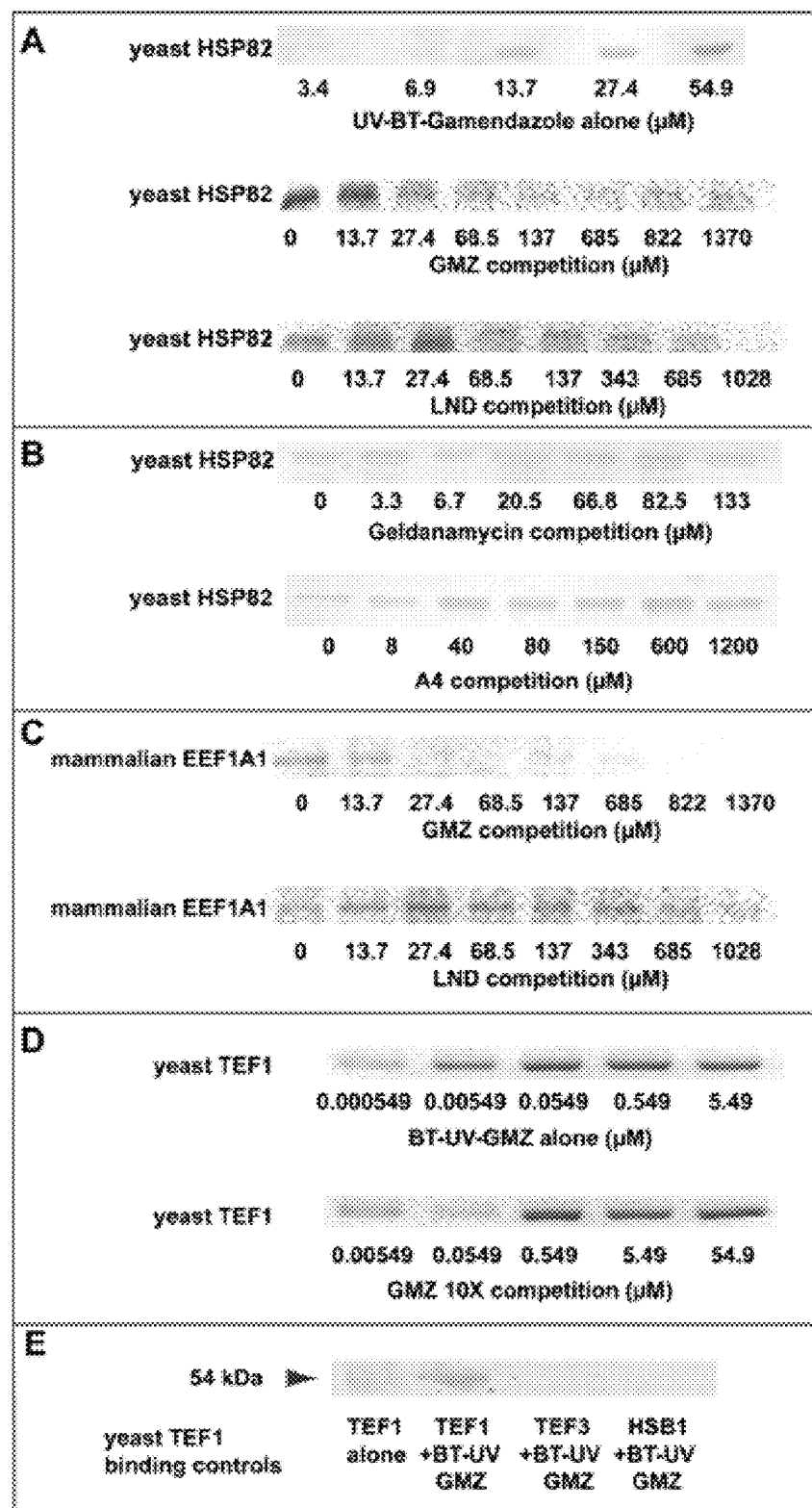
FIG. 15 panel A shows direct binding of BT-UV-gamendazole to purified *S. cerevisae* HSP82 and competition by gamendazole and LND.

A similar affinity purification experiment using cytosol from 60-day old rat testis also revealed HSP90AB1 and EEF1A1 in the gamendazole binding proteins (FIG. 14 panel B). Comparison of the gamendazole-eluted protein profiles from the testis cytosols incubated without and with excess gamendazole revealed a 90 kDa protein that was eluted from the column by gamendazole (FIG. 14 panel B, lanes 3-4), but absent in the gamendazole eluate that was pre-blocked by excess gamendazole (FIG. 14 panel B, lanes 6-7). Western blot analysis of the eluted samples confirmed the presence of HSP90 in a elution pattern that matched the 90 kDa Coomassie-stained band. A western signal corresponding to 90 kDa band HSP90 present in the starting precleared cytosols (FIG. 14 panel B, lanes 1-2), was eluted by 1.5 and 3.0 mM gamendazole (FIG. 14 panel B, lanes 3-4), but absent in the eluates from the cytosol pre-incubated with 10-fold excess gamendazole (FIG. 14 panel B, lanes 3-4). There is also a HSP90 western signal corresponding to the 90 kDa Coomassie-stained band in the salt eluate (FIG. 14 panel B, lane 7), that is absent in the excess gamendazole binding control (FIG. 14 panel B, lane 8). These results demonstrate that the 90 kDa band in the pre-high salt eluates contains HSP90, and that the binding of the protein(s) in this band, and its elution are dependent upon gamendazole binding either directly to the 90 kDa band itself or to a binding partner. MALDI-TOF analysis of the 90 kDa bands confirmed that this band contained HSP90AB1. As observed with TM-4 cells, there is also a component of proteins at 90 kDa that are resistant to gamendazole-dependent binding and elution that require high-salt to be removed from the column (FIG. 14 panel B, lanes 6-7). The western blot data suggest that HSP90 is present in the 600 mM salt eluate (FIG. 14 panel B, lane 7) and its binding to the column was still gamendazole-dependent (FIG. 15 panel B, lane 8). Thus it may have required higher levels of gamendazole or longer exposure to competing compound to elute from the column before application of the high salt.

A band containing EEF1A1 in the high-salt-eluate, that was blocked by excess gamendazole, was confirmed by Western blot. The Western blot also revealed EEF1A1 in the gamendazole pre-blocked sample that eluted from the column with higher concentrations of gamendazole (3.0 mM). The elution pattern for the EEF1A1 signal suggests that the gamendazole-dependent binding to the column is tighter than for HSP90 since the EEF1A1 band was eluted not with 1.5 mM gamendazole but higher concentrations and mainly in the high salt eluate from the column after Gamendazole had already been applied to the column. The presence of a western signal for EEF1A1 in the 6 mM gamendazole eluate from the excess gamendazole pre-incubated control could be explained by a high affinity binding site in EEF1A1 combined with the presence of large quantities of EEF1A1 in the cytosol.

HSP90 and EEF1A1 have been proposed as drug targets for anti-cancer therapeutic agents. Thus we examined the possibility that gamendazole could bind to the same protein targets in a cancer cell. We have already shown that ID8 cells show growth inhibition when cultured in the presence of gamendazole. As shown in FIG. 14 panel C, two very prominent and clean protein bands were eluted from the column and behaved identically to HSP90AB1 and EEF1A1, respectively, with regard to elution, relative molecular weight, and competition of binding by excess gamendazole.

The affinity purification of HSP90AB1 and EEF1A1 from testis and Sertoli cell cytosols using gamendazole-BT suggests either direct or indirect binding of HSP90 and EEF1A1 by gamendazole. Direct binding of HSP90 was confirmed using purified recombinant S. cerevisiae HSP82 (homologue to HSP90AB1) and gamendazole-BT-UV (FIG. 15 panel A). In the presence a fixed amount of HSP82, as the concentration of gamendazole-BT-UV increased, the signal of bound compound increased (FIG. 15 panel A, top lane). The signal for gamendazole-BT-UV was reduced in the presence of competing gamendazole indicating specific gamendazole binding (FIG. 15 panel A, middle lane). Competition of gamendazole binding by LND was not achieved until 10 mM LND and above (FIG. 15 panel A, bottom lane). This suggests that binding of HSP82 by gamendazole is much tighter than for LND. This conclusion was supported by attempts to affinity purify targets from testis using biotinylated UV-crosslinking LND. No LND-specific binding could be achieved following similar procedures (data not shown).

The direct binding of gamendazole to HSP82 was explored further by testing whether known inhibitors of HSP90 could compete for gamendazole-BT-UV binding (FIG. 15 panel B). HSP90 family members contain an N-terminal and a C-terminal ATP binding site. Two known inhibitors of HSP90 function are geldanamycin, an inhibitor of the N-terminal ATP site, and novobiocin, an inhibitor of the C-terminal ATP site. We have recently synthesized A4, an analogue of novobiocin, with a low μM affinity for HSP90 as opposed to the low mM affinity of novobiocin for HSP90. Neither geldanamycin nor A4 competed for binding of gamendazole-BT-UV by HSP82. This suggests that either gamendazole binds to HSP90 with much higher affinity than either geldanamycin or A4, or that gamendazole binds to a different site on HSP90 than the other compounds.

Example 16

In Vitro Binding and UV-Crosslinking of Gamendazole to Purified Bacterially Expressed Yeast HSP82 (HSP90) and Purified Yeast and Mammalian EEF1A1

Purified recombinant Saccharomyces cerevisiae HSP82 (5 μg in 20 μl), S. cerevisiae TEF1, TEF3, HBS1, or O. caniculus EEF1A1 were incubated with the gamendazole-BT-UV for 1 hr at 4° C., then cross-linked for 20 min at 4° C. with long-wave UV. Competition incubations were carried out with 10-fold molar excess gamendazole, lonidamine (LND), geldanamycin, and A4 (a novobiocin analogue) prior to UV-exposure. The protein was then run on a 7.5% SDS-PAGE gel, transferred to a PVDF membrane, and blocked with 0.1% BSA in TTBS (50 mM Tris-HCl, pH 7.4, 50 mM NaCl, 5 mM EDTA, and 50 mM NaF). The sheet was then incubated with horseradish peroxidase (HRP)-avidin, washed with TTBS, then incubated for 20 min with AEC substrate for HRP (Zymed Invitrogen, Carlsbad, Calif.) to visualize the gamendazole-coupled protein.

Direct binding and competition of gamendazole binding to purified O. caniculus EEF1A1 (FIG. 15 panel C) and its homologue S. cerevisiae TEF1 (FIG. 15 panel D) was also confirmed following similar procedures. In the presence fixed amounts of TEF1, concentrations of gamendazole-BT-UV alone at 54.9 nM and above showed no additional increase in signal indicating saturation of the protein at these concentrations (FIG. 15 panel D, upper lane). At the sub-saturating concentrations of gamendazole-BT-UV, competition with 10× excess gamendazole competed binding as indicated by the lower binding signal (FIG. 15 panel D, lower panel). In order to control for the specificity of crosslinking to TEF1, reactions with gamendazole-BT-UV were also performed with two other purified yeast nucleotide binding proteins, HBS1, a GTP binding protein, and TEF3, an ATP binding protein. At equal concentrations and ratios to BT-UV-GMZ as utilized for TEF1, no crosslinking to either protein could be observed (FIG. 15 panel E).

Example 17

Effect of gamendazole on HSP90 Client Proteins in MCF-7 Cells and HSP90-Mediated Luciferase Refolding The affinity purification results and in vitro HSP90 binding studies above demonstrate that gamendazole binds directly to HSP90. To determine whether gamendazole produces a functional change in HSP90, we undertook a series of cell-based and in vitro experiments that have been previously used to measure distinct functional changes in HSP90 resulting from direct drug binding. In the presence of inhibitors, the substrate-bound HSP90 heteroprotein complex becomes destabilized and the client protein becomes a target for ubiquitin-proteasomal degradation. Thereby, disruption of HSP90-mediated protein folding processes result in the degradation of HSP90-dependent client proteins. We decided to test the MCF-7 breast cancer cell line, in which numerous HSP90 inhibitors have been analyzed, to provide the most appropriate confirmation of HSP90 inhibitory activity.

Figure 16:
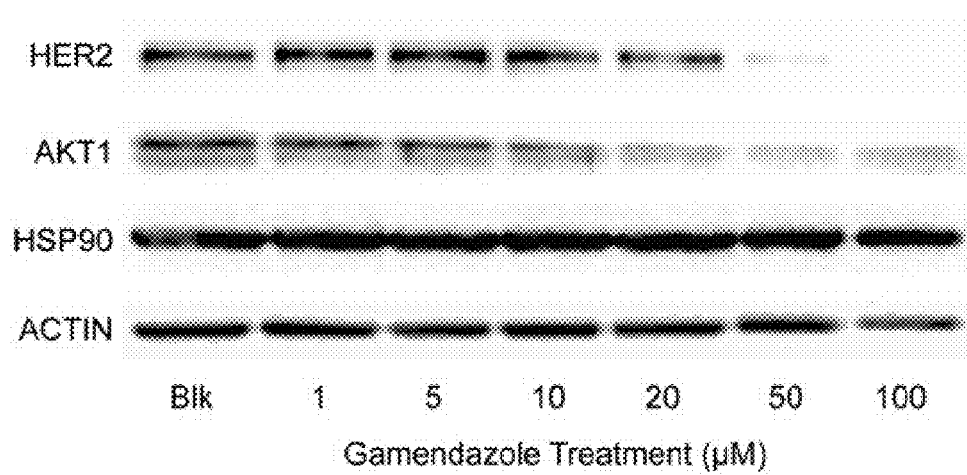
FIG. 16 shows a Western blot analysis of ERBB2, AKT1, HSP90, and actin in MCF-7 cells treated with gamendazole. All concentrations are reported in μM and geldanamycin (500 nM), a known HSP90 inhibitor, was used as a positive control.
Figure 17:
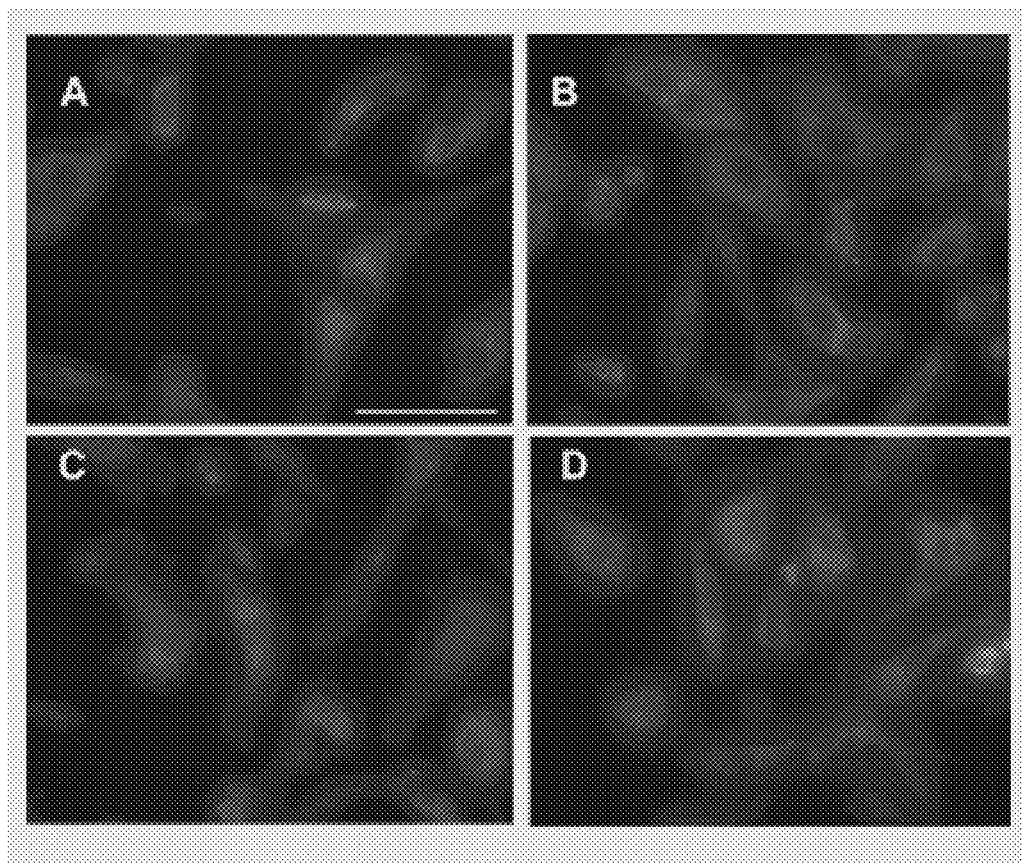
FIG. 17 shows immunohistochemistry of HSP90AB1 and EEF1A1 in primary Sertoli cells is not altered by gamendazole. Immunohistochemistry of HSP90AB1 in primary mouse Sertoli cells incubated for 24 hr in the absence (Panel A) or presence (Panel B) of gamendazole. Immunohistochemistry of EEF1A1 in primary mouse Sertoli cells incubated for 24 hr in the absence (Panel C) or presence (Panel D) of gamendazole. Bar=50 μm.

To determine whether gamendazole affects the HSP90-mediated protein folding process, Western analyses of MCF-7 breast cancer cell lysates was performed (FIG. 16). ERBB2 (HER2) and AKT1 are known HSP90-dependent client proteins that require HSP90 for conformational maturation. Gamendazole caused the degradation of these two HSP90 substrates in a dose-dependent manner (FIG. 16). Actin is not a substrate for the HSP90 protein folding process and in the presence of gamendazole, levels of actin remained the same, supporting the hypothesis that gamendazole's effects are related to destabilization of the substrate bound HSP90 heteroprotein complex. Even though gamendazole produced a decline in AKT1 and ERBB2, there was no accompanying increase in HSP90, suggesting that gamendazole is not dismantling the HSP90-HSF1 heteroprotein complex and is thus not inducing the expression of the inducible form of HSP90, HSP90AA1. Since most HSP90 drugs induce HSP90AA1 synthesis, it was important to examine the possibility that localization changes might occur since western blots indicated no change in levels of the protein in MCF-7 cells. Immunofluorescence analysis of primary Sertoli cells treated with gamendazole also demonstrates no change in localization or level of the HSP90AB1 or EEF1A1 (FIG. 17). Similarly, no change in EEF1A1 levels or localization was observed (FIG. 17). Similar diffuse cytoplasmic patterns of distribution for HSP90 and EEF1A1 have been reported previously.

Example 18

Figure 18A:
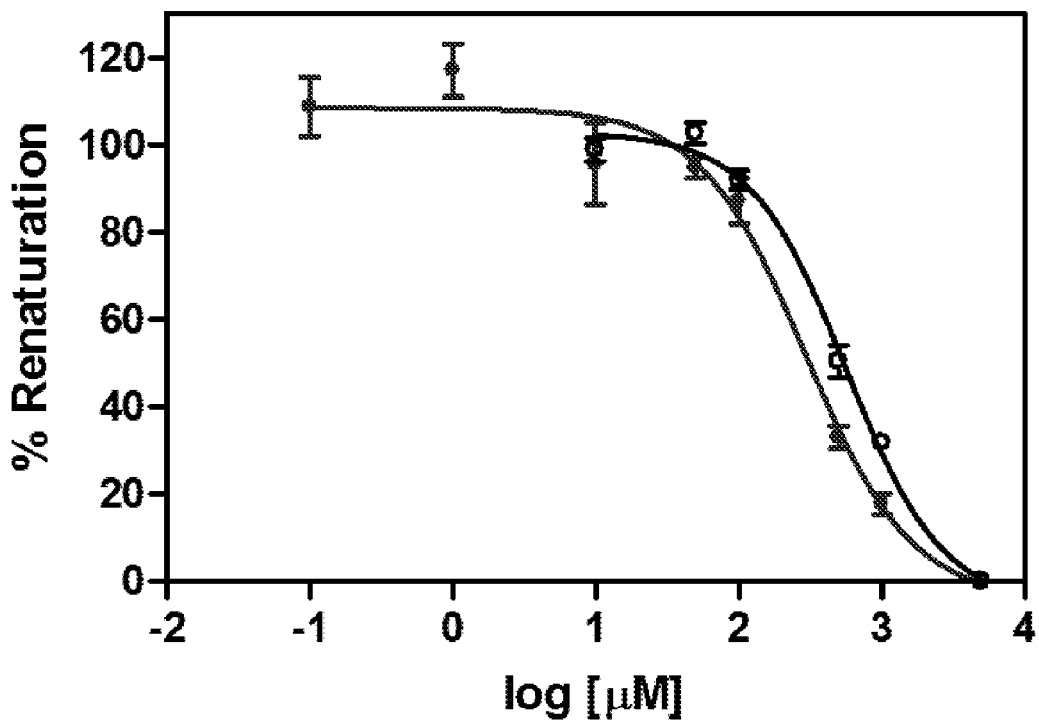
FIG. 18A-18B includes graphs that show the effect of HSP90 inhibition on the renaturation of firefly luciferase in rabbit reticulocyte lysate and cell proliferation.

Gamendazole Inhibits HSP90-Dependent Luciferase Refolding In Vitro and Proliferation of MCF-7 Cells The refolding of thermally denatured firefly luciferase in rabbit reticulocyte lysate is an HSP90-dependent process. We have recently demonstrated that this is a robust, reproducible assay capable of identifying inhibitors of HSP90 that bind at either the N- or C-terminus. Gamendazole inhibited the refolding of denatured luciferase in this assay ($IC_{50}$=330±38 μM), demonstrating its ability to functionally inhibit HSP90 activity (FIG. 18A). The $IC_{50}$ value for novobiocin (552±12 μM) was higher than previously estimated in our high-throughput screen (~400 μM), however, slight differences in lysate batches and experimental conditions could explain this effect.

Figure 18B:
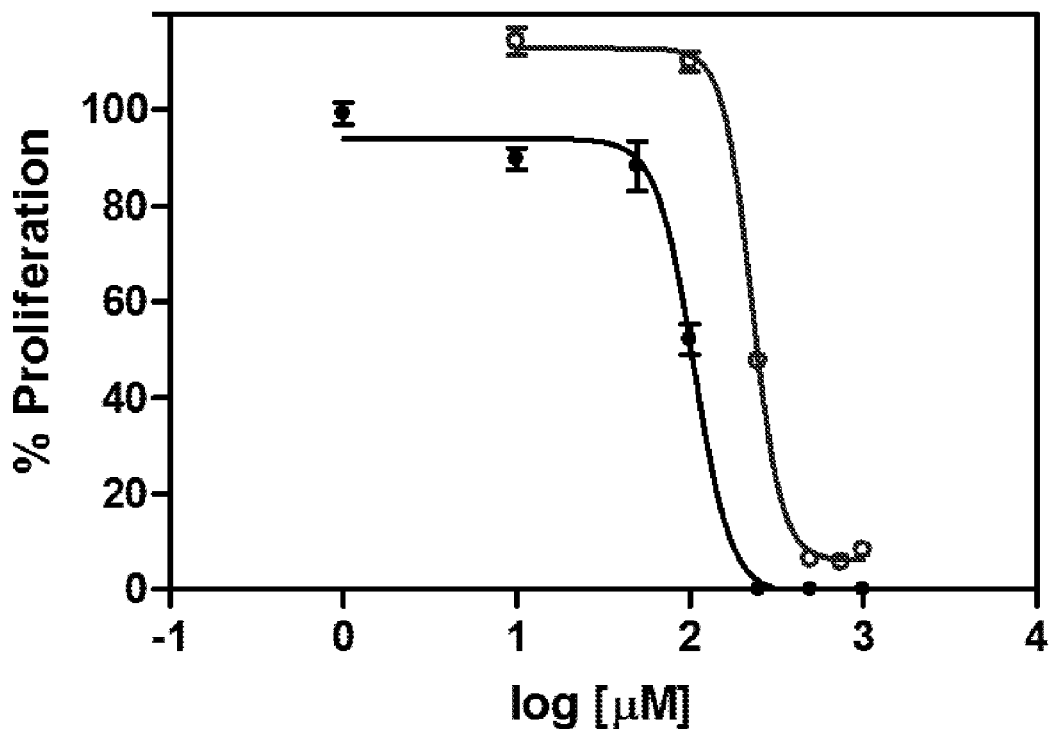

LND, from which gamendazole was designed, was initially developed as an anti-cancer therapeutic agent. Since gamendazole displays inhibitory affects on HSP90 client proteins similar to other HSP90 anti-cancer agents, we examined whether gamendazole inhibits proliferation of MCF-7 cells in vitro (FIG. 18B). The IC50 value for inhibition of MCF-7 cell proliferation by gamendazole was 101±4 μM. Whereas, for novobiocin, the IC50 was over 2-fold higher at 224±5 μM.

Example 19

Mant-GMPPNP and Mant-GDP Binding Assay for TEF1

The binding affinity for 2'-(or 3')—O—N-methylanthraniloyl (mant)-GDP and mant-GMPPNP to *S. cerevisiae* TEF1 in the presence and absence of gamendazole were determined by a fluorometric titration assay. To examine whether gamendazole inhibits nucleotide binding of TEF1, 50 μM of gamendazole was incubated with TEF1-binding buffer mix for 30 min at 25° C. before adding fluorescently labeled nucleotides. Increased fluorescence of mant-nucleotides was observed by fluorescence resonance energy transfer (FRET) which excited tryptophans or tyrosines of TEF1 at 280 nm and used emission wavelength of 440 nm for the mant moiety of the nucleotides. The protein and nucleotide complex-dependent fluorescence values were plotted against mant-GMPPNP or mant-GDP concentrations and fit to a hyperbolic curve to give $K_d$ values.

Figure 19A:
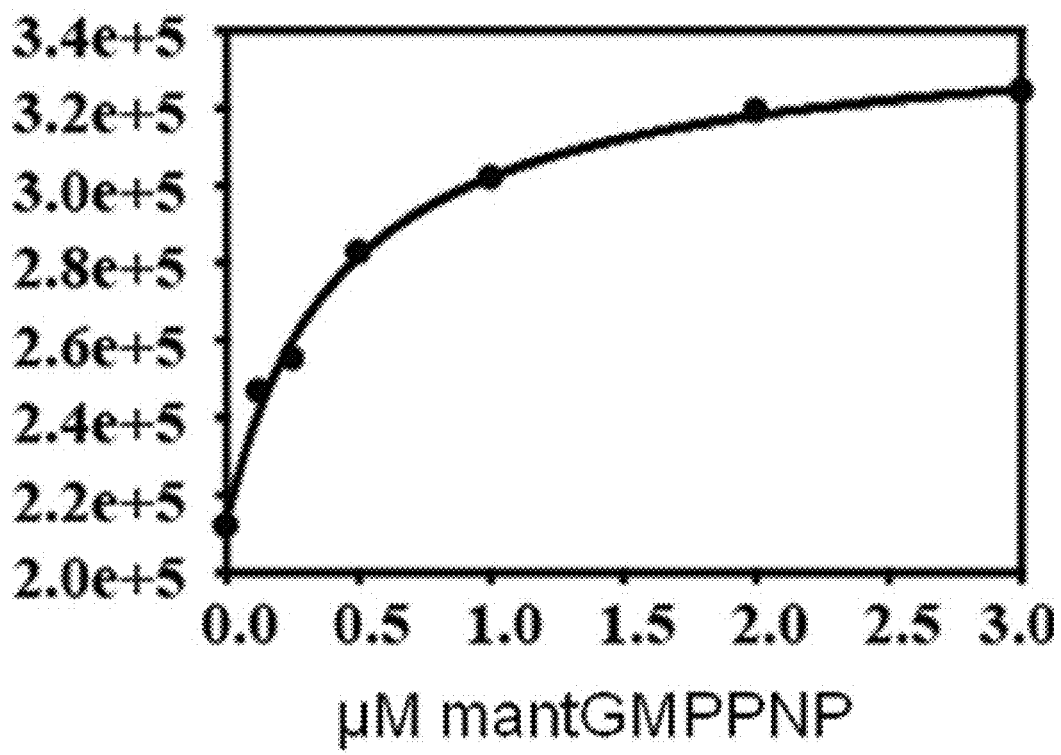
FIG. 19A-19B includes graphs that show TEF1 nucleotide binding assays. Aliquots of mant-GMPPNP (A) and mant-GDP (B) were added to the binding buffer and TEF1 (1 μM) with 50 μM gamendazole. The fluorescence was measured by FRET via excitation at 280 nm and emission of 440 nm for the mant moiety. Data was fit to a hyperbolic curve to give a $K_d$ value.
Figure 19B:
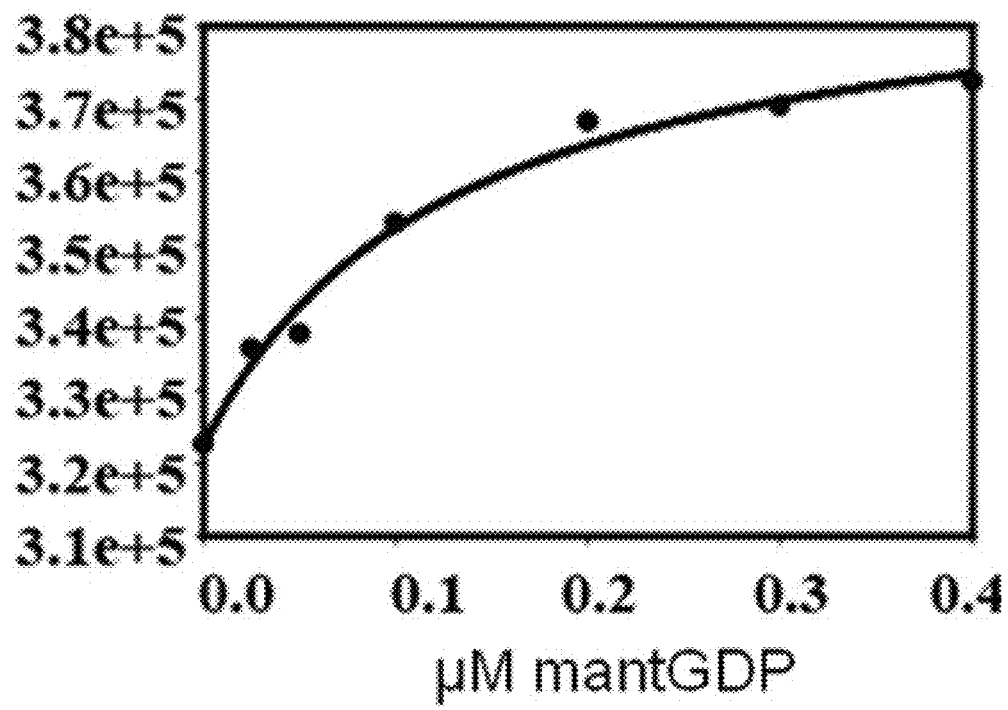

Two known functions of EEF1A1 and TEF1 are elongation during protein synthesis and actin bundling. The canonical translation function requires exchange of GDP and GTP in a nucleotide binding pocket of the protein, while actin bundling is nucleotide independent. The latter of these two functions requires exchange of GDP and GTP in a nucleotide binding pocket of the protein. To determine the effect of gamendazole on nucleotide binding affinities of TEF1, the equilibrium dissociation constant of ($K_d$) of TEF1 for mant-GDP and mant-GMPPNP was measured in the presence of 50 μM drug (FIG. 19A-19B). The $K_d$ value of TEF1 for mant-GDP in the absence of drug is 0.18 μM. Stopped-flow kinetics using mant-GDP showed TEF1 binds to mant-GDP in the presence of the gamendazole with a similar affinity ($K_d$=0.12). The $K_d$ of TEF1 for mant-GMPPNP with and without gamendazole was determined as 0.43 μM and 0.52 μM respectively. The similar $K_d$ values indicate that gamendazole does not affect nucleotide-binding properties of EEF1A1.

Example 20

Immunofluorescence of HSP90AB1 and EEF1A1 in Gamendazole-Treated Primary Sertoli Cells Primary Sertoli cells were plated on acid-washed poly-L-lysine coated glass cover slips in 6-well plates. The cells were treated with 20 μM gamendazole at 37° C. Controls were treated with solvent carrier (final concentration of 0.2% DMSO). After 24 hr, the media was aspirated and the cells were washed three times with 2 ml of TBS (10 mM Tris-HCl, pH 7.4, 0.9% (w/v) NaCl). The cells were then fixed with 10% formaldehyde in TBS for 20 min at room temperature (R.T.), washed three times for 10 min with TBS, then permeabilized with 1% NP-40 in TBS for 15 mins. The cells were then washed with TBS+0.1% NP-40, and blocked for 1 hr at R.T. with 10% goat serum in TBS-NP-40. After rinsing with TBS, the cells were incubated for 1 hr at 37° C. with primary antibody: either 1:1000 dilution of mouse monoclonal IgG anti-EEF1A1 (05-235, Upstate, Waltham, Mass.), or 1:1000 dilution of mouse monoclonal IgM anti-HSP90AB1 (SPA-843, Stressgen Biotechnologies, San Diego, Calif.), in 2% Goat serum and 0.1% bovine serum albumin in TBS-NP-40. After three washes with TBS-NP-40, the cells were incubated in the dark for 1 hr at R.T. with TRITC-tagged secondary antibody (in the same buffer as primary antibody): for EEF1A1, 1:200 goat anti-mouse IgG (115-025-003, Jackson Immunologicals, West Grove, Pa.), and for HSP90AB1, 1:200 goat anti-mouse IgM (115-025-020, Jackson Immunologicals, West Grove, Pa.). After the final three washes with TBS-NP-40 (10 min each), cover slips were mounted with Vectashield Hardset mounting media for fluorescence (Vector Laboratories, Burlingame, Calif.).

Example 21

Figure 20:
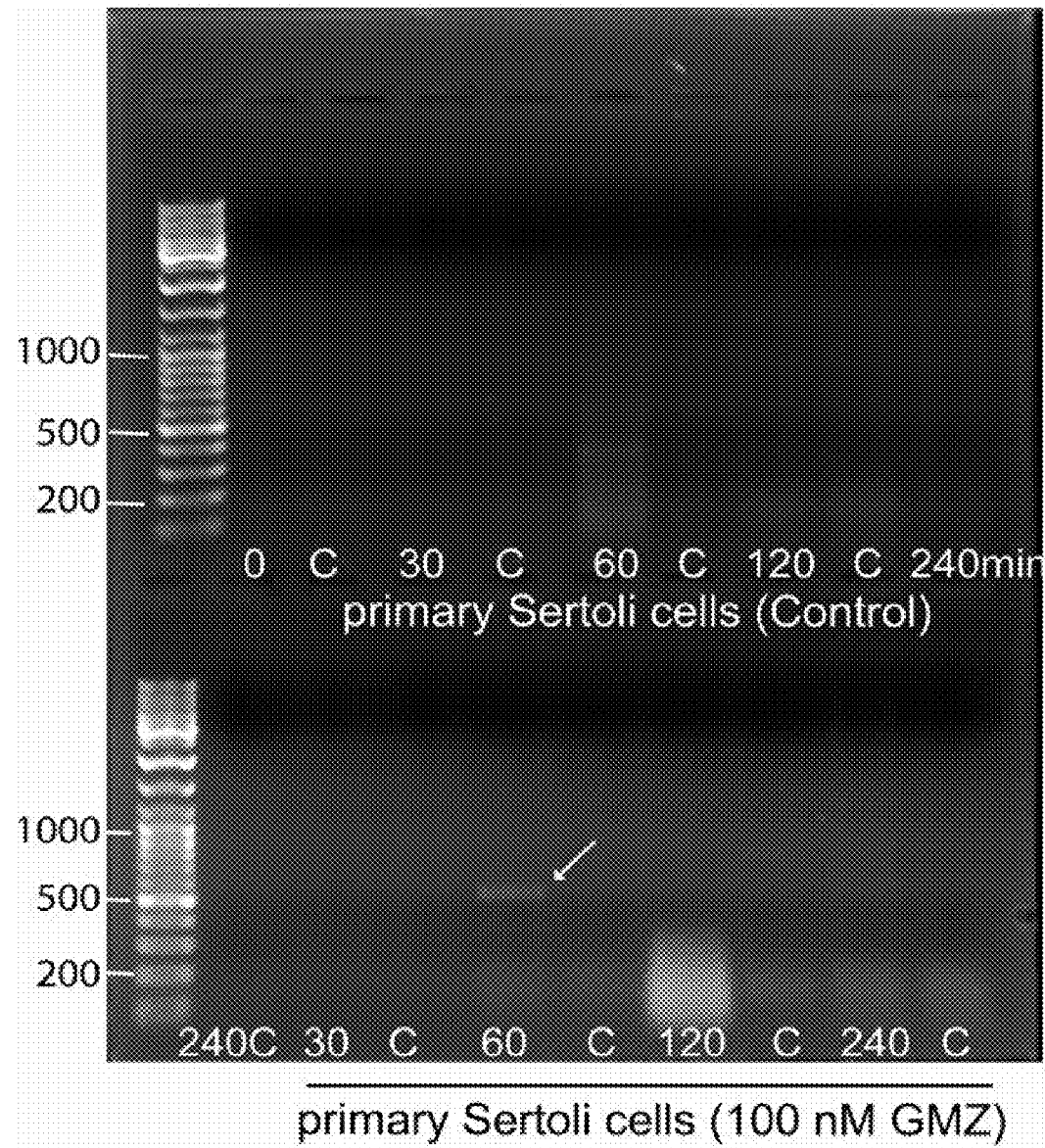
FIG. 20 shows results of RT-PCR of IIIa in primary Sertoli cells treated with and without gamendazole (10 nM) for 0-240 min.

Confirmation of Interleukin 1-alpha (Il1a) as Early Response Gene in Primary Sertoli Cells Treated With gamendazole Il1a is a known disruptor of Sertoli cell-spermatid junction integrity and has been proposed as an important regulator of Sertoli cell-spermatogenic cell interactions. Three interleukin 1 genes were among the most rapidly and dramatically increased genes in response to gamendazole. The primary hypothesis driving the proposed research is that Sertoli cells are the primary target cell for gamendazole's anti-spermatogenic effect. To provide further support for this hypothesis, we confirmed Il1a as an early response gene to gamendazole in primary Sertoli cells. We performed RT-PCR using RNA prepared from primary Sertoli cells cultured in the absence and presence of 100 nM gamendazole for 0, 30, 60, 120, and 240 min (FIG. 20). This dose of gamendazole is well within the concentration range used to test lonidamine effects in vitro in previous studies. At 60 min of gamendazole treatment, a spike of amplified product of approximately 500 bp, the size expected for IIIa, was observed (FIG. 20). In the absence of gamendazole, no amplified product was detected at any time point. The product was also absent in reactions performed without added reverse transcriptase (indicated by a C at the lane next to each positive time point), confirming the signal was derived from amplified mRNA.

Example 22

Female Fertility Management

Figure 21:
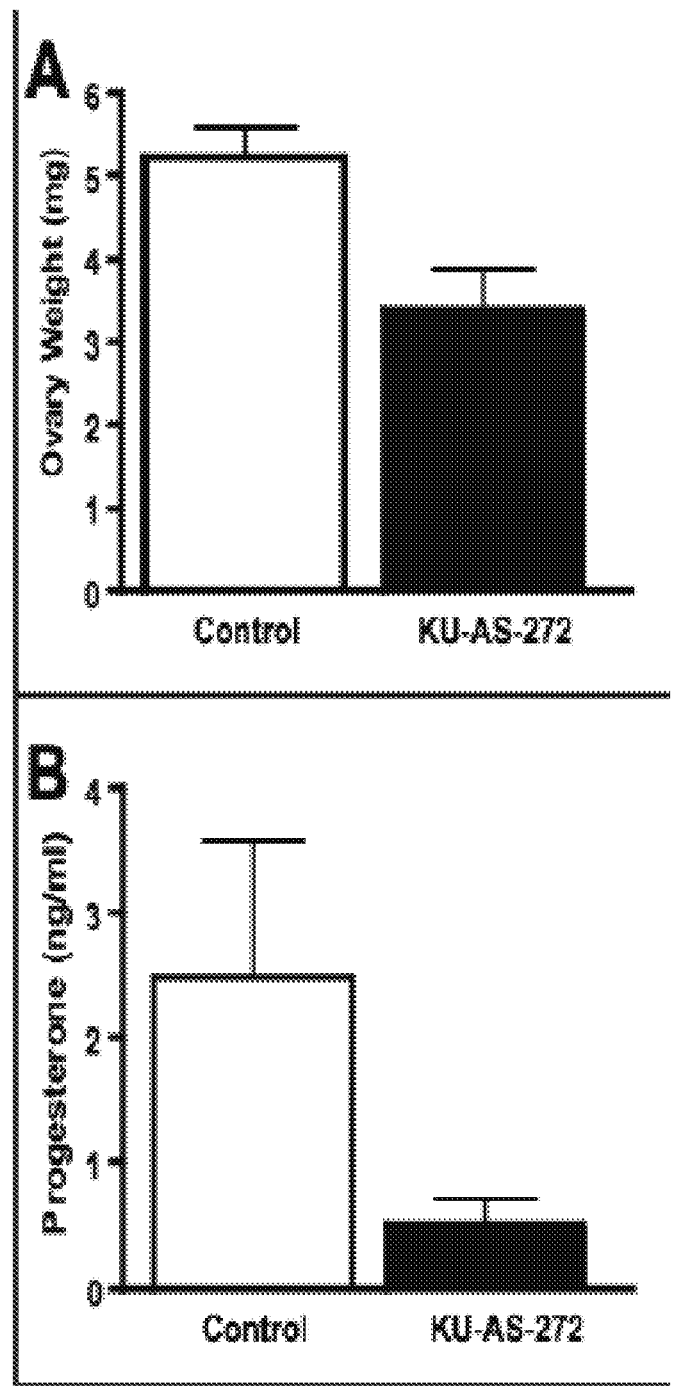
FIG. 21 includes graphs that show that after 5 days of a single oral dose (100 mg/kg) of H2-gamendazole female mice had reduced ovary weight (FIG. 21 panel A) and reduced serum levels of progesterone (FIG. 21 panel B).
Figure 22:
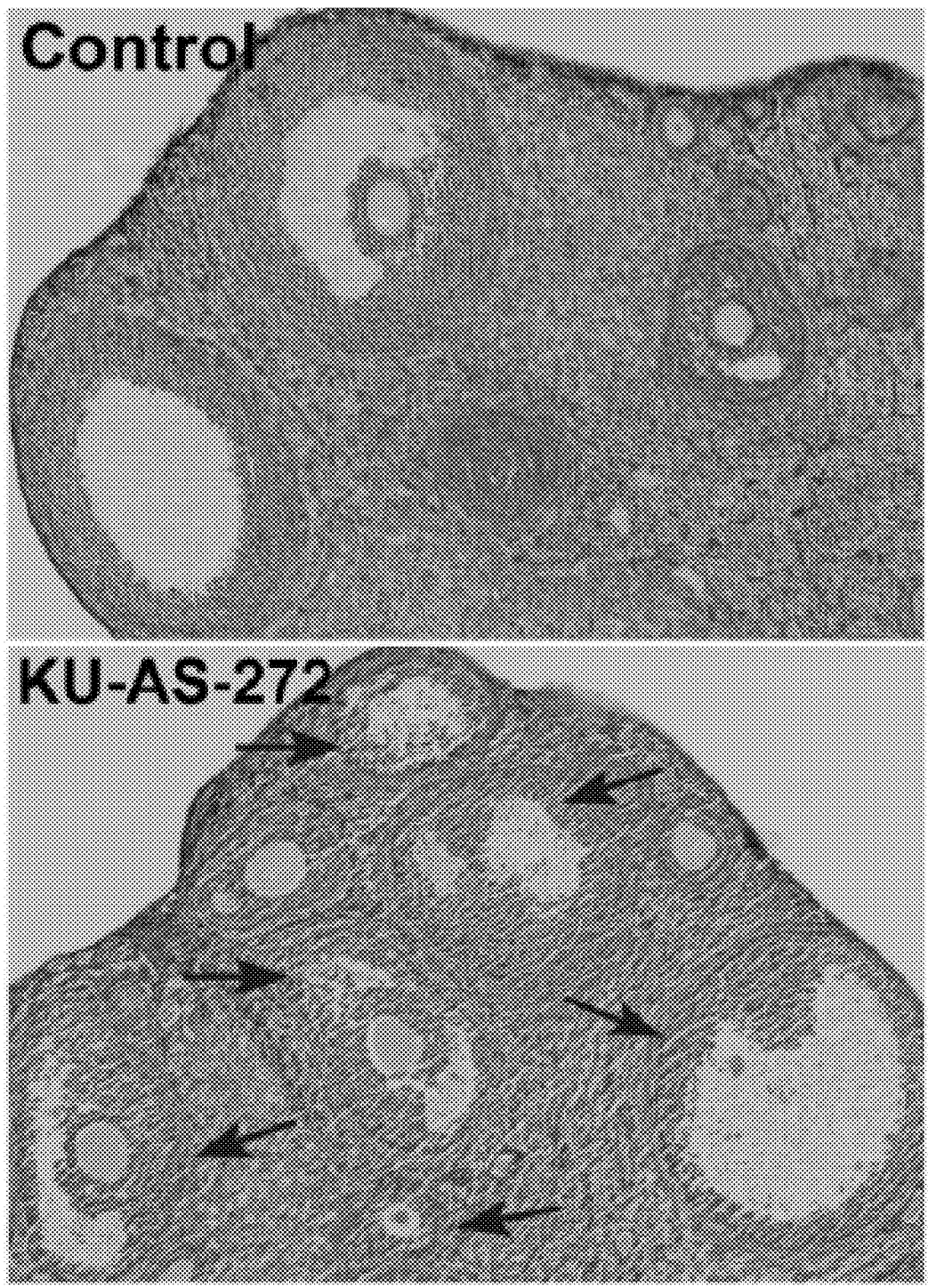
FIG. 22 includes images of ovarian histology that reveal the presence of multiple atretic/dying follicles after 5 days following H2-gamendazole administration (100 mg/kg).

The ability to modulate female fertility was investigated. The H2-gamendazole was administered to adult cycling C57BI6 female mice in a single oral dose of 100 mg/kg. The total weight, ovary weight, and serum levels of progesterone were measured. It was found that after 6 days ovarian weight (FIG. 21 panel A) and steroid (e.g., progesterone) production (FIG. 21 panel B) rapidly decreased after administration of H2-gamendazole. However, the total weight of the mice stayed about the same (data not shown) and did not change after a single oral dose, which indicates that the dose was not toxic. Histology (FIG. 22) shows that H2-gamendazole causes ovarian follicles to impaired and to die (e.g., atretic) compared to a control of carrier as described herein. These data indicate a single dose of H2-GMZ exerts a rapid and significant effect on the ovary.

Example 23

Probability of Effect of Compounds

Figure 23:
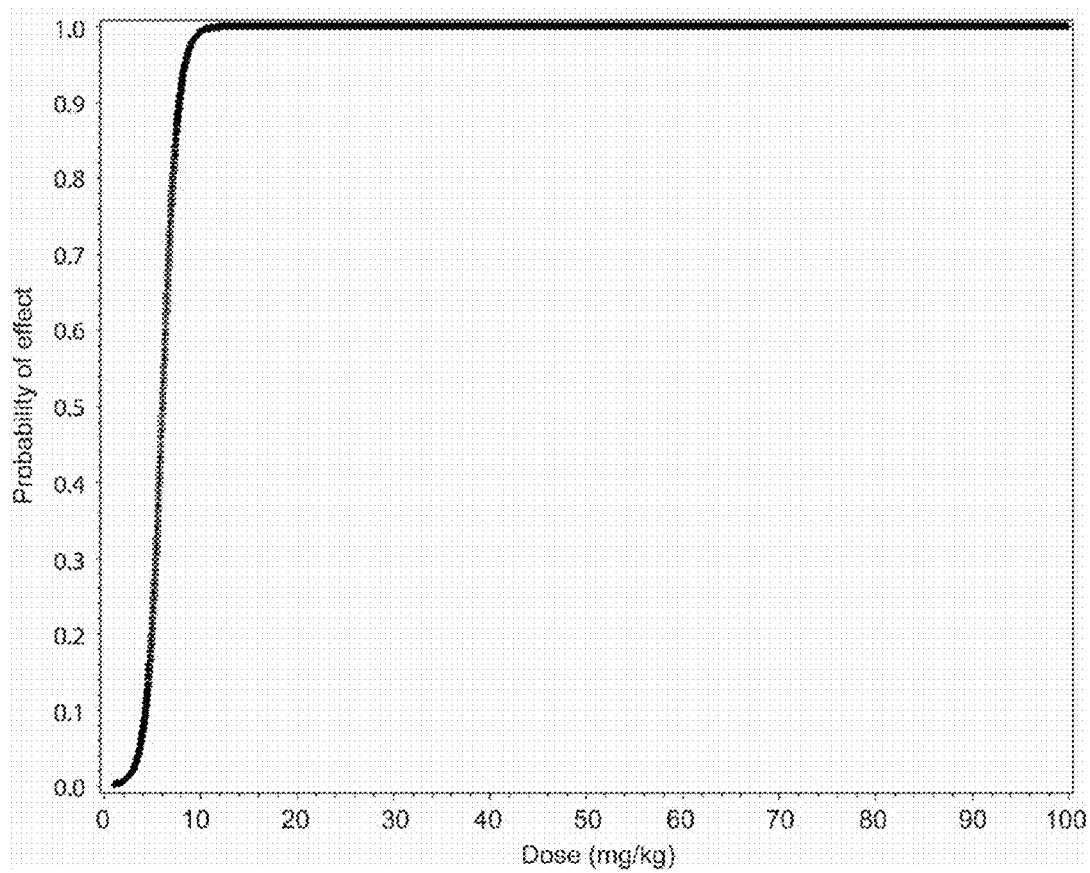
FIG. 23 includes a graph that shows the probability of inhibiting fertility for increasing dose amounts.

The mating trial data for rats using all doses for gamendazole tested thus far shows that testes weight decreases by approximately 50% with a standard deviation of 3.5% at a 6 mg/kg dose in rats. The changes in ovary weights were 35% and 8% (SD) in female mice, respectively. A logistic model predicting success (sterility) using dose level was fit to data (FIG. 23) assuming a 50% success rate at a dose rate of 6 mg/kg and 100% success at levels of 12 mg/kg to 100 mg/kg which is what the investigator expects. Since the biological efficacy of gamendazole (RC-MC-110) and H2-gamendazole (JWS-2-72) are similar, the model predicts a success rate of 99.95% at a dose level of 12 mg/kg for each compound: sterility=$e^{-7.5415+1.2569*dose}$

The invention claimed is:

1. A method for inducing irreversible sterility in a subject, the method comprising:
    administering to the subject one or more doses of a compound according to Formula I so as to reduce fertility in the subject:

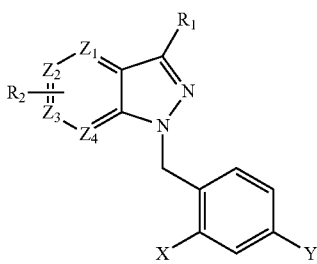

Formula I wherein $R_1$ is carboxyl, acryl, or carboxylic acid hydrazide;
wherein $R_2$ is halogen, alcohol, alkoxy, aralkyl, cycloalkyl, haloalkyl, haloalkoxy, amino, or carboxyl;
wherein X and Y are the same or different from each other and are halogen or lower alkyl;
wherein $Z_1$, $Z_2$, $Z_3$, and $Z_4$ are carbon; and
pharmaceutically acceptable salts and esters thereof.

2. A method as in claim 1, wherein
$R_1$ includes one or more of a carboxylic acid, carboxylic acid ester, propionic acid, 2-methyl propionic acid, oxirane-carboxylic acid, cyclopropane carboxylic acid, propionic acid methyl ester, 2-methyl propionic acid methyl ester, oxirane-carboxylic acid methyl ester, or cyclopropane carboxylic acid methyl ester; and/or
$R_2$ includes a halogen, haloalkyl, or haloalkoxy.

3. A method as in claim 1, wherein the, compound is selected from the group consisting of:
3-[1-(2,4-dichlorobenzyl)-6-trifluoromethyl-1H-indazol-3-yl]-acrylic acid;
6-chloro-1-(2,4-dichlorobenzyl)-1H-indazole-3-carboxylic acid hydrazide;
1-(2,4-dichlorobenzyl)-6-fluoro-1H-indazole-3-carboxylic acid methyl ester;
6-fluoro-1-(2,4-dichlorobenzyl)-1H-indazole-3-carboxylic acid hydrazide;
3-[1-(2,4-dichlorobenzyl)-6-fluoro-1H-indazol-3-yl]-acrylic acid;
3-[1-(2,4-dichlorobenzyl)-6-chloro-1H-indazol-3-yl]-acrylic acid;
3-[1-(2,4-dichlorobenzyl)-6-trifluoromethoxy-1H-indazol-3-yl]acrylic acid; 341-(2,4-dichlorobenzyl)-6-chloro-1H-indazol-3-ylJ-propionic acid;
3-[1-(2,4-dichlorobenzyl)-6-trifluoromethyl-1H-indazol-3-yl]-propionic acid; and pharmaceutically acceptable salts and esters thereof.

4. A method as in claim 1, wherein the compound is selected from the group consisting of:
gamendazole;
3-[1-(2,4-dichlorobenzyl)-6-trifluoromethyl-1H-indazol-3-yl]-propionic acid (JVVS-2-72 or H2-gamendazole);
3-[1-(2,4-dichlorobenzyl)-6-chloro-1H-indazol-3-yl]-acrylic acid (JWS 1-190);
1-(2-chloro-4-fluorobenzyl)-6-chloro-1H-indazole-3-carboxylic acid hydrazide (JWS 2-22);
1-(2,4-difluorobenzyl)-6-chloro-1H-indazole-3-carboxylic acid hydrazide (JWS 1-282);
and
pharmaceutically acceptable salts and esters thereof.

5. A method as in claim 1, wherein the compound is administered in an effective amount to inhibit spermatogenesis in the subject.

6. A method as in claim 5, wherein the compound is administered in an effective amount to impair Sertoli cell function in the subject.

7. A method as in claim 5, wherein the compound is administered in an effective amount to reduce testis weight in the subject.

8. A method as in claim 5, wherein the compound is administered in a therapeutically effective amount for causing reversible infertility in the subject, the method further comprising:
ceasing administration of the compound to the subject so as to return fertility in the subject.

9. A method as in claim 5, wherein the compound is administered in an effective amount for irreversibly sterilizing the subject.

10. A method as in claim 9, wherein the compound is administered in an effective amount to induce irreversible sterility in the subject in a single dose.

11. A method as in claim 9, wherein the compound is administered in a multi-dose regimen to induce irreversible sterility in the subject.

12. A method for inducing irreversible sterility in a male subject, the method comprising:
   administering to the male subject one or more doses of a composition having a pharmaceutically acceptable carrier and a compound according to Formula I so as to irreversibly inhibit spermatogenesis:

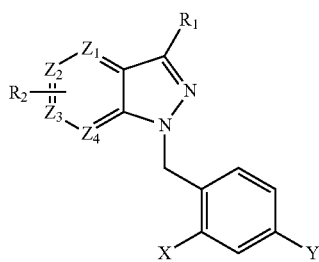

Formula I wherein $R_1$ is carboxyl, acryl, or carboxylic acid hydrazide;
wherein $R_2$ is halogen, alcohol, alkoxy, aralkyl, cycloalkyl, haloalkyl, haloalkoxy, amino, or carboxyl;
wherein X and Y are the same or different from each other and are halogen or lower alkyl;
wherein $Z_1$, $Z_2$, $Z_3$, and $Z_4$ are carbon; and
pharmaceutically acceptable salts and esters thereof.

13. A method as in claim 12, wherein the compound is selected from the group consisting of:
   3-[1-(2,4-dichlorobenzyl)-6-trifluoromethyl-1H-indazol-3-yl]-acrylic acid;
   6-chloro-1-(2,4-dichlorobenzyl)-1H-indazole-3-carboxylic acid hydrazide;
   1-(2,4-dichlorobenzyl)-6-fluoro-1H-indazole-3-carboxylic acid methyl ester;
   6-fluoro-1-(2,4-dichlorobenzyl)-1H-indazole-3-carboxylic acid hydrazide;
   3-[1-(2,4-dichlorobenzyl)-6-fluoro-1H-indazol-3-yl]-acrylic acid;
   3-[1-(2,4-dichlorobenzyl)-6-chloro-1H-indazol-3-yl]-acrylic acid;
   3-[1-(2,4-dichlorobenzyl)-6-trifluoromethoxy-1H-indazol-3-yl]acrylic acid;
   3-[1-(2,4-dichlorobenzyl)-6-chloro-1H-indazol-3-yl]-propionic acid;
   3-[1-(2,4-dichlorobenzyl)-6-trifluoromethyl-1H-indazol-3-yl]-propionic acid;
   gamendazole;
   3-[1-(2,4-dichlorobenzyl)-6-trifluoromethyl-1H-indazol-3-yl]-propionic acid;
   3-[1-(2,4-dichlorobenzyl)-6-chloro-1H-indazol-3-yl]-acrylic acid;
   1-(2-chloro-4-fluorobenzyl)-6-chloro-1H-indazole-3-carboxylic acid hydrazide;
   1-(2,4-difluorobenzyl)-6-chloro-1H-indazole-3-carboxylic acid hydrazide; and
   and pharmaceutically acceptable salts and esters thereof.

14. A method as in claim 13, wherein the compound is selected from the group consisting of:
   gamendazole;
   3-[1-(2,4-dichlorobenzyl)-6-trifluoromethyl-1H-indazol-3-yl]-propionic acid (JVVS-2-72 or H2-gamendazole).

15. A method as in claim 12, wherein the compound is administered in an effective amount to irreversibly sterilize the male subject and maintain bodyweight of the subject.

16. A method as in claim 12, wherein the compound is administered in an effective amount to irreversibly sterilize the male subject and inhibiting production of inhibin B.

17. A method as in claim 12, wherein the compound is administered in an effective amount to irreversibly sterilize the male subject and increase circulating follicle-stimulating hormone (FSH).

18. A method as in claim 12, wherein the compound is administered in an effective amount to irreversibly sterilize the male subject and reduce one or more of: structured spermatogenic cell-type layering; spermatozoa; spermatids; spermatagonia; germinal epithelium; amount of germ cells; or testis weight.

19. A method as in claim 12, wherein the compound is administered in an effective amount to irreversibly sterilize the male subject and inhibiting: heat shock protein HSP90AB1; and/or eukaryotic translation elongation factor 1 alpha 1 (EEF1A1).

20. A method as in claim 12, wherein the compound is administered in an effective amount to irreversibly sterilize the male subject and increase: production of an interleukin 1 protein; or increasing production of NF-KappaB inhibitor alpha (Nfkbia).

21. A method as in claim 12, wherein the compound is administered in an effective amount to induce irreversible sterility in the subject in a single dose.

22. A method as in claim 12, wherein the compound is administered in a multi-dose regimen to induce irreversible sterility in the subject.

23. A method for inducing irreversible sterility in a male subject, the method comprising:
   administering to a male subject a single dose of at least 6 mg/kg of a compound according to Formula I so as to irreversibly inhibit spermatogenesis:

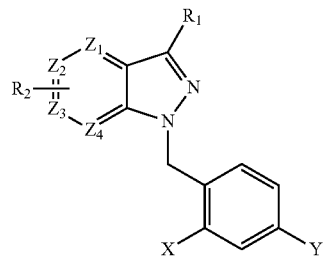

Formula I wherein $R_1$ is carboxyl, acryl, or carboxylic acid hydrazide;
wherein $R_2$ is halogen, alcohol, alkoxy, aralkyl, cycloalkyl, haloalkyl, haloalkoxy, amino, or carboxyl;
wherein X and Y are the same or different from each other and are halogen or lower alkyl;
wherein $Z_1$, $Z_2$, $Z_3$, and $Z_4$ are carbon; and
pharmaceutically acceptable salts and esters thereof.

24. A method as in claim 23, wherein the compound of Formula I is administered to the male subject from about 12 mg/kg to about 100 mg/kg.

* * * * *

UNITED STATES PATENT AND TRADEMARK OFFICE
CERTIFICATE OF CORRECTION

| | |
|---|---|
| PATENT NO. | : 8,377,958 B2 |
| APPLICATION NO. | : 12/830681 |
| DATED | : February 19, 2013 |
| INVENTOR(S) | : Georg et al. |

It is certified that error appears in the above-identified patent and that said Letters Patent is hereby corrected as shown below:

In the Specification:

In Column 6, Line 10, delete "FIG. 9A-9B" and insert -- FIGS. 9A-9B --, therefor.

In Column 6, Line 30, delete "mm." and insert -- μm. --, therefor.

In Column 6, Line 42, delete "FIG. 12A-12B" and insert -- FIGS. 12A-12B --, therefor.

In Column 7, Line 27, delete "cerevisae" and insert -- cerevisiae --, therefor.

In Column 7, Line 53, delete "FIG. 18A-18B" and insert -- FIGS. 18A-18B --, therefor.

In Column 8, Line 3, delete "FIG. 19A-19B" and insert -- FIGS. 19A-19B --, therefor.

In Column 8, Line 10, delete "IIIa" and insert -- Il1a --, therefor.

In Column 8, Line 33, delete "(EEF1A 1)" and insert -- (EEF1A1) --, therefor.

In Column 16, Line 33, delete "provided" and insert -- provided. --, therefor.

In Column 19, Line 16, delete "Gamandazole)" and insert -- Gamendazole) --, therefor.

In Column 30, Lines 66-67, delete "provided" and insert -- provided. --, therefor.

In Column 40, Line 39, delete "3-carboxylic," and insert -- 3-carboxylic --, therefor.

Signed and Sealed this
First Day of October, 2013

Teresa Stanek Rea
*Deputy Director of the United States Patent and Trademark Office*

CERTIFICATE OF CORRECTION (continued)
U.S. Pat. No. 8,377,958 B2

In Column 42, Lines 1-12, delete " 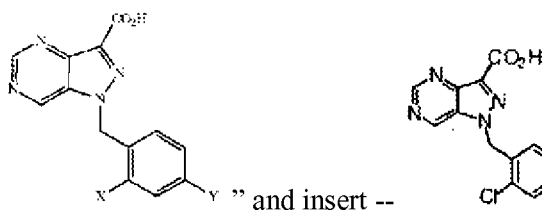 " and insert -- 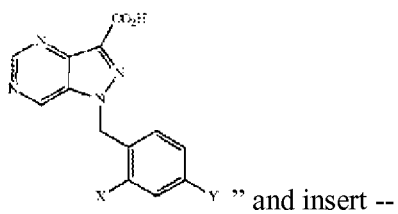 --, therefor.

In Column 51, Line 25, delete "conspectuses." and insert -- conceptuses. --, therefor.

In Column 53, Line 26, delete "propanetriol (glycerol), i-1,2,3,4-butanetetrol" and insert -- propantriol (glycerol), i-1,2,3,4-butantetrol --, therefor.

In Column 65, Line 37, delete "product." and insert -- product --, therefor.

In Column 70, Line 31, delete "$C_{18}H_{11}O_2F_3N_2O_2$ 415.01." and insert -- $C_{18}H_{11}Cl_2F_3N_2O_2$ 415.01, --, therefor.

In Column 75, Line 18, delete "322.0150." and insert -- 322.0150, --, therefor.

In Column 86, Line 48, delete "rates" and insert -- rales --, therefor.

In Column 98, Line 32, delete "Chemy J," and insert -- Cherry J, --, therefor.

In Column 99, Line 23, delete "(FIG. 9A-9B)." and insert -- (FIGS. 9A-9B). --, therefor.

In Column 112, Line 11, delete "(FIG. 19A-19B)" and insert -- (FIGS. 19A-19B) --, therefor.

In Column 113, Lines 46, delete "$e^{-7.5415+1.2569*dose}$" and insert -- $e^{-7.5415+1.2569*dose}$ . --, therefor.

In the Claims:

In Column 114, Lines 29-30, in Claim 3, delete "341-(2,4-dichlorobenzyl)-6-chloro-1H-indazole-3-ylJ-propionic acid;" and insert -- 3-[1-(2,4-dichlorobenzyl)-6-chloro-1H-indazole-3-yl]-propionic acid; --, therefor.

In Column 114, Line 39, in Claim 4, delete "(JVVS-2-72 or H2-gamendazole);" and insert -- (JWS-2-72 or H2-gamendazole); --, therefor.

In Column 115, Line 56, in Claim 13, delete "and pharmaceutically" and insert -- pharmaceutically --, therefor.

In Column 115, Line 61, in Claim 14, delete "(JVVS-2-72 or H2-gamendazole);" and insert -- (JWS-2-72 or H2-gamendazole); --, therefor.